US009533977B2

United States Patent
Park et al.

(10) Patent No.: US 9,533,977 B2
(45) Date of Patent: Jan. 3, 2017

(54) OXAZOLIDINONE DERIVATIVE AS CETP INHIBITOR, ITS PREPARATION METHOD, AND PHARMACEUTICAL COMPOSITION COMPRISING THE SAME

(71) Applicant: DONG-A ST CO., LTD., Seoul (KR)

(72) Inventors: Jang Hyun Park, Gyeonggi-do (KR); Seung Hyun Song, Gyeonggi-do (KR); Han Kook Chung, Gyeonggi-do (KR); Heung Jae Kim, Gyeonggi-do (KR); Ji Hye Lee, Gyeonggi-do (KR); Byung Jun Jang, Seoul (KR); Eun Jung Kim, Seoul (KR); Hae Hum Jung, Gyeonggi-do (KR); Chae Lim Ryu, Gyeonggi-do (KR); Jae-Sung Hwang, Gyeonggi-do (KR); Hyung Ki Lee, Gyeonggi-do (KR); Kyung Koo Kang, Gyeonggi-do (KR); Soon-Hoe Kim, Gyeonggi-do (KR)

(73) Assignee: DONG-A ST CO., LTD. (KR)

( * ) Notice: Subject to any disclaimer, the term of this patent is extended or adjusted under 35 U.S.C. 154(b) by 0 days.

(21) Appl. No.: 14/779,534

(22) PCT Filed: Mar. 28, 2014

(86) PCT No.: PCT/KR2014/002677
§ 371 (c)(1),
(2) Date: Sep. 23, 2015

(87) PCT Pub. No.: WO2014/157994
PCT Pub. Date: Oct. 2, 2014

(65) Prior Publication Data
US 2016/0039804 A1    Feb. 11, 2016

(30) Foreign Application Priority Data

Mar. 29, 2013  (KR) .................. 10-2013-0034713
Mar. 27, 2014  (KR) .................. 10-2014-0036344

(51) Int. Cl.
*C07D 413/06*   (2006.01)
*C07D 413/14*   (2006.01)
*C07D 417/14*   (2006.01)

(52) U.S. Cl.
CPC ........... *C07D 413/06* (2013.01); *C07D 413/14* (2013.01); *C07D 417/14* (2013.01)

(58) Field of Classification Search
None
See application file for complete search history.

(56) References Cited

FOREIGN PATENT DOCUMENTS

| CN | 103958484 A | 7/2014 |
|---|---|---|
| WO | 2007-081569 A2 | 7/2007 |
| WO | 2007-081571 A2 | 7/2007 |
| WO | 2014-012428 A1 | 1/2014 |

OTHER PUBLICATIONS

Barter et al., "Cholesteryl ester transfer protein: A novel target for raising HDL and inhibiting atherosclerosis", Artwrioscler Thrombosis, and Vascular Biology, 2003; 23:160-167.
Cockerill et al., "High-density lipoproteins inhibit cytokine-induced expression of endothelial cell adhesion molecules", Received Jul. 10, 1995, Accepted Aug. 18, Arterioscler. Thromb. Vasc. Biol. 1995; 15; 1987-1994.
Dorman, Susan E., "Clinical features of dominant and recessive interferon Y receptor 1 deficiencies", Lancet 2004, 364: 2113-2121.
Fonarow, Gregg C., "Treating to goal: new strategies for initiating and optimizing lipid-lowering therapy in patients with atherosclerosis", Vascular Medicine, 2002, 7: 187-194.
Gordon et al., "High density lipoprotein as a protective factor against coronary heart disease / The Framingham study", The American Journal of Medicine, May 1977, vol. 62, pp. 707-714.
Inazu et al., "Cholesteryl ester transfer protein and atherosclerosis", Current Opinion in Lipidology 2000, 11:389-396.
JAMA, Executive summary of the third report of the National Cholesterol Education program (NCEP) expert panel on detection, evaluation, and treatment of high blood cholesterol in adults (adult treatment panel III), May 16, 2001, 2001, vol. 285, No. 19, pp. 2486-2497.
Kuhar, Marsha Bernard, "Update on managing hypercholesterolemia: The New NCEP Guidelines", AAOHN Journal, Aug. 2002, 50, 8, pp. 360-364.
LaRosa et al., "Effect of statins on risk of Coronary Disease: A Meta-analysis of randomized controlled trials", JAMA, Dec. 22/29, 1999, vol. 282, No. 24, pp. 2340-2346
Miller et al., "The Tromso Heart-study / High-density lipoprotein and coronary heart-disease: A prospective case-control study", The Lancet, May 7, 1977, pp. 965-968.
Mineo et al., "Endothelial and antithrombotic actions of HDL", Circulation Research, Jun. 9, 2006; 98: pp. 1352-1364.
Negre-Salvayre, Anne et al., "Antioxidant and cytoprotective properties of high-density lipoproteins in vascular cells", Free Radical Biology & Medicine 41 (2006) 1031-1040.
Pedersen et al., "Randomised trial of cholesterol lowering in 4444 patients with coronary heart disease" the Scandinavian Simvastatin Survival Study (4S), The Lancet, Nov. 19, 1994; 344, 8934; ProQuest pp. 1383-1389.

(Continued)

*Primary Examiner* — Timothy R Rozof
(74) *Attorney, Agent, or Firm* — Lerner, David, Littenberg, Krumholz & Mentlik, LLP

(57) ABSTRACT

Disclosed are a novel oxazolidinone derivative exhibiting inhibitory activity against CETP, a preparation method thereof, and a pharmaceutical composition comprising the same. Exhibiting excellent inhibitory activity against CETP, the oxazolidinone derivative can be effectively applied to the prevention or treatment of various CETP enzyme activity- or HDL cholesterol level-related diseases such as dyslipidemia, atherosclerosis, and coronary heart disease.

23 Claims, No Drawings

(56) References Cited

OTHER PUBLICATIONS

Rhoads et al., "Serum lipoproteins and coronary heart disease in a population study of Hawaii Japanese men", The New England Journal of Medicine, Feb. 5, 1976, vol. 294, No. 6, pp. 293-298.
Tall, Alan R., "Plasma cholesteryl ester transfer protein", Journal of Lipid Research, vol. 34, 1993, pp. 1255-1274.
Tangirala et al., "Regression of atherosclerosis induced by liver-directed gene transfer of Apolipoprotein A-I in mice", Circulation 1999; 100:1816-1822.
The Lancet, "MRC/BHF heart protection study of cholesterol lowering with simvastatin in 20 536 high-risk individuals: a randomised placebo-controlled trial", Jul. 6, 2002, vol. 360, pp. 7-22.
International Search Report from International Publication PCT/KR2014/002677 mailed Jul. 30, 2014.
Search Report of Chinese Patent Application No. 201480018703.5 dated Sep. 5, 2016.
Extended European Search Report for Application No. 14775848.6 dated Aug. 5, 2016.

OXAZOLIDINONE DERIVATIVE AS CETP INHIBITOR, ITS PREPARATION METHOD, AND PHARMACEUTICAL COMPOSITION COMPRISING THE SAME

CROSS-REFERENCE TO RELATED APPLICATION

This application is a national phase entry under 35 U.S.C. §371 of International Application No. PCT/KR2014/002677, filed Mar. 28, 2014, which claims priority to Korean Patent Application No. 10-2013-0034713, filed Mar. 29, 2013 and Korean Patent Application No. 10-2014-0036344, filed Mar. 27, 2014, the disclosures of which are incorporated herein by reference.

TECHNICAL FIELD

The present invention relates to a novel oxazolidinone derivative with inhibitory activity against CETP, a preparation method thereof, and a pharmaceutical composition comprising the same.

BACKGROUND ART

Coronary heart disease (CHD), also known as atherosclerotic heart disease, is caused by plaque being deposited and building up along the inner walls of the arteries of the heart. The risk of arteries narrowing increases with smoking, insufficient exercise, obesity, diabetes, high blood pressure, and dyslipidemia. CHD is the leading cause of death irrespective of sex and accounts for approximately 500,000 deaths in the United States every year out of 15.8 million CHD patients.

According to the guidelines of NCEP (National Cholesterol Education Program) ATP-III (Adult Treatment Panel III), management of blood cholesterol levels is very important for the prevention or improvement of CHD. NCEP classified persons with CHD history or CHD-equivalent risk factors into three groups according to the 10-year risk of CHD onset (<10%, 10-20%, >20%), and proposed criteria/goals of living behavior improvement and drug treatment for reducing LDL-cholesterol levels in each group (*JAMA* 2001; 285: 2486-2497, *AAOHN J* 2002; 50: 360-364, *Vascular Medicine* 2002; 7: 187-194). 3-Hydroxy-3-methylglutaryl-CoA (HMG-CoA) reductase inhibitors, such as statins, are reported to lower blood cholesterol levels by inhibiting the synthesis of cholesterol and increasing the expression of LDL receptors, and make a contribution to the treatment or prevention of cardiovascular diseases irrespective of sex and age by reducing the incidence of cardiac diseases by as high as approximately 30% (*Lancet* 1994; 344: 1383-1389, *Lancet* 2002; 360: 7-22, *Lancet* 2004; 364: 7-22, *JAMA* 1999; 282: 2340-2346). However, these statin-lineage drugs are not sufficiently efficacious for the treatment or prevention of atherosclerosis-caused CHD.

Since the report that the incidence risk of CHD increases with a decrease in HDL cholesterol level (N. Engl. J. Med. 1976; 294: 293-298, *Lancet*. 1977; 1: 965-968, *Am. J. Med.* 1977; 62: 707-714), HDL cholesterol-increasing drugs such as fibrate or niacin have been developed (*Vasc Med* 2002; 7: 187-194, *JAMA* 2001; 285: 2486-2497). Particularly, as HDL was revealed to have various functions including the inhibition of LDL oxidation (*Free Radic. Biol. Med.* 41: 1031-1040), anti-thrombotic/anti-inflammatory activity (*Circ. Res.* 98: 1352-1364, *Arterioscler. Thromb. Vasc. Biol.* 15: 1987-1994), and the prevention and improvement of arteriosclerosis (*Circulation*. 100: 1816-1822) as well as reverse cholesterol transport, the use of HLD cholesterol-increasing drugs alone or in combination with statins has been expected as a novel therapy for CHD. However, this therapy is reported to produce a safety problem such as drug resistance, and its efficacy is, in fact, not as high as expected. Therefore, there is a need for more potent HDL cholesterol-increasing drugs.

In response to this need, CETP (cholesterylester transfer protein) inhibitors have been developed as HDL cholesterol-increasing agents with a novel mechanism. CETP is a hydrophobic glycoprotein which circulates mostly in association with HDL in blood (Tall A R et al., *J Lipid Res.* 1993; 34: 1255-1274). This plasma protein performs a homoexchange by collecting triglycerides from very low density lipoprotein (VLDL) and LDL, and exchanges them for cholesteryl esters from HLD, thus contributing to the redistribution of cholesterols and the remodeling of lipoproteins. Consistent with this in vivo activity of CETP, it is reported that blood HDL cholesterol levels decrease with an increase in blood CETP activity (*Curr Opin. Lipidol.* 11; 4: 389-396). Also, decreased CETP activity brings about an increase in HDL cholesterol levels which, in turn, facilitate reverse cholesterol transport, resulting in a preventive arteriosclerosis effect (Philip J et al., *Arterioscler Thromb Vasc Biol.* 2003; 23: 160-167). The suggestion of the improvement of HDL cholesterol through CETP inhibition has incited pharmaceutical companies to develop drugs for preventing or treating CHD, including anacetrapib of Merck, torcetrapib of Pfizer, and dalcetrapib of Roche. During clinical trials, torcetrapib was first to be dropped due to safety problems, followed by dalcetrapib due to its weak inhibitory activity against CETP and insufficient clinical efficacy.

Therefore, there is an urgent need for a CETP inhibitor that is safes and more potent, allowing for the development of a drug for preventing or treating CHD with excellent efficacy.

DISCLOSURE

Technical Problem

The present invention is to provide a novel oxazolidinone derivative, a preparation method thereof, and a pharmaceutical composition comprising the same.

Technical Solution

An aspect of the present invention provides a compound represented by the following Chemical Formula 1, an isomer thereof, or a pharmaceutically acceptable salt thereof:

[Chemical Formula 1]

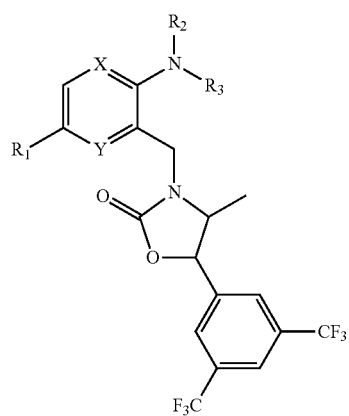

wherein,

X is N, Y is N or CH;

$R_1$ is selected from the group consisting of hydrogen, cyano, halogen, halogen-substituted or unsubstituted C1 to C6 alkyl, —$NR_4R_5$, —$(O)SO_2R_6$ which is optionally substituted with C1-C4 alkyl or may not be, substituted or unsubstituted C3 to C20 cycloalkyl, substituted or unsubstituted C3 to C20 heterocyclic, substituted or unsubstituted C6 to C40 aryl, and substituted or unsubstituted C3 to C40 heteroaryl;

$R_4$ and $R_5$ are independently selected from the group consisting of hydrogen, C1 to C4 alkyl, and C3 to C6 cycloalkyl with a proviso that when $R_4$ and $R_5$ are independently C1 to C4 alkyl, $R_4$ and $R_5$ may be linked to each other to form a hetero cycle containing N;

the substituted C3 to C20 cycloalky or the C3 to C20 heterocyclic in $R_1$ may be substituted with a functional radical selected from the group consisting of halogen, halogen-substituted or unsubstituted C1 to C4 alkyl, C1 to C4 hydroxyalkyl, —$(CH_2)nCOR_7$, and —$(CH_2)nCO(O)R_7$;

the substituted C6 to C40 aryl in $R_1$ may be substituted with a functional radical selected from the group consisting of halogen, cyano, nitryl, C1 to C4 alkyl, C1 to C4 hydroxyalkyl, and C1 to C4 alkoxy;

the C3 to 40 heteroaryl in $R_1$ may be substituted with cyano, nitryl, oxo, —$NR_8R_9$, halogen, halogen-substituted or unsubstituted C1 to C4 alkyl, C1 to C4 hydroxyalkyl, C1 to C4 alkoxy, —$(CH_2)nCOR_{10}$, and —$(CH_2)nCO(O)R_{10}$;

$R_2$ is selected from the group consisting of hydrogen, hydroxy-substituted or unsubstituted C1 or C6 alkyl, C3 to C7 cycloalkyl, and —$(CH_2)nCO(O)R_{11}$;

$R_3$ is selected from the group consisting of C1 to C6 alkyl which may be substituted with substituted or unsubstituted C3 to C7 cycloalkyl or may not be, substituted or unsubstituted C3 to C7 cycloalkyl, substituted or unsubstituted C3 to C20 heterocyclic, and substituted or unsubstituted C6 to C20 spirocyclic heterocyclic;

$R_2$ and $R_3$ may be linked to each other to form a heterocycle containing N, said heterocycle being substituted with halogen-substituted or unsubstituted C1 to C4 alkyl or not;

the C3 to C7 cycloalkyl in $R_3$ may be substituted with a functional radical selected from the group consisting of oxo, —$NR_{12}R_{13}$, C1 to C4 hydroxyalkyl, and —$(CH_2)nCO(O)R_{14}$;

the substituted C3 to C20 heterocycle and the substituted C6 to C20 spirocyclic heterocyclic in $R_3$ may be independently substituted with a functional radical selected from the group consisting of oxo, C1 to C4 alkyl, C1 to C4 alkoxy, —$(CH_2)nCO(O)R_{15}$, —$COR_{16}$, and —$SO_2R_{17}$;

$R_{16}$ and $R_{17}$ are independently C1 to C4 alkyl or —$NR_{18}R_{19}$;

$R_6$, $R_7$, $R_8$, $R_9$, $R_{10}$, $R_{11}$, $R_{12}$, $R_{13}$, $R_{14}$, $R_{15}$, $R_{18}$ and $R_{19}$ are independently hydrogen or C1 to C4 alkyl;

n is an integer of 0, 1 or 2.

Provided in accordance with another aspect of the present invention are a method for preparing the novel compound of Chemical Formula 1, and a pharmaceutical composition with inhibitory activity against CETP, comprising the novel compound of Chemical Formula 1.

As supported in the following Example section, the compound of Chemical Formula 1 is a novel oxazolidinone derivative and is demonstrated to exhibit excellent inhibitory activity against CETP, compared to known CETP inhibitors. Thus, the compound of Chemical Formula 1, and a pharmaceutical composition comprising the same is effectively applicable to the prevention or treatment of various diseases related to CETP activity or HDL cholesterol level, including dyslipidemia, atherosclerosis, and coronary heart disease (CHD).

Below, a detailed description will be given of a novel compound, a preparation method thereof, and a pharmaceutical composition comprising the same in accordance with embodiments of the present invention.

According to one embodiment thereof, the present invention provides a novel compound of Chemical Formula 1 exhibiting CETP inhibition activity, an isomer thereof, or a pharmaceutically acceptable salt thereof.

The compound of Chemical Formula 1 is characterized by the heterocyclic structure in which X is N and Y is N or CH. This specific heterocyclic structure may affect properties of the compound of Chemical Formula 1 such as CETP inhibition activity and safety. Accordingly, the compound of Chemical Formula 1 with such a specific heterocyclic structure can be more effectively used in preventing or treating various diseases related with CETP enzyme activity or HDL cholesterol levels, compared to those without such heterocyclic structures.

Preferable in terms of CETP inhibition activity or safety is the heterocyclic structure wherein X is N, and Y is N. In this regard, in Chemical Formula 1, $R_1$ is unsubstituted C3 to C20 cycloalkyl, or C3 to C40 heteroaryl substituted with C1 to C4 alkyl; $R_2$ is C1 to C6 alkyl or C3 to C7 cycloalkyl, $R_3$ is C3 to C7 cycloalkyl, or C1 to C6 alkyl substituted with substituted C3 to C7 cycloalkyl; $R_2$ and $R_3$ are linked to each other to form a heterocycle which may be substituted with halogen-substituted or unsubstituted C1 to C4 alkyl or may not be.

Meanwhile, the novel compounds according to the embodiment may have one or more chiral centers and may exist as racemates or individual optical isomers, all of which fall within the scope of the present invention. As used herein, the term "isomer" generally refers to compounds with the same molecular formula but different chemical structures, and the term "optical isomer" is intended to encompass any stereoisomer which may be possible for the compound of one embodiment, including the same geometrical isomers.

It is understood that in the compound of Chemical Formula 1 according to one embodiment, each substituent may be attached to a chiral center of carbon atoms. The asymmetric carbon atoms on the compound according to the embodiment may be in the form of (R)-, (S)- or (R,S)-configuration. Suitably, the compound may exist as an enantiomer taking either (R)- or (S)-configuration. Further, the compound according to one embodiment of the present invention may take the form of any possible isomer or a mixture of possible isomers, for example, a pure geometrical isomer, a diastereomer, an enantiomer, a racemate, or a mixture thereof. In addition, when the compound according to one embodiment has a double bond, substituents attached to the double bond may take E or Z configuration. Moreover, when the compound of one embodiment contains bi-substituted cycloalkyl, each substituent on the cycloalkyl moiety may take cis- or trans-configuration As used herein, the term "pharmaceutically acceptable salt" refers to any salt which possesses the same biological activity and properties of the compound of Chemical Formula 1 according to one embodiment of the present invention and which is preferable in terms of pharmaceutical, biological or other characteristics. Non-limiting examples of the salt include inorganic or organic base addition salts or acid addition salts of the compound of Chemical Formula 1. In greater detail, the existence of an amine group or a similar alkaline group on Chemical Formula 1 makes it feasible to form an acid addition salt with an organic acid or inorganic acid. Examples of the organic acid applicable to the formation of an acid addition salt include acetic acid, propionic acid, glycolic acid, pyrubic acid, oxalic acid, maleic acid, malonic acid, succinic acid, furmaric acid, tartaric acid, citric acid, benzoic acid, cinnamic acid, manelic acid, methanesulfonic acid, ethanesulfonic acid, p-toluene sulfonic acid, and salicylic acid. Among the inorganic acids useful in the present invention are hydrochloric acid, hydrobromic acid, sulfonic acid, nitric acid and phosphoric acid. With regard to other pharmaceutically acceptable salts, reference may be made to literature such as [Remington's Pharmaceutical Sciences, 20th ed., Mack Publishing Company, Easton, Pa., (1985)].

The pharmaceutically acceptable salt of the compound according to one embodiment of the present invention may be synthesized by a typical chemical method from either a compound in the form of a free base, or an alkaline or acidic residue derived therefrom. Further, a second pharmaceutically acceptable salt may be synthesized from a first pharmaceutically acceptable salt. For example, a compound in a free base form may be reacted with a stoichiometric amount of a suitable acid to give an acid addition salt of the compound of one embodiment of the present invention. In this regard, the reaction may be carried out in water, an organic solvent or a mixture thereof, for example, in a non-aqueous medium such as ether, ethyl acetate, ethanol, isopropanol or acetonitrile. Furthermore, other pharmaceutically acceptable salts may be obtained using typical reactions obvious to those skilled in the art.

Concrete examples of the compound of Chemical Formula 1 include the compounds listed in Table 1, below, isomers thereof, and pharmaceutically acceptable salts thereof. In Table 1, compounds 1 to 93 have heterocyclic structures in which X is N and is CH while compounds 94 to 131 have heterocyclic structures in which X is N and Y is N. Exhibiting excellent inhibitory activity against CETP, these compounds of Chemical Formula 1 can be effectively applied to the prevention or treatment of various diseases related with CETP enzyme activity or HDL cholesterol levels, with preference for the compounds wherein X is N and Y is N:

TABLE 1

1  (4S,5R)-5-[3,5-bis(trifluoromethyl)phenyl]-4-methyl-3-[(2-(methyl (tetrahydrofuran-3-yl)amino)-5-(trifluoromethyl)pyridin-3-yl)methyl]-oxazolidin-2-one
2  (4S,5R)-5-[3,5-bis(trifluoromethyl)phenyl]-4-methyl-3-{(2-[ethyl(tetrahydrofuran-3-yl)amino]-5-(trifluoromethyl)pyridin-3-yl)methyl}-oxazolidin-2-one
3  (4S,5R)-5-[3,5-bis(trifluoromethyl)phenyl]-4-methyl-3-({2-[(3R,4R)-4-ethoxytetrahydrofuran-3-yl)(methyl)amino]-5-(trifluoromethyl)pyridin-3-yl}methyl)-oxazolidin-2-one
4  (4S,5R)-5-[3,5-bis(trifluoromethyl)phenyl]-4-methyl-3-({2-[(3S,4R)-ethoxytetrahydrofuran-3-yl)(methyl)amino]-5-(trifluoromethyl)pyridin-3-yl}methyl)-oxazolidin-2-one
5  (4S,5R)-5-[3,5-bis(trifluoromethyl)phenyl]-4-methyl-3-({2-[(tetrahydro-2H-pyran-4-yl)amino]-5-(trifluoromethyl)pyridin-3-yl}methyl)-oxazolidin-2-one
6  (4S,5S)-5-[3,5-bis(trifluoromethyl)phenyl]-4-methyl-3-({[2-(methyl)(tetrahydro-2H-pyran-4-yl)amino]-5-(trifluoromethyl)pyridin-3-yl}methyl)-oxazolidin-2-one
7  (4S,5R)-5-[3,5-bis(trifluoromethyl)phenyl]-4-methyl-3-({[2-(ethyl)(tetrahydro-2H-pyran-4-yl)amino]-5-(trifluoromethyl)pyridin-3-yl}methyl)-oxazolidin-2-one
8  (4S,5R)-5-[3,5-bis(trifluoromethyl)phenyl]-4-methyl-3-({[2-(propyl)(tetrahydro-2H-pyran-4-yl)amino]-5-(trifluoromethyl)pyridin-3-yl}methyl)-oxazolidin-2-one
9  (4S,5R)-5-[3,5-bis(trifluoromethyl)phenyl]-4-methyl-3-({[2-(butyl)(tetrahydro-2H-pyran-4-yl)amino]-5-(trifluoromethyl)pyridin-3-yl}methyl)-oxazolidin-2-one
10 (4S,5R)-5-[3,5-bis(trifluoromethyl)phenyl]-4-methyl-3-{[2-(cyclopropyl)(tetrahydro-2H-pyran-4-yl)amino]-5-(trifluoromethyl)pyridin-3-yl}methyl)-oxazolidin-2-one
11 (4S,5R)-5-[3,5-bis(trifluoromethyl)phenyl]-4-methyl-3-({[2-(cyclobutyl)(tetrahydro-2H-pyran-4-yl)amino]-5-(trifluoro)methylpyridin-3-yl}methyl)-oxazolidin-2-one
12 t-butyl [3-({(4S,5R)-5-[3,5-bis(trifluoromethyl)phenyl]-4-methyl-2-oxo-oxazolidin-3-yl}methyl)-5-(trifluoromethyl)pyridin-2-yl]-(tetrahydro-2H-pyran-4-yl)-carbamate
13 ethyl [3-({(4S,5R)-5-[3,5-bis(trifluoromethyl)phenyl]-4-methyl-2-oxo-oxazolidin-3-yl}methyl)-5-(trifluoromethyl)pyridin-2-yl]-(tetrahydro-2H-pyran-4-yl)-carbamate
14 (4S,5R)-5-[3,5-bis(trifluoromethyl)phenyl]-4-methyl-3-({[2-ethyl(tetrahydro-2H-pyran-4-yl)amino]-pyridin-3-yl}methyl)-oxazolidin-2-one
15 (4S,5R)-5-[3,5-bis(trifluoromethyl)phenyl]-4-methyl-3-({[2-ethyl(tetrahydro-2H-pyran-3-yl)amino]-5-(trifluoromethyl)pyridin-3-yl}methyl)-oxazolidin-2-one
16 (4S,5R)-5-[3,5-bis(trifluoromethyl)phenyl]-4-methyl-3-({2-[ethyl(tetrahydro-2H-pyran-4-yl)amino]-5-fluoropyridin-3-yl}methyl)-oxazolidin-2-one
17 t-butyl 2-([3-({(4S,5R)-5-[3,5-bis(trifluoromethyl)phenyl]-4-methyl-2-oxo-oxazolidin-3-yl}methyl)-5-(trifluoromethyl)pyridin-2-yl]-(tetrahydro-2H-pyran-4-yl)amino)-acetate
18 (4S,5R)-5-[3,5-bis(trifluoromethyl)phenyl]-4-methyl-3-({[2-(hydroxyethyl)(tetrahydro-2H-pyran-4-yl)amino]-5-(trifluoromethyl)pyridin-3-yl}methyl)-oxazolidin-2-one
19 (4S,5R)-5-[3,5-bis(trifluoromethyl)phenyl]-4-methyl-3-({[2-(oxepan-4-yl)amino]-5-(trifluoromethyl)pyridin-3-yl}methyl)-oxazolidin-2-one
20 (4S,5R)-5-[3,5-bis(trifluoromethyl)phenyl]-4-methyl-3-({[2-(methyl)(oxepen-4-yl)amino]-5-(trifluoromethyl)pyridin-3-yl}methyl)-oxazolidin-2-one
21 (4S,5R)-5-[3,5-bis(trifluoromethyl)phenyl]-4-methyl-3-({[2-(ethyl)(1,4-dioxaspiro[4.5]decan-8-yl)amino]-5-trifluoromethylpyridin-3-yl}methyl)-oxazolidin-2-one
22 (4S,5R)-5-[3,5-bis(trifluoromethyl)phenyl]-4-methyl-3-({[2-(ethyl)(4-oxocyclohexyl)amino]-5-(trifluoromethyl)pyridin-3-yl}methyl)-oxazolidin-2-one
23 (4S,5R)-5-[3,5-bis(trifluoromethyl)phenyl]-4-methyl-3-({[2-(ethyl)(4-ethylaminocyclohexyl)amino]-5-(trifluoromethyl)pyridin-3-yl}methyl)-oxazolidin-2-one
24 methyl 2-(4-{[3-({(4S,5R)-5-[3,5-bis(trifluoromethyl)phenyl]-4-methyl-2-oxo-oxazolidin-3-yl}methyl)-5-(trifluoromethyl)pyridin-2-yl](ethyl)amino}cyclohexyl)acetate
25 (4S,5R)-5-[3,5-bis(trifluoromethyl)phenyl]-4-methyl-3-({[2-(ethyl)(tetrahydro-2H-thiopyran-4-yl)amino]-5-(trifluoromethyl)pyridin-3-yl}methyl)-oxazolidin-2-one
26 (4S,5R)-5-[3,5-bis(trifluoromethyl)phenyl]-4-methyl-3-({[2-(ethyl)(1-oxidotetrahydro-2H-thiopyran-4-yl)amino]-5-(trifluoromethyl)pyridin-3-yl}methyl)-oxazolidin-2-one TABLE 1-continued

| | |
|---|---|
| 27 | t-butyl 4-{[3-({(4S,5R)-5-[3,5-bis(trifluoromethyl)phenyl]-4-methyl-2-oxo-oxazolidin-3-yl}methyl)-5-(trifluoromethyl)pyridin-2-yl](ethyl)amino}piperidine-1-carboxylate |
| 28 | (4S,5R)-5-[3,5-bis(trifluoromethyl)phenyl]-3-({[2-(ethyl)(piperidin-4-yl)amino]-5-(trifluoromethyl)pyridin-3-yl}methyl)-4-methyloxazolidin-2-one |
| 29 | (4S,5R)-5-[3,5-bis(trifluoromethyl)phenyl]-4-methyl-3-({[2-(ethyl)(1-methylpiperidin-4-yl)amino]-5-(trifluoromethyl)pyridin-3-yl}methyl)-oxazolidin-2-one |
| 30 | (4S,5R)-5-[3,5-bis(trifluoromethyl)phenyl]-4-methyl-3-({[2-(ethyl)(1,1-dimethylpiperidin-4-yl)amino]-5-(trifluoromethyl)pyridin-3-yl}methyl)-oxazolidin-2-one |
| 31 | ((4S,5R)-5-[3,5-bis(trifluoromethyl)phenyl]-4-methyl-3-({[2-(ethyl)(1-propylpiperidin-4-yl)amino]-5-trifluoromethylpyridin-3-yl}methyl)-oxazolidin-2-one |
| 32 | (4S,5R)-5-[3,5-bis(trifluoromethyl)phenyl]-4-methyl-3-({[2-(ethyl)(1-methanesulfonylpiperidin-4-yl)amino]-5-trifluoromethylpyridin-3-yl}methyl)-oxazolidin-2-one |
| 33 | (4S,5R)-5-[3,5-bis(trifluoromethyl)phenyl]-4-methyl-3-({[2-(ethyl)(1-acetylpiperidin-4-yl)amino]-5-(trifluoromethyl}pyridin-3-yl}methyl)-oxazolidin-2-one |
| 34 | (4S,5R)-5-[3,5-bis(trifluoromethyl)phenyl]-4-methyl-3-({[2-(ethyl)(1-propionylpiperidin-4-yl)amino]-5-(trifluoromethyl)pyridin-3-yl}methyl)-oxazolidin-2-one |
| 35 | methyl 4-{[3-({(4S,5R)-5-[3,5-bis(trifluoromethyl)phenyl]-4-methyl-2-oxo-oxazolidin-3-yl}methyl)-5-(trifluoromethyl)pyridin-2-yl](ethyl)amino}piperidine-1-carboxylate |
| 36 | ethyl 4-{[3-({(4S,5R)-5-[3,5-bis(trifluoromethyl)phenyl]-4-methyl-2-oxo-oxazolidin-3-yl}methyl)-5-(trifluoromethyl)pyridin-2-yl](ethyl)amino}piperidine-1-carboxylate |
| 37 | methyl 4-{[3-({(4S,5R)-5-[3,5-bis(trifluoromethyl)phenyl]-4-methyl-2-oxo-oxazolidin-3-yl}methyl)-5-(trifluoromethyl)pyridin-2-yl](ethyl)amino}-N,N-dimethylpiperidine-1-carboxamide |
| 38 | methyl 2-(4-{[3-({(4S,5R)-5-[3,5-bis(trifluoromethyl)phenyl]-4-methyl-2-oxo-oxazolidin-3-yl}methyl)-5-(trifluoromethyl)pyridin-2-yl](ethyl)amino}piperidin-1-yl)acetate |
| 39 | 2-(4-{[3-({(4S,5R)-5-[3,5-bis(trifluoromethyl)phenyl]-4-methyl-2-oxo-oxazolidin-3-yl}methyl)-5-(trifluoromethyl)pyridin-2-yl](ethyl)amino}piperidin-1-yl)acetic acid |
| 40 | (4S,5R)-5-[3,5-bis(trifluoromethyl)phenyl]-4-methyl-3-({[2-(ethyl)(tetrahydro-2H-pyran-4-yl)amino]-5-bromopyridin-3-yl}methyl)-oxazolidin-2-one |
| 41 | (4S,5R)-5-[3,5-bis(trifluoromethyl)phenyl]-4-methyl-3-({[2-(ethyl)(tetrahydro-2H-pyran-4-yl)amino]-5-(pyrrolidin-1-yl)pyridin-3-yl}methyl)-oxazolidin-2-one |
| 42 | methyl 2-(4-{5-({(4S,5R)-5-[3,5-bis(trifluoromethyl)phenyl]-4-methyl-2-oxo-oxazolidin-3-yl}methyl)-6-[ethyl(tetrahydro-2H-pyran-4-yl)amino]pyridin-3-yl}piperazin-1-yl)acetate |
| 43 | (4S,5R)-5-[3,5-bis(trifluoromethyl)phenyl]-4-methyl-3-({[2-(ethyl)(tetrahydro-2H-pyran-4-yl)amino]-5-(azetidin-1-yl)pyridin-3-yl}methyl)-oxazolidin-2-one |
| 44 | (4S,5R)-5-[3,5-bis(trifluoromethyl)phenyl]-4-methyl-3-({[2-(ethyl)(tetrahydro-2H-pyran-4-yl)amino]-5-(piperidin-1-yl)pyridin-3-yl}methyl)-oxazolidin-2-one |
| 45 | (4S,5R)-5-[3,5-bis(trifluoromethyl)phenyl]-4-methyl-3-({[2-(ethyl)(tetrahydro-2H-pyran-4-yl)amino]-5-phenylpyridin-3-yl}methyl)-oxazolidin-2-one |
| 46 | (4S,5R)-5-[3,5-bis(trifluoromethyl)phenyl]-4-methyl-3-({[2-(ethyl)(tetrahydro-2H-pyran-4-yl)amino]-5-(3-methylphenyl)pyridin-3-yl}methyl)-oxazolidin-2-one |
| 47 | (4S,5R)-5-[3,5-bis(trifluoromethyl)phenyl]-4-methyl-3-({[2-(ethyl)(tetrahydro-2H-pyran-4-yl)amino]-5-(3-fluorophenyl)pyridin-3-yl}methyl)-oxazolidin-2-one |
| 48 | (4S,5R)-5-[3,5-bis(trifluoromethyl)phenyl]-4-methyl-3-({[2-(ethyl)(tetrahydro-2H-pyran-4-yl)amino]-5-(3-ethoxyphenyl)pyridin-3-yl}methyl)-oxazolidin-2-one |
| 49 | (4S,5R)-5-[3,5-bis(trifluoromethyl)phenyl]-4-methyl-3-({[2-(ethyl)(tetrahydro-2H-pyran-4-yl)amino]-5-(furan-2-yl)pyridin-3-yl}methyl)-oxazolidin-2-one |
| 50 | (4S,5R)-5-[3,5-bis(trifluoromethyl)phenyl]-4-methyl-3-({[2-(ethyl)(tetrahydro-2H-pyran-4-yl)amino]-5-(1-methyl-1H-pyrrol-2-yl)pyridin-3-yl}methyl)-oxazolidin-2-one |
| 51 | (4S,5R)-5-[3,5-bis(trifluoromethyl)phenyl]-4-methyl-3-({[2-(ethyl)(tetrahydro-2H-pyran-4-yl)amino]-5-(3,5-dimethyl-isoxazol-4-yl}methyl)-oxazolidin-2-one |
| 52 | (4S,5R)-5-[3,5-bis(trifluoromethyl)phenyl]-4-methyl-3-({[2-(ethyl)(tetrahydro-2H-pyran-4-yl)amino]-pyridin-3-yl}methyl)-oxazolidin-2-one |
| 53 | (4S,5R)-5-[3,5-bis(trifluoromethyl)phenyl]-4-methyl-3-({[2-(ethyl)(cyclohexyl)amino]-5-(trifluoromethyl)pyridin-3-yl}methyl)-oxazolidin-2-one |
| 54 | 5-({4S,5R)-5-[3,5-bis(trifluoromethyl)phenyl]-4-methyl-2-oxo-1,3-oxazolidin-3-yl}methyl)-6-[(cyclohexyl)(ethyl)amino]nicotinonitrile |
| 55 | 5-{[(4S,5R)-5-[3,5-bis(trifluoromethyl)phenyl]-4-methyl-2-oxo-oxazolidin-3-yl]methyl}-6-[(cyclohexyl)(ethyl)amino]-pyridin-3-yl methanesulfonate |
| 56 | (4S,5R)-5-[3,5-bis(trifluoromethyl)phenyl]-4-methyl-3-({[2-(ethyl)(cyclohexyl-4-yl)amino]-5-(1-methyl-1H-pyrrol-2-yl)pyridin-3-yl}methyl)-oxazolidin-2-one |
| 57 | (4S,5R)-5-[3,5-bis(trifluoromethyl)phenyl]-4-methyl-3-({[2-(methyl)(cyclohexyl-4-yl)amino]-5-(3,5-dimethylisoxazol-4-yl)pyridin-3-yl}methyl)-oxazolidin-2-one |
| 58 | (4S,5R)-5-[3,5-bis(trifluoromethyl)phenyl]-4-methyl-3-({[2-(ethyl)(cyclohexyl)amino]-5-(3,5-dimethylisoxazol-4-yl)pyridin-3-yl}methyl)-oxazolidin-2-one |
| 59 | (4S,5R)-5-[3,5-bis(trifluoromethyl)phenyl]-4-methyl-3-({[2-(ethyl)(cyclohexyl)amino]-5-(1-methyl-1H-pyrazol-5-yl)pyridin-3-yl}methyl)-oxazolidin-2-one |
| 60 | (4S,5R)-5-[3,5-bis(trifluoromethyl)phenyl]-4-methyl-3-({[2-(ethyl)(cyclohexyl-4-yl)amino]-5-(1-methyl-1H-3-(trifluoromethyl)-pyrazol-5-yl)pyridin-3-yl}methyl)-oxazolidin-2-one |
| 61 | ethyl (2-{4-[5-({(4S,5R)-5-[3,5-bis(trifluoromethyl)phenyl]-4-methyl-2-oxo-oxazolidin-3-yl}methyl)]-6-[(cyclohexyl)(ethyl)amino]pyridin-3-yl}-1H-pyrazol-1-yl)acetate |
| 62 | (4S,5R)-5-[3,5-bis(trifluoromethyl)phenyl]-4-methyl-3-({[2-(ethyl)(cyclohexyl)amino]-5-(1-methyl-1H-pyrazol-4-yl)pyridin-3-yl}methyl)-oxazolidin-2-one |
| 63 | (4S,5R)-5-[3,5-bis(trifluoromethyl)phenyl]-4-methyl-3-({[2-(ethyl)(cyclohexyl)amino]-5-(3-methyl-thiophen-5-yl)pyridin-3-yl}methyl)-oxazolidin-2-one |
| 64 | (4S,5R)-5-[3,5-bis(trifluoromethyl)phenyl]-3-({[2-(ethyl)(cyclohexyl)amino]-5-(1,3,5-trimethyl-1H-pyrazol-4-yl}pyridin-3-yl}methyl)-oxazolidin-2-one |
| 65 | (4S,5R)-5-[3,5-bis(trifluoromethyl)phenyl]-4-methyl-3-({[2-(ethyl)(cyclohexyl-4-yl)amino]-5-(3,5-dimethyl-1H-pyrazol-4-yl)pyridin-3-yl}methyl)-oxazolidin-2-one |

TABLE 1-continued

| | |
|---|---|
| 66 | (4S,5R)-5-[3,5-bis(trifluoromethyl)phenyl]-4-methyl-3-({[2-(ethyl)(cyclohexyl)amino]-5-(1-methyl-1H-tetrazol-5-yl)pyridin-3-yl}methyl)-oxazolidin-2-one |
| 67 | (4S,5R)-5-[3,5-bis(trifluoromethyl)phenyl]-4-methyl-3-({[2-(ethyl)(cyclohexyl)amino]-5-(1-isobutyl-1H-pyrazol-4-yl)pyridin-3-yl}methyl)-oxazolidin-2-one |
| 68 | (4S,5R)-5-[3,5-bis(trifluoromethyl)phenyl]-4-methyl-3-({[2-(ethyl)(cyclohexyl)amino]-5-(1H-pyrazol-4-yl)pyridin-3-yl}methyl)-oxazolidin-2-one |
| 69 | (4S,5R)-5-[3,5-bis(trifluoromethyl)phenyl]-4-methyl-3-({[2-(ethyl)(cyclohexyl)amino]-5-(1,3-dimethyl-1H-pyrazol-4-yl)pyridin-3-yl}methyl)-oxazolidin-2-one |
| 70 | (4S,5R)-5-[3,5-bis(trifluoromethyl)phenyl]-4-methyl-3-({[2-(ethyl)(cyclohexyl)amino]-5-(3-methoxy-thiophen-2-yl)pyridin-3-yl}methyl)-oxazolidin-2-one |
| 71 | 5-{5-({(4S,5S)-5-[3,5-bis(trifluoromethyl)phenyl]-4-methyl-2-oxo-oxazolidin-3-yl}methyl)-6-[(cyclohexyl)(ethyl)amino]pyridin-3-yl}-thiophene-2-carbonitrile |
| 72 | (4S,5R)-5-[3,5-bis(trifluoromethyl)phenyl]-4-methyl-3-({[2-(ethyl)(cyclohexyl)amino]-5-(3-(trifluoromethyl)-1H-pyrazol-4-yl)pyridin-3-yl}methyl)-oxazolidin-2-one |
| 73 | ethyl 4-{5-({(4S,5R)-5-[3,5-bis(trifluoromethyl)phenyl]-4-methyl-2-oxo-oxazolin-3-yl}methyl)-6-[(cyclohexyl)(ethyl)amino)]pyridin-3-yl}-3-methylisoxazole-5-carboxylate |
| 74 | ethyl 5-{5-({(4S,5R)-5-[3,5-bis(trifluoromethyl)phenyl]-4-methyl-2-oxo-oxazolin-3-yl}methyl)-6-[(cyclohexyl)(ethyl)amino)]pyridin-3-yl}-3-methylisoxazole-4-carboxylate |
| 75 | (4S,5R)-5-[3,5-bis(trifluoromethyl)phenyl]-4-methyl-3-({[2-(ethyl)(cyclohexyl)amino]-5-(2-methyl-furan-5-yl)pyridin-3-yl}methyl)-oxazolidin-2-one |
| 76 | t-butyl 2-{5-({(4S,5S)-5-[3,5-bis(trifluoromethyl)phenyl]-4-methyl-2-oxo-oxazolidin-3-yl}methyl)-6-[(cyclohexyl)(ethyl)amino]pyridin-3-yl}-1H-pyrrole-1-carboxylate |
| 77 | (4S,5R)-5-[3,5-bis(trifluoromethyl)phenyl]-4-methyl-3-({[2-(ethyl)(cyclohexyl)amino]-5-(thiophen-3-yl)pyridin-3-yl}methyl)-oxazolidin-2-one |
| 78 | (4S,5R)-5-[3,5-bis(trifluoromethyl)phenyl]-4-methyl-3-({[2-(ethyl)(cyclohexyl)amino]-5-(3-methyl-thiophen-2-yl)pyridin-3-yl}methyl)-oxazolidin-2-one |
| 79 | (4S,5R)-5-[3,5-bis(trifluoromethyl)phenyl]-4-methyl-3-({[2-(ethyl)(cyclohexyl)amino]-5-(2-methyl-thiophen-5-yl)pyridin-3-yl}methyl)-oxazolidin-2-one |
| 80 | (4S,5R)-5-[3,5-bis(trifluoromethyl)phenyl]-4-methyl-3-({[2-(ethyl)(cyclohexyl)amino]-5-(thiophen-2-yl)pyridin-3-yl}methyl)-oxazolidin-2-one |
| 81 | (4S,5R)-5-[3,5-bis(trifluoromethyl)phenyl]-4-methyl-3-({[2-(ethyl)(cyclohexyl)amino]-5-(thiazol-4-yl)pyridin-3-yl}methyl)-oxazolidin-2-one |
| 82 | 3-{5-({(4S,5S)-5-[3,5-bis(trifluoromethyl)phenyl]-4-methyl-2-oxo-oxazolidin-3-yl}methyl)-6-[(cyclohexyl)(ethyl)amino]pyridin-3-yl}-thiophene-2-carbonitrile |
| 83 | t-butyl 4-[5-({(4S,5S)-5-[3,5-bis(trifluoromethyl)phenyl]-4-methyl-2-oxo-oxazolidin-3-yl}methyl)-6-[cyclohexyl(ethyl)amino]pyridin-3-yl]-5-methylisoxazol-3-yl-carbamate |
| 84 | (4S,5R)-5-[3,5-bis(trifluoromethyl)phenyl]-4-methyl-3-({[2-(ethyl)(cyclohexyl)amino]-5-(2,4-dimethyl-thiazol-5-yl)pyridin-3-yl}methyl)-oxazolidin-2-one |
| 85 | (4S,5R)-5-[3,5-bis(trifluoromethyl)phenyl]-4-methyl-3-({[2-(ethyl)(cyclohexyl)amino]-5-(3-amino-5-methyl-isoxazol-4-yl)pyridin-3-yl}methyl)-oxazolidin-2-one |
| 86 | (4S,5R)-5-[3,5-bis(trifluoromethyl)phenyl]-4-methyl-3-({[2-(ethyl)(cyclohexyl)amino]-5-(3-methyl-thiophen-4-yl)pyridin-3-yl}methyl)-oxazolidin-2-one |
| 87 | (4S,5R)-5-[3,5-bis(trifluoromethyl)phenyl]-4-methyl-3-({[2-(ethyl)(cyclohexyl)amino]-5-(3-methyl-isothioxazol-4-yl)pyridin-3-yl}methyl)-oxazolidin-2-one |
| 88 | (4S,5R)-5-[3,5-bis(trifluoromethyl)phenyl]-4-methyl-3-({[2-(ethyl)(cyclohexyl)amino]-5-(pyrrolidin-1-yl)pyridin-3-yl}methyl)-oxazolidin-2-one |
| 89 | (4S,5R)-5-[3,5-bis(trifluoromethyl)phenyl]-4-methyl-3-({[2-(ethyl)(cyclohexyl)amino]-5-(2-methyl-pyrrolidin-1-yl)pyridin-3-yl}methyl)-oxazolidin-2-one |
| 90 | (4S,5R)-5-[3,5-bis(trifluoromethyl)phenyl]-4-methyl-3-({[2-(ethyl)(cyclohexyl)amino]-5-(2-ethyl-pyrrolidin-1-yl)pyridin-3-yl}methyl)-oxazolidin-2-one |
| 91 | (4S,5R)-5-[3,5-bis(trifluoromethyl)phenyl]-4-methyl-3-({[2-(ethyl)(cyclohexyl)amino]-5-(3,3-difluoro-pyrrolidin-1-yl)pyridin-3-yl}methyl)-oxazolidin-2-one |
| 92 | (4S,5R)-5-[3,5-bis(trifluoromethyl)phenyl]-4-methyl-3-({[2-(ethyl)(cyclohexyl)amino]-5-(2-(trifluoromethyl)-pyrrolidin-1-yl)pyridin-3-yl}methyl)-oxazolidin-2-one |
| 93 | 3-[5-({(4S,5R)-5-[3,5-bis(trifluoromethyl)phenyl]-4-methyl-2-oxo-oxazolidin-3-yl}methyl)-6-[(cyclohexyl)(ethyl)amino]pyridin-3-yl]-1,2,4-oxadiazol-5(4H)-one |
| 94 | (4S,5R)-5-[3,5-bis(trifluoromethyl)phenyl]-4-methyl-3-{[2-(cyclohexylamino)-5-(3,5-dimethyl-isoxazol-4-yl)pyrazin-3-yl]methyl}-oxazolidin-2-one |
| 95 | (4S,5R)-5-[3,5-bis(trifluoromethyl)phenyl]-4-methyl-3-({[2-(methyl)(cyclohexyl)amino]-5-(3,5-dimethyl-isoxazol-4-yl)pyrazin-3-yl}methyl)-oxazolidin-2-one |
| 96 | (4S,5R)-5-[3,5-bis(trifluoromethyl)phenyl]-4-methyl-3-({[2-(ethyl)(cyclohexyl)amino]-5-(3,5-dimethyl-isoxazol-4-yl)pyrazin-3-yl}methyl)-oxazolidin-2-one |
| 97 | (4S,5R)-5-[3,5-bis(trifluoromethyl)phenyl]-3-({[2-(cyclopropyl)(cyclohexyl)amino]-5-(3,5-dimethyl-isoxazol-4-yl)pyrazin-3-yl}methyl)-4-methyloxazolidin-2-one |
| 98 | (4S,5S)-5-[3,5-bis(trifluoromethyl)phenyl]-3-{[6-(3,5-dimethylisoxazol-4-yl)-3-(piperidin-1-yl)pyrazin-2-yl]methyl}-4-methyloxazolidin-2-one |
| 99 | (4S,5S)-5-[3,5-bis(trifluoromethyl)phenyl]-3-{[6-(3,5-dimethylisoxazol-4-yl)-3-(2,6-dimethylmorpholino)pyrazin-2-yl]methyl}-4-methyloxazolidin-2-one |
| 100 | (4S,5S)-5-[3,5-bis(trifluoromethyl)phenyl]-3-{[6-(3,5-dimethylisoxazol-4-yl)-3-[3-(trifluoromethyl)piperidin-1-yl]pyrazin-2-yl]methyl}-4-methyloxazolidin-2-one |
| 101 | (4S,5R)-5-[3,5-bis(trifluoromethyl)phenyl]-3-({[3-(cyclopentylmethyl)(ethyl)amino]-4-methyl6-(3,5-dimethylisoxazol-4-yl)pyrazin-3-yl}methyl)-oxazolidin-2-one |
| 102 | trans-4-({[3-({(4S,5S)-5-[3,5-bis(trifluoromethyl)phenyl]-4-methyl-2-oxazolidin-3-yl}methyl)-5-(3,5-dimethyloxazol-4-yl)pyrazin-2-yl]{N-(ethyl)aminomethyl]cyclohexyl})acetic acid |
| 103 | trans-4-({[3-({(4S,5S)-5-[3,5-bis(trifluoromethyl)phenyl]-4-methyl-2-oxazolidin-3-yl}methyl)-5-(pyrrolidin-1-yl)pyrazin-2-yl]{N-(ethyl)aminomethyl]cyclohexyl})acetic acid |
| 104 | trans-4-({[3-({(4S,5S)-5-[3,5-bis(trifluoromethyl)phenyl]-4-methyl-2-oxazolidin-3-yl}methyl)-5-(1-methyl-1H-pyrrol-2-yl)pyrazin-2-yl]{N-(ethyl)aminomethyl]cyclohexyl})acetic acid |

TABLE 1-continued

| | |
|---|---|
| 105 | trans-4-({[3-({[4S,5S)-5-[3,5-bis(trifluoromethyl)phenyl]-methyl-2-oxazolidin-3-yl}methyl)-5-(thiophen-3-yl)pyrazin-2-yl]{[N-(ethyl)aminomethyl]cyclohexyl)}acetic acid |
| 106 | trans-4-({[3-({(4S,5S)-5-[3,5-bis(trifluoromethyl)phenyl]-4-methyl-2-oxazolidin-3-yl}methyl)-5-(1-methyl-1H-pyrazol-5-yl)pyrazin-2-yl]{[N-(ethyl)aminomethyl]cyclohexyl)}acetic acid |
| 107 | trans-4-({[3-({(4S,5S)-5-[3,5-bis(trifluoromethyl)phenyl]-4-methyl-2-oxazolidin-3-yl}methyl)-5-(1,3-dimethyl-1H-pyrazol-5-yl)pyrazin-2-yl]{[N-(ethyl)aminomethyl]cyclohexyl)}acetic acid |
| 108 | trans-4-({[3-({(4S,5S)-5-[3,5-bis(trifluoromethyl)phenyl]-4-methyl-2-oxazolidin-3-yl}methyl)-5-(1,3-dimethyl-1H-pyrazol-4-yl)pyrazin-2-yl]{[N-(ethyl)aminomethyl]cyclohexyl)}acetic acid |
| 109 | trans-4-({[3-({(4S,5S)-5-[3,5-bis(trifluoromethyl)phenyl]-4-methyl-2-oxazolidin-3-yl}methyl)-5-(3-methoxythiophen-2-yl)pyrazin-2-yl]{[N-(ethyl)aminomethyl]cyclohexyl)}acetic acid |
| 110 | trans-4-({[3-({(4S,5S)-5-[3,5-bis(trifluoromethyl)phenyl]-4-methyl-2-oxazolidin-3-yl}methyl)-5-(4-methylthiophen-2??-yl)pyrazin-2-yl]{[N-(ethyl)aminomethyl]cyclohexyl)}acetic acid |
| 111 | trans-4-({[3-({(4S,5S)-5-[3,5-bis(trifluoromethyl)phenyl]-4-methyl-2-oxazolidin-3-yl}methyl)-5-(3-methylthiophen-2-yl)pyrazin-2-yl]{[N-(ethyl)aminomethyl]cyclohexyl)}acetic acid |
| 112 | trans-4-({[3-({(4S,5S)-5-[3,5-bis(trifluoromethyl)phenyl]-4-methyl-2-oxazolidin-3-yl}methyl)-5-(thiazol-2-yl)pyrazin-2-yl]{[N-(ethyl)aminomethyl]cyclohexyl)}acetic acid |
| 113 | trans-4-({[3-({(4S,5S)-5-[3,5-bis(trifluoromethyl)phenyl]-4-methyl-2-oxazolidin-3-yl}methyl)-5-(thiazol-4-yl)pyrazin-2-yl]{[N-(ethyl)aminomethyl]cyclohexyl)}acetic acid |
| 114 | trans-4-({[3-({[4S,5S)-5-[3,5-bis(trifluoromethyl)phenyl]-4-methyl-2-oxazolidin-3-yl}methyl)-5-(thiophen-2-yl)pyrazin-2-yl]{[N-(ethyl)aminomethyl]cycbhexyl)}acetic acid |
| 115 | trans-4-({[3-({(4S,5S)-5-[3,5-bis(trifluoromethyl)phenyl]-4-methyl-2-oxazolidin-3-yl}methyl)-5-(5-acetylthiophen-2-yl)pyrazin-2-yl]{[N-(ethyl)aminomethyl]cyclohexyl)}acetic acid |
| 116 | trans-4-({[3-({(4S,5S)-5-[3,5-bis(trifluoromethyl)phenyl]-4-methyl-2-oxazolidin-3-yl}methyl)-5-phenylpyrazin-2-yl]{[N-(ethyl)aminomethyl]cyclohexyl)}acetic acid |
| 117 | trans-4-({[3-({(4S,5S)-5-[3,5-bis(trifluoromethyl)phenyl]-4-methyl-2-oxazolidin-3-yl}methyl)-5-(4-cyanophenyl)pyrazin-2-yl]{[N-(ethyl)aminomethyl]cyclohexyl)}acetic acid |
| 118 | trans-4-({[3-({(4S,5S)-5-[3,5-bis(trifluoromethyl)phenyl]-4-methyl-2-oxazolidin-3-yl}methyl)-5-(4-hydroxymethylphenyl)pyrazin-2-yl]{[N-(ethyl)aminomethyl]cyclohexyl)}acetic acid |
| 119 | trans-4-({[3-({(4S,5S)-5-[3,5-bis(trifluoromethyl)phenyl]-4-methyl-2-oxazolidin-3-yl}methyl)-5-(pyridin-3-yl)pyrazin-2-yl]{[N-(ethyl)aminomethyl]cyclohexyl)}acetic acid |
| 120 | trans-4-({[3-({(4S,5S)-5-[3,5-bis(trifluoromethyl)phenyl]-4-methyl-2-oxazolidin-3-yl}methyl)-5-(5-fluoropyridin-3-yl)pyrazin-2-yl]{[N-(ethyl)aminomethyl]cyclohexyl)}acetic acid |
| 121 | trans-4-({[3-({(4S,5S)-5-[3,5-bis(trifluoromethyl)phenyl]-4-methyl-2-oxazolidin-3-yl}methyl)-5-(cyclopropylpyrazin-2-yl)]{[N-(ethyl)aminomethyl]cyclohexyl)}acetic acid |
| 122 | trans-4-({[3-({(4S,5S)-5-[3,5-bis(trifluoromethyl)phenyl]-4-methyl-2-oxazolidin-3-yl}methyl)-5-(cyclobutylpyrazin-2-yl)]{[N-(ethyl)aminomethyl]cyclohexyl)}acetic acid |
| 123 | trans-4-({[3-({(4S,5S)-5-[3,5-bis(trifluoromethyl)phenyl]-4-methyl-2-oxazolidin-3-yl}methyl)-5-(3,5-dimethyloxazol-4-yl)pyrazin-2-yl]{[N-(propyl)aminomethyl]cyclohexyl)}acetic acid |
| 124 | trans-4-({[3-({(4S,5S)-5-[3,5-bis(trifluoromethyl)phenyl]-4-methyl-2-oxazolidin-3-yl}methyl)-5-(pyrrolidin-1-yl)pyrazin-2-yl]{[N-(propyl)aminomethyl]cyclohexyl)}acetic acid |
| 125 | trans-4-({[3-({(4S,5S)-5-[3,5-bis(trifluoromethyl)phenyl]-4-methyl-2-oxazolidin-3-yl}methyl)-5-(cyclohexylpyrazin-2-yl)]{[N-(propyl)aminomethyl]cyclohexyl)}acetic acid |
| 126 | trans-4-({[3-({(4S,5S)-5-[3,5-bis(trifluoromethyl)phenyl]-4-methyl-2-oxazolidin-3-yl}methyl)-5-(3,5-dimethyloxazol-4-yl)pyrazin-2-yl]{[N-(methyl)aminomethyl]cyclohexyl)}acetic acid |
| 127 | trans-4-({[3-({(4S,5S)-5-[3,5-bis(trifluoromethyl)phenyl]-4-methyl-2-oxazolidin-3-yl}methyl)-5-(pyrrolidin-1-yl)pyrazin-2-yl]{[N-(methyl)aminomethyl]cyclohexyl)}acetic acid |
| 128 | trans-4-({[3-({(4S,5S)-5-[3,5-bis(trifluoromethyl)phenyl]-4-methyl-2-oxazolidin-3-yl}methyl)-5-(cyclobutylpyrazin-2-yl)]{[N-(methyl)aminomethyl]cyclohexyl)}acetic acid |
| 129 | trans-4-({[3-({(4S,5S)-5-[3,5-bis(trifluoromethyl)phenyl]-4-methyl-2-oxazolidin-3-yl}methyl)-5-(cyclopentylpyrazin-2-yl)]{[N-(methyl)aminomethyl]cyclohexyl)}acetic acid |
| 130 | trans-4-({[3-({(4S,5S)-5-[3,5-bis(trifluoromethyl)phenyl]-4-methyl-2-oxazolidin-3-yl}methyl)-5-(3,5-dimethyloxazol-4-yl)pyrazin-2-yl]{[N-(ethyl)aminomethyl]cyclohexyl)}propanol |
| 131 | trans-4-({[3-({(4S,5S)-5-[3,5-bis(trifluoromethyl)phenyl]-4-methyl-2-oxazolidin-3-yl}methyl)-5-(pyrrolidin-4-yl)pyrazin-2-yl]{[N-(ethyl)aminomethyl]cyclohexyl)}propanol |

Contemplated in accordance with a further aspect of the present invention is a method for preparing the compound of Chemical Formula 1. In one embodiment, the preparation method comprises: introducing a leaving group to a compound of Chemical Formula 2-1 to give a compound of Chemical Formula 2-2; reacting the compound of Chemical Formula 2-2 with (4S,5R)-5-[3,5-bis(trifluoromethyl)phenyl])-4-methyl-oxazolidin-2-one to form a compound of Chemical Formula 3; and coupling the compound of Chemical Formula 3 with an amine group (—NR$_2$R$_3$) to afford the compound of Chemical Formula 1:

[Chemical Formula 2-1]

[Chemical Formula 2-2]

[Chemical Formula 3]

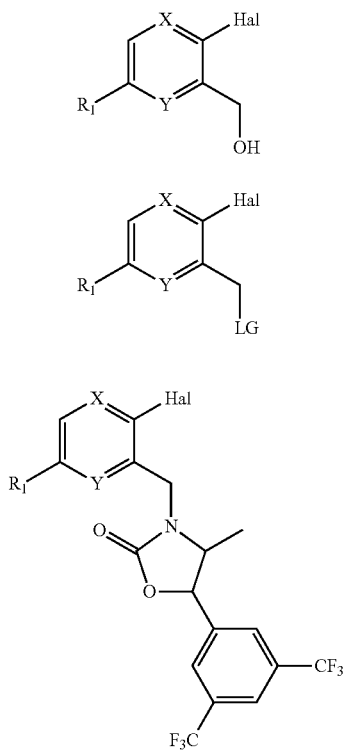

wherein, Hal represents halogen, LG represents a leaving group selected from among halogen or methanesulfonyl, and X, Y, R$_1$, R$_2$ and R$_3$ are as defined in Chemical Formula 1.

In this preparation method, the compound of Chemical Formula 2-1 may be obtained by reducing a compound of Chemical Formula 2:

[Chemical Formula 2]

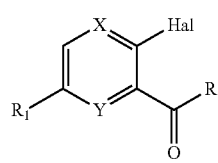

wherein, R is hydrogen or C1 to C4 alkoxy, for example, methoxy, and Hal and R$_1$ are as defined in Chemical Formula 2-1.

The preparation method described above may be summarized as illustrated in the following Reaction Scheme 1:

[Reaction Scheme 1]

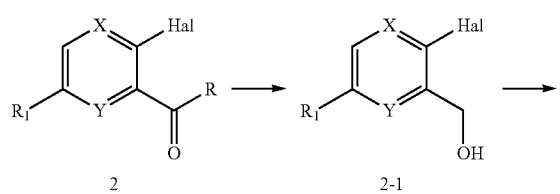

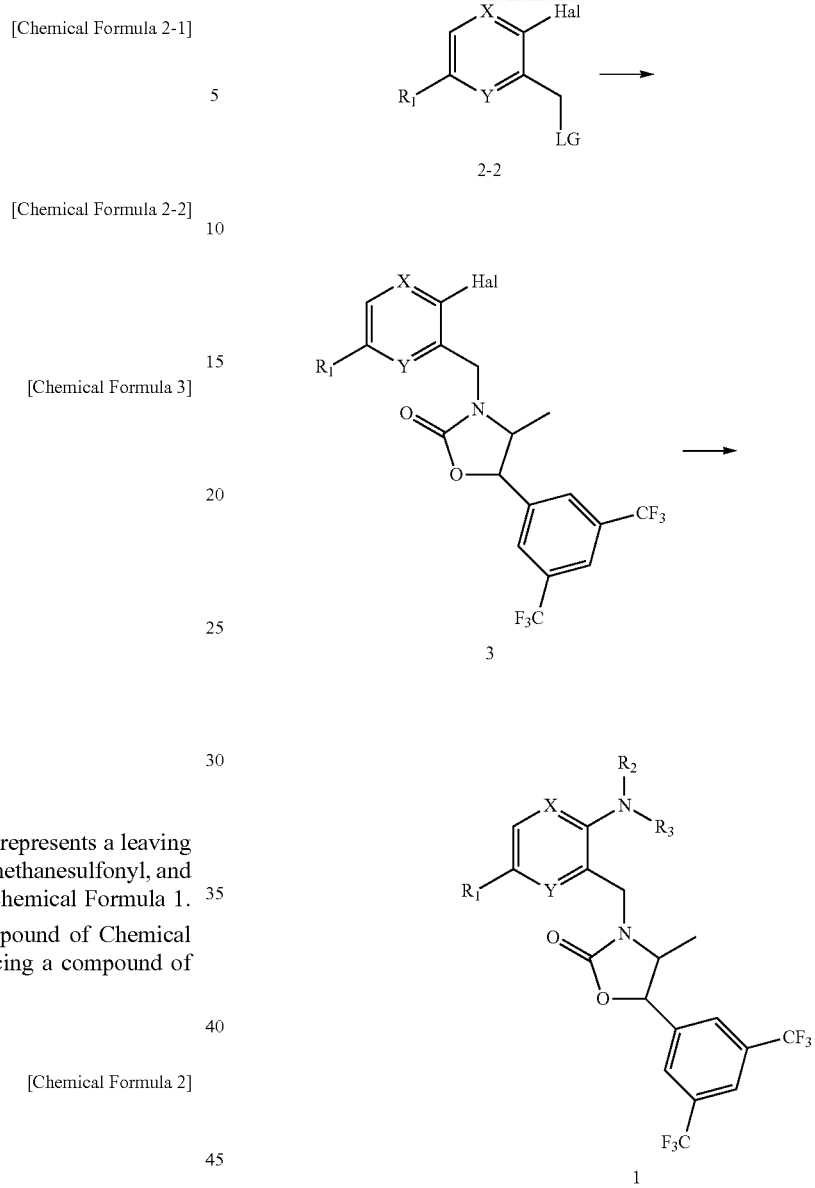

In this preparation method, the coupling of the amine group (—NR$_2$R$_3$) may be carried out in a single process using NHR$_2$R$_3$ as a reactant, or in a multi-step process first by using NHR$_2$ or NHR$_3$ as a reactant, followed by introducing R$_2$ or R$_3$. This additional introduction of R$_2$ or R$_3$ may be achieved using alkylation or other cycloalkyl or heterocyclic coupling reactions known to those skilled in the art according to the kind of each substituent. When R$_2$ is a hydroxy-containing substituent, for example, hydroxy-substituted C1 to C6 alkyl, the preparation method may further comprises protecting the hydroxy group with a protecting group such as t-butyldimethylsilyl group, and this hydroxy-protecting group may be finally removed to afford the compound of Chemical Formula 1.

In another embodiment, the method for preparing the compound of Chemical Formula 1 comprises introducing a leaving group to a compound of Chemical Formula 4-1 to give a compound of Chemical Formula 4-2; and reacting the compound of Chemical Formula 4-2 with (4S,5R)-5-[3,5-bis(trifluoromethyl)phenyl])-4-methyl-oxazolidin-2-one:

[Chemical Formula 4-1]

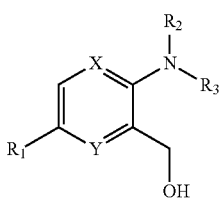

[Chemical Formula 4-2]

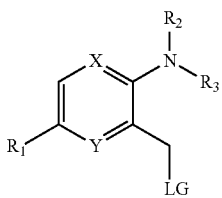

wherein, LG represents a leaving group selected from among halogen and sulfanyl group, and X, Y, $R_1$, $R_2$ and $R_3$ are as defined in Chemical Formula 1.

This preparation method may further comprise, prior to the formation of the compound of Chemical Formula 4-2, coupling a compound of Chemical Formula 2 with an amine group (—$NR_2R_3$) to form a compound of Chemical Formula 4; and reducing the compound of Chemical Formula 4 into the compound of Chemical Formula 4-1:

[Chemical Formula 2]

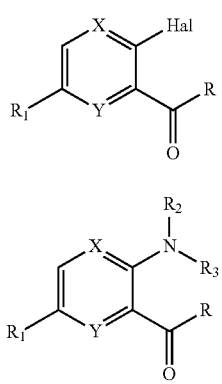

[Chemical Formula 4]

wherein, Hal represents halogen, R is hydrogen or C1 to C4 alkoxy, and X, Y, $R_1$, $R_2$ and $R_3$ are as defined in Chemical Formula 1.

This method may be summarized as illustrated in the following Reaction Scheme 2:

[Reaction Scheme 2]

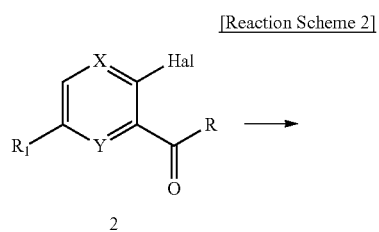

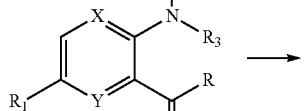

4

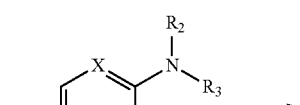

4-1

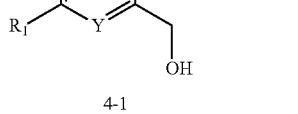

4-2

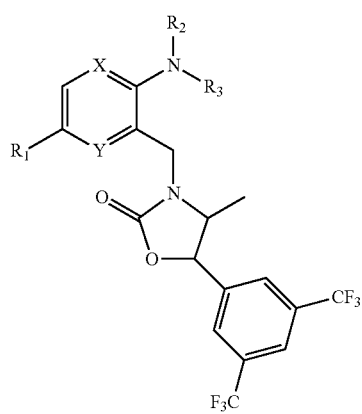

1

In accordance with a further embodiment, the preparation method may further comprise, before the formation of the compound of Chemical Formula 4-2, introducing at least one of $R_2$ and $R_3$ to the amine group on a compound of Chemical Formula 5 to give a compound of Chemical Formula 6; performing acyl substitution on the compound of Chemical Formula 6 to form a compound of Chemical Formula 4; and reducing the compound of Chemical Formula 4 to a compound of Chemical Formula 4-1. For the acyl substitution, the halogen of the compound of Chemical Formula 6 may substituted by an aldehyde or alkylcarbonyl group:

[Chemical Formula 5]

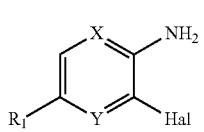

[Chemical Formula 6]

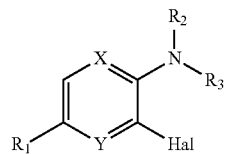

[Chemical Formula 4]

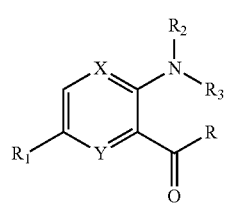

[Chemical Formula 4-1]

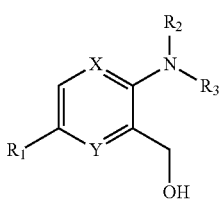

wherein, Hal represents halogen, R is hydrogen or C1 to C4 alkoxy, and X, Y, $R_1$, $R_2$ and $R_3$ are as defined in Chemical Formula 1.

This preparation method may be summarized as illustrated in the following Reaction Scheme 3:

[Reaction Scheme 3]

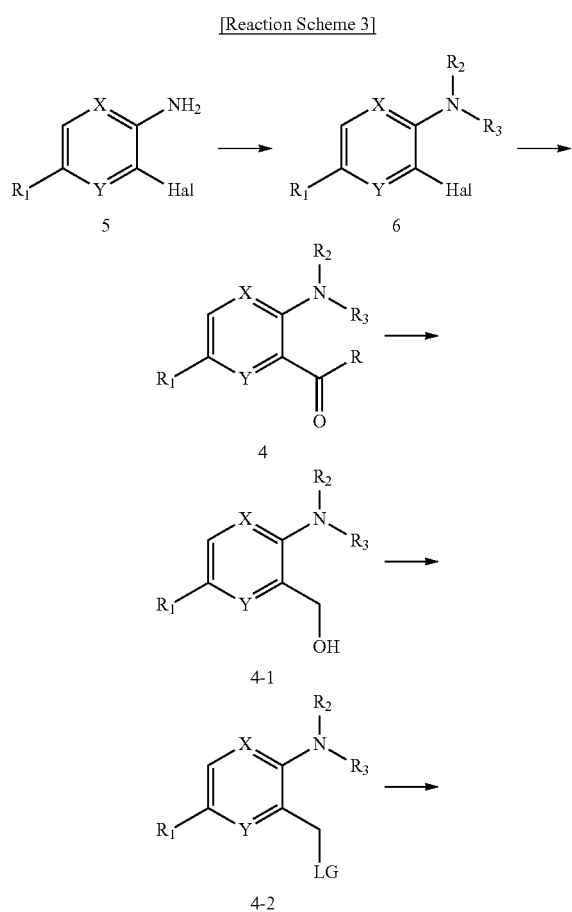

In a still further embodiment, the preparation method may comprises, prior to the formation of the compound of Chemical Formula 4-2, coupling a compound of Chemical Formula 2b with an amine group (—$NR_2R_3$) to give a compound of Chemical Formula 4b'; introducing $R_1$ to the compound of Chemical Formula 4b' to form a compound of Chemical Formula 4 (exception that $R_1$ is hydrogen or halogen); and reducing the compound of Chemical Formula 4 to a compound of Chemical Formula 4-1:

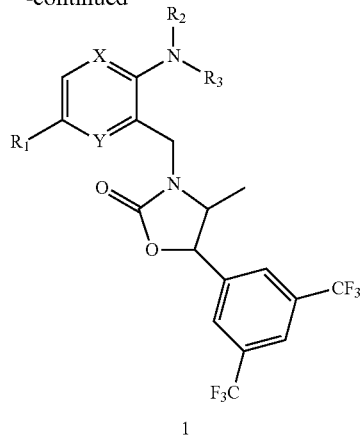

[Chemical Formula 2b]

[Chemical Formula 4b']

[Chemical Formula 4]

[Chemical Formula 4-1]

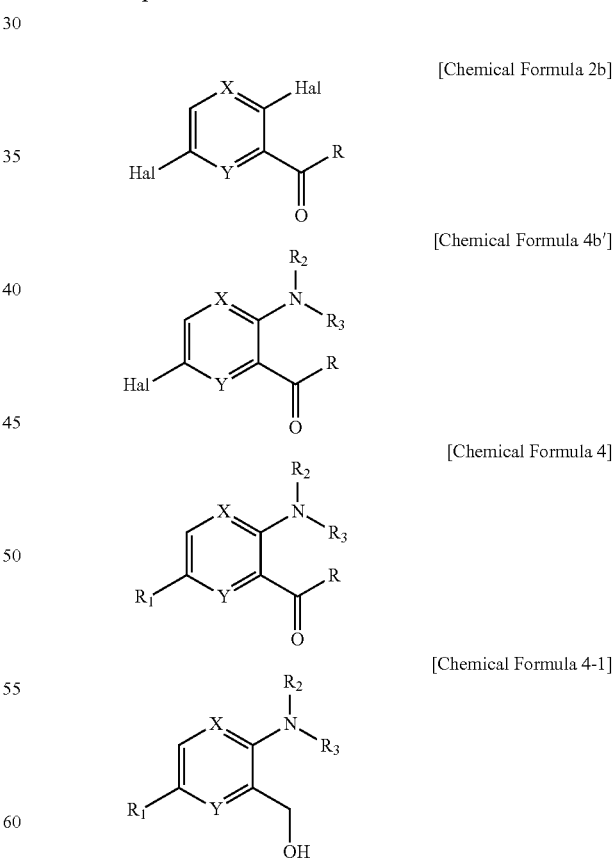

wherein, Hal represents halogen, R is hydrogen or C1 to C4 alkoxy, and X, Y, $R_1$, $R_2$ and $R_3$ are as defined in Chemical Formula 1, with the exception that $R_1$ is hydrogen or halogen.

This preparation method may be summarized as illustrated in the following Reaction Scheme 4, by which the compound of Chemical Formula 1 can be suitably prepared, with the exception that $R_1$ is hydrogen or halogen:

[Reaction Scheme 4]

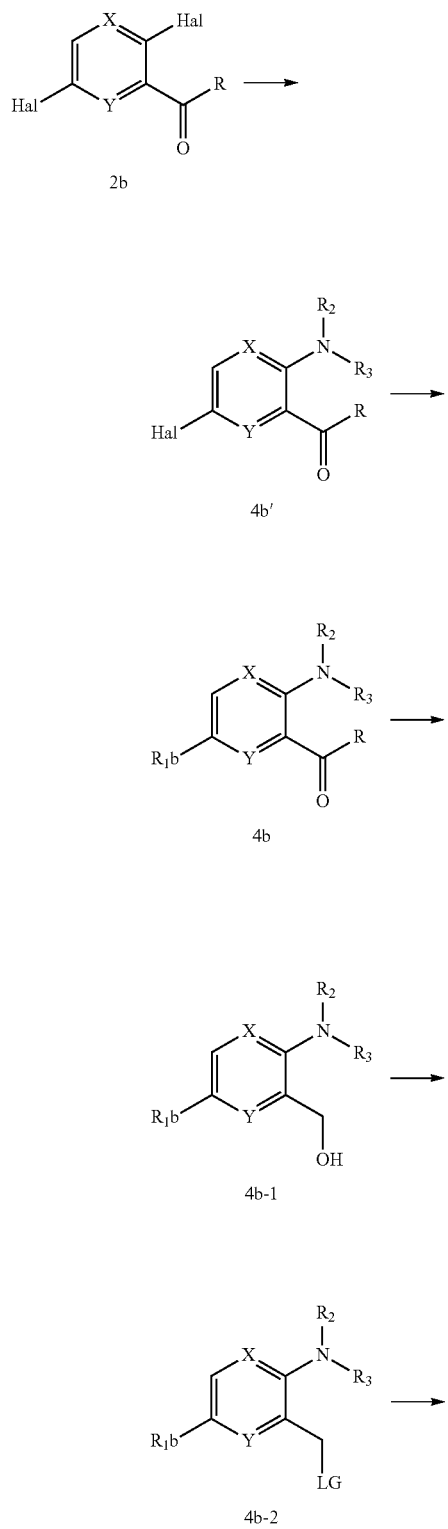

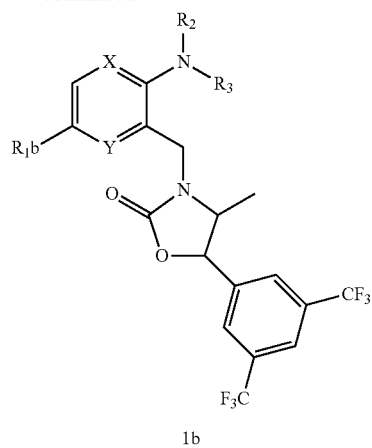

In Reaction Scheme 4, $R_{1b}$ is the same as $R_1$ except that $R_1$ is hydrogen or halogen.

Also in the preparation methods illustrated in Reaction Schemes 2 to 4, the coupling of the amine group ($-NR_2R_3$) may be carried out in a single process using $NHR_2R_3$ as a reactant or in a multi-step process first by using $NHR_2$ or $NHR_3$ as a reactant, followed by introducing $R_2$ or $R_3$. When $R_2$ is a hydroxy-containing substituent, the preparation method may further comprises protecting the hydroxy group with a protecting group such as t-butyldimethylsilyl group, and this hydroxy-protecting group may be finally removed to afford the compound of Chemical Formula 1.

According to a still further aspect thereof, the present invention provides a method for preparing the compound of Chemical Formula 1 wherein $R_1$ is not hydrogen.

In one embodiment, this preparation method comprises introducing a leaving group to a compound of Chemical Formula 2a-1 to form a compound of Chemical Formula 2a-2; reacting the compound of Chemical Formula 2a-2 with (4S,5R)-5-[3,5-bis(trifluoromethyl)phenyl])-4-methyl-oxazolidin-2-one to form a compound of Chemical Formula 3a; coupling the compound of Chemical Formula 3a with an amine group ($-NR_2R_3$) to form a compound of Chemical Formula 1a'; and introducing $R_1$ to the compound of Chemical Formula 1a' to afford the compound of Chemical Formula 1 (with the exception that $R_1$ is hydrogen):

[Chemical Formula 2a-1]

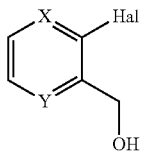

[Chemical Formula 2a-2]

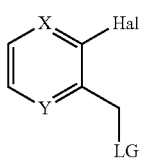

[Chemical Formula 3a]

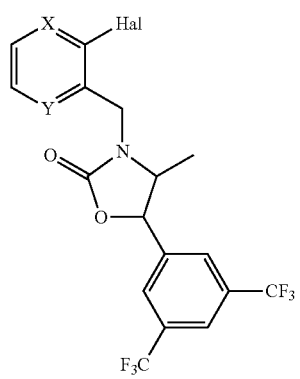

[Chemical Formula 1a']

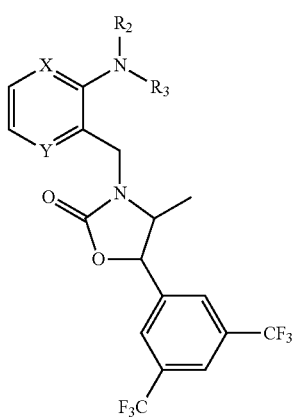

Wherein, Hal represents halogen, LG represents a leaving group selected from among halogen and methanesulfonyl, and X, Y, $R_1$, $R_2$ and $R_3$ are as defined in Chemical Formula 1, with the proviso that $R_1$ is not hydrogen.

More exemplary embodiment of this preparation may be summarized as illustrated in the following Reaction Scheme 5:

[Reaction Scheme 5]

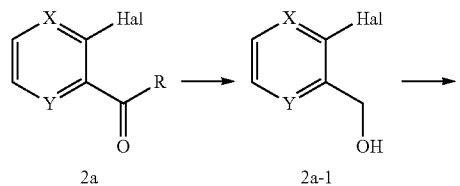

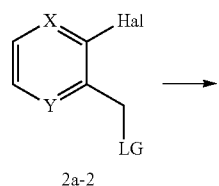

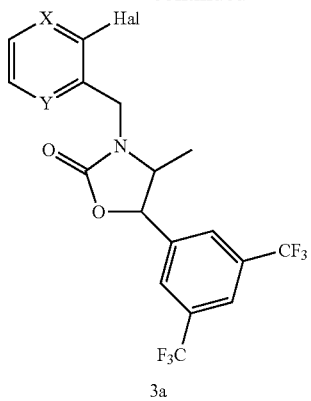

3a

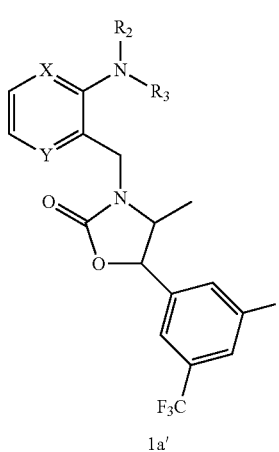

1a'

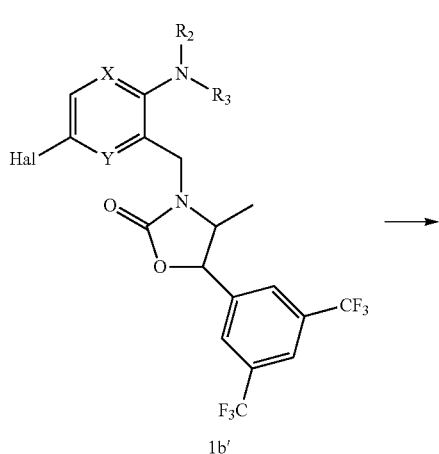

1b'

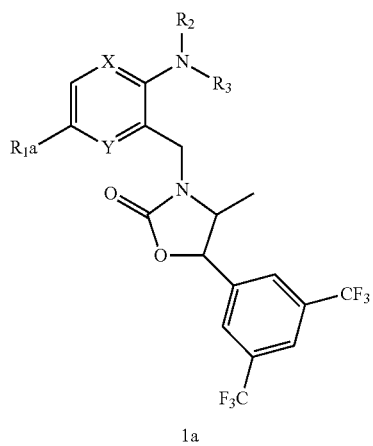

1a wherein $R_{1a}$ is the same as $R_1$, with the proviso that $R_1$ is not hydrogen.

In the preparation method of Reaction Scheme 5, the compound of Chemical Formula 2a may be reduced to a compound of Chemical Formula 2a-1, which is then prepared into the compound of Chemical Formula 1a' through the steps described above. In addition, the introduction of $R_1$ (e.g, $R_{1a}$, but not hydrogen) to the compound of Chemical Formula 1a' may be achieved by halogenating the compound of Chemical Formula 1a' to the compound of Chemical Formula 1b', and substituting the halogen on the compound of Chemical Formula 1b' with $R_1$ (e.g, $R_{1a}$, but not hydrogen).

In another embodiment, the method for preparing the compound of Chemical Formula 1 wherein $R_1$ is not hydrogen, comprises introducing a leaving group to the compound of Chemical Formula 4a-1 to give a compound of Chemical Formula 4a-2; reacting the compound of Chemical Formula 4a-2 with (4S,5R)-5-[3,5-bis(trifluoromethyl)phenyl])-4-methyl-oxazolidin-2-one to form a compound of Chemical Formula 1a'; and introducing $R_1$ to a compound of Chemical Formula 1a' to afford the compound of Chemical Formula 1 (with the exception that $R_1$ is hydrogen):

[Chemical Formula 4a-1]

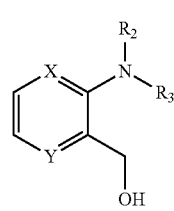

[Chemical Formula 4a-2]

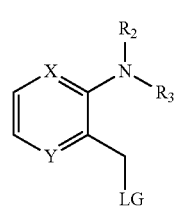

[Chemical Formula 1a']

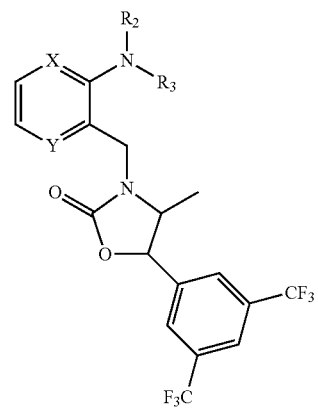

1a' wherein, LG represents a leaving group selected from among halogen and methanesulfonyl, and X, Y, $R_1$, $R_2$ and $R_3$ are as defined in Chemical Formula 1, with the provision that $R_1$ is not hydrogen.

An exemplary embodiment of this preparation may be summarized as illustrated in the following Reaction Scheme 6:

[Reaction Scheme 6]

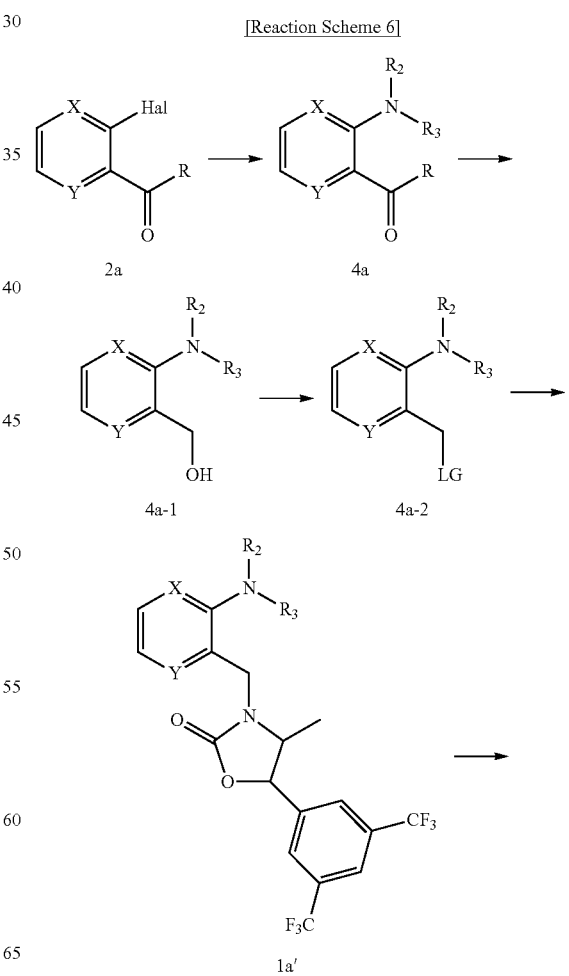

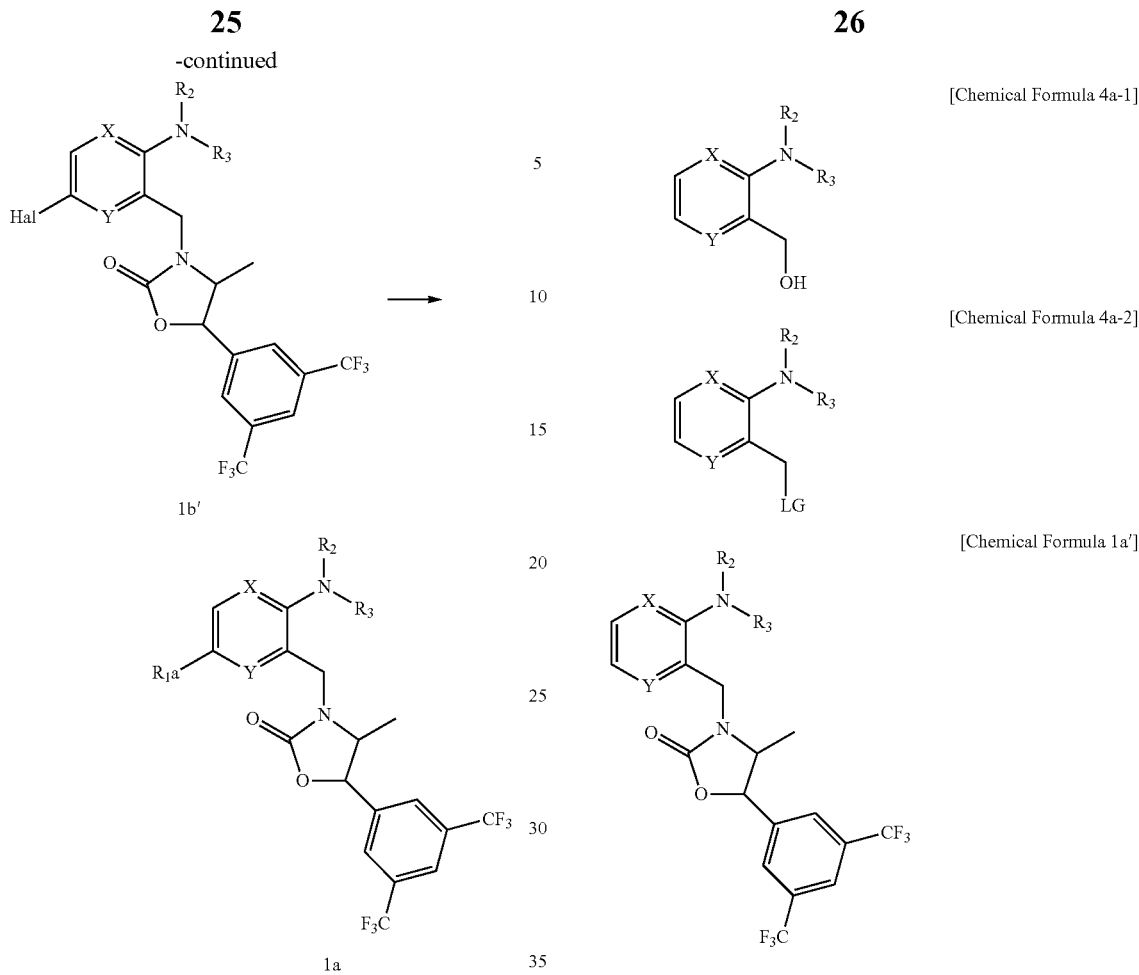

In Reaction Scheme 6, $R_{1a}$ is as defined in Reaction Scheme 5.

In the preparation method of Reaction Scheme 6, the compound of Chemical Formula 2a may be coupled with an amine group (—$NR_2R_3$) to form a compound of Chemical Formula 4a which is then reduced to a compound of Chemical Formula 4a-1, which is in turn prepared into the compound of Chemical Formula 1a' through the steps described above. In addition, the introduction of $R_1$ (e.g, $R_{1a}$, but not hydrogen) to the compound of Chemical Formula 1a' may be achieved by halogenating the compound of Chemical Formula 1a' to the compound of Chemical Formula 1b', and substituting the halogen on the compound of Chemical Formula 1b' with $R_1$ (e.g, $R_{1a}$, but not hydrogen), whereby the compound of Chemical Formula 1 where $R_1$ is not hydrogen (the compound of Chemical Formula 1a in Reaction Scheme 6) can be suitably prepared.

In accordance with another embodiment, the method for preparing the compound of Chemical Formula 1 wherein $R_1$ is not hydrogen, comprises: introducing a leaving group to a compound of Chemical Formula 4a-1 to give a compound of Chemical Formula 4a-2; reacting the compound of Chemical Formula 4a-2 with (4S,5R)-5-[3,5-bis(trifluoromethyl)phenyl])-4-methyl-oxazolidin-2-one to form a compound of Chemical Formula 1a'; and introducing $R_1$ to the compound of Chemical Formula 1a' to afford the compound of Chemical Formula 1 (with the exception that $R_1$ is hydrogen.):

wherein, LG represents a leaving group selected from among halogen and to methanesulfonyl, and X, Y, $R_1$, $R_2$ and $R_3$ are as defined in Chemical Formula 1, with the provision that $R_1$ is not hydrogen.

An exemplary embodiment of this preparation method may be summarized as illustrated in the following Reaction Scheme 7:

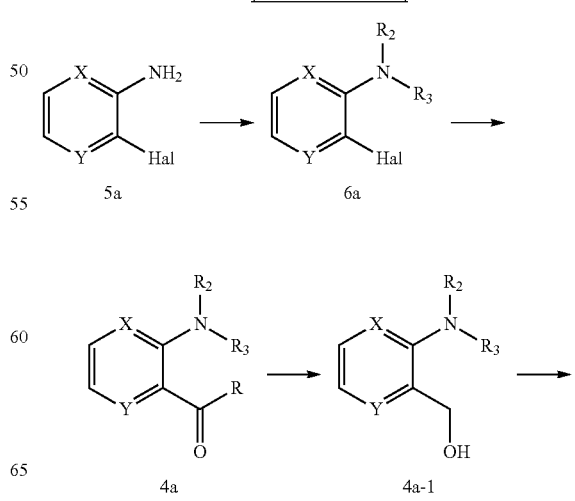

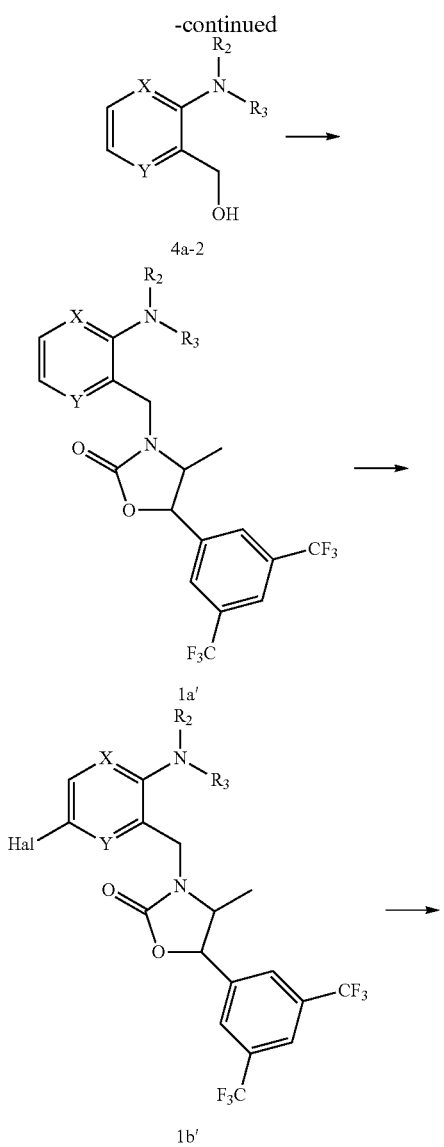

Chemical Formula 6a and then, the halogen on the compound of Chemical Formula 6 may be substituted to form a compound of Chemical Formula 4a. Subsequently, the compound of Chemical Formula 4a is reduced to a compound of Chemical Formula 4a-1 which is then prepared into the compound of Chemical Formula 1a' through the steps described above. In the preparation method of Reaction Scheme 7, the introduction of $R_1$ (e.g, $R_{1a}$, but not hydrogen) to the compound of Chemical Formula 1a' may be achieved by halogenating the compound of Chemical Formula 1a' to the compound of Chemical Formula 1b', and substituting the halogen on the compound of Chemical Formula 1b' with $R_1$ (e.g., $R_{1a}$, but not hydrogen), whereby the compound of Chemical Formula 1 where $R_1$ is not hydrogen (the compound of Chemical Formula 1a in Reaction Scheme 7) can be suitably prepared.

Also, in the preparation methods illustrated in Reaction Schemes 5 to 7, the coupling of the amine group ($-NR_2R_3$) may be carried out in a single process using $NHR_2R_3$ as a reactant or in a multi-step process first by using $NHR_2$ or $NHR_3$ as a reactant, followed by introducing $R_2$ or $R_3$. When $R_2$ is a hydroxy-containing substituent, the preparation method may further comprises protecting the hydroxy group with a protecting group such as t-butyldimethylsilyl group, and this hydroxy-protecting group may be finally removed to afford the compound of Chemical Formula 1.

In accordance with still another aspect thereof, the present invention provide a method for preparing the compound of Chemical Formula 1 wherein $R_1$ is not hydrogen.

According to one embodiment, the preparation method comprises: introducing a leaving group to a compound of Chemical Formula 4b'-1 to give a compound of Chemical Formula 4b'-2; reacting the compound of Chemical Formula 4b'-2 with (4S,5R)-5-[3,5-bis(trifluoromethyl)phenyl])-4-methyl-oxazolidin-2-one to form a compound of Chemical Formula 1b'; and substituting the halogen on the compound of Chemical Formula 1b' with $R_1$ to afford the compound of Chemical Formula 1 (with the exception that $R_1$ is hydrogen.):

[Chemical Formula 4b'-1]

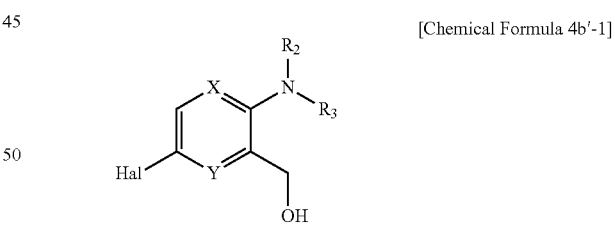

[Chemical Formula 4b'-2]

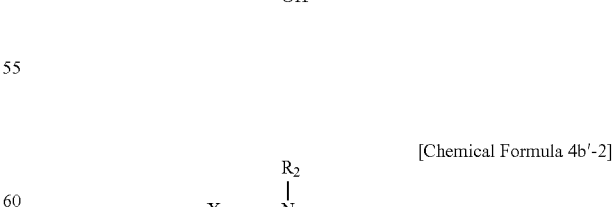

In Reaction Scheme 7, $R_{1a}$ is as defined in Reaction Scheme 5.

In the preparation of Reaction Scheme 7, at least one of $R_2$ and $R_3$, for example, $R_3$ and optionally $R_2$ which is not hydrogen, may be introduced to the amine group on the compound of Chemical Formula 5a to form a compound of

[Chemical Formula 1b']

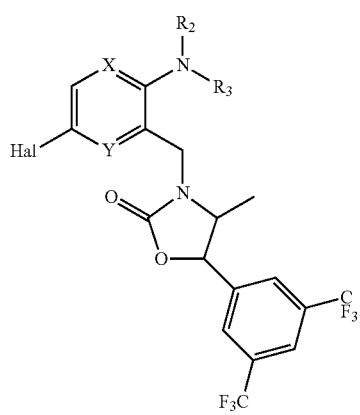

wherein Hal represents halogen, LG represents a leaving group selected from among halogen and methanesulfonyl, and X, Y, $R_1$, $R_2$ and $R_3$ are as defined in Chemical Formula 1, with the proviso that $R_1$ is not hydrogen nor halogen.

An exemplary embodiment of this preparation method may be summarized as illustrated in the following Reaction Scheme 8:

[Reaction Scheme 8]

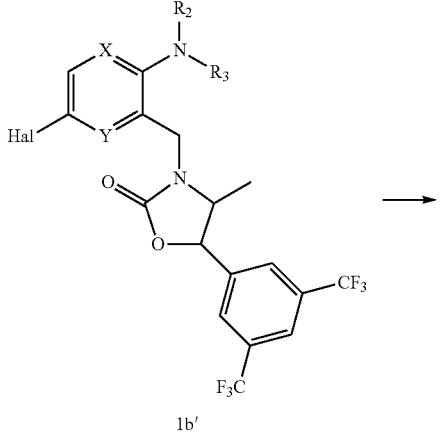

In Reaction Scheme 8, $R_{1b}$ is as defined in $R_1$, with the provision that $R_1$ is not hydrogen nor halogen.

In the preparation method of Reaction Scheme 8, the compound of Chemical Formula 2b may be coupled with an amine group (—$NR_2R_3$) to form a compound of Chemical Formula 4b' which is then reduced to a compound of Chemical Formula 1b', which is in turn prepared into the compound of Chemical Formula 1b' through the steps described above. In addition, the halogen on the compound of Chemical Formula 1b' may be substituted by $R_1$ (e.g, $R_{1b}$ but neither hydrogen nor halogen) to prepare the compound of Chemical Formula 1 where $R_1$ is not hydrogen nor halogen (the compound of Chemical Formula 1b in Reaction Scheme 8).

In accordance with another embodiment, the method for preparing the compound of Chemical Formula 1 wherein $R_1$ is not hydrogen nor halogen, comprises: introducing a leaving group to a compound of Chemical Formula 2b-1 to give a compound of Chemical Formula 2b-2; reacting the compound of Chemical Formula 2b-2 with (4S,5R)-5-[3,5-bis(trifluoromethyl)phenyl])-4-methyl-oxazolidin-2-one to form a compound of Chemical Formula 3b'; and coupling the compound of Chemical Formula 3b' with an amine group (—$NR_2R_3$) to form a compound of Chemical Formula 1b'; substituting the halogen on the compound of Chemical Formula 1b' with $R_1$ to afford the compound of Chemical Formula 1 (with the exception that $R_1$ is hydrogen or halogen):

[Chemical Formula 2b-1]

[Chemical Formula 2b-2]

[Chemical Formula 3b']

[Chemical Formula 1b']

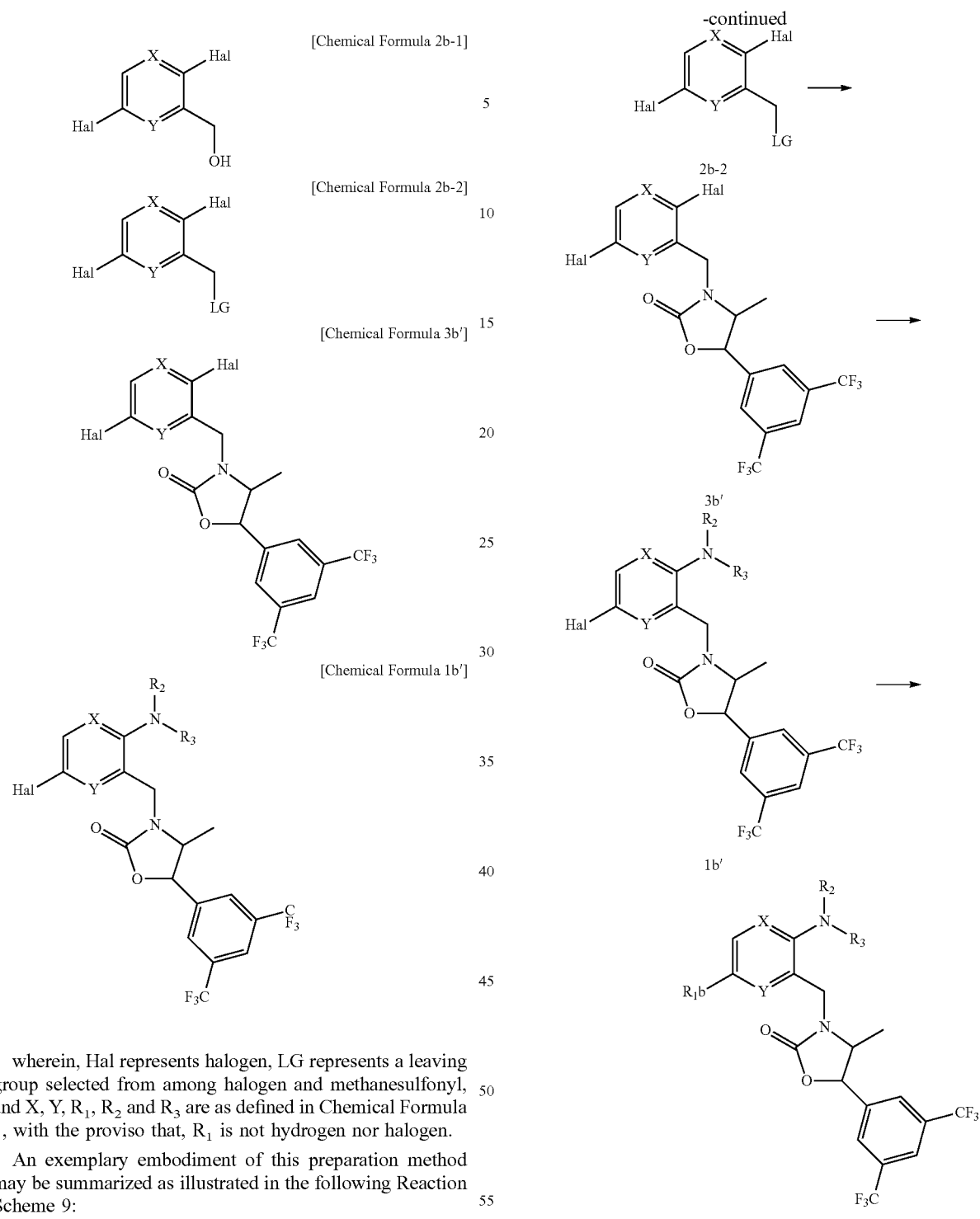

wherein, Hal represents halogen, LG represents a leaving group selected from among halogen and methanesulfonyl, and X, Y, $R_1$, $R_2$ and $R_3$ are as defined in Chemical Formula 1, with the proviso that, $R_1$ is not hydrogen nor halogen.

An exemplary embodiment of this preparation method may be summarized as illustrated in the following Reaction Scheme 9:

[Reaction Scheme 9]

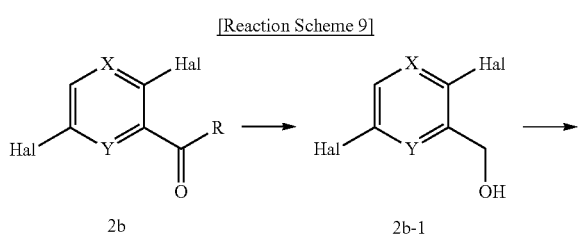

In Reaction Scheme 9, $R_{1b}$ is as defined in Reaction Scheme 8.

In this preparation method, the compound of Chemical Formula 2b may be reduced to a compound of Chemical Formula 2b-1 which is then prepared into the compound of Chemical Formula 1b' through the steps described above. Also in this preparation method, the halogen on the compound of Chemical Formula 1b' may be substituted by $R_1$ ($R_{1b}$, but neither hydrogen nor halogen) to produce the compound of Chemical Formula 1 wherein $R_1$ is not hydrogen nor halogen (compound of Chemical Formula 1b in Reaction Scheme 9).

In accordance with another embodiment, the method for preparing the compound of Chemical Formula 1 wherein $R_1$ is not hydrogen nor halogen, comprises: introducing a leaving group to a compound of Chemical Formula 2b-1 to give a compound of Chemical Formula 2b-2; reacting the compound of Chemical Formula 2b-2 with (4S,5R)-5-[3,5-bis(trifluoromethyl)phenyl])-4-methyl-oxazolidin-2-one to form a compound of Chemical Formula 3b'; substituting the halogen on the compound of Chemical Formula 3b' with $R_1$ to form a compound of Chemical Formula 3 (with the exception that $R_1$ is not hydrogen nor halogen); and coupling the compound of Chemical Formula 3 with an amine group (—$NR_2R_3$) to afford a compound of Chemical Formula 1:

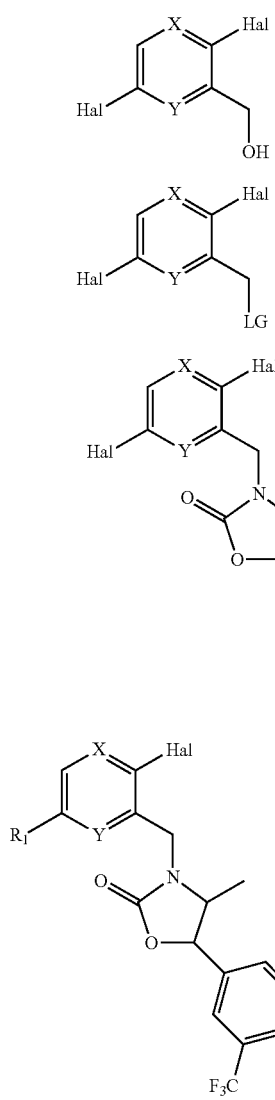

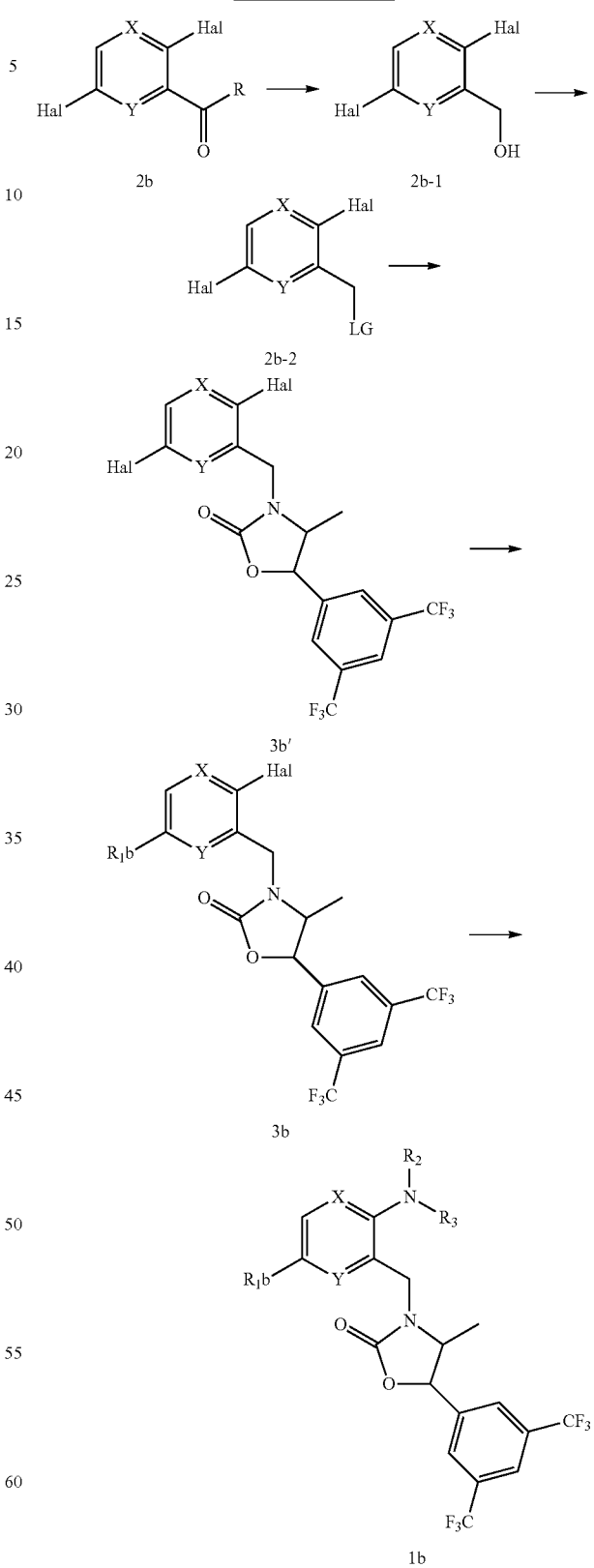

wherein, Hal represents halogen, LG represents a leaving group selected from among halogen and methanesulfonyl, and X, Y, $R_1$, $R_2$ and $R_3$ are as defined in Chemical Formula 1, with the provision that $R_1$ is not hydrogen nor halogen.

An exemplary embodiment of this preparation method may be summarized as illustrated in the following Reaction Scheme 10:

In Reaction Scheme 10, $R_{1b}$ is as defined in Reaction Scheme 8.

In this preparation method, the compound of Chemical Formula 2b is reduced to the compound of Chemical Formula 2b-1 which is, in turn, prepared into the compound of Chemical Formula 3b' through the steps described above. Subsequently, the substitution of the halogen on the compound of Chemical Formula 3b' with $R_1$ (e.g., $R_{1b}$, but neither hydrogen nor halogen) produces the compound of Chemical Formula 3 wherein $R_1$ is not hydrogen nor halogen (the compound of Chemical Formula 3b in Reaction Scheme 10), followed by coupling with an amine group (—$NR_2R_3$) to prepare the compound of Chemical Formula 1 (the compound of Chemical Formula 1b in Reaction Scheme 10).

Also in the preparation methods illustrated in Reaction Schemes 8 to 10, the coupling of the amine group (—$NR_2R_3$) may be carried out in a single process using $NHR_2R_3$ as a reactant or in a multi-step process first by using $NHR_2$ or $NHR_3$ as a reactant, followed by introducing $R_2$ or $R_3$. When $R_2$ is a hydroxy-containing substituent, the preparation method may further comprises protecting the hydroxy group with a protecting group such as t-butyldimethylsilyl group, and this hydroxy-protecting group may be finally removed to afford the compound of Chemical Formula 1.

It should be noted that in the preparation methods illustrated in Reaction Schemes 1 to 10, the compound of Chemical Formula 1 (or the compound of Chemical Formula 1a or 1b), that is, the final product may be obtained as isomers or a mixture of isomers. Hence, an additional process may be conducted to separate pure isomers. Reaction procedures and conditions for isomer separation may follow the methods and conditions well known in the art.

As a reactant used in each preparation method, (4S,5R)-5-[3,5-bis(trifluoromethyl)phenyl])-4-methyl-oxazolidin-2-one may be synthesized using a well-known method, for example, according to the disclosure of U.S. Pat. No. 7,781,426. The preparation method may be summarized as illustrated in the following Reaction Scheme 11:

[Reaction Scheme 11]

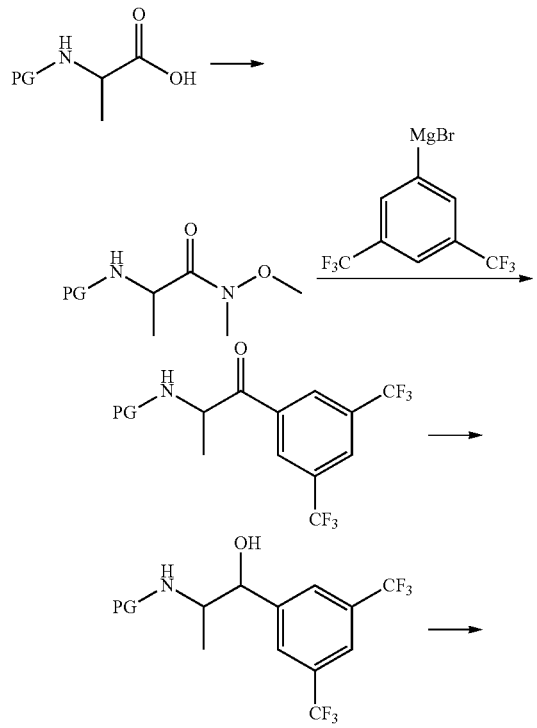

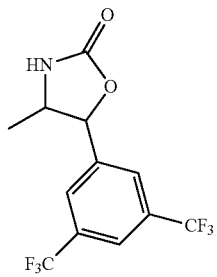

In Reaction Scheme 11, PG represents a protecting group for an amine group, and may be for example, t-Boc or Cbz.

With reference to Reaction Scheme 11, the preparation of (4S,5R)-5-[3,5-bis(trifluoromethyl)phenyl])-4-methyl-oxazolidin-2-one starts with amine-protected 2-aminopropionic acid, followed by coupling with dimethyl hydroxyl amine, a Grignard reaction, a reduction, and treatment with a base, in the order, to form an oxazolidinone ring.

In accordance with a yet further aspect thereof, the present invention addresses a pharmaceutical composition with CETP inhibition activity, comprising the compound of Chemical Formula 1, an isomer thereof, or a pharmaceutically acceptable salt thereof as an active ingredient. Exhibiting excellent inhibitory activity against CETP, the pharmaceutical composition can be effectively applied to the prevention or treatment of various CETP enzyme activity- or HDL cholesterol level-related diseases such as dyslipidemia, atherosclerosis, and coronary heart disease.

The pharmaceutical composition may take a typical drug formulation. That is, the pharmaceutical composition may be administered in various forms such as oral or non-oral dosage forms, with preference for an oral dosage form. In this regard, the pharmaceutical composition of the present invention may be formulated in combination with a diluent or excipient such as a filler, a thickener, a binder, a humectant, a disintegrant, a surfactant, etc.

Solid preparations intended for oral administration may be in the form of tablets, pills, powders, granules, capsules, and the like. In regards to these solid agents, the active ingredient of the present invention is formulated in combination with at least one excipient such as starch, calcium carbonate, sucrose, lactose, or gelatin. In addition to a simple excipient, a lubricant such as magnesium stearate, talc, etc. may be used. Among liquid preparations intended for oral administration are suspensions, internal use solutions, emulsion, syrups, and the like. Plus a simple diluent such as water or liquid paraffin, various excipients, such as humectants, sweeteners, aromatics, preservatives, and the like may be contained in the liquid preparations. Also, the pharmaceutical composition of the present invention may be in a parenteral dosage form such as sterile aqueous solutions, non-aqueous solvents, suspensions, emulsions, lyophilizates, suppositories, and the like. Injectable propylene glycol, polyethylene glycol, vegetable oils such as olive oil, and esters such as ethyl oleate may be suitable for the non-aqueous solvents and suspensions. The basic materials of suppositories include Witepsol, macrogol, Tween 61, cacao butter, laurin butter, and glycerogelatin.

Advantageous Effects

The present invention can provide a novel compound as a potent CETP inhibitor useful for the treatment or prevention of dyslipidemia, atheriosclerosis, and coronary heart disease, a preparation method thereof, and a pharmaceutical composition comprising the same.

MODE FOR INVENTION

A better understanding of the present invention may be obtained through the following examples which are set forth to illustrate, but are not to be construed as limiting the present invention.

Example 1

(4S,5R)-5-[3,5-bis(trifluoromethyl)phenyl]-4-methyl-3-[[2-(methyl(tetrahydrofuran-3-yl)amino)-5-(trifluoromethyl)pyridin-3-yl)methyl]-oxazolidin-2-one

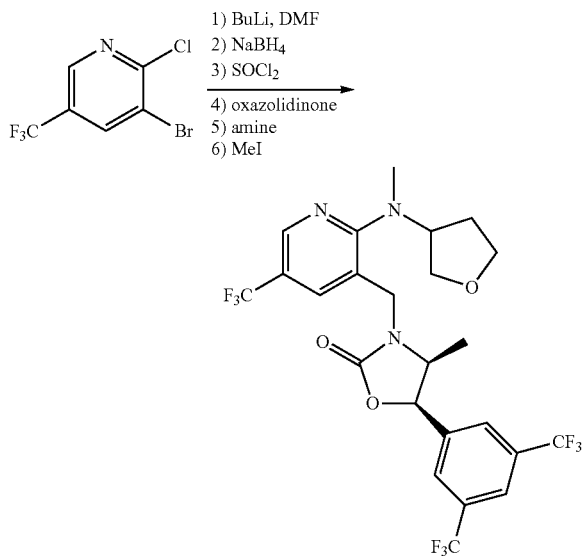

[Step 1] Preparation of 2-chloro-5-(trifluoromethyl)pyridin-3-yl-methane chloride

[Step 1-1] Preparation of 2-chloro-5-(trifluoromethyl)pyridine-3-carbaldehyde

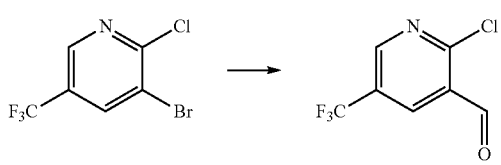 [SMILES: FC(F)(F)c1cnc(Cl)c(Br)c1 ; O=Cc1cc(C(F)(F)F)cnc1Cl]

To a solution of 3-bromo-2-chloro-5-(trifluoromethyl)pyridine (20.00 g, 0.077 mol) in toluene (400 ml), DMF (dimethylformaldehyde) (7.72 ml, 0.10 mol) was dropwise added at −65° C., followed by the addition of n-BuLi (1.57M solution in hexane; 64 ml, 0.10 mol). After stirring for 30 min, the reaction was terminated with 1 N HCl, and then, the reaction mixture was extracted with ethyl acetate. The organic layer was washed with water, dried over anhydrous magnesium sulfate, filtered, and concentrated in a vacuum to obtain 2-chloro-5-(trifluoromethyl)pyridine-3-carbaldehyde. This produce was used in the subsequent reaction without further purification.

[Step 1-2] Preparation of 2-chloro-5-(trifluoromethyl)pyridin-3-yl-methanol

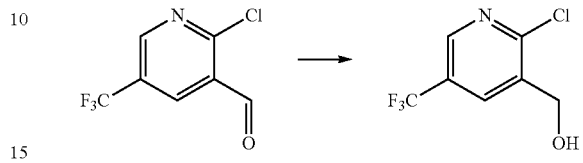

To a solution of 2-chloro-5-(trifluoromethyl)pyridine-3-carbaldehyde of step 1-1 in ethanol (60 ml) was dropwise added NaBH$_4$ (2.90 g, 0.077 mol) while stirring for 30 min at room temperature. After the reaction was terminated with a saturated ammonium solution, extraction with ethylacetate was carried out. The organic layer was dried over anhydrous magnesium sulfate, filtered, and concentrated. The residue was purified by chromatography to give 2-chloro-5-(trifluoromethyl)pyridin-3-yl-methanol (12.3 g, 76%).

[Step 1-3] Preparation of 2-chloro-5-(trifluoromethyl)pyridin-3-yl-methane chloride

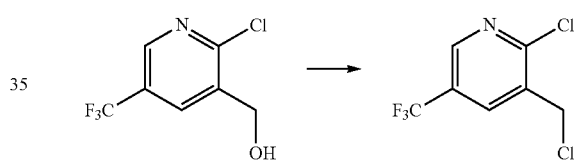

A solution of 2-chloro-5-(trifluoromethyl)pyridin-3-yl-methanol (46 g, 135.0 mol) of step 1-2 in DMF (300 ml) was cooled to 0° C. SOCl$_2$ (thionyl chloride) (17.6 g, 148 mol) was dropwise added to the solution over 1 hr with stirring. The reaction mixture was diluted with acetate ethyl (200 ml), and then added with water to terminate the reaction. The organic layer thus formed was dried over Na$_2$SO$_4$, filtered, and concentrated to give 2-chloro-5-(trifluoromethyl)pyridin-3-yl-methane chloride which was then used in a subsequent reaction without further purification.

[Step 2] Preparation of (4S,5R)-5-[3,5-bis(trifluoromethyl)phenyl]-4-methyl-oxazolidin-2-one

[Step 2-1] Preparation of (S)-benzyl 1-(N,O-dimethylhydroxylamine)-1-oxopropan-2-yl carbamate

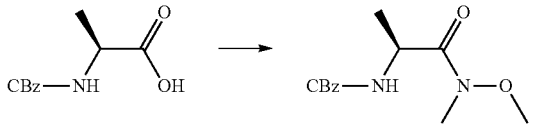

To a solution of Cbz-L-alanine (21.38 g, 95.78 mmol) in tetrahydrofuran (THF) (200 ml) were dropwise added HOBT.H$_2$O (17.60 g, 114.93 mmol), Weinreb's amine.HCl (12.15 g, 124.51 mmol), Hunig's base (30.95 g, 239.45 mmol), and EDC.HCl (23.87 g, 124.51 mmol) at 0° C. After being stirred at room temperature for 18 hrs, the reaction mixture was cooled to 0° C. and added with 2 N HCl to terminate the reaction. After extraction with ethyl acetate, the organic layer thus formed was washed once with 1N HCl and a saturated sodium carbonate solution, each. The organic layer was dried over anhydrous magnesium sulfate, filtered, and concentrated in a vacuum. The concentrate was re-crystallized in hexane, and filtered at a reduced pressure to obtain the title compound (23.39 g, 92%).

¹H NMR (400 MHz, CDCl₃) δ 7.21-7.35 (m, 5H), 5.55 (m, 1H), 5.07 (m, 2H), 4.72 (m, 1H), 3.75 (s, 3H), 3.18 (s, 3H), 1.32 (d, J=7.2 Hz, 3H).

[Step 2-2] Preparation of (S)-benzyl-1-[3,5-bis(trifluoromethyl)phenyl]-1-oxopropan-2-yl carbamate

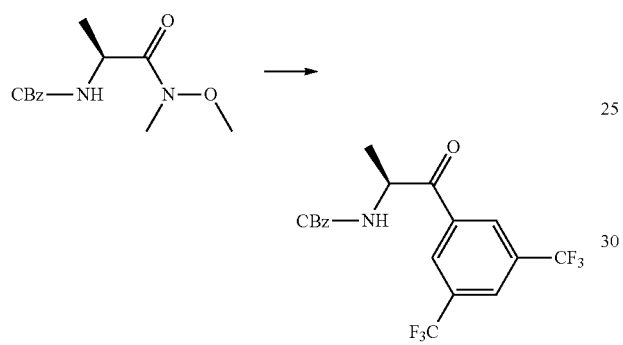

To a solution of (S)-benzyl-1-(N,O-dimethylhydroxylamine)-1-oxopropan-2-yl carbamate (1.00 g, 3.75 mmol) of step 2-1 in THF (tetrahydrofuran) (10 ml) was slowly added drops of 3,5-bis(trifluoromethyl)phenyl MgBr (0.5M in THF, 18.8 mL, 9.38 mmol) at 0° C. After stirring the reaction mixture at room temperature for 2 hrs, the reaction was terminated with a saturated ammonium chloride solution, and then, the reaction mixture was extracted with ethyl acetate. The organic layer thus formed was dried over anhydrous magnesium sulfate, filtered, and concentrated. The residue was purified by chromatography to afford the title compound (1.2 g, 76%).

1H NMR (400 MHz, CDCl3) δ 8.32-8.40 (m, 2H), 8.09 (brs, 1H), 7.21-7.38 (m, 5H), 5.66 (m, 1H), 5.34 (m, 1H), 5.12 (s, 2H), 1.44 (d, J=7.2 Hz, 3H).

[Step 2-3] Preparation of (1R,2S)-benzyl-[3,5-bis(trifluoromethyl)phenyl]-1-hydroxypropan-2-yl carbamate

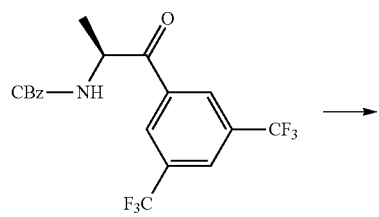

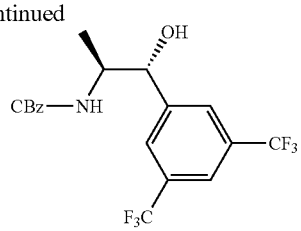

A solution of (S)-benzyl-1-[3,5-bis(trifluoromethyl)phenyl]-1-oxopropan-2-yl carbamate (0.3 g, 0.72 mmol), obtained in step 2-2, in toluene (5.4 mL) and isopropyl alcohol (3.6 mL) was added with drops of Al(OPri)₃ (0.22 g, 1.08 mmol) at room temperature, and refluxed at 50° C. for 15 hrs with stirring. The reaction mixture was cooled to room temperature, and the reaction was terminated with 2 N HCl, followed by extraction with ethyl acetate. The organic layer thus formed was dried over anhydrous magnesium sulfate, filtered, and concentrated. The residue was re-crystallized in hexane, and filtered at a reduced pressure to afford the title compound (0.3 g, 99%).

¹H NMR (400 MHz, CDCl₃) δ 7.75-7.82 (m, 3H), 7.26-7.40 (m, 5H), 5.12 (s, 2H), 5.03 (brs, 1H), 4.85 (d, J=7.2 Hz, 1H), 4.04 (m, 1H), 3.24 (brs, 1H), 0.99 (d, J=7.2 Hz, 3H).

[Step 2-4] Preparation of (4S,5R)-5-[3,5-bis(trifluoromethyl)phenyl])-4-methyl-oxazolidin-2-one

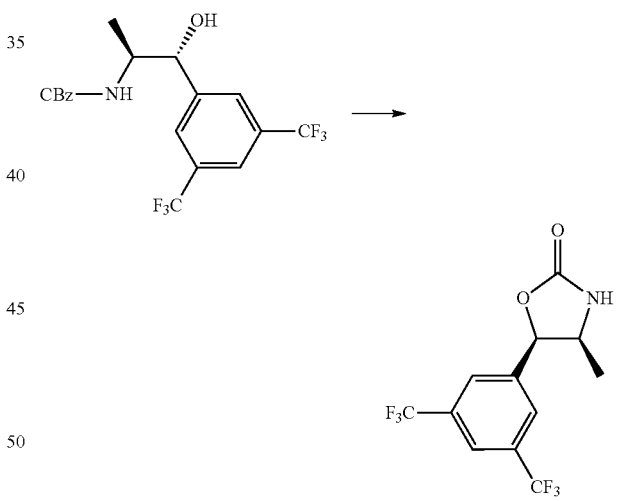

A solution of (1R,2S)-benzyl-[3,5-bis(trifluoromethyl)phenyl]-1-hydroxypropan-2-yl carbamate (0.3 g, 0.71 mmol) of step 2-3 in 5 ml of isopropyl alcohol was added with drops of KOH (0.1 g, 1.78 mmol), and then stirred at room temperature for 4 hrs. The reaction was terminated with water, followed by extraction with ethyl acetate. The organic layer thus formed was dried over anhydrous magnesium sulfate, filtered, and concentrated. The residue was re-crystallized in hexane, and filtered at a reduced pressure to afford the title compound (0.28 g, 90%).

¹H NMR (400 MHz, CDCl₃) δ 7.88 (br s, 1H), 7.77 (br s, 2H), 5.81 (d, J=8.0 Hz, 1H), 5.32 (br s, 1H), 4.29 (m, 1H), 0.82 (d, J=6.4 Hz, 3H).

[Step 3] Preparation of (4S,5R)-5-[3,5-bis(trifluoromethyl)phenyl]-4-methyl-3-[(2-chloro-5-trifluoromethylpyridin-3-yl)methyl]-oxazolidin-2-one

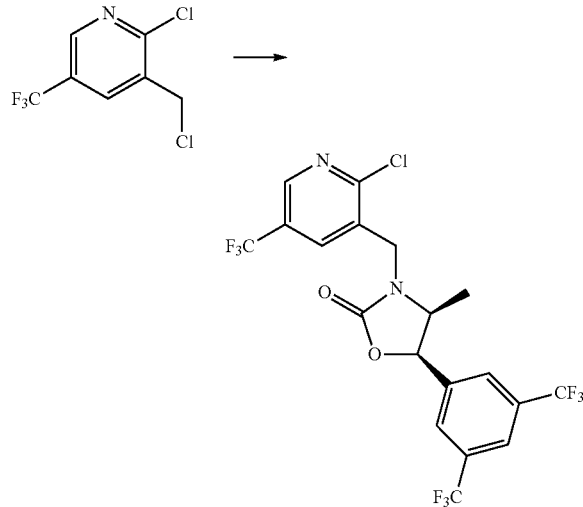

To a solution of (4S,5R)-5-[3,5-bis(trifluoromethyl)phenyl]-4-methyloxazolidin-2-one (46 g, 147 mol), obtained in step 2, in DMF (150 ml) was dropwise added NaHMDS (sodium hexamethyldisilazide) (176 ml, 176 mol) at −40° C. The reaction mixture was stirred for 30 min, and slowly added with drops of a dilution of 2-chloro-5-(trifluoromethyl)pyridin-3-yl-methane chloride, obtained in step 1, in DMF (30 ml). The resulting reaction mixture was heated to room temperature, stirred for 3 hrs, diluted with ethyl acetate (200 ml), and added with water (500 ml) to terminate the reaction. The organic layer thus formed was withdrawn, washed with water (2.5 l), and filtered through silica-selite pad at a reduced pressure to afford the title compound (60 g, 67%).

1H NMR (400 MHz, CDCl$_3$) 8.64 (s, 1H), 8.01 (s, 1H), 7.90 (s, 1H), 7.82 (s, 2H), 5.76 (d, J=8.0 Hz, 1H), 4.84 (d, J=16.0 Hz, 1H), 4.47 (d, J=16.4 Hz, 1H), 4.22 (m, 1H), 083 (d, 3H).

[Step 4] Preparation of (4S,5R)-5-[3,5-bis(trifluoromethyl)phenyl]-4-methyl-3-[(2-(tetrahydrofuran-3-yl)amino-5-(trifluoromethyl)pyridin-3-yl)methyl]-oxazolidin-2-one

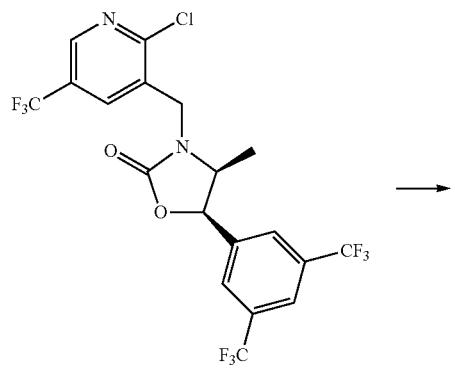

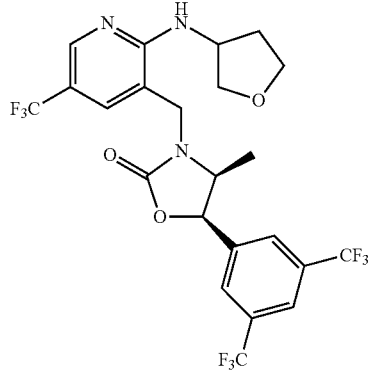

Tetrahydrofuran amine (198 mg, 1.92 mmol) was dropwise added to (4S,5R)-5-[3,5-bis(trifluoromethyl)phenyl]-4-methyl-3-[(2-chloro-5-trifluoromethylpyridin-3-yl)methyl]-oxazolidin-2-one obtained in step 3. This reaction mixture was refluxed at 130° C. for 4 hrs with stirring, cooled to room temperature, diluted with ethyl acetate, and then extracted with water. The organic layer thus formed was washed with brine, dried over anhydrous magnesium sulfate, filtered, and concentrated. The residue was purified by chromatography to afford the title compound (130 mg, 36%).

1H NMR (400 MHz, CDCl$_3$) 8.36 (s, 1H), 7.89 (s, 1H), 7.71 (d, J=2.8 Hz, 2H), 7.36 (s, 1H), 5.71 (d, J=8.0 Hz, 1H), 4.68 (m, 2H), 4.13-3.97 (m, 4H), 3.90 (m, 2H), 3.76 (m, 2H), 2.33 (m, 1H), 1.99 (m, 1H), 0.88 (t, 3H), 0.80 (m, 3H).

[Step 5] Preparation of (4S,5R)-5-[3,5-bis(trifluoromethyl)phenyl]-4-methyl-3-[(2-(methyl(tetrahydrofuran-3-yl)amino)-5-(trifluoromethyl)pyridin-3-yl)methyl]-oxazolidin-2-one

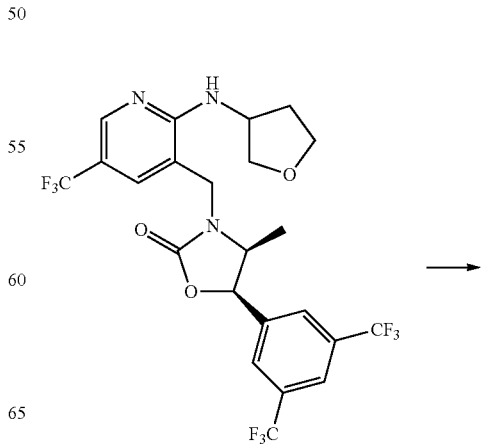

-continued

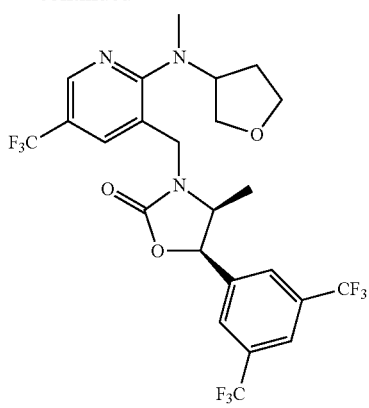

A solution of (4S,5R)-5-[3,5-bis(trifluoromethyl)phenyl]-4-methyl-3-[(2-(tetrahydrofuran-3-yl)amino-5-(trifluoromethyl)pyridin-3-yl)methyl]-oxazolidin-2-one (70 mg, 0.13 mmol), obtained in step 4, in DMF (1 ml) was cooled to 0° C. This solution was stirred for 5 min in the presence of NaH (15 mg, 0.38 mmol). After addition of methyl iodide (27 mg, 0.19 mmol) thereto, the reaction mixture was stirred at room temperature for 2 hrs. The reaction was terminated with a saturated ammonium solution, followed by extraction with ethyl acetate. The organic layer thus obtained was dried filtered, and concentrated in a vacuum. The residue was purified by chromatography to afford the title compound (65 mg, 90%).

$^1$H NMR (400 MHz, CDCl$_3$) 8.46 (s, 1H), 7.87 (s, 1H), 7.77 (d, J=2.0 Hz, 1H), 7.73 (s, 2H), 5.72 (t, J=6.8 Hz, 1H), 4.84 (m, 1H), 4.34-4.24 (m, 2H), 4.01-3.85 (m, 4H), 3.75 (m, 2H), 3.63 (m, 1H), 2.80 (s, 3H), 2.79 (s, 3H), 2.27 (m, 2H), 1.99 (m, 2H), 0.66 (m, 3H)

Example 2

(4S,5R)-5-[3,5-bis(trifluoromethyl)phenyl]-4-methyl-3-{(2-[ethyl(tetrahydrofuran-3-yl)amino]-5-(trifluoromethyl)pyridin-3-yl)methyl}-oxazolidin-2-one

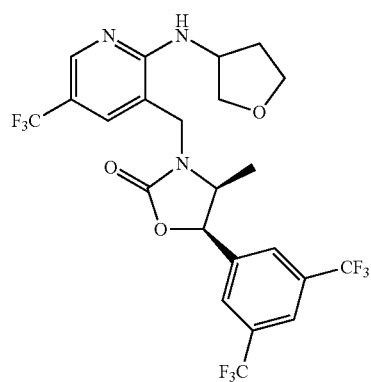

-continued

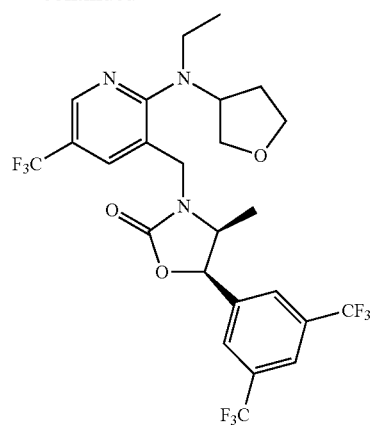

The title compound was prepared in the same manner as in Example 1, with the exception that ethyl iodide, instead of the methyl iodide in step 5, was employed. 38 mg (93%).

$^1$H NMR (400 MHz, CDCl$_3$) 8.51 (s, 1H, major), 8.47 (s, 1H, minor), 7.89 (s, 1H, minor), 7.81 (s, 1H, major), 7.80 (s, 1H, minor), 7.76 (s, 2H, minor), 7.74 (s, 2H, major), 5.74 (d, 1H, minor), 5.71 (d, 1H, major), 4.83 (d, 1H, minor), 4.78 (d, 1H, major), 4.33 (m, 1H), 4.29 (m, 1H), 3.99 (m, 4H), 3.76 (m, 2H), 3.63 (m, 1H, minor), 3.49 (m, 1H, major), 3.30 (m, 3H), 2.24 (m, 1H), 1.98 (m, 2H), 0.94 (t, 6H), 0.62 (d, 3H, major), 0.63 (d, 3H, minor).

Example 3

(4S,5R)-5-[3,5-bis(trifluoromethyl)phenyl]-4-methyl-3-({2-[(3R,4R)-4-ethoxytetrahydrofuran-3-yl)(methyl)amino]-5-(trifluoromethyl)pyridin-3-yl}methyl)-oxazolidin-2-one

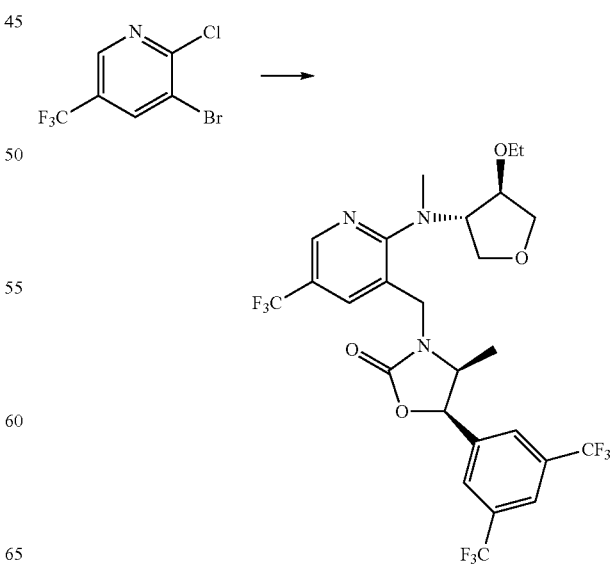

[Step 1] Preparation of 3-bromo-N-(4R-ethoxy-tetrahydrofuran-3-yl)-5-(trifluoromethyl)pyridine-2-amine

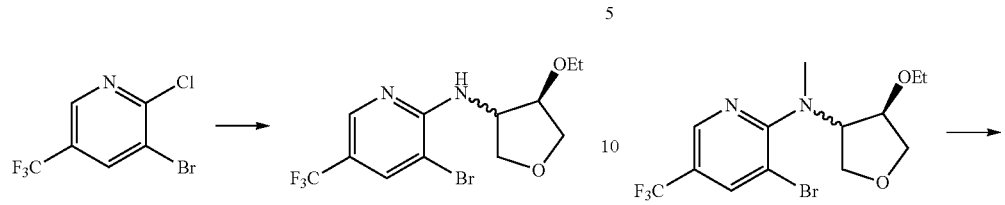

A solution of 2-chloro-3-bromo-5-trifluoromethyl pyridine (1.17 g, 4.48 mmol) in DMF (4 ml) was added with drops of TEA (triethylamine) (1.24 ml, 8.96 mmol) and then with (4R)-3-ethoxy-4-tetrahydrofuranamine (824 mg, 4.93 mmol), refluxed at 110° C. for 5 hrs with stirring, cooled to room temperature, and quenched with water, followed by extraction with ethyl acetate. The organic layer was dried, filtered, and concentrated. The residue was purified by chromatography to afford the title compound (537 mg, 34%).

$^1$H NMR (400 MHz, CDCl$_3$) 8.32 (s, 1H), 7.80 (s, 1H), 5.41 (d, J=6.0 Hz, 1H), 5.58 (t, J=5.2 Hz, 1H), 4.11-4.07 (m, 2H), 3.93 (d, J=4.4 Hz, 1H), 3.86-3.78 (m, 2H), 3.74 (d, J=8.4 Hz, 1H), 3.62 (ddd, J=7.2, 6.0, 6.0 Hz, 1H), 1.23 (t, 3H).

[Step 2] Preparation of 3-bromo-N-(4R-ethoxy-tetrahydrofuran-3-yl)-N-methyl-5-(trifluoromethyl)pyridine-2-amine

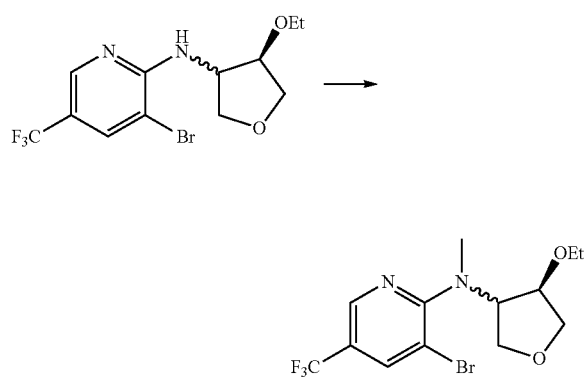

A solution of 3-bromo-N-(4R-ethoxy-tetrahydrofuran-3-yl)-5-(trifluoromethyl)pyridine-2-amine (537 mg), obtained in step 1, in DMF (6 ml) was added with NaH (2.0 eq) and methyl iodide (1.5 eq), and stirred for 1 hr at room temperature. The reaction was terminated with an aqueous ammonium solution, followed by extraction with ethyl acetate. The organic layer was dried, filtered, and concentrated. The residue was purified by chromatography to afford the title compound (470 mg, 79%).

$^1$H NMR (400 MHz, CDCl$_3$) 8.38 (s, 1H0, 7.94 (d, J=1.2 Hz, 1H), 4.57 (ddd, J=6.8, 6.8, 4.0 Hz, 1H), 4.26-4.17 (m, H), 4.11 (dd, J=10.0, 4.8 Hz, 1H), 3.86 (dd, J=10.0, 4.8 Hz, 1H), 3.73 (dd, J=10.0, 4.4 Hz, 1H), 3.49-3.39 (m, 1H), 3.0 (s, 3H), 1.15 (t, 3H).

[Step 3] Preparation of 2-[(4R-ethoxytetrahydrofuran-3-yl)(methyl)amino]-5-(trifluoromethyl)pyridin-3-yl-methanol

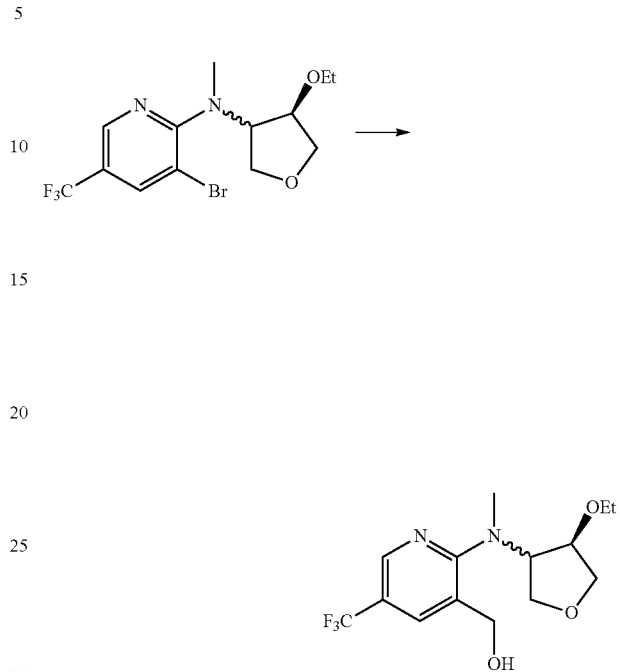

A solution of 3-bromo-N-(4R-ethoxy-tetrahydrofuran-3-yl)-N-methyl-5-(trifluoromethyl)pyridine-2-amine (100 mg, 0.27 mmol), obtained in step 2, in DMF (30 mg, 1.23 mmol) and toluene (0.5 ml) was added with n-BuLi (0.6 ml, 1.23 mmol) at −78° C., and stirred for 3 hrs. The reaction was terminated with an aqueous ammonium solution, followed by extraction with ethyl acetate. The organic layer was dried, filtered, and concentrated. The concentrate was dissolved in ethanol (2 ml). The reaction mixture was cooled to 0° C., and added with drops of NaBH$_4$ (20 mg, 0.54 mmol). After 30 min, the reaction was terminated with a saturated aqueous ammonium solution, followed by extraction with ethyl acetate. The organic layer thus formed was dried, filtered, and concentrated in a vacuum. The residue was purified by chromatography to afford the title compound (33 mg, 38%).

$^1$H NMR (400 MHz, CDCl$_3$) 8.43 (s, 1H), 7.89 (s, 1H), 4.73 (q, 2H), 4.25 (m, 1H), 4.22 (m, 1H), 4.15-4.01 (m, 2H), 3.78-3.68 (m, 2H), 3.53 (m, 2H), 2.86 (s, 3H), 1.18 (t, 3H).

[Step 4] Preparation of (4S,5R)-5-[3,5-bis(trifluoromethyl)phenyl]-4-methyl-3-({2-[(3R,4R)-ethoxytetrahydrofuran-3-yl)(methyl)amino]-5-(trifluoromethyl)pyridin-3-yl}methyl)-oxazolidin-2-one

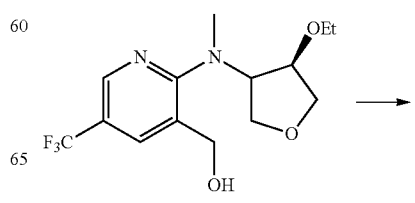

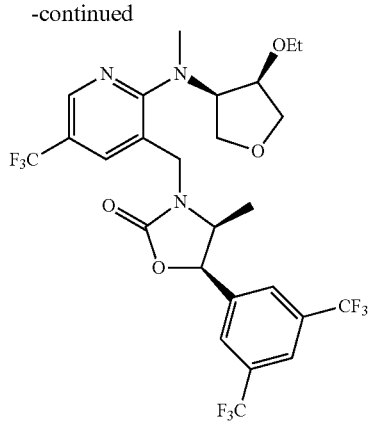

2-[(4R-ethoxytetrahydrofuran-3-yl)(methyl)amino]-5-(trifluoromethyl)pyridin-3-yl-methanol (33 mg) obtained in step 3 was reacted with $SOCl_2$ (thionyl chloride) in DMF (1 ml), and then with (4S,5R)-5-[3,5-bis(trifluoromethyl)phenyl])-4-methyl-oxazolidin-2-one in the same manner as in step 3 of Example 1 to afford the title compound (14.7 mg, 23%).

$^1$H NMR (400 MHz, $CDCl_3$) 8.48 (s, 1H), 7.87 (s, 1H), 7.75-7.73 (m, 3H), 5.72 (d, 1H), 4.91 (d, 1H), 4.21-4.06 (m, 4H), 3.87 (m, 1H), 3.77 (m, 1H), 3.70 (m, 1H), 3.50 (m, 2H), 2.87 (s, 3H), 1.14 (t, 3H), 0.65 (d, 3H).

Example 4

(4S,5R)-5-[3,5-bis(trifluoromethyl)phenyl]-4-methyl-3-({2-[(3S,4R)-ethoxytetrahydrofuran-3-yl)(methyl)amino]-5-(trifluoromethyl)pyridin-3-yl}methyl)-oxazolidin-2-one The same procedure as in Example 3 was repeated to afford the title compound (35.6 mg, 57%).

$^1$H NMR (400 MHz, $CDCl_3$) 8.48 (s, 1H), 7.87 (s, 1H), 7.77 (s, 1H), 7.73 (s, 2H), 5.69 (d, 1H), 4.85 (d, 1H), 4.35 (d, 1H), 4.28 (m, 4H), 3.89 (m, 1H), 3.72 (m, 2H), 3.55 (m, 2H), 2.85 (s, 3H).

Example 5

(4S,5R)-5-[3,5-bis(trifluoromethyl)phenyl]-4-methyl-3-({2-[(tetrahydro-2H-pyran-4-yl)amino]-5-(trifluoromethyl)pyridin-3-yl}methyl)-oxazolidin-2-one

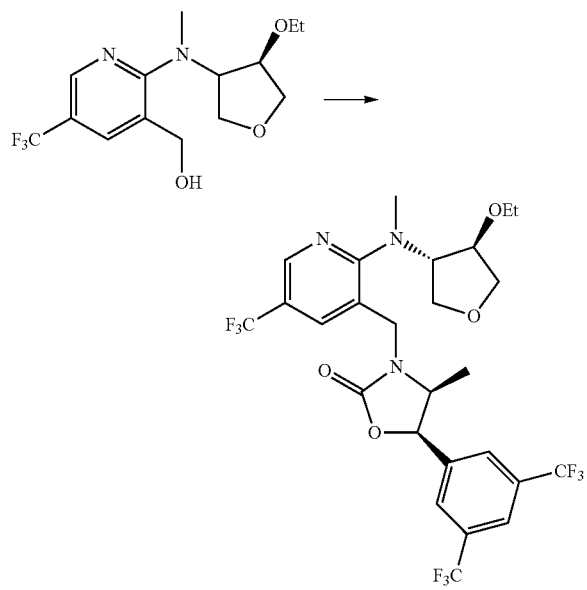

(4S,5R)-5-[3,5-bis(trifluoromethyl)phenyl]-4-methyl-3-[(2-chloro-5-(trifluoromethyl)pyridin-3-yl)methyl]-oxazolidin-2-one (500 mg, 0.99 mmol), obtained in step 3 of Example 1, and TEA (270 mg, 1.98 mmol) were dissolved in DMF (3 ml), and added with drops of tetrahydropyran amine (0.3 ml, 2.96 mmol). The reaction mixture was refluxed at 120° C. for 48 hrs with stirring, and then cooled to the room temperature. The cooled mixture was diluted with 50 ml of acetate chloride, and washed twice with brine. The organic layer was dried over anhydrous magnesium sulfate, filtered, and concentrated. The residue was purified by chromatography to afford the title compound (368 mg, 65%).

$^1$H NMR (400 MHz, $CDCl_3$) 8.334 (d, J=0.8 Hz, 1H), 7.88 (s, 1H), 7.70 (s, 2H), 7.34 (d, J=4.0 Hz, 1H), 6.17 (d, J=8.0 Hz, 1H), 5.69 (d, J=8.0 Hz, 1H), 4.64 (AB, $J_{AB}$=14.8 Hz, $\Delta_{AB}$=215.4, 1H), 4.24-4.20 (m, 1H), 4.11-4.04 (m, 2H), 4.01-3.98 (m, 2H), 3.58-3.53 (m, 2H), 2.05-1.68 (m, 2H), 1.68-1.51 (m, 2H), 0.80 (d, J=6.0 Hz, 3H).

Example 6

(4S,5S)-5-[3,5-bis(trifluoromethyl)phenyl]-4-methyl-3-({[2-(methyl)(tetrahydro-2H-pyran-4-yl)amino]-5-(trifluoromethyl)pyridin-3-yl}methyl)-oxazolidin-2-one

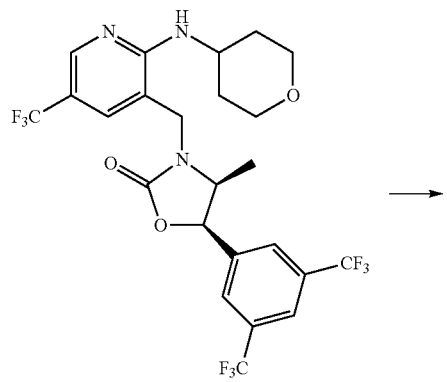

(4S,5R)-5-[3,5-bis(trifluoromethyl)phenyl]-4-methyl-3-({2-[(tetrahydro-2H-pyran-4-yl)amino]-5-trifluoromethyl-pyridin-3-yl}methyl)-oxazolidin-2-one (214 mg, 0.37 mmol) of Example 5 was dissolved in DMSO (dimethyl sulfoxide) (10 ml), and cooled to 0° C. The reaction mixture was added with drops of NaH (22.4 mg, 0.56 mmol), and stirred for 5 min. Then, methyl iodide (68.27 mg, 0.48 mmol) was dropwise added. The resulting mixture was stirred for 30 min, added with brine to terminate the reaction, and diluted with 50 ml of ethyl acetate. The organic layer was washed twice with brine, dried over anhydrous magnesium sulfate. The residue was purified by chromatography to afford the title compound (190 mg, 88%).

$^1$H NMR (400 MHz, CDCl$_3$) 8.442 (s, 1H), 7.88 (s, 1H), 7.73 (s, 3H), 5.70 (d, J=8.0 Hz, 1H), 4.82 (AB, J$_{AB}$=15.6 Hz, Δ$_{AB}$=222.8, 1H), 4.26 (AB, J$_{AB}$=15.6 Hz, Δ$_{AB}$=222.8, 1H), 4.06-3.978 (m, 2H), 3.89 (dddd, J=6.4, 13.2, 13.2 Hz, 1H), 3.49-3.37 (m, 2H), 2.82 (s, 3H), 1.96-1.74 (m, 3H), 1.62-1.58 (m, 1H), 0.63 (d, J=6.8 Hz, 3H).

Example 7

(4S,5R)-5-[3,5-bis(trifluoromethyl)phenyl]-4-methyl-3-({[2-(ethyl)(tetrahydro-2H-pyran-4-yl)amino]-5-(trifluoromethyl)pyridin-3-yl}methyl)-oxazolidin-2-one

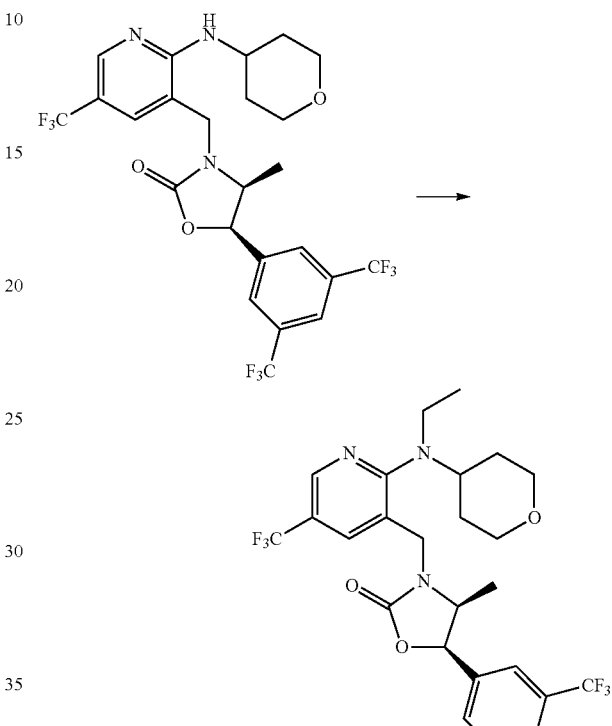

Method 1

The same procedure as in Example 6 was repeated, with the except that ethyl iodide, instead of methyl iodide, was reacted with (4S,5R)-5-[3,5-bis(trifluoromethyl)phenyl]-4-methyl-3-({2-[(tetrahydro-2H-pyran-4-yl)amino]-5-trifluoromethylpyridin-3-yl}methyl)-oxazolidin-2-one, to afford the title compound (6 mg, 15%).

Method 2

[Step 1] Preparation 2-[ethyl(tetrahydro-2H-pyran-4-yl)amino]-5-(trifluoromethyl)nicotine aldehyde

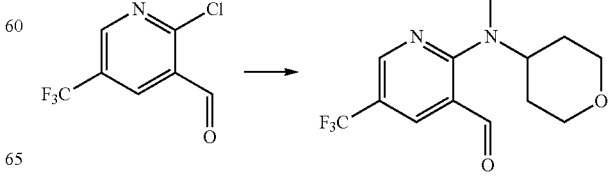

2-chloro-5-trifluoromethylpyridine carbaldehyde (1.2 g, 5.5 mmol), obtained in step 1-1 of Example 1, was dissolved together with N-ethyl-N-(tetrahydro-2H-pyran-4-yl)-amine (1.3 g, 16.5 mmol) and $K_2CO_3$ (3.03 g, 22 mmol), in toluene (15 ml), and refluxed at 130° C. for 48 hrs with stirring. The reaction mixture cooled to room temperature, and added with water to terminate the reaction, followed by extraction with ethyl acetate. The organic layer was dried over anhydrous magnesium sulfate, filtered, and concentrated. The residue was purified by chromatography to afford the title compound (1.1 g, 50%).

$^1$H NMR (400 MHz, $CDCl_3$) 8.51 (s, 1H), 7.88 (s, 1H), 7.79 (d, J=2.0 Hz, 1H), 7.77 (s, 2H), 5.72 (d, J=8.0 Hz, 1H), 4.75 (d, J=16.0 Hz, 1H), 4.34 (d, J=16.0 Hz, 1H), 4.00 (m, 2H), 3.46 (m, 6H), 1.86 (m, 4H), 0.93 (t, 3H), 0.63 (d, 3H).

[Step 2] Preparation of (2-[ethyl(tetrahydro-2H-pyran-4-yl)amino)-5-(trifluoromethyl)pyridin-3-yl) methanol

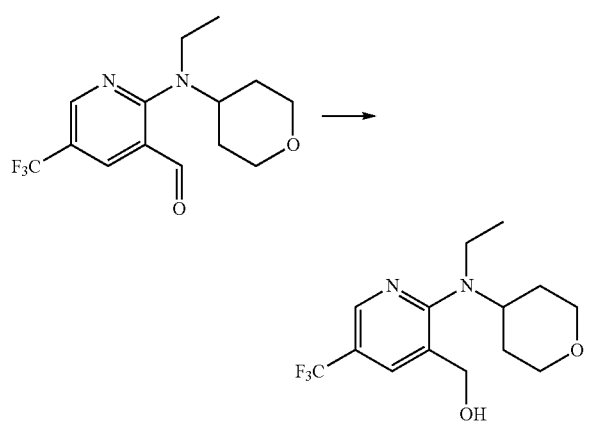

A solution of 2-[ethyl(tetrahydro-2H-pyran-4-yl)amino]-5-(trifluoromethyl)nicotine aldehyde of step 1 (1.0 g, 3.31 mmol) in methanol (10 ml) was cooled to 0° C., and added with drops of $NaBH_4$ (188 mg, 4.96 mmol). 30 min later, the reaction was terminated with a saturated aqueous ammonium solution, followed by extraction with ethyl acetate. The organic layer thus formed was dried, filtered, and concentrated at a reduced pressure. The residue was purified by chromatography to afford the title compound (986 mg, 98%).

[Step 3] Preparation of 3-(chloromethyl)-N-ethyl-N-(tetrahydro-2H-pyran-4-yl)-5-(trifluoromethyl)pyridine-2-amine

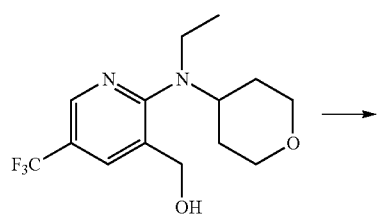

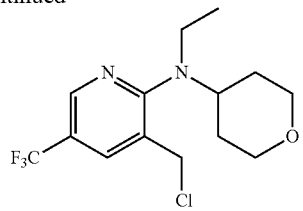

A solution of (2-[ethyl(tetrahydro-2H-pyran-4-yl)amino)-5-(trifluoromethyl)pyridin-3-yl) methanol of step 2 (1.57 g, 5.16 mmol) in DMF (10 ml) was added with drops of $SOCl_2$ (739 mg, 6.19 mmol) at 0° C., and stirred at room temperature for 30 min. The reaction was terminated with water. The reaction mixture was extracted with ethyl acetate, dried, and concentrated at a reduced pressure. The residue was used in the subsequent reaction without further purification.

[Step 4] Preparation of (4S,5R)-5-[3,5-bis(trifluoromethyl)phenyl]-4-methyl-3-({2-[ethyl(tetrahydro-2H-pyran-4-yl)amino]-5-(trifluoromethyl)pyridin-3-yl}methyl)-oxazolidin-2-one

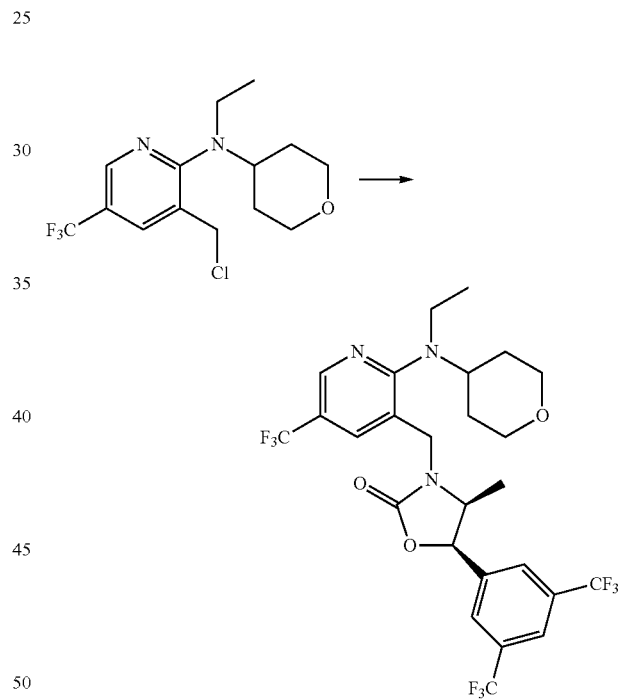

A solution of (4S,5R)-5-[3,5-bis(trifluoromethyl)phenyl])-4-methyl-oxazolidin-2-one (1.78 g, 5.68 mmol), obtained in step 2 of Example 1, in DMF (10 ml) was added with drops of NaHMDS (5.16 ml, 5.16 mmol) at −40° C., and stirred for 30 min. To this mixture was slowly added a solution of 3-(chloromethyl)-N-ethyl-N-(tetrahydro-2H-pyran-4-yl)-5-(trifluoromethyl)pyridine-2-amine, obtained in step 3, in DMF (5 ml), after which the reaction mixture was stirred at room temperature for 2 hrs. The reaction was terminated with a saturated aqueous ammonium solution, followed by extraction with ethyl acetate. The residue was purified by chromatography to afford the title compound (1.92 g, 64%).

$^1$H NMR (400 MHz, $CDCl_3$) 8.51 (s, 1H), 7.88 (s, 1H), 7.79 (d, J=2.0 Hz, 1H), 7.77 (s, 2H), 5.72 (d, J=8.0 Hz, 1H), 4.75 (d, J=16.0 Hz, 1H), 4.34 (d, J=16.0 Hz, 1H), 4.00 (m, 2H), 3.46 (m, 6H), 1.86 (m, 4H), 0.93 (t, 3H), 0.63 (d, 3H).

Example 8

(4S,5R)-5-[3,5-bis(trifluoromethyl)phenyl]-4-methyl-3-({[2-(propyl)(tetrahydro-2H-pyran-4-yl)amino]-5-(trifluoromethyl)pyridin-3-yl}methyl)-oxazolidin-2-one

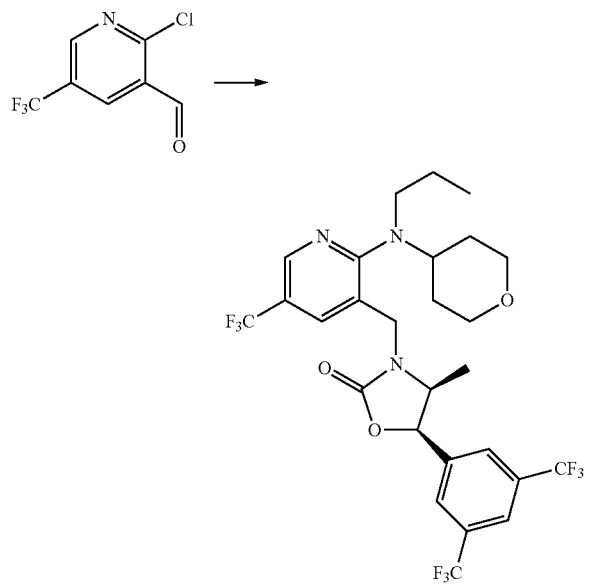 [SMILES: O=Cc1cc(C(F)(F)F)cnc1Cl ; CCN(c1ncc(C(F)(F)F)cc1CN1C(=O)O[C@H](c2cc(C(F)(F)F)cc(C(F)(F)F)c2)[C@@H]1C)C1CCSCC1]

The same procedure as in method 2 of Example 7 was repeated, with the exception that N-propyl-N-(tetrahydro-2H-pyran-4-yl)-amine (2.36 g, 16.5 mmol) was used instead of N-ethyl-N-(tetrahydro-2H-pyran-4-yl)-amine, to afford the title compound (2.4 g, 58%).

¹H NMR (400 MHz, CDCl₃) 8.49 (s, 1H), 7.88 (s, 1H), 7.77 (s, 1H), 7.74 (s, 2H), 5.73 (d, J=8.0 Hz, 1H), 4.75 (d, J=16.4 Hz, 1H), 4.33 (d, J=16.4 Hz, 1H), 4.03 (m, 3H), 3.46-3.27 (m, 4H), 3.18 (m, 1H), 3.08 (m, 1H), 1.92 (m, 1H), 1.82 (m, 2H), 1.35 (m, 2H), 0.86 (s, 3H), 0.62 (d, 3H).

Example 9

(4S,5R)-5-[3,5-bis(trifluoromethyl)phenyl]-4-methyl-3-({[2-(butyl)(tetrahydro-2H-pyran-4-yl)amino]-5-(trifluoromethyl)pyridin-3-yl}methyl)-oxazolidin-2-one

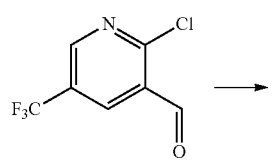

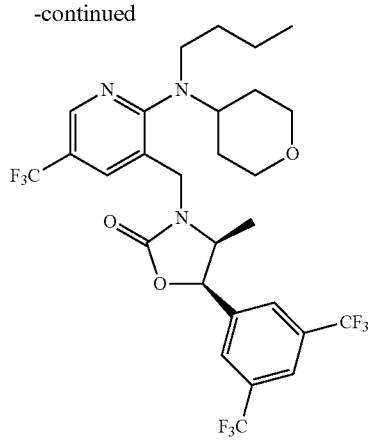

The same procedure as in method 2 of Example 7 was repeated, with the exception that N-butyl-N-(tetrahydro-2H-pyran-4-yl)-amine was used instead of N-ethyl-N-(tetrahydro-2H-pyran-4-yl)-amine, to afford the title compound (84.6 mg, 90%).

¹H NMR (400 MHz, CDCl₃) 8.49 (s, 1H), 7.88 (s, 1H), 7.77-7.71 (m, 4H), 5073 (d, J=8.0 Hz, 1H), 4.74 (d, J=16.0 Hz, 1H), 4.32 (d, J=16.0 Hz, 1H), 4.04 (m, 3H), 3.47-3.06 (m, 5H), 1.92-1.71 (m, 4H), 0.81 (t, 3H), 0.61 (d, J=6.8 Hz, 3H)

Example 10

(4S,5R)-5-[3,5-bis(trifluoromethyl)phenyl]-4-methyl-3-{[2-(cyclopropyl)(tetrahydro-2H-pyran-4-yl)amino]-5-(trifluoromethyl)pyridin-3-yl}methyl)-oxazolidin-2-one

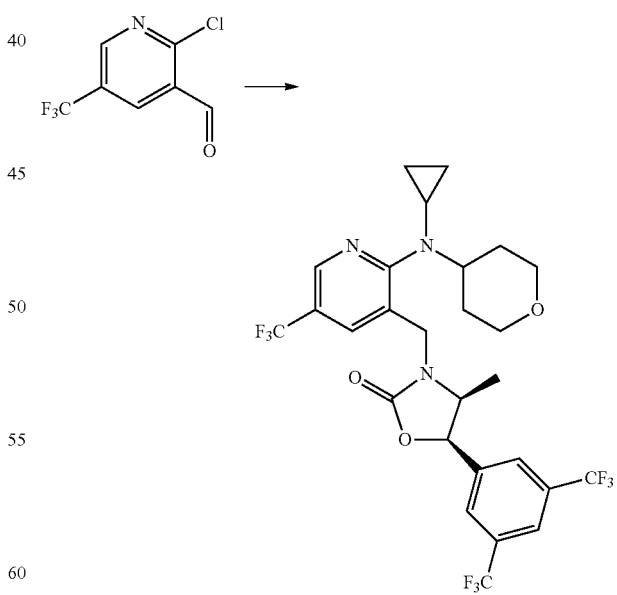

The same procedure as in method 2 of Example 7 was repeated, with the exception that N-cyclopropyl-N-(tetrahydro-2H-pyran-4-yl)-amine was used instead of N-ethyl-N-(tetrahydro-2H-pyran-4-yl)-amine, to afford the title compound (50 mg, 45%).

¹H NMR (400 MHz, CDCl₃) 8.53 (s, 1H), 7.90 (s, 1H), 7.78 (s, 1H), 7.75 (s, 2H), 5.73 (d, 1H), 4.84 (d, 1H), 4.32 (d, 1 h), 4.04 (m, 2H), 3.91 (m, 1H), 3.6 (m, 3H), 2.83 (m, 1H), 2.13 (m, 2 h), 1.89 (m, 2H), 1.78 (m 2H), 0.82 (m, 3H), 0.65 (d, 3H).

Example 11

(4S,5R)-5-[3,5-bis(trifluoromethyl)phenyl]-4-methyl-3-({[2-(cyclobutyl)(tetrahydro-2H-pyran-4-yl)amino]-5-(trifluoro)methylpyridin-3-yl}methyl)-oxazolidin-2-one

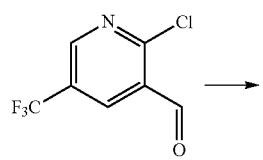

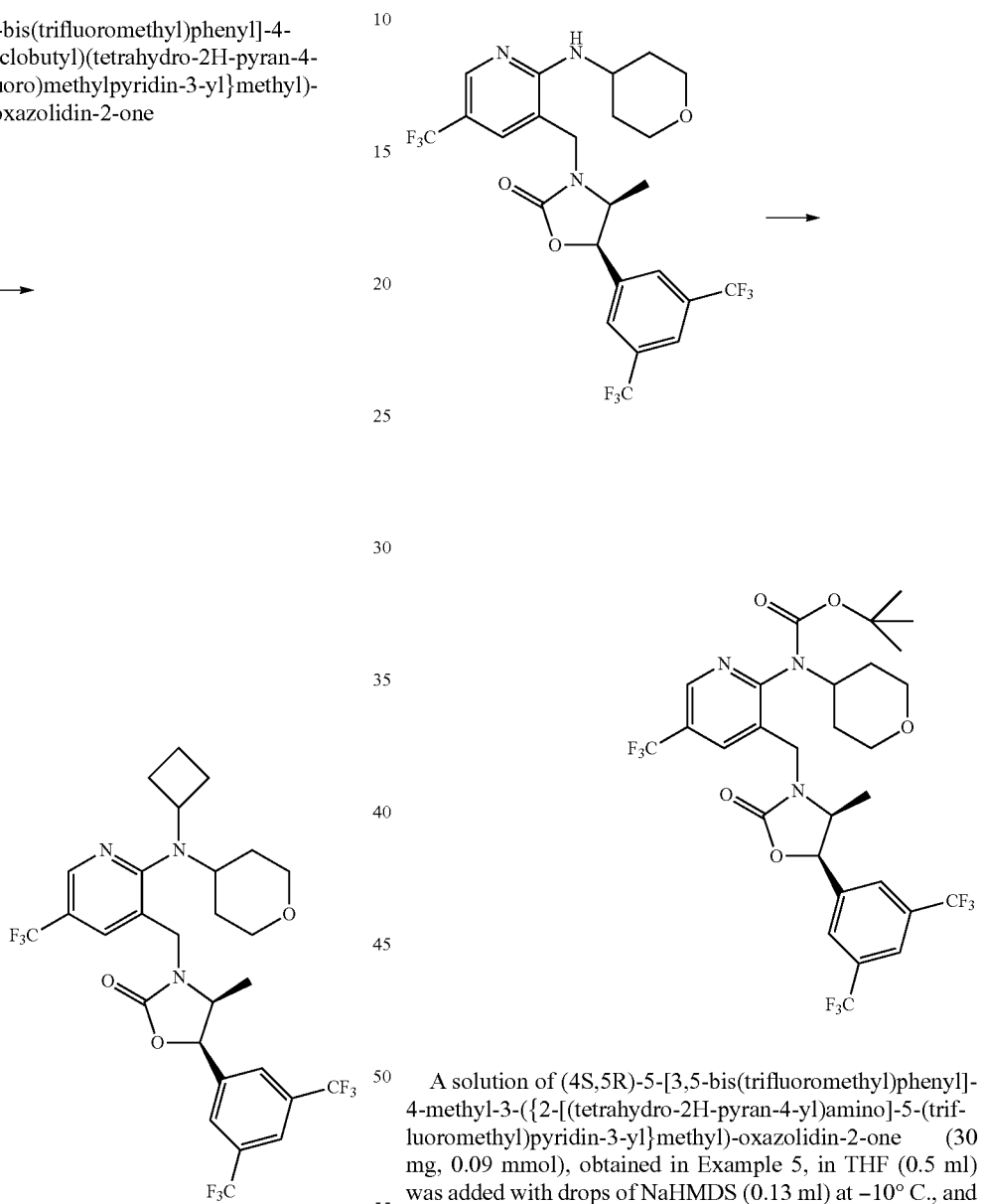

The same procedure as in method 2 of Example 7 was repeated, with the exception that N-cyclobutyl-N-(tetrahydro-2H-pyran-4-yl)-amine was used instead of N-ethyl-N-(tetrahydro-2H-pyran-4-yl)-amine, to afford the title compound (22 mg, 70%).

¹H NMR (400 MHz, CDCl₃) 8.57 (s, 1H), 7.89 (s, 1H), 7.83 (s, 1H), 7.76 (s, 2H), 5.74 (d, J=8.0 Hz, 1H), 4.75 (d, J=16.4 Hz, 1H), 4.50 (d, J=16.4 Hz, 1H), 4.13 (m, 1H), 3.97 (m, 3H), 3.34 (m, 2H), 3.08 (m, 1H), 2.15 (m, 2H), 1.81-1.40 (m, 8H), 0.73 (d, 3H).

Example 12 t-butyl [3-({(4S,5R)-5-[3,5-bis(trifluoromethyl)phenyl]-4-methyl-2-oxo-oxazolidin-3-yl}methyl)-5-(trifluoromethyl)pyridin-2-yl]-(tetrahydro-2H-pyran-4-yl)-carbamate A solution of (4S,5R)-5-[3,5-bis(trifluoromethyl)phenyl]-4-methyl-3-({2-[(tetrahydro-2H-pyran-4-yl)amino]-5-(trifluoromethyl)pyridin-3-yl}methyl)-oxazolidin-2-one (30 mg, 0.09 mmol), obtained in Example 5, in THF (0.5 ml) was added with drops of NaHMDS (0.13 ml) at −10° C., and stirred for 10 min. Then, the solution was added with (BOC)₂O (di-t-butyl dicarbonate) (29 mg, 0.131 mmol), and stirred for 4 hrs. The reaction was terminated with water, followed by extraction with ethyl acetate. The organic layer was dried over anhydrous magnesium sulfate, filtered, and concentrated at a reduced pressure. The residue was purified by chromatography to afford the title compound 13.3 mg (23%).

¹H NMR (400 MHz, CDCl₃) 8.46 (s, 1H), 7.75 (s, 3H), 7.51 (s, 1H), 5.87 (d, J=6.0 Hz, 1H), 4.76 (m, 1H), 4.62 (m, 1H), 4.26 (q, 2H), 4.09 (m, 2H), 3.51 (m, 2H), 2.88 (m, 2H), 1.32-1.23 (m, 14H).

Example 13

Ethyl [3-({(4S,5R)-5-[3,5-bis(trifluoromethyl)phenyl]-4-methyl-2-oxo-oxazolidin-3-yl}methyl)-5-(trifluoromethyl]pyridin-2-yl]-(tetrahydro-2H-pyran-4-yl)-carbamate

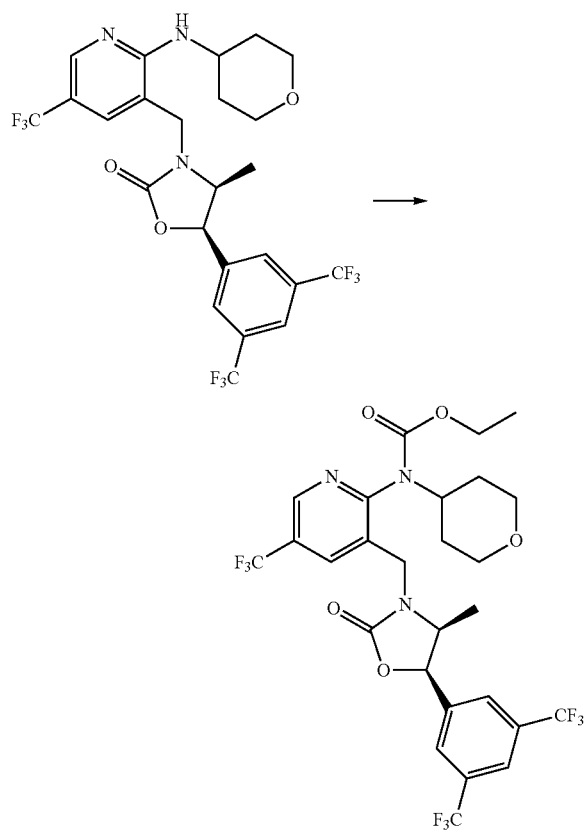

The same procedure as in Example 12 was repeated, with the exception that diethyl pyrocarbonation was used instead of (BOC)₂O, to afford the title compound (11.2 mg, 20%).

$^1$H NMR (400 MHz, CDCl$_3$) 8.46 (s, 1H), 7.76 (s, 3H), 7.50 (s, 1H), 5.95 (d, J=6.0 Hz, 1H), 4.78 (m, 1H), 4.62 (m, 1H), 4.25 (m, 8H), 3.51 (m, 2H), 2.87 (m, 2H), 1.31 (m, 6H).

Example 14

(4S,5R)-5-[3,5-Bis(trifluoromethyl)phenyl]-4-methyl-3-({[2-ethyl(tetrahydro-2H-pyran-4-yl)amino]-pyridin-3-yl}methyl)-oxazolidin-2-one

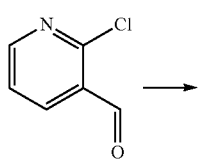

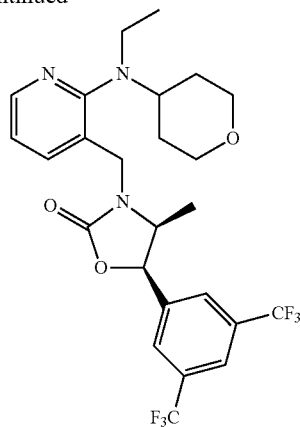

The same procedure as in method 2 of Example 7 was repeated, with the exception that 2-chloro-pyridine carbaldehyde was used instead of 2-chloro-5-trifluoromethylpyridine carbaldehyde, to afford the title compound (15 mg, 9%).

$^1$H NMR (400 MHz, CDCl$_3$) 8.32 (dd, J=4.8, 1.6 Hz, 1H), 7.87 (s, 1H), 7.73 (s, 2H), 7.67 (d, J=7.8 Hz, 1H), 7.05 (dd, J=7.2, 4.8 Hz, 1H), 5.69 (d, J=8.0 Hz, 1H), 4.73 (d, J=16.4 Hz, 1H), 4.42 (d, J=16.4 Hz, 1H), 3.94 (m, 3H), 3.37 (m, 3H), 3.13 (m, 2H), 1.75 (m, 2H), 1.64 (m, 2H), 0.90 (t, 3H), 0.65 (d, 3H).

Example 15

(4S,5R)-5-[3,5-bis(trifluoromethyl)phenyl]-4-methyl-3-({[2-ethyl(tetrahydro-2H-pyran-3-yl)amino]-5-(trifluoromethyl)pyridin-3-yl}methyl)-oxazolidin-2-one

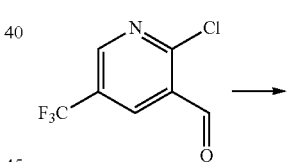

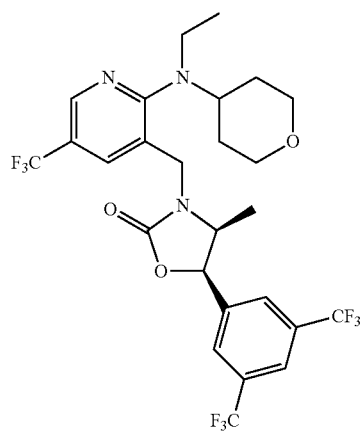

The same procedure as in method 2 of Example 7 was repeated, with the exception that N-ethyl-N-(tetrahydro-2H-pyran-3-yl)-amine was used instead of N-ethyl-N-(tetrahydro-2H-pyran-4-yl)-amine, to afford the title compound (70 mg, 45%).

¹H NMR (400 MHz, CDCl₃) 8.50 (s, 1H), 7.87 (s, 1H), 7.80 (m, 1H), 7.74 (s, 2H), 5.71 (d, J=8.4 Hz, 1H), 4.78 (m, 1H), 4.34 (m, 1H), 3.94-3.79 (m, 3H), 3.52-3.14 (m, 6H), 1.93-1.59 (m, 4H), 0.93 (m, 3H), 0.64 (m, 3H).

Example 16

(4S,5R)-5-[3,5-Bis(trifluoromethyl)phenyl]-4-methyl-3-({2-[ethyl(tetrahydro-2H-pyran-4-yl)amino]-5-fluoropyridin-3-yl}methyl)-oxazolidin-2-one

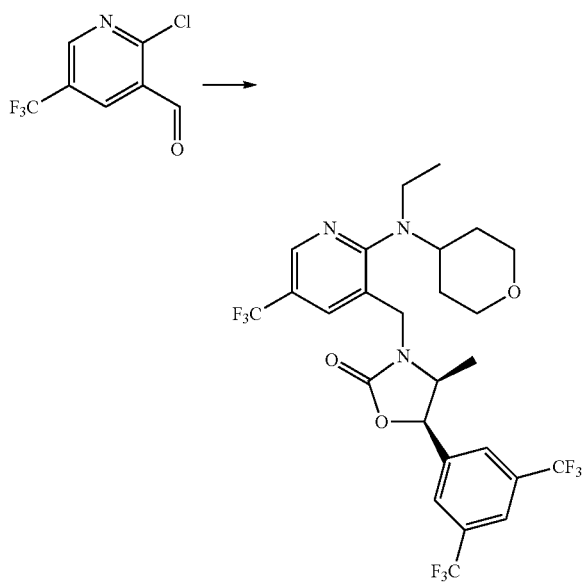

The same procedure as in method 2 of Example 7 was repeated, with the exception that 2-chloro-5-fluoropyridine carbaldehyde was used instead of 2-chloro-5-(trifluoromethyl)pyridine carbaldehyde, to afford the title compound (100 mg, 47%).

¹H NMR (400 MHz, CDCl₃) 8.18 (d, 1H, J=3.2 Hz), 7.87 (s, 1H), 7.74 (s, 2H), 7.43-7.40 (m, 1H), 5.72 (d, 1H, J=8.0 Hz), 4.70 (d, 1H, J=16.4 Hz), 4.63 (d, 1H, J=16.4 Hz), 4.01-3.90 (m, 3H), 3.39-3.22 (m, 4H), 3.12-3.04 (m, 2H), 1.74-1.69 (m, 2H), 1.61-1.57 (m, 2H), 0.84 (t, 3H, J=7.2 Hz), 0.67 (d, 3H, J=6.4 Hz).

Example 17 t-butyl 2-([3-({(4S,5R)-5-[3,5-bis(trifluoromethyl)phenyl]-4-methyl-2-oxo-oxazolidin-3-yl}methyl)-5-(trifluoromethyl)pyridin-2-yl]-(tetrahydro-2H-pyran-4-yl)amino)-acetate

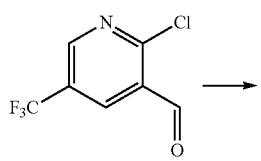

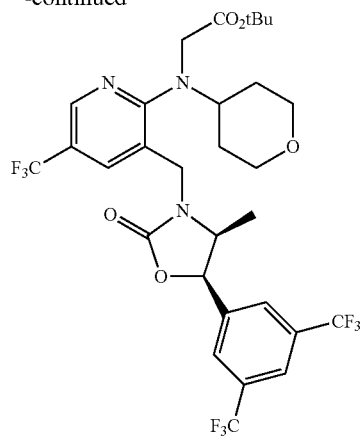

The same procedure as in method 2 of Example 7, with the exception that t-butyl 2-[(tetrahydro-2H-pyran-4-yl)amino]-acetate was used instead of N-ethyl-N-cyclohexylamine, to afford the title compound (70 mg, 45%).

¹H NMR (400 MHz, CDCl₃) 8.42 (s, 1H), 7.85 (s, 1H), 7.76 (s, 2H), 5.78 (d, J=7.8 Hz, 1H), 4.98 (d, J=15.6 Hz, 1H), 4.36 (d, J=15.6 Hz, 1H), 4.06-3.99 (m, 5H), 3.41 (m, 3H), 1.74 (m, 2H), 1.8 (s, 9H), 0.56 (d, 3H).

Example 18

(4S,5R)-5-[3,5-Bis(trifluoromethyl)phenyl]-4-methyl-3-({[2-(hydroxyethyl)(tetrahydro-2H-pyran-4-yl)amino]-5-(trifluoromethyl)pyridin-3-yl}methyl)-oxazolidin-2-one

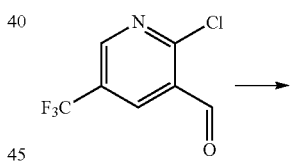

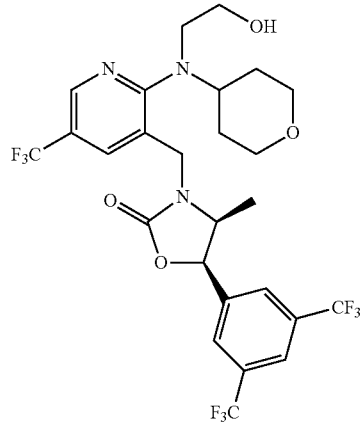

[Step 1] 2-{[2-(t-butyldimethylsiloxy)ethyl](tetrahydro-2H-pyran-4-yl)amino}-5-(trifluoromethyl)nicotine aldehyde

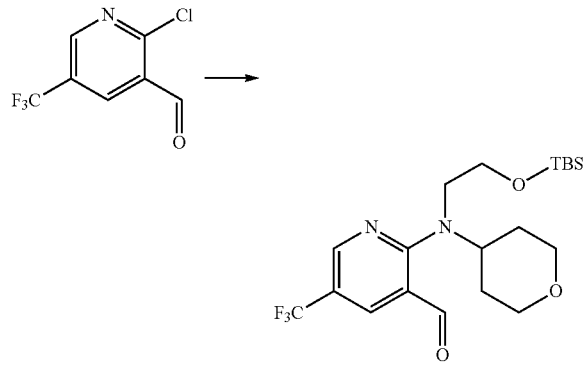

The same procedure as in step 1 of method 2 of Example 7 was repeated, with the exception that N-[(t-butyldimethylsiloxy)ethyl]-N-(tetrahydro-2H-pyran-4-yl)-amine was used instead of N-ethyl-N-(tetrahydro-2H-pyran-4-yl)-amine, to afford the title compound (110 mg, 58%).

$^1$H NMR (400 MHz, CDCl$_3$) 9.90 (s, 1H), 8.50 (s, 1H), 8.15 (s, 1H), 4.04 (m, 2H), 3.71 (m, 3H), 3.39 (m, 2H), 2.03 (m, 2H), 1.77 (m, 2H), 0.82 (s, 9H), −0.05 (s, 6H).

[Step 2] Preparation of [2-{[2-(t-butyldimethylsiloxy)ethyl](tetrahydro-2H-pyran-4-yl)amino}-5-(trifluoromethyl)pyridin-3-yl]methyl methanesulfonate

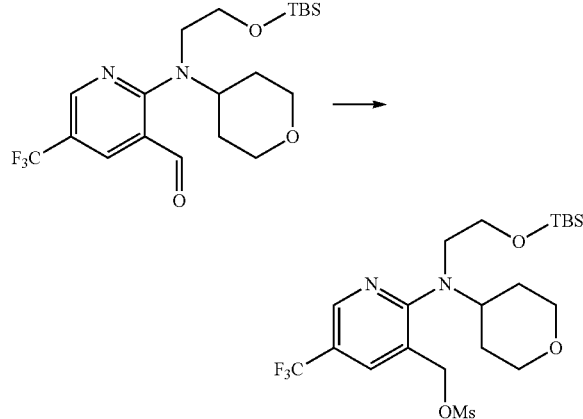

A solution of 2-{[2-(t-butyldimethylsiloxy)ethyl](tetrahydro-2H-pyran-4-yl)amino}-5-(trifluoromethyl)nicotine aldehyde (50 mg, 0.12 mmol) of step 1 in ethanol (2 ml) was added with drops of NaBH$_4$ (5.2 mg) at 0° C., and stirred at room temperature for 1 hr. The reaction was terminated with a saturated aqueous ammonium solution, followed by extraction with ethyl acetate. The organic layer was dried over anhydrous magnesium sulfate, filtered, and concentrated at a reduced pressure. The concentrate was dissolved in 2 ml of dichloromethane, and added with TEA (14 mg, 0.14 mmol) and then with drops of MsCl (16 mg, 0.14 mmol). After stirring at room temperature for 1 hr, the reaction was terminated with water. The reaction mixture was diluted with ethyl acetate and extracted. The organic layer was dried over anhydrous magnesium sulfate, filtered, and concentrated at a reduced pressure. The residue was used in a subsequent reaction without further purification.

[Step 3] Preparation of (4S,5R)-5-[3,5-bis(trifluoromethyl)phenyl]-3-{[2-{[2-(t-butyldimethylsiloxy)ethyl](tetrahydro-2H-pyran-4-yl)amino}-4-methyl-5-(trifluoromethyl)pyridin-3-yl]methyl}-oxazolidin-2-one

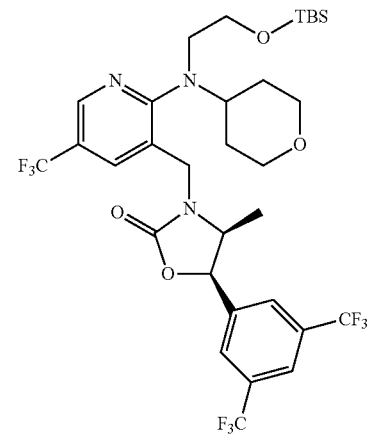

[2-{[2-(t-butyldimethylsiloxy)ethyl]tetrahydro-2H-pyran-4-yl)amino}-5-(trifluoromethyl)pyridin-3-yl]methyl methanesulfonate of step 2 and (4S,5R)-5-[3,5-bis(trifluoromethyl)phenyl])-4-methyl-oxazolidin-2-one were used in the same manner as in step 4 of Example 3 to afford the title compound (55 mg, 63%).

$^1$H NMR (400 MHz, CDCl$_3$) 8.46 (s, 1H), 7.88 (s, 1H), 7.77 (s, 1H), 7.73 (s, 2H), 5.72 (d, J=8.0 Hz, 1H), 4.75 (d, J=16.0 Hz, 1H), 4.33 (d, J=16.0 Hz, 1H), 4.04-3.87 (m, 3H), 3.67 (m, 1H), 3.50 (m, 2H), 3.38-3.17 (m, 6H), 1.91-1.72 (m, 4H), 0.78 (s, 9H), 0.61 (d, 3H), −0.03 (d, 3H).

63

[Step 4] Preparation of (4S,5R)-5-[3,5-bis(trifluoromethyl)phenyl]-4-methyl-3-({[2-(hydroxyethyl)(tetrahydro-2H-pyran-4-yl)amino]-5-(trifluoromethyl)pyridin-3-yl}methyl)-oxazolidin-2-one

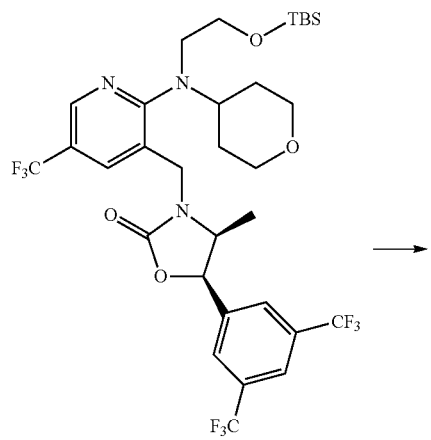

→

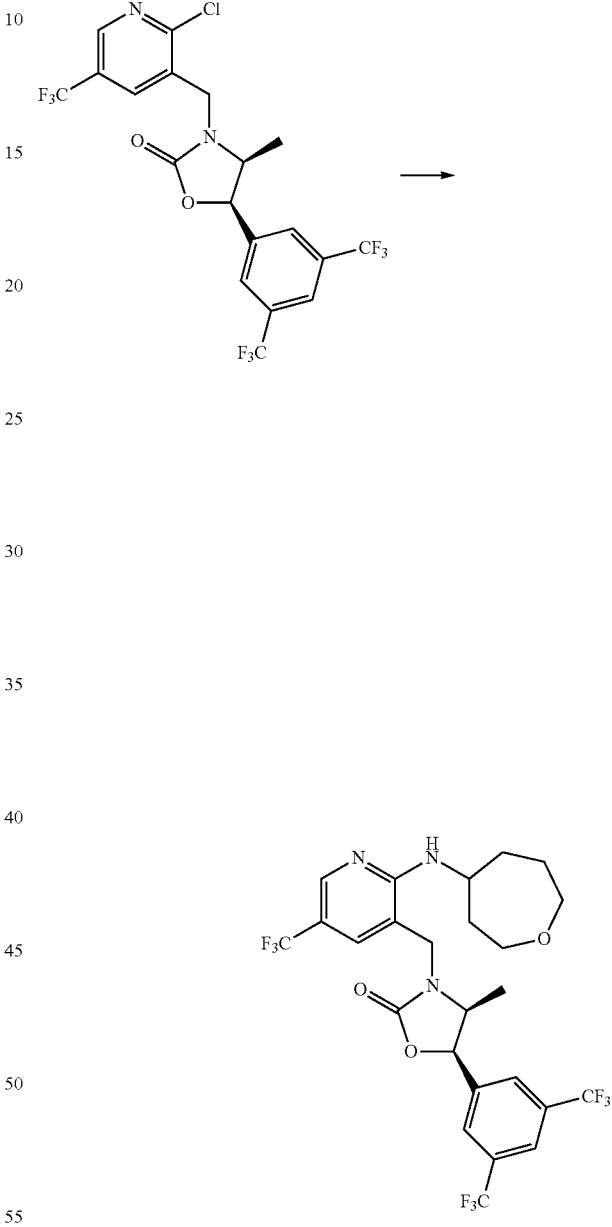

To a solution of (4S,5R)-5-[3,5-bis(trifluoromethyl)phenyl]-3-{[2-{[2-(t-butyldimethylsiloxy)ethyl](tetrahydro-2H-pyran-4-yl)amino}-4-methyl-5-(trifluoromethyl)pyridin-3-yl]methyl}-oxazolidin-2-one (28 mg, 0.038 mmol) of step 3 in THF/H2O (1/3, 2 ml) was dropwise added TFA (22 mg, 0.38 mmol) at 0° C. This solution was stirred at room temperature for 1 hr, diluted with ethyl acetate, and added with water to terminate the reaction, followed by extraction. The organic layer thus formed was washed with a saturated aqueous sodium carbonate, dried over anhydrous magnesium sulfate, 20 filtered, and concentrated at a reduced pressure to obtain the title compound (24 mg, 100%).

$^1$H NMR (400 MHz, CDCl$_3$) 8.49 (s, 1H), 7.88 (s, 1H), 7.80 (d, J=1.6 Hz, 1H), 7.74 (s, 2H), 5.75 (d, J=8.0 Hz, 1H), 4.82 (d, J=16.0 Hz, 1H), 4.31 (d, J=16.0 Hz, 1H), 4.03 (m, 3H), 3.66-3.46 (m, 4H), 3.39 (m, 2H), 3.13 (m, 1H), 1.95 (m, 2H), 1.69 (m, 2H), 0.68 (d, 3H).

64

Example 19

(4S,5R)-5-[3,5-bis(trifluoromethyl)phenyl]-4-methyl-3-({[2-(oxepan-4-yl)amino]-5-(trifluoromethyl)pyridin-3-yl}methyl)-oxazolidin-2-one The same procedure as in step 4 of Example 1 was repeated, with the exception that oxepane-4-amine was used instead of tetrahydrofuran-3-amine, to afford the title compound (26 mg, 68%).

$^1$H NMR (400 MHz, CDCl$_3$) 8.37 (s, 1H), 8.03 (s, 1H), 7.79 (s, 2H), 7.36 (s, 1H), 6.13 (dd, 1H), 5.73 (dd, 1H), 4.70 (dd, 1H), 4.09 (m, 3H), 3.86 (m, 4H), 2.04 (m, 2H), 1.89 (m, 2H), 1.60 (m, 2H), 0.99 (d, 3H).

Example 20

(4S,5R)-5-[3,5-bis(trifluoromethyl)phenyl]-4-methyl-3-({[2-(methyl)(oxepen-4-yl)amino]-5-(trifluoromethyl)pyridin-3-yl}methyl)-oxazolidin-2-one

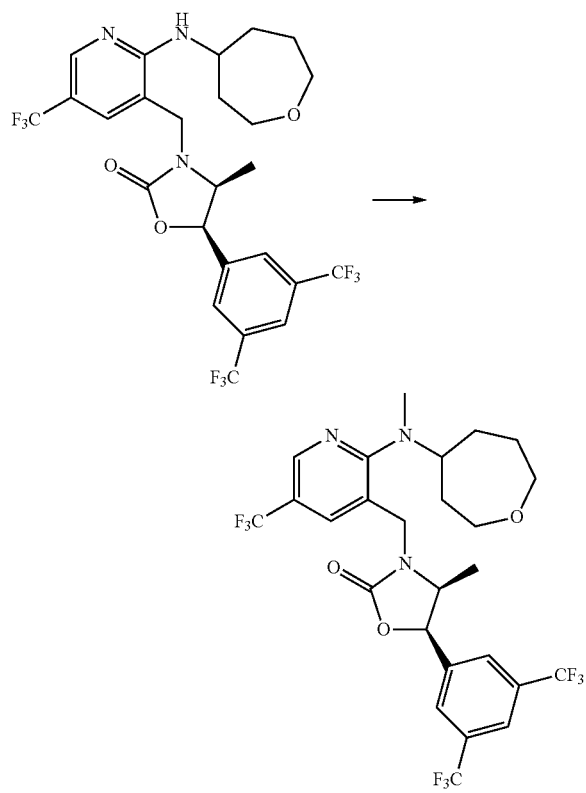

The same procedure as in step 5 of Example 1, with the exception that (4S,5R)-5-[3,5-bis(trifluoromethyl)phenyl]-4-methyl-3-({[2-(oxepan-4-yl)amino]-5-(trifluoromethyl)pyridin-3-yl}methyl)-oxazolidin-2-one was used instead of (4S,5R)-5-[3,5-bis(trifluoromethyl)phenyl]-4-methyl-3-[(2-(tetrahydrofuran-3-yl)amino-5-(trifluoromethyl)pyridin-3-yl)methyl]-oxazolidin-2-one, to afford the title compound (3.4 mg, 28%).

$^1$H NMR (400 MHz, CDCl$_3$) 8.45 (s, 1H), 7.89 (s, 1H), 7.75 (s, 2H), 7.72 (m, 1H), 5.71 (dd, 1H), 4.84 (dd, 1H), 4.26 (dd, 1H), 3.83 (m, 3H), 3.66 (m, 2H), 2.83 (s, 3H), 2.07 (m, 4H), 1.84 (m, 2H), 1.02 (d, 3H).

Example 21

(4S,5R)-5-[3,5-bis(trifluoromethyl)phenyl]-4-methyl-3-({[2-(ethyl)(1,4-dioxaspiro[4.5]decan-8-yl)amino]-5-trifluoromethylpyridin-3-yl}methyl)-oxazolidin-2-one

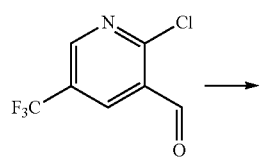

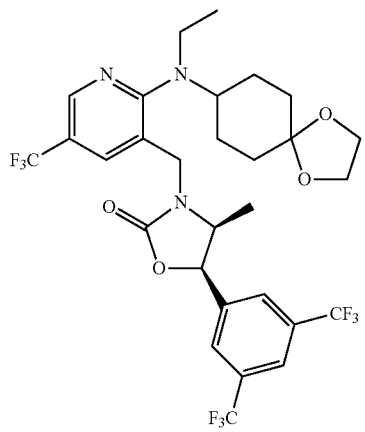

The same procedure as in method 2 of Example 7 was repeated, with the exception that N-ethyl-N-(1,4-dioxaspiro[4.5]decan-8-yl)-amine was used instead of N-ethyl-N-(tetrahydro-2H-pyran-4-yl)amine, to afford the title compound (1.39 g, 80%).

$^1$H NMR (400 MHz, CDCl$_3$) 8.49 (s, 1H), 7.87 (s, 1H), 7.77 (s, 1H), 7.73 (s, 2H), 5.70 (d, 1H, J=8.0 Hz), 4.71 (d, 1H, J=15.6 Hz), 4.29 (d, 1H, J=15.6 Hz), 3.92 (s, 5H), 3.49 (m, 1H), 3.18 (m, 1H), 3.03 (m, 1H), 1.43-2.00 (m, 8H), 0.90 (m, 3H), 0.60 (m, 3H).

Example 22

(4S,5R)-5-[3,5-bis(trifluoromethyl)phenyl]-4-methyl-3-({[2-(ethyl)(4-oxocyclohexyl)amino]-5-(trifluoromethyl)pyridin-3-yl}methyl)-oxazolidin-2-one

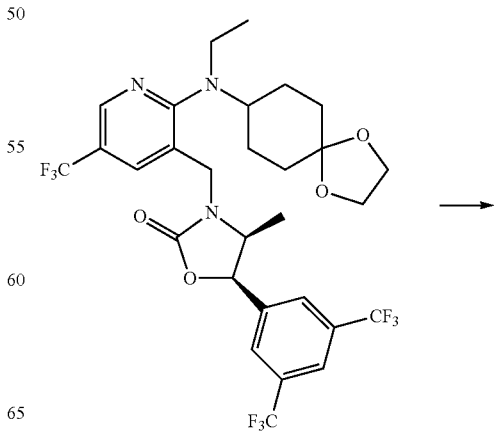

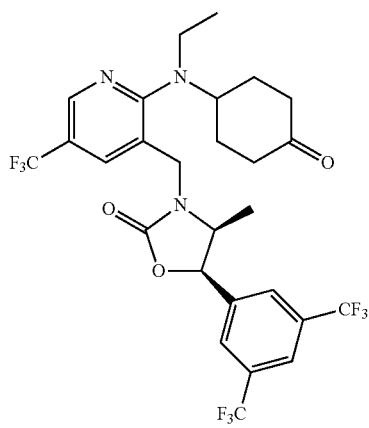

A solution of (4S,5R)-5-[3,5-bis(trifluoromethyl)phenyl]-4-methyl-3-({[2-(ethyl)(1,4-dioxaspiro[4.5]decan-8-yl)amino]-5-trifluoromethylpyridin-3-yl}methyl)-oxazolidin-2-one (820 mg, 1.25 mmol) of Example 21 in 1,4-dioxene (6 ml) was added with drops of 2N HCl (3 ml), refluxed at 70° C. for 4 hrs with stirring, and cooled to room temperature, followed by extraction with ethyl acetate and water. The organic layer was dried, filtered, and concentrated. The residue was purified by chromatography to afford the title compound (650 mg, 85%).

$^1$H NMR (400 MHz, CDCl$_3$) 8.55 (s, 1H), 7.90 (s, 1H), 7.82 (s, 1H), 7.76 (s, 2H), 5.74 (d, 1H, J=8.0 Hz), 4.80 (d, 1H, J=16.0 Hz), 4.37 (d, 1H, J=16.0 Hz), 3.93 (m, 1H), 3.62 (m, 1H), 3.45 (m, 1H), 3.19 (m, 1H), 2.29~2.50 (m, 4H), 1.90-2.21 (m, 4H), 0.97 (m, 3H), 0.62 (m, 3H)

To a solution of (4S,5R)-5-[3,5-bis(trifluoromethyl)phenyl]-4-methyl-3-({[2-(ethyl)(4-oxocyclohexyl)amino]-5-(trifluoromethyl)pyridin-3-yl}methyl)-oxazolidin-2-one (160 mg, 0.26 mmol) of Example 22 in dichloromethane (10 ml) were added ethylamine hydrochloride (32 mg, 0.392 mmol) and NaBH(OAc)$_3$ (110 mg, 0.52 mmol), followed by stirring at room temperature for 24 hrs. The reaction was terminated with water before extraction with dichloromethane. The organic layer was dried over magnesium sulfate, filtered, and concentrated at a reduced pressure. The residue was re-crystallized in n-hexane to afford the title compound (100 mg, 52%).

$^1$H NMR (400 MHz, CDCl$_3$) 8.48 (s, 1H), 7.87 (s, 1H), 7.77 (s, 1H), 7.73 (s, 2H), 5.70 (m, 1H), 4.73 (m, 1H), 4.33 (m, 1H), 3.87 (m, 1H), 3.50 (m, 1H), 3.14 (m, 1H), 2.93 (m, 1H), 2.66 (m, 2H), 2.42 (m, 1H), 2.03 (m, 4H), 1.84-1.23 (m, 4H), 1.23 (m, 3H), 0.93 (m, 3H), 0.62 (d, 3H).

Example 23

(4S,5R)-5-[3,5-bis(trifluoromethyl)phenyl]-4-methyl-3-({[2-(ethyl)(4-ethylaminocyclohexyl)amino]-5-(trifluoromethyl)pyridin-3-yl}methyl)-oxazolidin-2-one

Example 24 methyl 2-(4-{[3-({(4S,5R)-5-[3,5-bis(trifluoromethyl)phenyl]-4-methyl-2-oxo-oxazolidin-3-yl}methyl)-5-(trifluoromethyl)pyridin-2-yl](ethyl)amino}cyclohexyl)acetate

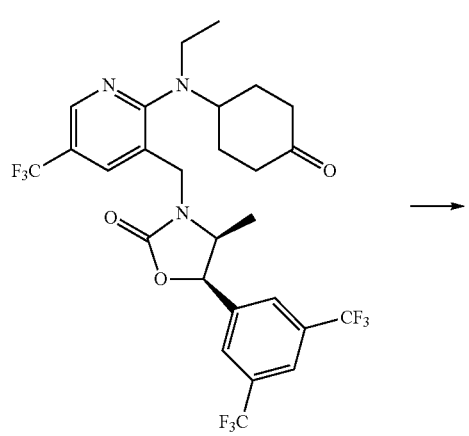

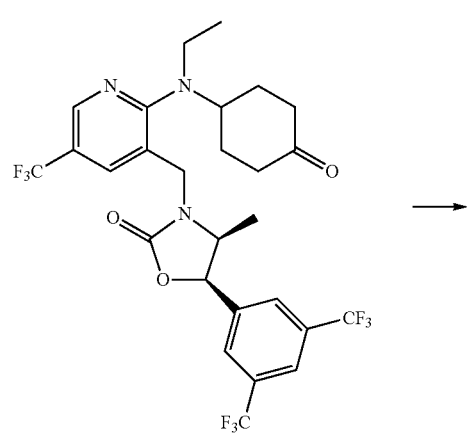

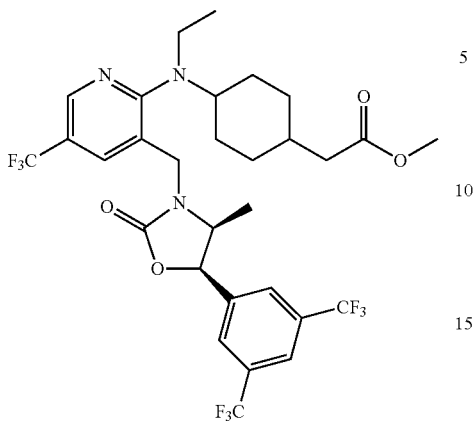

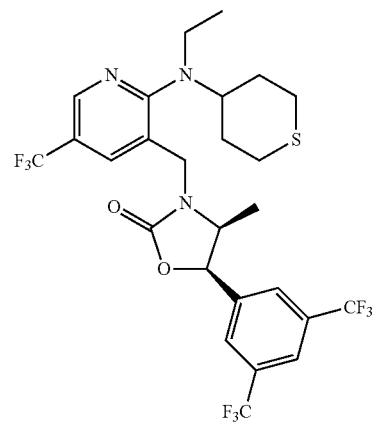

A solution of (4S,5R)-5-[3,5-bis(trifluoromethyl)phenyl]-4-methyl-3-({[2-(ethyl)(4-oxocyclohexyl)amino]-5-(trifluoromethyl)pyridin-3-yl}methyl)-oxazolidin-2-one (86 mg, 14.0 mmol) of Example 22 in THF (1 ml) was added with (carmethoxymethylene)triphenylphosphorane (73 mg, 0.21 mmol), and stirred at room temperature for 3 days. The reaction was terminated with water, followed by extraction with dichloromethane. The organic layer was dried over anhydrous magnesium sulfate, filtered, and concentrated at a reduced pressure. The residue was purified by chromatography and dissolved in methanol (1 ml). This solution was added with 10% Pd/C and provided with hydrogen gas from a hydrogen balloon. Stirring at room temperature for 6 hrs were followed by filtration through Celite pad. The filtrate was concentrated to afford the title compound (20 mg, 30%).

$^1$H NMR (400 MHz, CDCl$_3$) 8.50 (s, 1H), 7.90 (s, 1H), 7.70~7.89 (m, 3H), 5.73 (m, 1H), 4.72 (m, 1H), 4.30 (m, 1H), 4.04~4.20 (m, 4H), 3.89 (m, 1H), 3.42~3.61 (m, 2H), 3.16 (m, 2H), 2.87 (m, 1H), 2.17 (m, 1H), 1.40~1.90 (m, 6H), 1.22 (m, 3H), 0.96 (m, 3H), 0.62 (m, 3H)

Example 25

(4S,5R)-5-[3,5-bis(trifluoromethyl)phenyl]-4-methyl-3-({[2-(ethyl)(tetrahydro-2H-thiopyran-4-yl)amino]-5-(trifluoromethyl)pyridin-3-yl}methyl)-oxazolidin-2-one

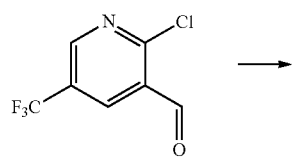

The same procedure as in method 2 of Example 7 was repeated, with the exception that N-(tetrahydro-2H-thiopyran-4-yl)-amine was used instead of N-ethyl-N-(tetrahydro-2H-pyran-4-yl)amine of step 1 to afford the title compound (450 mg, 58%).

$^1$H NMR (400 MHz, CDCl3) 8.48 (s, 1H), 7.87 (s, 1H), 7.77 (s, 1H), 7.73 (s, 2H), 4.69 (d, 1H), 4.24 (d, 1H), 3.88-3.48 (m, 1H), 3.57-3.52 (m, 1H), 3.20-3.15 (m, 1H), 2.86-2.83 (m, 1H), 2.73-2.59 (m, 4H), 2.05-1.89 (m, 4H), 0.92-0.86 (m, 3H), 0.60 (d, 3H).

Example 26

(4S,5R)-5-[3,5-bis(trifluoromethyl)phenyl]-4-methyl-3-({[2-(ethyl)(1-oxidotetrahydro-2H-thiopyran-4-yl)amino]-5-(trifluoromethyl)pyridin-3-yl}methyl)-oxazolidin-2-one

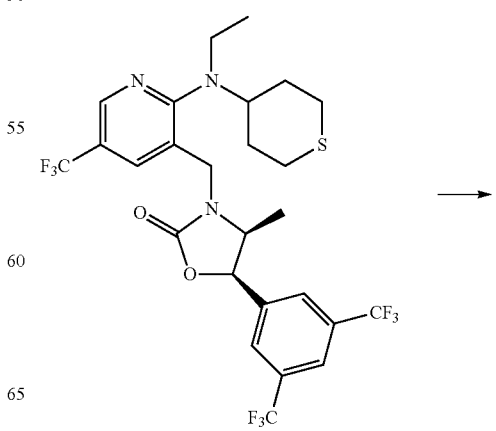

-continued

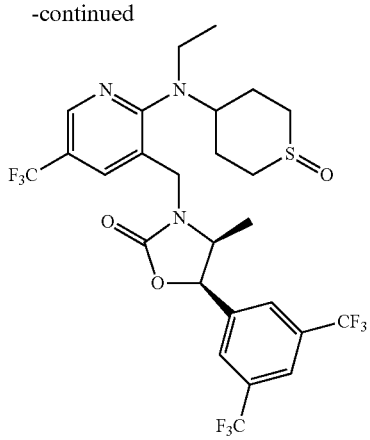

To a solution of (4S,5R)-5-[3,5-bis(trifluoromethyl)phenyl]-4-methyl-3-({[2-(ethyl)(tetrahydro-2H-thiopyran-4-yl)amino]-5-(trifluoromethyl)pyridin-3-yl}methyl)-oxazolidin-2-one (100 mg, 0.16 mmol) of Example 25 in dichloromethane (20 ml) was added $H_2O_2$ (54 mg, 0.48 mmol) at 0° C. Stirring at room temperature for 4 days were followed by extraction with dichloromethane. The extract was purified by chromatography to afford the title compound (80 mg, 78%).

$^1$H NMR (400 MHz, CDCl$_3$) 8.52 (s, 1H), 7.88 (s, 1H), 7.74 (s, 3H), 5.73 (d, 1H), 4.76-4.70 (m, 1H), 4.30-4.24 (m, 1H), 3.93-3.92 (m, 1H), 3.37-3.04 (m, 4H), 2.74-2.36 (m, 4H), 2.22-1.87 (m, 3H), 0.86 (d, 3H), 0.66-0.62 (m, 3H).

Example 27 t-butyl 4-{[3-({(4S,5R)-5-[3,5-bis(trifluoromethyl)phenyl]-4-methyl-2-oxo-oxazolidin-3-yl}methyl)-5-(trifluoromethyl)pyridin-2-yl](ethyl)amino}piperidine-1-carboxylate

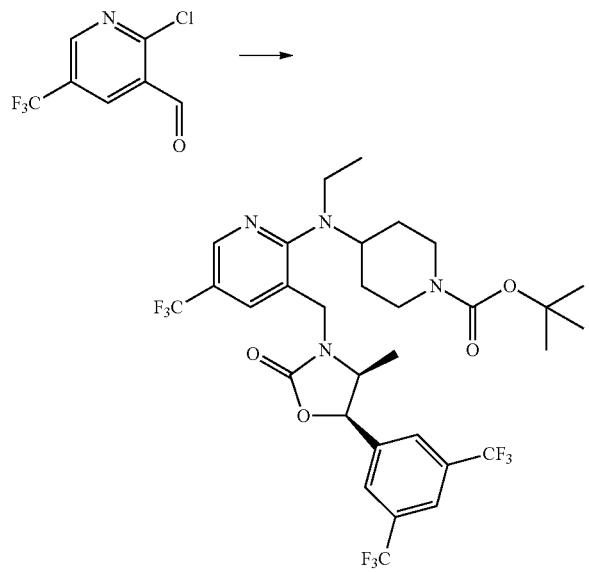

The same procedure as in method 2 of Example 7 was repeated, with the exception that t-butyl 4-(ethylamino)piperidine-1-carboxylate was used instead of N-ethyl-N-(tetrahydro-2H-pyran-4-yl)amine, to afford the title compound (80 mg, 46%).

$^1$H NMR (400 MHz, CDCl$_3$) 8.50 (s, 1H), 7.88 (s, 1H), 7.79 (d, J=2.0 Hz, 1H), 7.73 (s, 2H), 5.71 (d, J=8.0 Hz, 1H), 4.74 (d, J=16.0 Hz, 1H), 4.32 (d, J=16.0 Hz, 1H), 4.13 (m, 2H), 3.90 (m, 1H), 3.47 (m, 1H), 3.17 (m, 2H), 2.71 (m, 2H), 1.76 (m, 4H), 1.43 (s, 9H), 0.93 (t, 3H), 0.63 (d, 3H).

Example 28

(4S,5R)-5-[3,5-bis(trifluoromethyl)phenyl]-3-({[2-(ethyl)(piperidin-4-yl)amino]-5-(trifluoromethyl)pyridin-3-yl}methyl)-4-methyloxazolidin-2-one

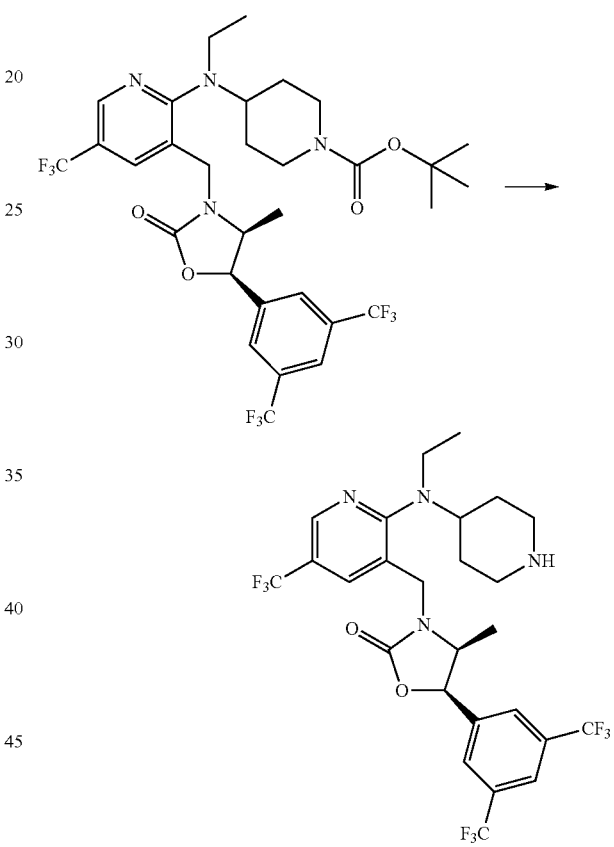

To a solution of t-butyl 4-{[3-({(4S,5R)-5-[3,5-bis(trifluoromethyl)phenyl]-4-methyl-2-oxo-oxazolidin-3-yl}methyl)-5-(trifluoromethyl)pyridin-2-yl](ethyl)amino}piperidine-1-carboxylate of Example 27 in dichloromethane (0.75 ml) was dropwise added TFA (trifluoroacetic acid) (0.25 ml, 0.36 mmol). The reaction mixture was stirred at room temperature for 2 hrs, diluted with dichloromethane, and added with water to terminate the reaction. An organic layer obtained by extraction was dried over anhydrous magnesium sulfate, filtered, and concentrated at a reduced pressure to afford the title compound (48 mg, 82%).

$^1$H NMR (400 MHz, CDCl$_3$) 8.49 (s, 1H), 7.88 (s, 1H), 7.78 (s, 1H), 7.73 (s, 2H), 5.71 (d, J=8.0 Hz, 1H), 4.74 (d, J=16.0 Hz, 1H), 4.32 (d, J=16.0 Hz, 1H), 3.87 (m, 1H), 3.54 (m, 1H), 3.20 (m, 4H), 2.62 (m, 2H), 1.78 (m, 4H), 0.94 (t, 3H), 0.62 (d, 3H).

Example 29

(4S,5R)-5-[3,5-bis(trifluoromethyl)phenyl]-4-methyl-3-({[2-(ethyl)(1-methylpiperidin-4-yl)amino]-5-(trifluoromethyl)pyridin-3-yl}methyl)-oxazolidin-2-one

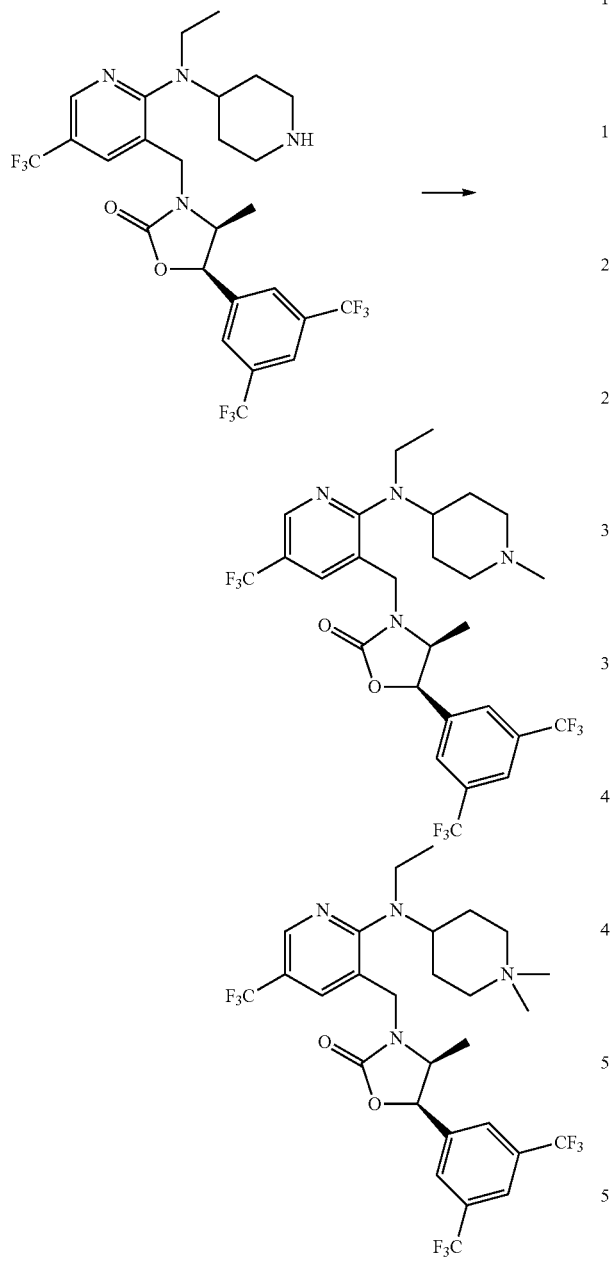

To a solution of (4S,5R)-5-[3,5-bis(trifluoromethyl)phenyl]-3-({[2-(ethyl)(piperidin-4-yl)amino]-5-(trifluoromethyl)pyridin-3-yl}methyl)-4-methyloxazolidin-2-one (35 mg, 0.058 mmol) of Example 28 in THF (0.5 ml) were added TEA (8.8 mg, 0.09 mmol) and methyl iodide (12.4 mg, 0.09 mmol). The reaction mixture was stirred at room temperature for 2 hrs and extracted with ethyl acetate and water. The organic layer was dried over anhydrous magnesium sulfate, filtered, and concentrated at a reduced pressure, followed by chromatographic purification to afford the title compound (7 mg, 2%).

$^1$H NMR (400 MHz, CDCl$_3$) 8.50 (s, 1H), 7.87 (s, 1H), 7.79 (s, 1H), 7.74 (s, 2H), 5.73 (d, J=8.4 Hz, 1H), 4.72 (d, J=15.6 Hz, 1H), 4.32 (d, J=15.6 Hz, 1H), 3.91 (m, 1H), 3.47 (m, 1H), 3.47 (m, 1H), 3.21-3.00 (m, 4H), 2.34 (bs, 3H), 2.02-1.65 (m, 6H), 0.92 (t, 3H), 0.63 (d, 3H).

Example 30

(4S,5R)-5-[3,5-bis(trifluoromethyl)phenyl]-4-methyl-3-({[2-(ethyl)(1,1-dimethylpiperidin-4-yl)amino]-5-(trifluoromethyl)pyridin-3-yl}methyl)-oxazolidin-2-one

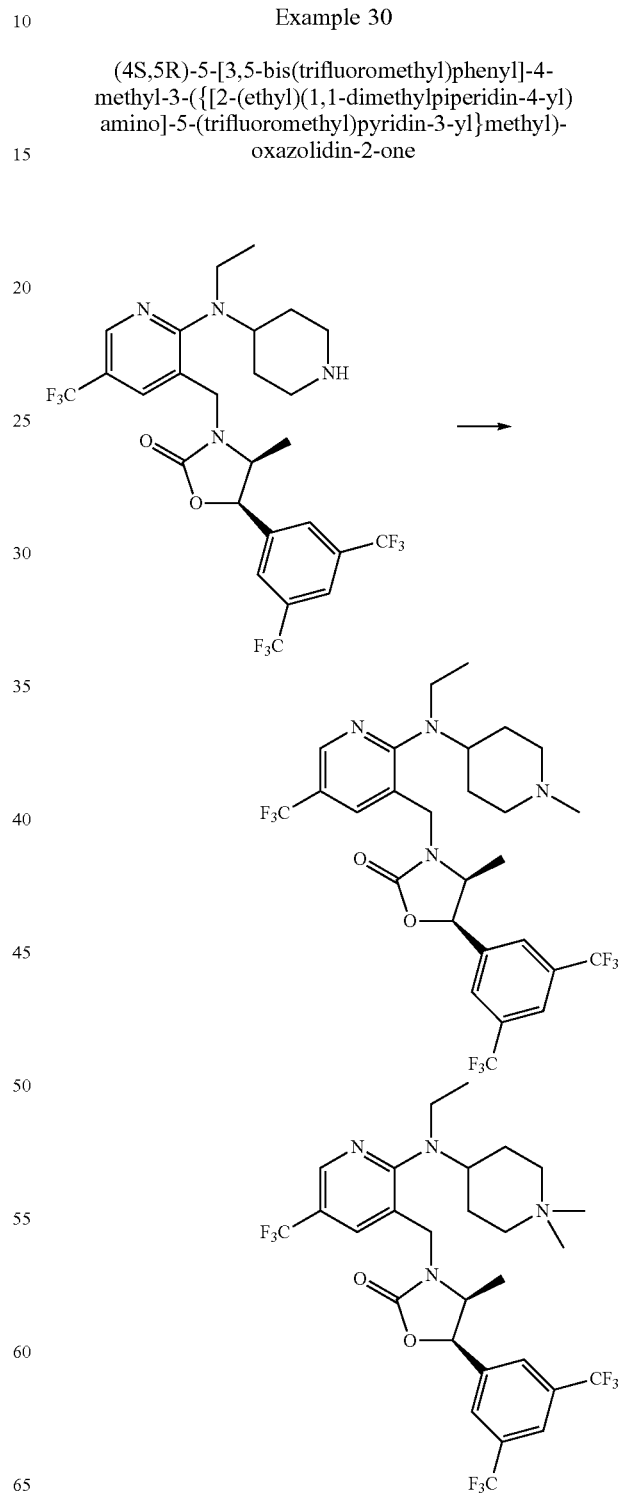

The title compound was prepared in the same manner as in Example 29 and purified by chromatography (20 mg, 57%).

¹H NMR (400 MHz, CDCl₃) 8.49 (s, 1H), 7.87 (s, 1H), 7.79 (s, 2H), 7.77 (s, 2H), 5.90 (d, J=8.0 Hz, 1H), 4.81 (d, J=16.4 Hz, 1H), 4.44 (d, J=16.4 Hz, 1H), 4.28 (m, 1H), 4.02-3.71 (m, 5H), 3.46 (s, 3H), 3.37 (s, 3H), 3.26 (m, 2H), 2.44 (m, 2H), 2.17 (m, 2H), 1.03 (t, 3H), 0.53 (d, 3H).

Example 31

((4S,5R)-5-[3,5-bis(trifluoromethyl)phenyl]-4-methyl-3-({[2-(ethyl)(1-propylpiperidin-4-yl)amino]-5-trifluoromethylpyridin-3-yl}methyl)-oxazolidin-2-one

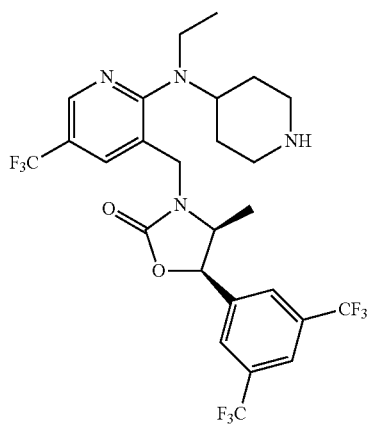

To a solution of (4S,5R)-5-[3,5-bis(trifluoromethyl)phenyl]-3-({[2-(ethyl)(piperidin-4-yl)amino]-5-(trifluoromethyl)pyridin-3-yl}methyl)-4-methyloxazolidin-2-one (70 mg, 0.12 mol) of Example 28 in dichloromethane (2 ml) were added propionaldehyde (14 mg, 0.234 mmol) and NaBH(OAc)₃ (50 mg, 0.234 mmol). Stirring at room temperature for 4 hrs was followed by adding water to terminate the reaction. Then, extraction was performed with dichloromethane. The organic layer thus formed was dried, and concentrated in a vacuum. The residue was purified by chromatography to afford the title compound (22 mg, 29%).

¹H NMR (400 MHz, CDCl₃) 8.49 (s, 1H), 7.87 (s, 1H), 7.77 (s, 1H), 7.74 (s, 2H), 5.71 (d, 1H), 4.70 (d, 1H), 4.29 (d, 1H), 4.15-4.12 (m, 1H), 3.90-3.84 (m, 1H), 3.52-3.44 (m, 1H), 3.22-3.14 (m, 1H), 3.04-2.86 (m, 4H), 2.32-2.22 (m, 2H), 1.78-1.47 (m, 5H), 0.97-0.79 (m, 6H), 0.68 (d, 3H).

Example 32

(4S,5R)-5-[3,5-bis(trifluoromethyl)phenyl]-4-methyl-3-({[2-(ethyl)(1-methanesulfonylpiperidin-4-yl)amino]-5-trifluoromethylpyridin-3-yl}methyl)-oxazolidin-2-one

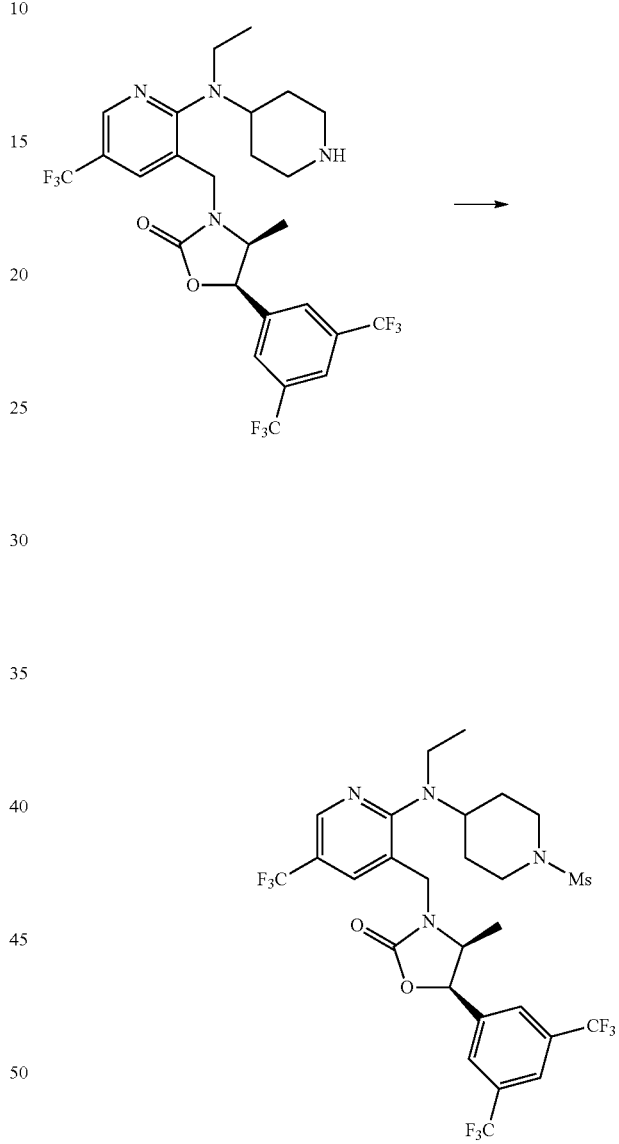

(4S,5R)-5-[3,5-bis(trifluoromethyl)phenyl]-3-({[2-(ethyl)(piperidin-4-yl)amino]-5-(trifluoromethyl)pyridin-3-yl}methyl)-4-methyloxazolidin-2-one of Example 28, and MsCl were used in the same manner as in step 2 of Example 18 to afford the title compound (20 mg, 35%).

¹H NMR (400 MHz, CDCl3) 8.53 (s, 1H), 7.91 (s, 1H), 7.80 (s, 1H), 7.76 (s, 2H), 5.74 (d, 1H, J=8.0 Hz), 4.73 (d, 1H, J=16.0 Hz), 4.31 (d, 1H, J=16.0 Hz), 3.95-3.83 (m, 3H), 3.49-3.44 (m, 1H), 3.21-3.16 (m, 2H), 2.79 (s, 3H), 2.76-2.60 (m, 2H), 1.95-1.78 (m, 4H), 0.94 (t, 3H, J=6.8 Hz), 0.64 (d, 3H, J=6.8 Hz).

Example 33

(4S,5R)-5-[3,5-bis(trifluoromethyl)phenyl]-4-methyl-3-({[2-(ethyl)(1-acetylpiperidin-4-yl)amino]-5-(trifluoromethyl)pyridin-3-yl}methyl)-oxazolidin-2-one

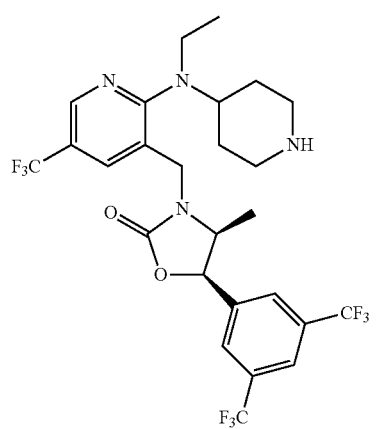

→

A solution of (4S,5R)-5-[3,5-bis(trifluoromethyl)phenyl]-3-({[2-(ethyl)(piperidin-4-yl)amino]-5-(trifluoromethyl)pyridin-3-yl}methyl)-4-methyloxazolidin-2-one (50 mg, 0.084 mmol) of Example 28 in dichloromethane (0.5 ml) was added with TEA (13 mg, 0.126 mmol) and then with drops of acetyl chloride (7.9 mg, 0.10 mmol). The reaction mixture was stirred at room temperature for 30 min, and quenched with water, followed by extraction with dichloromethane. The organic layer thus formed was washed with a saturated aqueous sodium carbonate solution, dried over anhydrous sodium sulfate, and filtered. The filtrate was concentrated in a vacuum to afford the title compound (46 mg, 86%).

$^1$H NMR (400 MHz, CDCl$_3$) 8.51 (s, 1H), 7.88 (s, 1H), 7.78 (s, 1H), 7.73 (s, 2H), 5.72 (d, J=8.0 Hz, 1H), 4.86 (m, 2H), 4.34 (m, 1H), 3.91 (m, 3H), 3.45-2.97 (m, 4H), 2.53 (m, 2H), 2.07 (s, 3H), 1.85-1.60 (m, 2H), 0.91 (m, 3H), 0.60 (bs, 3H).

Example 34

(4S,5R)-5-[3,5-bis(trifluoromethyl)phenyl]-4-methyl-3-({[2-(ethyl)(1-propionylpiperidin-4-yl)amino]-5-(trifluoromethyl)pyridin-3-yl}methyl)-oxazolidin-2-one

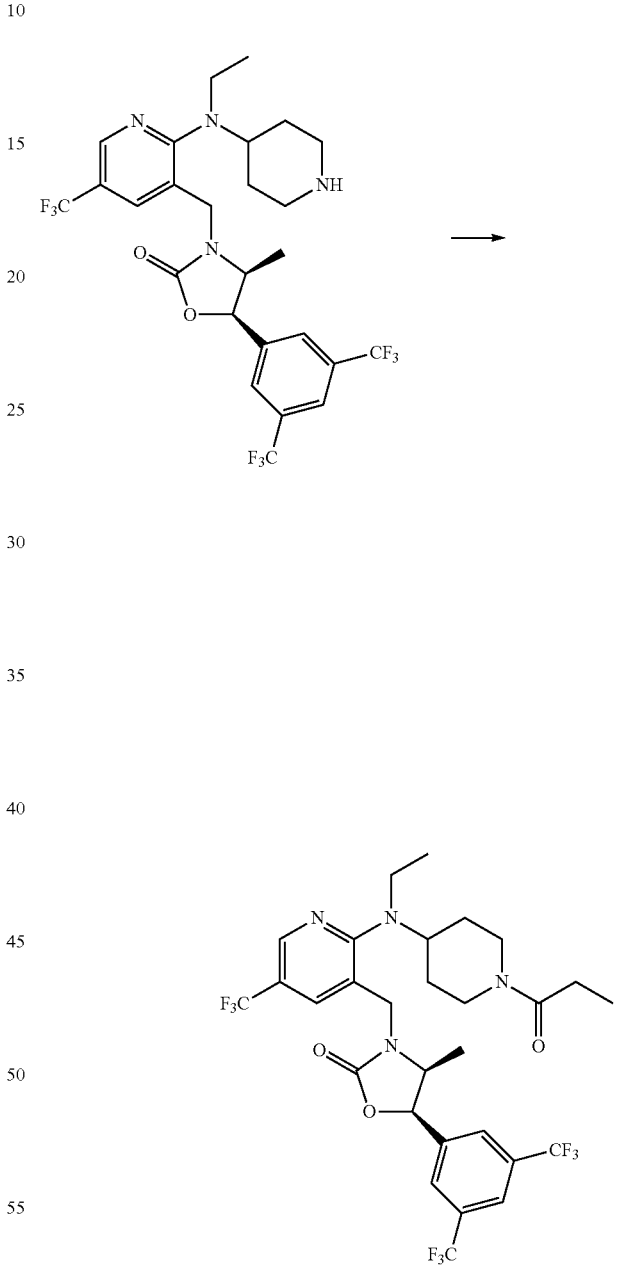

The same procedure as in Example 33 was repeated, with the exception that propionyl chloride was used instead of acetyl chloride to afford the title compound (48 mg, 90%).

$^1$H NMR (400 MHz, CDCl$_3$) 8.51 (s, 1H), 7.88 (s, 1H), 7.78 (s, 1H), 7.74 (s, 2H), 5.72 (d, J=8.0 Hz, 1H), 4.72 (m, 2H), 4.30 (m, 1H), 3.91 (m, 2H), 3.46-2.90 (m, 4H), 2.55 (m, 2H), 2.36 (m, 2H), 1.85 (m, 4H), 1.18 (m, 3H), 0.96 (m, 3H), 0.55 (m, 3H).

Example 35 methyl 4-{[3-({(4S,5R)-5-[3,5-bis(trifluoromethyl)phenyl]-4-methyl-2-oxo-oxazolidin-3-yl}methyl)-5-(trifluoromethyl)pyridin-2-yl](ethyl)amino}piperidine-1-carboxylate

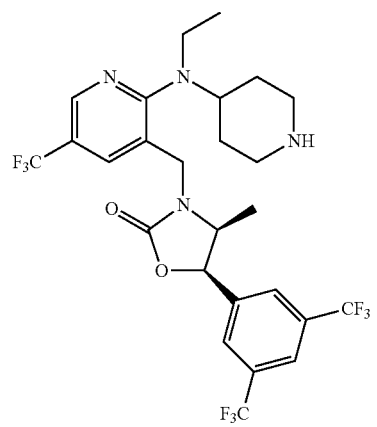

→

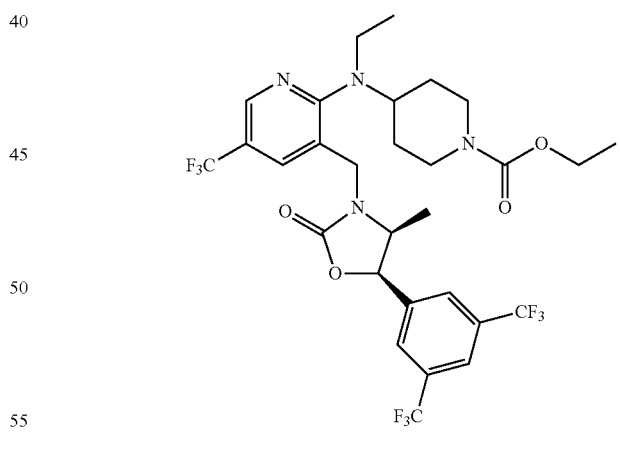

The same procedure as in Example 33, with the exception that methyl chloroformate was used instead of acetyl chloride, to afford the title compound (480 mg, 65%).

$^1$H NMR (400 MHz, CDCl$_3$) 8.52 (s, 1H), 7.90 (s, 1H), 7.81 (d, J=2.0 Hz, 1H), 7.53 (s, 2H), 5.74 (d, J=16.0 Hz, 1H), 4.34 (d, J=16.0 Hz, 1H), 3.92 (m, 1H), 3.69 (s, 3H), 3.4 (m, 1H), 3.19 (m, 2H), 2.79 (m, 2H), 1.80 (m, 4H), 0.94 (t, 3H), 0.64 (d, 3H).

Example 36 ethyl 4-{[3-({(4S,5R)-5-[3,5-bis(trifluoromethyl)phenyl]-4-methyl-2-oxo-oxazolidin-3-yl}methyl)-5-(trifluoromethyl)pyridin-2-yl](ethyl)amino}piperidine-1-carboxylate

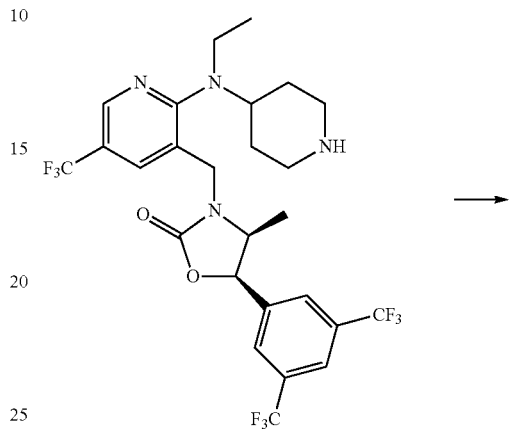

→

The same procedure as in Example 33 was repeated, with the exception that ethyl chloroformate was used instead of acetyl chloride, to afford the title compound (20 mg, 36%).

$^1$H NMR (400 MHz, CDCl$_3$) 8.50 (s, 1H), 7.88 (s, 1H), 7.78 (s, 1H), 7.73 (s, 2H), 5.70 (d, 1H, J=8.0 Hz), 4.71 (d, 1H, J=16.0 Hz), 4.29 (d, 1H, J=16.0 Hz), 4.18-4.08 (m, 4H), 3.90-3.86 (m, 1H), 3.48-3.39 (m, 1H), 3.16-3.11 (m, 2H), 2.80-2.60 (m, 2H), 1.84-1.68 (m, 2H), 1.68-1.56 (m, 2H), 1.25-1.22 (m, 3H), 0.90 (t, 3H, J=10.8 Hz), 0.61 (d, 3H, J=6.4 Hz).

Example 37 methyl 4-{[3-({(4S,5R)-5-[3,5-bis(trifluoromethyl)phenyl]-4-methyl-2-oxo-oxazolidin-3-yl}methyl)-5-(trifluoromethyl)pyridin-2-yl](ethyl)amino}-N,N-dimethylpiperidine-1-carboxamide

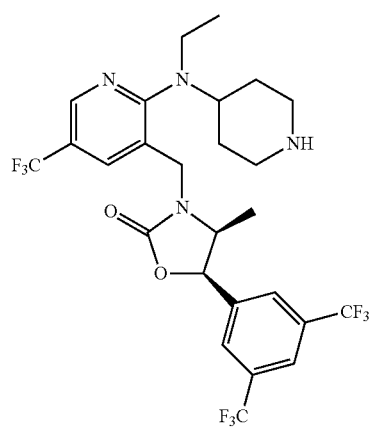

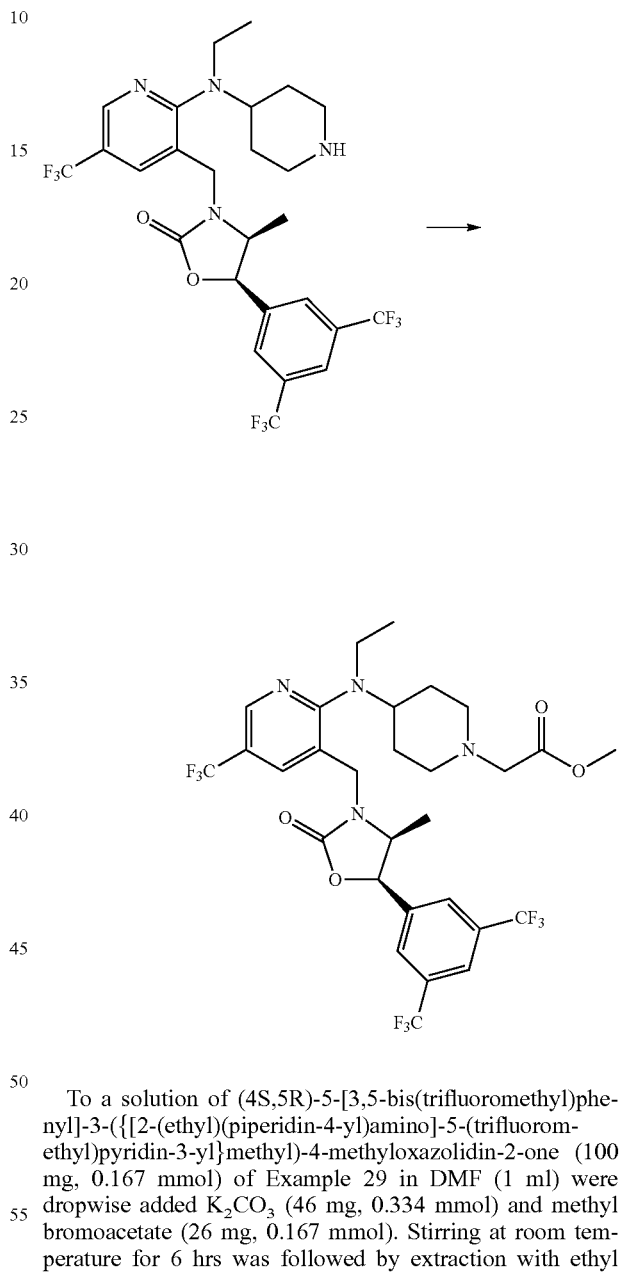

The same procedure as in Example 33, with the exception that dimethylcarbamic chloride was used instead of acetyl chloride, to afford the title compound (40 mg, 71%).

$^1$H NMR (400 MHz, CDCl$_3$) 8.52 (s, 1H), 7.90 (s, 1H), 7.80 (s, 1H), 7.76 (s, 2H), 5.73 (d, 1H), 4.74 (d, 1H), 4.38 (d, 1H), 3.92-3.89 (m, 1H), 3.77-3.68 (m, 2H), 3.52-3.43 (m, 1H), 3.20-3.15 (m, 2H), 2.78-2.66 (m, 4H), 2.81 (s, 6H), 1.81-1.66 (m, 4H), 0.94-0.91 (m, 3H), 0.64 (d, 3H).

Example 38 methyl 2-(4-{[3-({(4S,5R)-5-[3,5-bis(trifluoromethyl)phenyl]-4-methyl-2-oxo-oxazolidin-3-yl}methyl)-5-(trifluoromethyl)pyridin-2-yl](ethyl)amino}piperidin-1-yl)acetate To a solution of (4S,5R)-5-[3,5-bis(trifluoromethyl)phenyl]-3-({[2-(ethyl)(piperidin-4-yl)amino]-5-(trifluoromethyl)pyridin-3-yl}methyl)-4-methyloxazolidin-2-one (100 mg, 0.167 mmol) of Example 29 in DMF (1 ml) were dropwise added K$_2$CO$_3$ (46 mg, 0.334 mmol) and methyl bromoacetate (26 mg, 0.167 mmol). Stirring at room temperature for 6 hrs was followed by extraction with ethyl acetate and water. The organic layer was dried over anhydrous sodium sulfate, filtered, and concentrated at a reduced pressure. The residue was purified by chromatography to afford the title compound (53 mg, 47%).

$^1$H NMR (400 MHz, CDCl$_3$) 8.51 (s, 1H), 7.89 (s, 1H), 7.79 (s, 1H), 7.75 (s, 2H), 5.72 (d, 1H, J=8.0 Hz), 4.72 (d, 1H, J=15.6 Hz), 4.31 (d, 1H, J=15.6 Hz), 4.13-4.11 (m, 1H), 3.91-3.87 (m, 1H), 3.72 (s, 2H), 3.53-3.47 (m, 1H), 3.22-3.17 (m, 2H), 3.02-2.94 (m, 4H), 2.24-1.78 (m, 5H), 0.92 (t, 3H, J=7.2 Hz), 0.62 (d, 3H, J=6.8 Hz).

Example 39

2-(4-{[3-({(4S,5R)-5-[3,5-bis(trifluoromethyl)phenyl]-4-methyl-2-oxo-oxazolidin-3-yl}methyl)-5-(trifluoromethyl)pyridin-2-yl](ethyl)amino}piperidin-1-yl)acetic acid

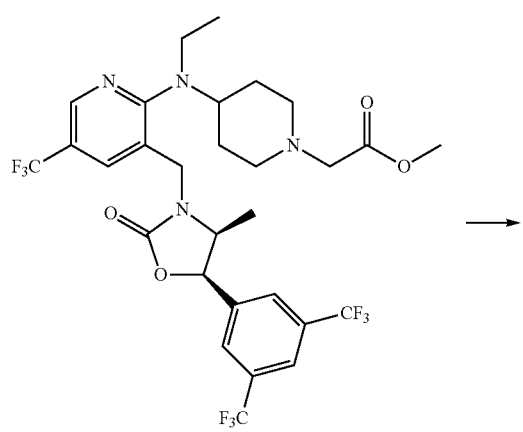

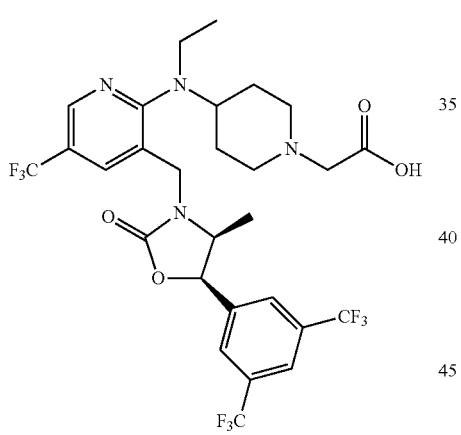

To a solution of methyl 2-(4-{[3-({(4S,5R)-5-[3,5-bis(trifluoromethyl)phenyl]-4-methyl-2-oxo-oxazolidin-3-yl}methyl)-5-(trifluoromethyl)pyridin-2-yl](ethyl)amino}piperidin-1-yl)acetate (25 mg, 0.037 mmol) of Example 38 in THF/H$_2$O (2/1, 0.75 ml) was added LiOH (1.79 mg, 0.07 mmol). The reaction mixture was stirred at room temperature for 6 hrs, and neutralized with 2 N HCl, followed by extraction with ethyl acetate. The organic layer was dried, and concentrated in a vacuum. The residue was purified by chromatography to afford the title compound (10 mg, 40%).

$^1$H NMR (400 MHz, CDCl$_3$) 8.51 (s, 1H), 7.89 (s, 1H), 7.79 (s, 1H), 7.75 (s, 2H), 5.72 (d, 1H, J=8.0 Hz), 4.72 (d, 1H, J=15.6 Hz), 4.31 (d, 1H, J=15.6 Hz), 4.13-4.11 (m, 1H), 3.91-3.87 (m, 1H), 3.72 (s, 2H), 3.53-3.47 (m, 1H), 3.22-3.17 (m, 2H), 3.02-2.94 (m, 4H), 2.24-1.78 (m, 5H), 0.92 (t, 3H, J=7.2 Hz), 0.62 (d, 3H, J=6.8 Hz).

Example 40

(4S,5R)-5-[3,5-bis(trifluoromethyl)phenyl]-4-methyl-3-({[2-(ethyl)(tetrahydro-2H-pyran-4-yl)amino]-5-bromopyridin-3-yl}methyl)-oxazolidin-2-one

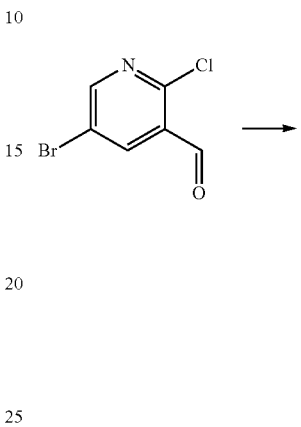

The same procedure as in method 2 of Example 7 was repeated, with the exception that 2-chloro-5-bromo-pyridine carbaldehyde, instead of 2-chloro-5-(trifluoromethyl)pyridine 3-carbaldehyde, was reacted with N-ethyl-N-(tetrahydro-2H-pyran-4-yl)-amine, to afford the title compound (3.5 g, 68%).

$^1$H NMR (400 MHz, CDCl$_3$) 8.53 (s, 1H), 7.90 (s, 1H), 7.81-7.77 (m, 3H), 5.74 (d, 1H), 4.71 (d, 1H), 4.35 (d, 1H), 4.14-4.09 (m, 1H), 4.02-3.94 (m, 3H), 3.41-3.28 (m, 3H), 3.12-3.06 (m, 2H), 1.81-1.62 (m, 3H), 0.90-0.87 (m, 3H), 0.68 (d, 3H).

Example 41

(4S,5R)-5-[3,5-bis(trifluoromethyl)phenyl]-4-methyl-3-({[2-(ethyl)(tetrahydro-2H-pyran-4-yl)amino]-5-(pyrrolidin-1-yl)pyridin-3-yl}methyl)-oxazolidin-2-one

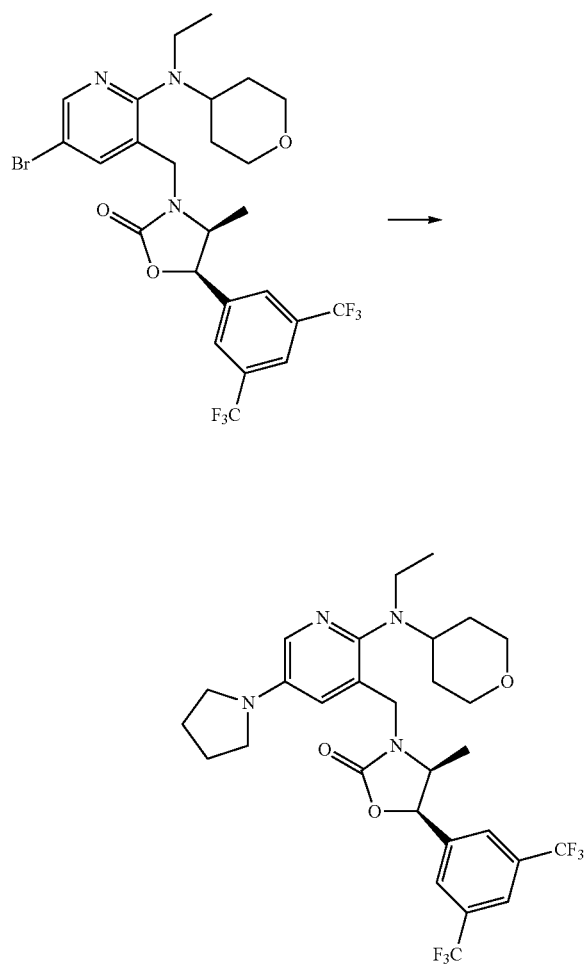

To a solution of (4S,5R)-5-[3,5-bis(trifluoromethyl)phenyl]-4-methyl-3-({[2-(ethyl)(tetrahydro-2H-pyran-4-yl)amino]-5-bromopyridin-3-yl}methyl)-oxazolidin-2-one (100 mg, 0.16 mmol) of Example 40 in toluene (4 ml) were added pyrrolidine (60 ul, 0.64 mmol), BINAP (20 mg, 0.032 mmol), NatOBu (22 mg, 0.22 mmol), and Pd$_2$(dba)$_3$ (219.8, 0.24 mmol). The reaction mixture was purged with nitrogen, stirred at 100° C. for 3 hrs and cooled to room temperature. Filtration through a Celite-pad filter was followed by extraction with dichloromethane. The organic layer thus formed was dried over anhydrous magnesium sulfate, filtered, and concentrated at a reduced pressure. The residue was purified by chromatography to afford the title compound (60 mg, 60%).

$^1$H NMR (400 MHz, CDCl$_3$) 7.89 (s, 1H), 7.79-7.77 (m, 3H), 6.82 (d, 1H), 5.68 (d, 1H), 4.52 (d, 1H), 4.01-3.91 (m, 3H), 3.35-3.18 (m, 6H), 3.05-3.02 (m, 2H), 2.04-2.02 (m, 3H), 1.69-1.50 (m, 6H), 0.87-0.80 (m, 3H), 0.73 (d, 3H).

Example 42 methyl 2-(4-{5-({(4S,5R)-5-[3,5-bis(trifluoromethyl)phenyl]-4-methyl-2-oxo-oxazolidin-3-yl}methyl)-6-[ethyl(tetrahydro-2H-pyran-4-yl)amino]pyridin-3-yl}piperazin-1-yl)acetate

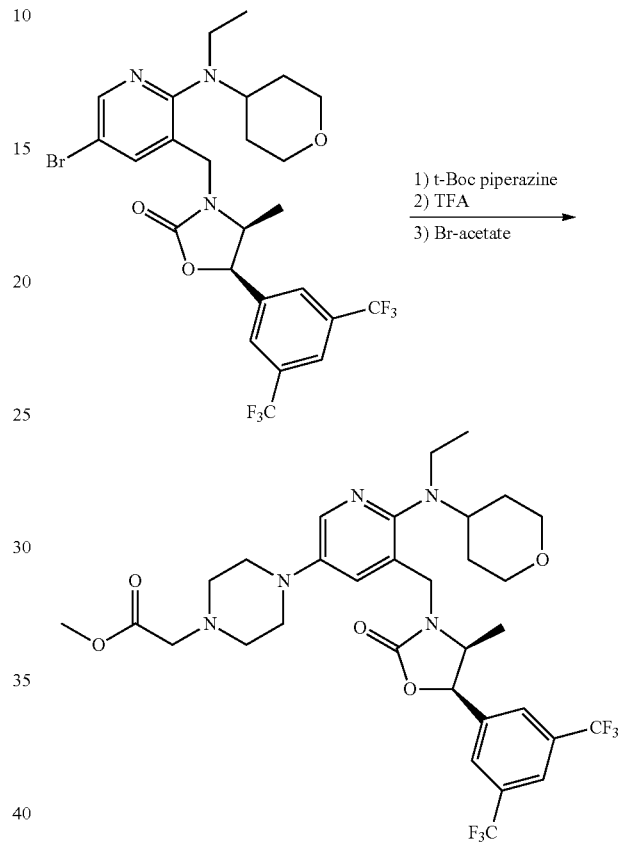

1) t-Boc piperazine
2) TFA
3) Br-acetate

[Step 1] Preparation of t-butyl 4-[5-({(4S,5R)-5-[3,5-bis(trifluoromethyl)phenyl]-4-methyl-2-oxooxazolidin-3-yl}methyl)-6-[ethyl(tetrahydro-2H-pyran-4-yl)amino]pyridin-3-yl]piperazine-1-carboxylate

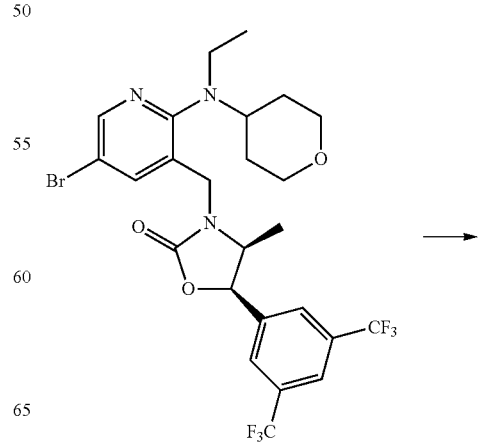

-continued

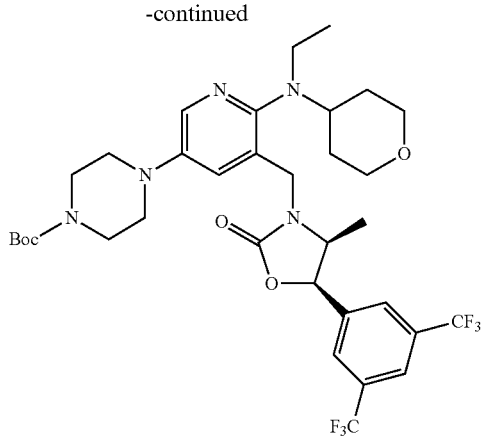

The same procedure as in Example 41 was repeated, with the exception that 1-t-Boc-piperazine was used instead of pyrrolidine, to afford the title compound (60 mg, 54%).

$^1$H NMR (400 MHz, CDCl$_3$) 8.04 (s, 1H), 7.89 (s, 1H), 7.76 (s, 3H), 5.70 (d, 1H), 4.67 (d, 1H), 4.47 (d, 1H), 4.00-3.95 (m, 2H), 3.65-3.58 (m, 4H), 3.37-3.29 (m, 4H), 3.18-3.12 (m, 6H), 1.75-1.37 (m, 12H), 1.49 (s, 9H), 0.89 (m, 3H), 0.72 (d, 3H).

[Step 2] (4S,5R)-5-[3,5-bis(trifluoromethyl)phenyl]-4-methyl-3-({2-[ethyl(tetrahydro-2H-pyran-4-yl)amino]-5-(piperazin-1-yl)pyridin-3-yl}methyl)oxazolidin-2-one

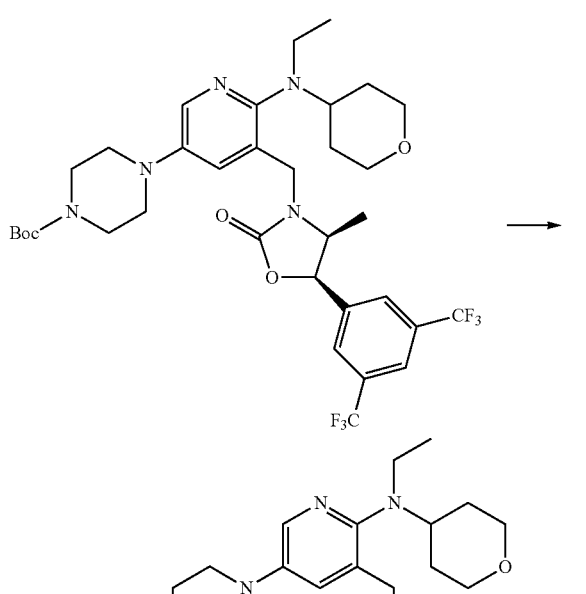

A solution of t-butyl 4-[5-({(4S,5R)-5-[3,5-bis(trifluoromethyl)phenyl]-4-methyl-2-oxooxazolidin-3-yl}methyl)-6-[ethyl(tetrahydro-2H-pyran-4-yl)amino]pyridin-3-yl]piperazine-1-carboxylate (60 mg, 0.08 mmol) of step 1 in dichloromethane was used in the same manner as in Example 33 to afford the title compound (52 mg, 100%).

$^1$H NMR (400 MHz, CDCl3) 8.48 (s, 1H), 7.87 (s, 1H), 7.77 (s, 1H), 7.73 (s, 2H), 4.69 (d, 1H), 4.24 (d, 1H), 3.88-3.48 (m, 1H), 3.57-3.52 (m, 1H), 3.20-3.15 (m, 1H), 2.86-2.83 (m, 1H), 2.73-2.59 (m, 4H), 2.05-1.89 (m, 4H), 0.92-0.86 (m, 3H), 0.60 (d, 3H).

[Step 3] Preparation of methyl 2-(4-{5-({(4S,5R)-5-[3,5-bis(trifluoromethyl)phenyl]-4-methyl-2-oxo-oxazolidin-3-yl}methyl)-6-[ethyl(tetrahydro-2H-pyran-4-yl)amino]pyridin-3-yl}piperazin-1-yl)acetate

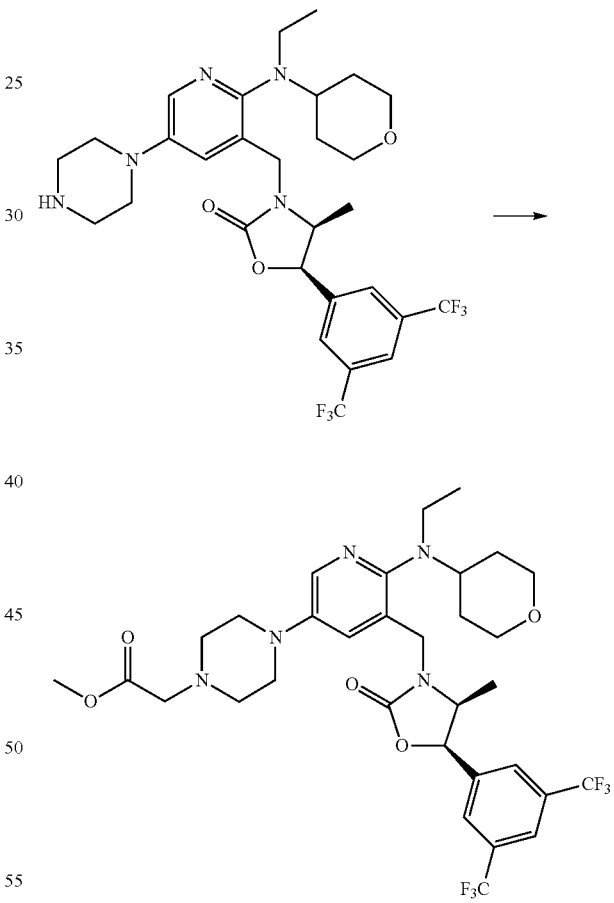

(4S,5R)-5-[3,5-bis(trifluoromethyl)phenyl]-4-methyl-3-({2-[ethyl(tetrahydro-2H-pyran-4-yl)amino]-5-(piperazin-1-yl)pyridin-3-yl}methyl)-oxazolidin-2-one of step 2 and methyl bromoacetate were used in the same manner as in Example 43 to afford the title compound (29 mg, 50%).

$^1$H NMR (400 MHz, CDCl3) 8.04 (s, 1H), 7.89 (s, 1H), 7.76 (s, 2H), 7.23 (s, 1H), 5.69 (d, 1H), 4.69 (d, 1H), 4.46 (d, 1H), 3.99-3.61 (m, 2H), 3.81 (s, 3H), 3.37-3.24 (m, 6H), 2.77 (m, 4H), 1.71-1.62 (m, 13H), 0.86 (s, 3H), 0.72 (d, 3H).

Example 43

(4S,5R)-5-[3,5-bis(trifluoromethyl)phenyl]-4-methyl-3-({[2-(ethyl)(tetrahydro-2H-pyran-4-yl)amino]-5-(azetidin-1-yl)pyridin-3-yl}methyl)-oxazolidin-2-one

Example 44

(4S,5R)-5-[3,5-bis(trifluoromethyl)phenyl]-4-methyl-3-({[2-(ethyl)(tetrahydro-2H-pyran-4-yl)amino]-5-(piperidin-1-yl)pyridin-3-yl}methyl)-oxazolidin-2-one

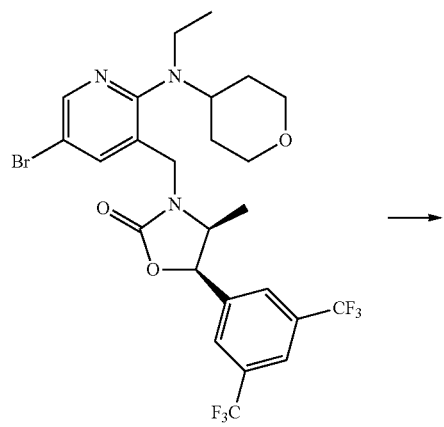 →

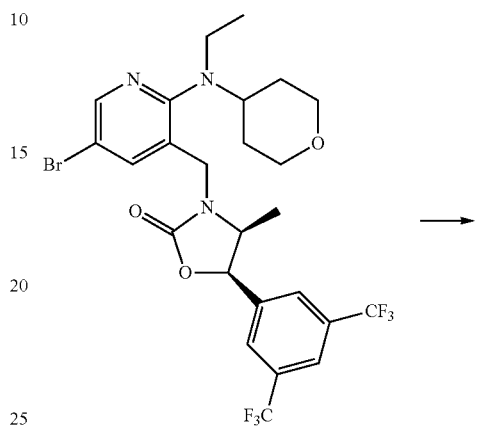 →

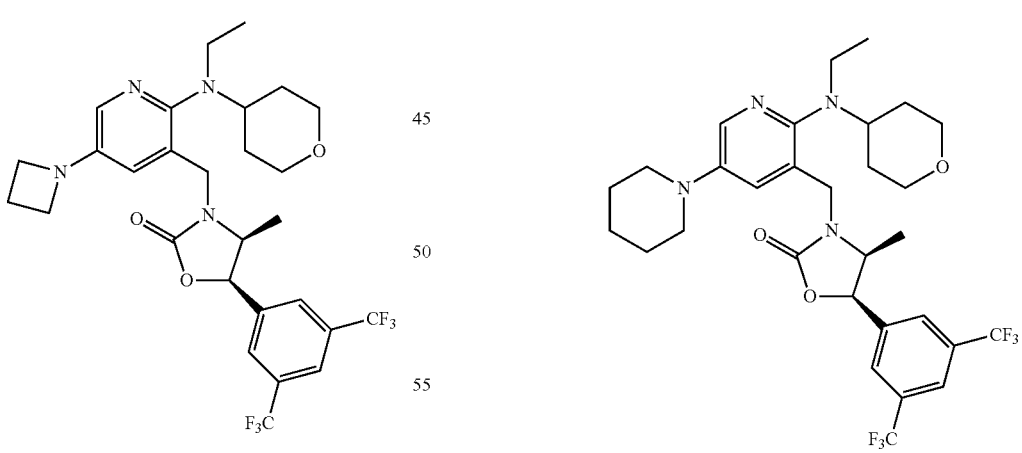

The same procedure as in Example 41 was repeated, with the exception that azetidine was used instead of pyrrolidine, to afford the title compound (18 mg, 8%).

$^{1}$H NMR (400 MHz, CDCl$_{3}$) 7.89 (s, 1H), 7.76 (s, 2H), 7.64 (s, 1H), 6.73 (s, 1H), 5.68 (d, 1H, J=8.0 Hz), 4.67 (d, 1H, J=16.0 Hz), 4.49 (d, 1H, J=16.0 Hz), 3.80~4.05 (m, 6H), 3.33 (m, 2H), 3.22 (m, 1H), 3.03 (m, 2H), 2.41 (m, 2H), 1.48~1.72 (m, 5H), 0.84 (m, 3H), 0.67 (m, 3H).

The same procedure as in Example 41 was repeated, with the exception that piperidine was used instead of pyrrolidine, to afford the title compound (19 mg, 13%).

$^{1}$H NMR (400 MHz, CDCl$_{3}$) 8.04 (s, 1H), 7.87 (s, 1H), 7.74 (s, 2H), 7.20 (s, 1H), 5.67 (d, 1H, J=8.0 Hz), 4.66 (d, 1H, J=15.2 Hz), 4.45 (d, 1H, J=15.6 Hz), 3.83~4.00 (m, 3H), 2.93~3.38 (m, 9H), 1.48~1.78 (m, 10H), 0.84 (t, 3H, J=6.8 Hz), 0.69 (d, 3H, J=6.4 Hz).

Example 45

(4S,5R)-5-[3,5-bis(trifluoromethyl)phenyl]-4-methyl-3-({[2-(ethyl)(tetrahydro-2H-pyran-4-yl)amino]-5-phenylpyridin-3-yl}methyl)-oxazolidin-2-one

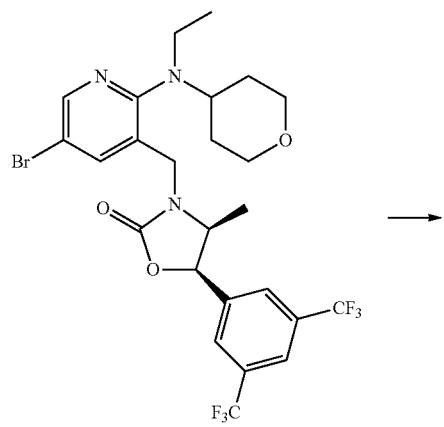

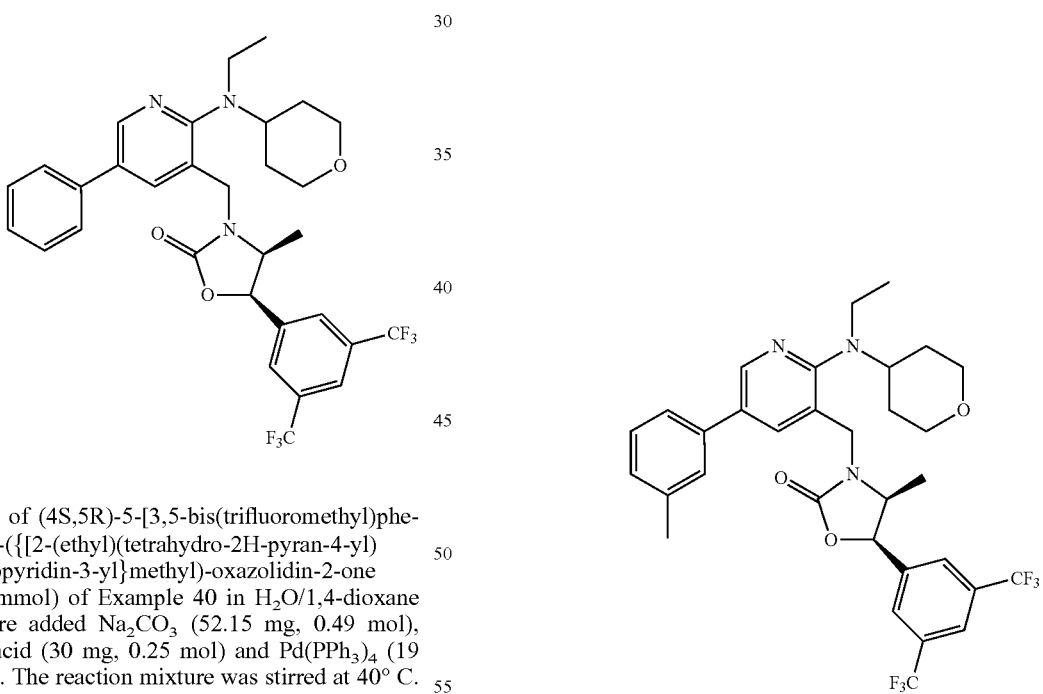

To a solution of (4S,5R)-5-[3,5-bis(trifluoromethyl)phenyl]-4-methyl-3-({[2-(ethyl)(tetrahydro-2H-pyran-4-yl)amino]-5-bromopyridin-3-yl}methyl)-oxazolidin-2-one (100 mg, 0.16 mmol) of Example 40 in $H_2O$/1,4-dioxane (1/2, 3 ml) were added $Na_2CO_3$ (52.15 mg, 0.49 mol), phenylboronic acid (30 mg, 0.25 mol) and $Pd(PPh_3)_4$ (19 mg, 0.02 mmol). The reaction mixture was stirred at 40° C. for 24 hrs and then cooled to room temperature, followed by extraction with ethyl acetate. The organic layer thus formed was dried over anhydrous magnesium sulfate, filtered, and concentrated at a reduced pressure. The residue was purified by chromatography to afford the title compound (70 mg, 70%).

$^1$H NMR (400 MHz, $CDCl_3$) 8.57 (s, 1H), 7.86 (d, 2H, J=11.6 Hz), 7.75 (s, 2H), 7.56-7.57 (m, 2H), 7.49 (t, 2H, J=7.6 Hz), 7.41 (s, 1H), 5.69 (d, 1H, J=8.0 Hz), 4.82 (d, 1H, J=15.6 Hz), 4.45 (d, 1H, J=15.6 Hz), 4.03 (m, 1H), 3.94 (m, 2H), 3.42 (m, 2H), 3.32 (m, 1H), 3.15 (m, 2H), 1.81 (m, 2H), 1.69 (m, 2H), 0.95 (m, 3H), 0.69 (m, 3H).

Example 46

(4S,5R)-5-[3,5-bis(trifluoromethyl)phenyl]-4-methyl-3-({[2-(ethyl)(tetrahydro-2H-pyran-4-yl)amino]-5-(3-methylphenyl)pyridin-3-yl}methyl)-oxazolidin-2-one

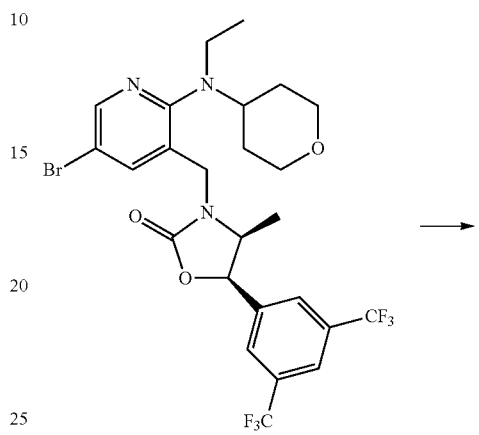

The same procedure as in Example 45 was repeated, with the exception that 2-methyltoluene boronic acid was used instead of phenyl boronic acid, to afford the title compound (80 mg, 51%).

$^1$H NMR (400 MHz, $CDCl_3$) 8.56 (s, 1H), 7.87 (s, 1H), 7.83 (s, 1H), 7.74 (s, 2H), 7.37 (s, 3H), 7.23 (s, 1H), 5.68 (d, 1H, J=7.6 Hz), 4.82 (d, 1H, J=15.6 Hz), 4.44 (d, 1H, J=15.6 Hz), 3.87~4.05 (m, 3H), 3.24-3.50 (m, 3H), 3.07~3.23 (m, 2H), 2.41 (s, 3H), 1.52~1.90 (m, 4H), 0.94 (m, 3H), 0.69 (m, 3H).

93
Example 47

(4S,5R)-5-[3,5-bis(trifluoromethyl)phenyl]-4-methyl-3-({[2-(ethyl)(tetrahydro-2H-pyran-4-yl)amino]-5-(3-fluorophenyl)pyridin-3-yl}methyl)-oxazolidin-2-one

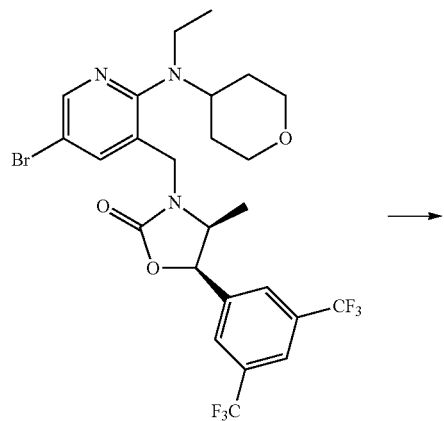

→

94
Example 48

(4S,5R)-5-[3,5-bis(trifluoromethyl)phenyl]-4-methyl-3-({[2-(ethyl)(tetrahydro-2H-pyran-4-yl)amino]-5-(3-ethoxyphenyl)pyridin-3-yl}methyl)-oxazolidin-2-one

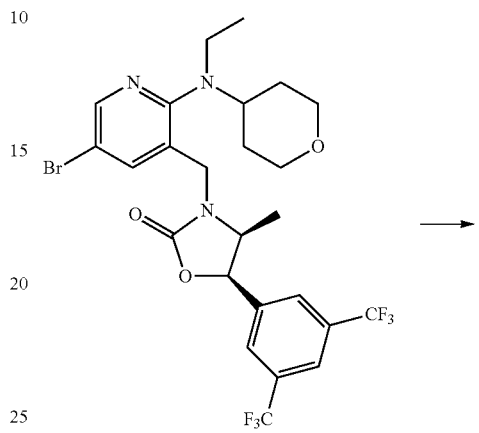

→

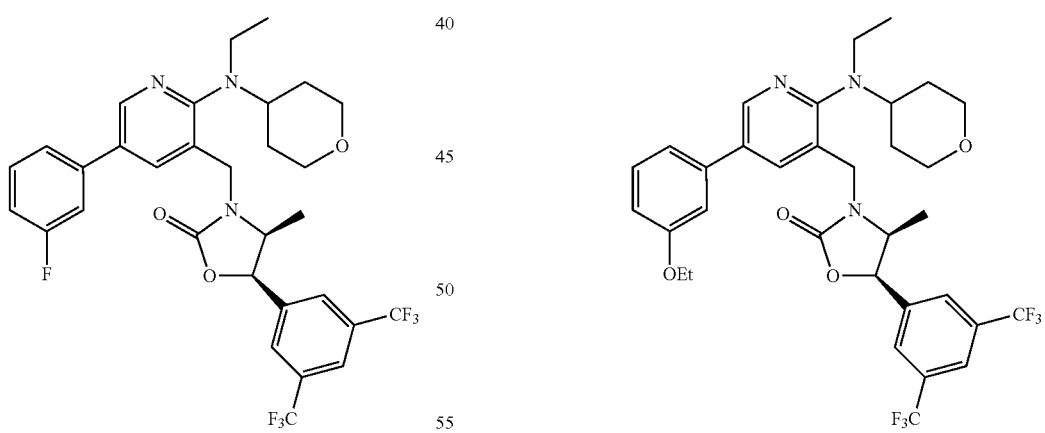

The same procedure as in Example 45 was repeated, with the exception that 3-fluorophenyl boronic acid was used instead of phenyl boronic acid, to afford the title compound (79 mg, 50%).

$^1$H NMR (400 MHz, CDCl$_3$) 8.52 (s, 1H), 7.86 (s, 1H), 7.80 (s, 1H), 7.73 (s, 3H), 7.44 (m, 1H), 7.31 (s, 1H), 7.08 (m, 1H), 5.68 (d, 1H, J=7.6 Hz), 4.79 (d, 1H, J=15.6 Hz), 4.41 (d, 1H, J=15.2 Hz), 3.83~4.02 (m, 3H), 3.22~3.50 (m, 3H), 3.16 (m, 2H), 1.60~1.89 (m, 4H), 0.93 (m, 3H), 0.68 (m, 3H).

The same procedure as in Example 45 was repeated, with the exception that 3-ethoxyphenylboronic acid was used instead of phenyl boronic acid, to afford the title compound (75.9 mg, 71%).

$^1$H NMR (400 MHz, CDCl$_3$) 8.56 (s, 1H), 7.88 (s, 1H), 7.83 (s, 1H), 7.75 (s, 2H), 7.49 (m, 1H), 7.03~7.16 (m, 2H), 6.93 (m, 1H), 5.69 (d, 1H, J=7.2 Hz), 4.82 (d, 1H, J=15.6 Hz), 4.43 (d, 1H, J=15.6 Hz), 3.86~4.16 (m, 5H), 3.26~3.50 (m, 3H), 3.08~3.26 (m, 2H), 1.40~1.90 (m, 4H), 1.25 (m, 3H), 0.91 (m, 3H), 0.68 (m, 3H)

Example 49

(4S,5R)-5-[3,5-bis(trifluoromethyl)phenyl]-4-methyl-3-({[2-(ethyl)(tetrahydro-2H-pyran-4-yl)amino]-5-(furan-2-yl)pyridin-3-yl}methyl)-oxazolidin-2-one

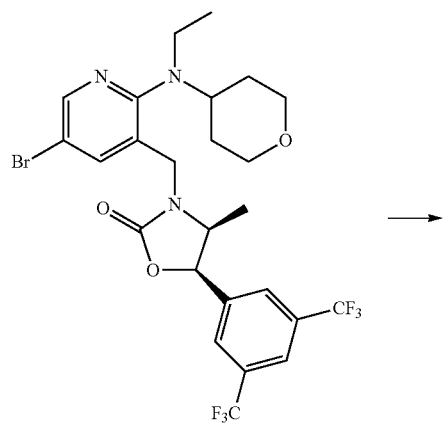

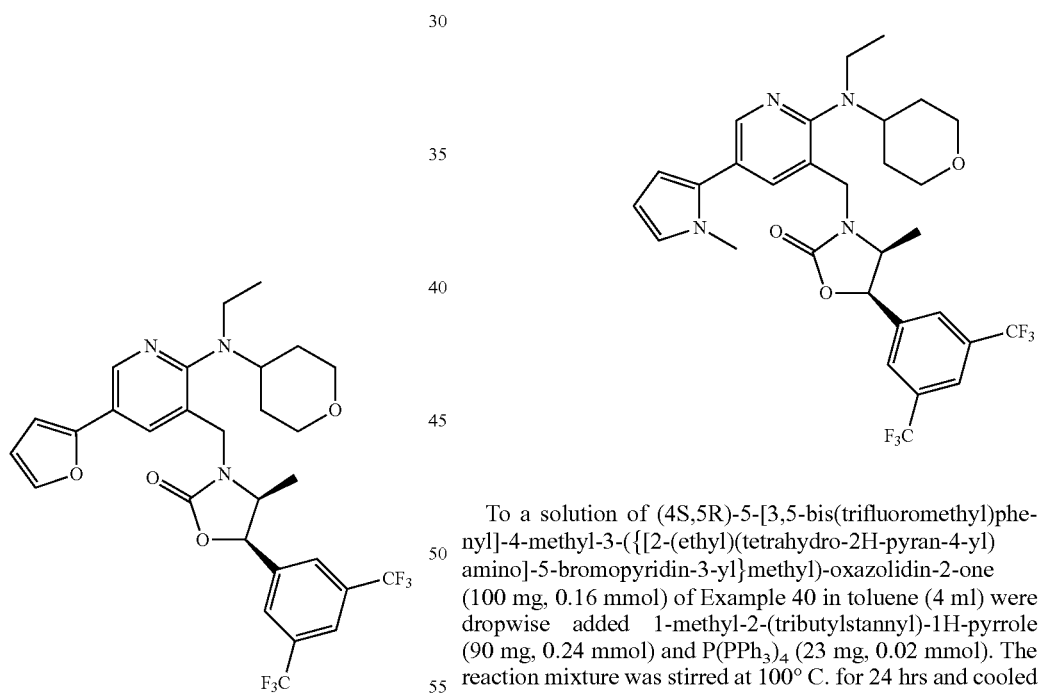

The same procedure as in Example 45 was repeated, with the exception that 1-furanyl boronic acid was used instead of phenyl boronic acid, to afford the title compound (33.8 mg, 34%).

$^1$H NMR (400 MHz, CDCl$_3$) 8.62 (s, 1H), 7.84~7.92 (m, 2H), 7.74 (s, 2H), 7.50 (s, 1H), 6.66 (d, 1H, J=2.8 Hz), 6.49 (s, 1H), 5.70 (d, 1H, J=8.4 Hz), 4.76 (d, 1H, J=16.4 Hz), 4.40 (d, 1H, J=15.6 Hz), 3.89~4.02 (m, 3H), 3.24~3.42 (m, 3H), 3.05~3.21 (m, 2H), 1.50~1.82 (m, 4H), 0.90 (m, 3H), 0.66 (m, 3H).

Example 50

(4S,5R)-5-[3,5-bis(trifluoromethyl)phenyl]-4-methyl-3-({[2-(ethyl)(tetrahydro-2H-pyran-4-yl)amino]-5-(1-methyl-1H-pyrrol-2-yl)pyridin-3-yl}methyl)-oxazolidin-2-one

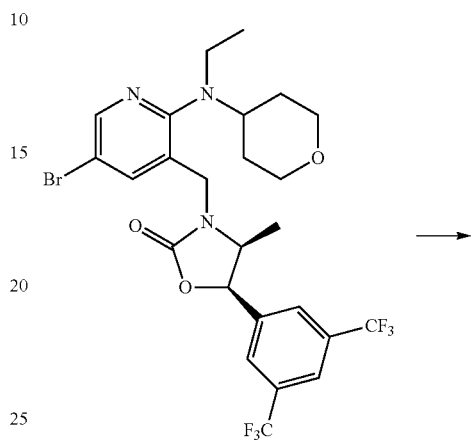

To a solution of (4S,5R)-5-[3,5-bis(trifluoromethyl)phenyl]-4-methyl-3-({[2-(ethyl)(tetrahydro-2H-pyran-4-yl)amino]-5-bromopyridin-3-yl}methyl)-oxazolidin-2-one (100 mg, 0.16 mmol) of Example 40 in toluene (4 ml) were dropwise added 1-methyl-2-(tributylstannyl)-1H-pyrrole (90 mg, 0.24 mmol) and P(PPh$_3$)$_4$ (23 mg, 0.02 mmol). The reaction mixture was stirred at 100° C. for 24 hrs and cooled to room temperature, followed by extraction with ethyl acetate and water. The organic layer thus formed was dried over anhydrous magnesium sulfate, filtered, and concentrated at a reduced pressure. The residue was purified by chromatography to afford the title compound (33.8 mg, 34%).

$^1$H NMR (400 MHz, CDCl$_3$) 8.41 (s, 1H), 7.89 (s, 1H), 7.75 (s, 2H), 7.68 (s, 1H), 6.78 (s, 1H), 6.21~6.29 (m, 2H), 5.70 (d, 1H, J=7.6 Hz), 4.79 (d, 1H, J=16.0 Hz), 4.41 (d, 1H, J=16.8 Hz), 3.89~4.03 (m, 3H), 3.70 (s, 3H), 3.26~3.43 (m, 3H), 3.07~3.23 (m, 2H), 1.62~1.86 (m, 4H), 0.95 (m, 3H), 0.68 (m, 3H).

Example 51

(4S,5R)-5-[3,5-bis(trifluoromethyl)phenyl]-4-methyl-3-({[2-(ethyl)(tetrahydro-2H-pyran-4-yl)amino]-5-(3,5-dimethyl-isoxazol-4-yl}methyl)-oxazolidin-2-one

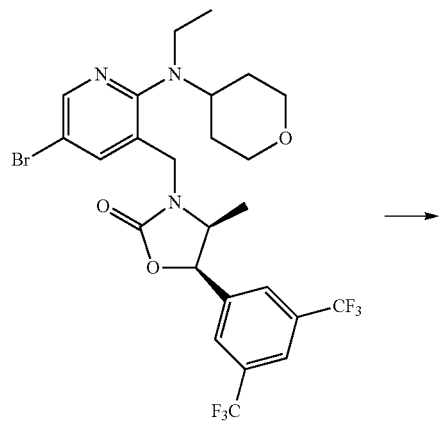

The same procedure as in Example 45 was repeated, with the exception that 3,5-dimethyl-4-(4,4,5,5-tetramethyl-1,3,2-dioxaborolan-2-yl)isoxazole was used instead of phenyl boronic acid, to afford the title compound (18 mg, 17%).

¹H NMR (400 MHz, CDCl₃) 8.24 (s, 1H), 7.87 (s, 1H), 7.67 (s, 2H), 7.58 (s, 1H), 5.68 (d, 1H, J=8.4 Hz), 4.74 (d, 1H, J=15.6 Hz), 4.40 (d, 1H, J=15.6 Hz), 3.84~4.03 (m, 3H), 3.24~3.42 (m, 4H), 3.14 (m, 1H), 2.44 (s, 3H), 2.29 (s, 3H), 1.49~2.88 (m, 4H), 0.92 (m, 3H), 0.67 (m, 3H).

Example 52

(4S,5R)-5-[3,5-bis(trifluoromethyl)phenyl]-4-methyl-3-({[2-(ethyl)(tetrahydro-2H-pyran-4-yl)amino]-pyridin-3-yl}methyl)-oxazolidin-2-one

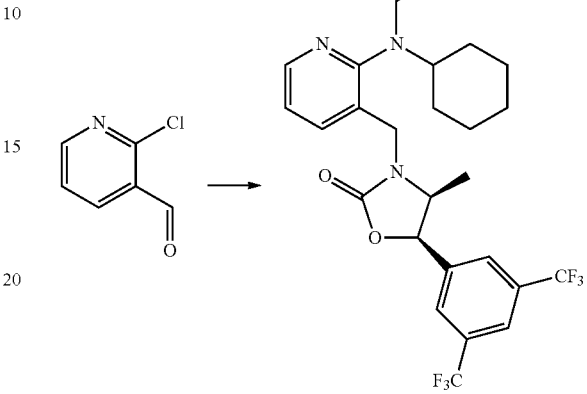

The same procedure as in method 2 of Example 7 was repeated, with the exception that 2-chloronicotine aldehyde was used instead of 2-chloro-5-(trifluoromethyl)pyridine carbaldehyde, to afford the title compound (15 mg, 9%).

¹H NMR (400 MHz, CDCl₃) 8.31 (dd, 1H), 7.88 (s, 1H), 7.75 (s, 2H), 7.66 (d, 1H), 7.00 (dd, 1H), 5.69 (d, 1H), 4.71 (d, 1H), 4.39 (d, 1H), 3.92 (m, 1H), 3.50 (m, 1H), 3.11 (m, 1H), 2.74 (m, 1H), 1.86~1.05 (m, 10H), 0.90 (t, 3H), 0.65 (d, 3H).

Example 53

(4S,5R)-5-[3,5-bis(trifluoromethyl)phenyl]-4-methyl-3-({[2-(ethyl)(cyclohexyl)amino]-5-(trifluoromethyl)pyridin-3-yl}methyl)-oxazolidin-2-one

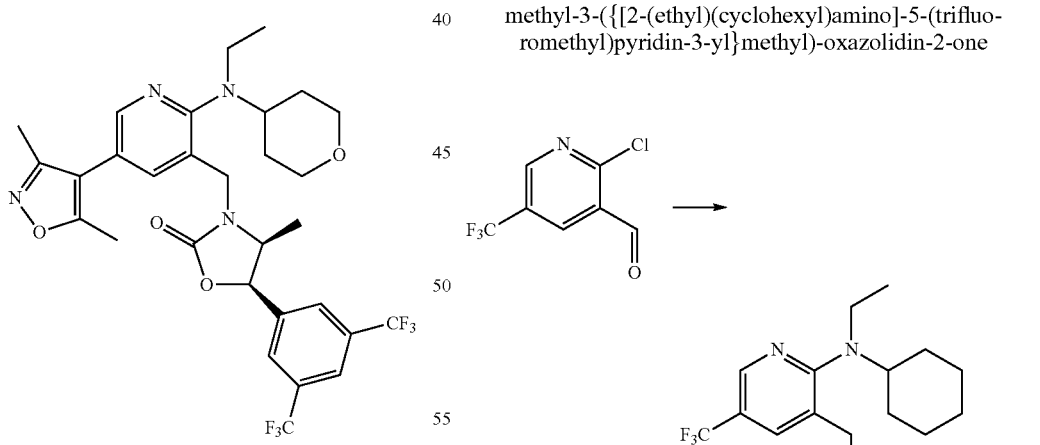

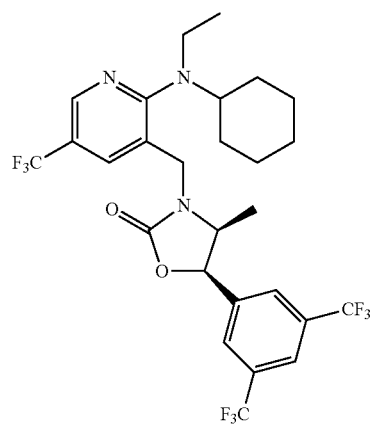

The same procedure as in method 2 of Example 7 was repeated, with the exception that N-ethyl-N-cyclohexylamine was used instead of N-ethyl-N-(tetrahydropyran-4-yl)amine, to afford the title compound (160 mg, 32%).

¹H NMR (400 MHz, CDCl₃) 8.47 (s, 1H), 7.87 (s, 1H), 7.76 (s, 2H), 7.24 (s, 1H), 5.69 (d, 1H, J=8.0 Hz), 4.70 (d, 1H, J=15.6 Hz), 4.27 (d, 1H, J=15.6 Hz), 3.84 (m, 1H), 3.55 (m, 1H), 3.15 (m, 1H), 2.82 (m, 1H), 1.38~1.81 (m, 6H), 1.00~1.36 (m, 4H), 0.92 (m, 3H), 0.80 (m, 3H)

Example 54

5-({4S,5R)-5-[3,5-bis(trifluoromethyl)phenyl]-4-methyl-2-oxo-1,3-oxazolidin-3-yl}methyl)-6-[(cyclohexyl)(ethyl)amino]nicotinonitrile

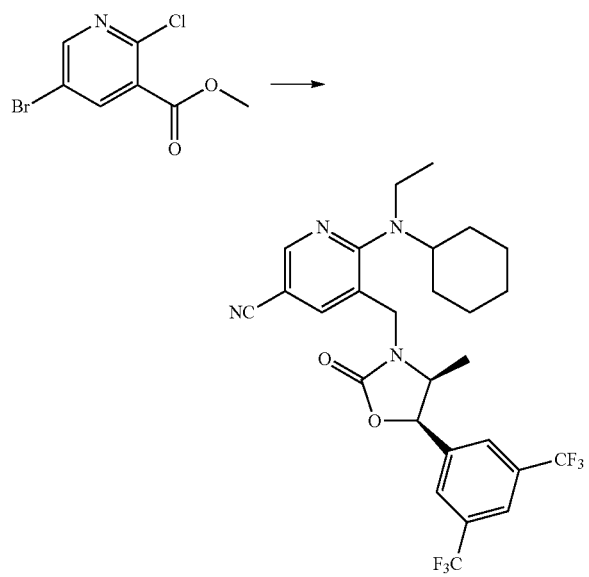

[Step 1] Preparation of methyl 5-bromo-2-[cyclohexyl(ethyl)amino]nicotinate

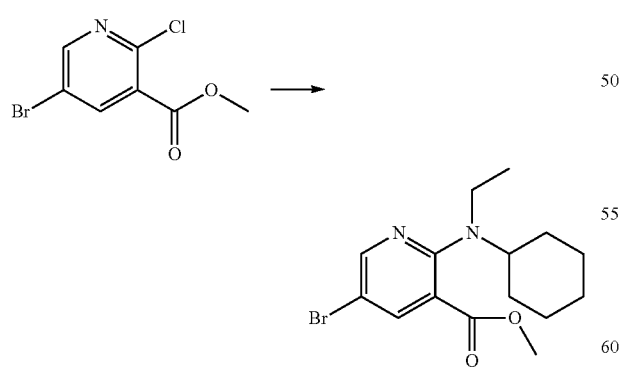

To a solution of methyl 2-chloro-5-bromo nicotinate (100 g, 399 mol) in toluene (400 ml, 1M) was dropwise added N-ethyl-N-cyclohexyl amine (62.2 g, 489 mol) at room temperature. The reaction mixture was refluxed at 140° C. for 6 hrs and further added with drops of N-ethyl-N-cyclohexyl amine (62.2 g, 489 mol). Again, the reaction mixture was refluxed for 20 hrs, cooled to the room temperature, diluted with ethyl acetate, and then washed with water, ammonium chloride and 2N HCl. Concentration in a vacuum afforded the title compound (130g, 95.5%).

¹H NMR (400 MHz, CDCl₃) 8.21 (s, 1H), 7.88 (s, 1H), 3.86 (s, 3H), 3.41 (m, 2H), 3.34 (m, 1H), 1.78 (m, 2H), 1.46~1.69 (m, 4H), 1.18~1.29 (m, 4H), 1.80 (t, 3H, J=6.8 Hz)

[Step 2] Preparation of {5-bromo-2-[cyclohexyl(ethyl)amino]pyridin-3-yl}methanol

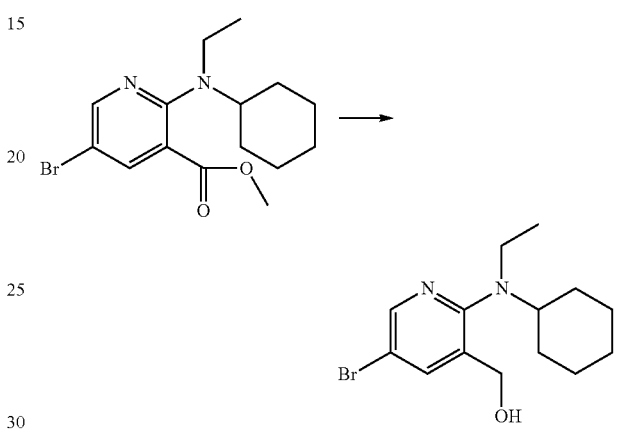

A solution of methyl 5-bromo-2-[cyclohexyl(ethyl)amino]nicotinate (226 g, 662 mol) of step 1 in tetrahydrofuran (700 ml, 0.9M) was cooled to 0° C., and slowly added with drops of LAH (25 g, 662 mol). The reaction mixture was stirred for 30 min, diluted with ethyl acetate, and added with drops of Na₂SO₄ decahydrate (430 g). Stirring at room temperature for 24 to hrs was followed by filtration in a vacuum. Concentration at a reduced pressure afforded the title compound (201 g, 97%).

¹H NMR (400 MHz, CDCl₃) 8.33 (d, 1H, J=2.4 Hz), 7.65 (s, 1H, J=2.4 Hz), 4.69 (s, 2H), 3.22 (m, 2H), 2.92 (m, 1H), 1.69~1.83 (m, 3H), 1.62 (m, 1H), 1.30~1.50 (m, 2H), 1.08~1.30 (m, 4H), 0.92 (t, 3H, J=7.2 Hz)

[Step 3] Preparation of 5-bromo-3-(chloromethyl)-N-cyclohexyl-N-ethylpyridine-2-amine

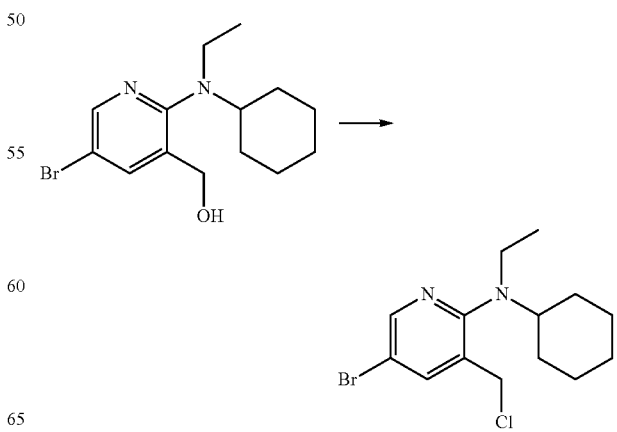

A solution of {5-bromo-2-[cyclohexyl(ethyl)amino]pyridin-3-yl}methanol (46 g, 135 mol) of step 2 in DMF (300 ml) was cooled to 0° C., and slowly added with drops of SOCl₂ (17.6 g, 148 mol) with stirring for 1 hr. The reaction solution was diluted with ethyl acetate (200 ml) before quenching with water. The organic layer thus formed was dried over anhydrous Na₂SO₄, and concentrated in a vacuum to give 5-bromo-3-(chloromethyl)-N-cyclohexyl-N-ethylpyridine-2-amine which was immediately used in a subsequent reaction without further purification.

[Step 4] Preparation of (4S,5R)-5-[3,5-bis(trifluoromethyl)phenyl]-4-methyl-3-({5-bromo-2-[cyclohexyl(ethyl)amino]pyridin-3-yl}methyl)-oxazolidin-2-one

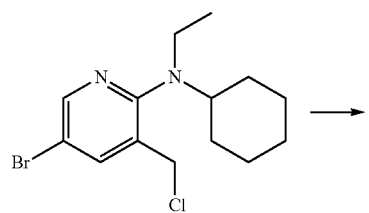

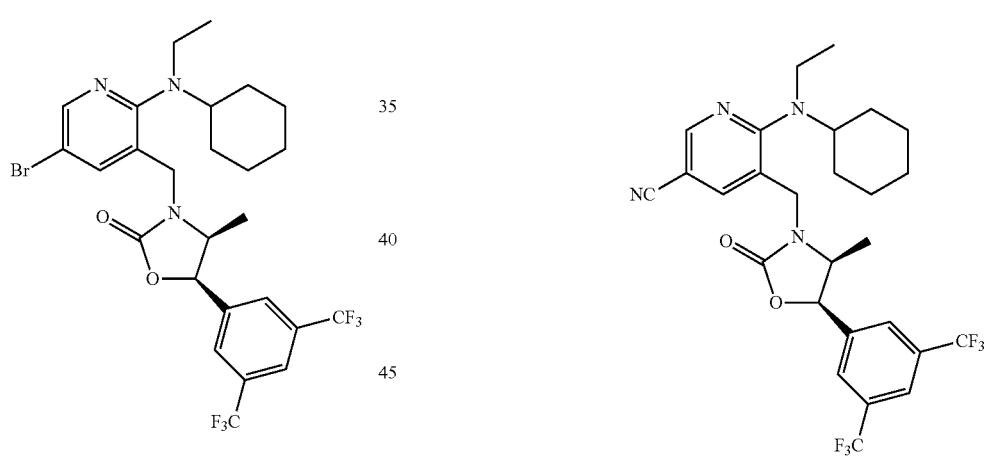

To a solution of (4S,5R)-5-[3,5-bis(trifluoromethyl)phenyl-4-methyloxazolidin-2-one (46 g, 147 mol) in DMF (150 ml) was dropwise added NaHMDS (176 ml, 176 mol) at −40° C. The reaction mixture was stirred for 30 min, and slowly added with drops of a dilution of 5-bromo-3-(chloromethyl)-N-cyclohexyl-N-ethyl pyridine-2-amine of step 3 in DMF (30 ml). The resulting reaction mixture was heated to room temperature, stirred for 3 hrs, and diluted with ethyl acetate (200 ml) before quenching with water (500 ml). The organic layer was withdrawn, washed with water (1.5 L), and filtered through a silica-selite pad in a vacuum to afford the title compound (60 g, 67%).

¹H NMR (400 MHz, CDCl₃) 8.31 (s, 1H), 7.89 (s, 1H), 7.76 (s, 2H), 7.74 (s, 1H), 5.73 (d, 1H, J=8.0 Hz), 4.68 (d, 1H, J=16.0 Hz), 4.30 (d, 1H, J=16.0 Hz), 3.93 (m, 1H), 3.44 (m, 1H), 3.03 (m, 1H), 2.68 (m, 1H), 1.44~1.86 (m, 5H), 1.02~1.44 (m, 5H), 0.86 (t, 3H, J=6.8 Hz), 0.66 (d, 3H, J=6.4 Hz).

[Step 5] Preparation of 5-({4S,5R)-5-[3,5-bis(trifluoromethyl)phenyl]-4-methyl-2-oxo-1,3-oxazolidin-3-yl}methyl)-6-[(cyclohexyl)(ethyl)amino]nicotinonitrile

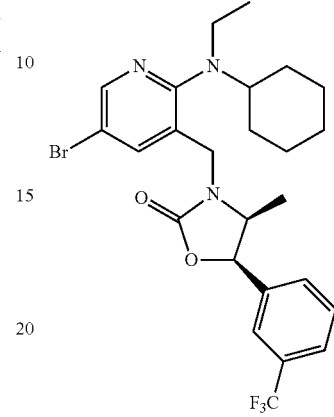

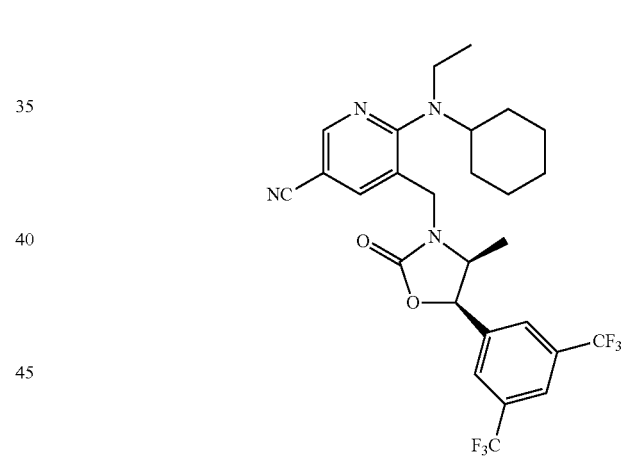

A solution of (4S,5R)-5-[3,5-bis(trifluoromethyl)phenyl]-4-methyl-3-({5-bromo-2-[cyclohexyl(ethyl)amino]pyridin-3-yl}methyl)-oxazolidin-2-one (500 mg, 0.82 mmol) of step 4 in DMF (3 ml) was added with CuCN (147 mg, 1.64 mmol) and CuI (232 mg, 1.23 mmol), and then refluxed for 24 hrs with stirring. The resulting reaction mixture was cooled to room temperature and extracted with ethyl acetate and water. The organic layer thus formed was dried over anhydrous magnesium sulfate, filtered, and concentrated at a reduced pressure. The residue was purified by chromatography to afford the title compound (200 mg, 44%).

¹H NMR (400 MHz, CDCl₃) 8.47 (s, 1H), 7.90 (s, 1H), 7.79 (s, 1H), 7.76 (s, 2H), 5.75 (d, 1H, J=8.0 Hz), 4.75 (d, 1H, J=15.6 Hz), 4.13 (d, 1H, J=16.4 Hz), 3.84 (m, 1H), 3.62 (m, 1H), 3.17 (m, 1H), 2.98 (m, 1H), 1.72~1.90 (m, 2H), 1.42~1.71 (m, 4H), 1.02~1.40 (m, 4H), 0.96 (t, 3H, J=6.4 Hz), 0.63 (d, 3H, J=6.0 Hz).

Example 55

5-{[(4S,5R)-5-[3,5-bis(trifluoromethyl)phenyl]-4-methyl-2-oxo-oxazolidin-3-yl]methyl}-6-[(cyclohexyl)(ethyl)amino]-pyridin-3-yl methanesulfonate

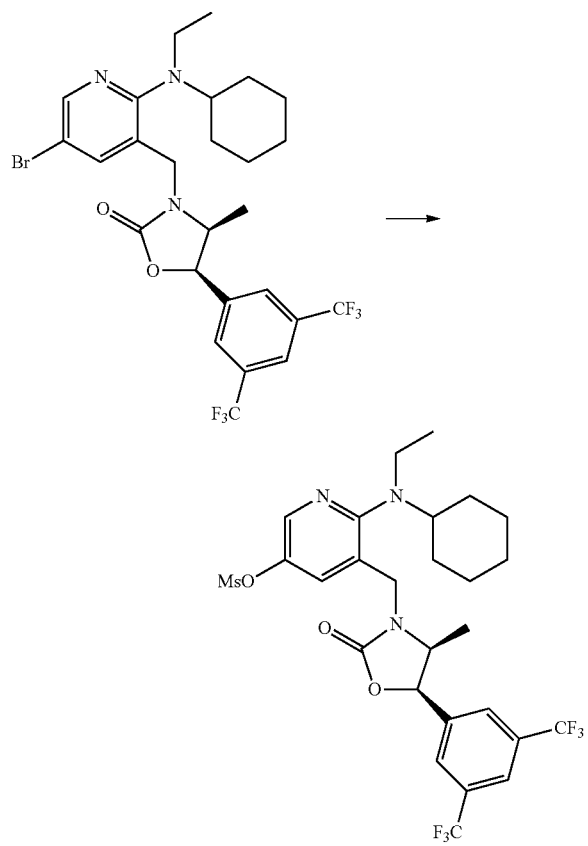

[Step 1] Preparation of (4S,5R)-5-[3,5-bis(trifluoromethyl)phenyl]-4-methyl 3-({2-[cyclohexyl(ethyl)amino]-5-hydroxypyridin-3-yl}methyl)-oxazolidin-2-one

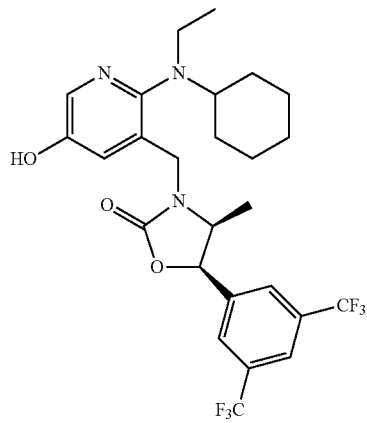

To a solution of (4S,5R)-5-[3,5-bis(trifluoromethyl)phenyl]-4-methyl-3-({5-bromo-2-[cyclohexyl(ethyl)amino]pyridin-3-yl}methyl)-oxazolidin-2-one (500 mg, 0.8 mmol) of step 3 of Example 54 in 1,4-dioxane/H20 (1/1, 8 ml) were added $Pd_2(dba)_3$ (90 mg, 0.08 mmol), KOH (135 mg, 2.4 mmol) and 2-di-t-butylphosphino-3,4,5,6-tetramethyl-2',4',6'-triisopropyl-1,1'-biphenyl (100 mg, 0.16 mmol). The reaction mixture was refluxed at 100° C. for 3 hrs with stirring, and then cooled to room temperature. Extraction was performed with dichloromethane and water. The organic layer thus formed was dried over anhydrous magnesium sulfate, filtered, and concentrated at a reduced pressure. The residue was purified by chromatography to afford the title compound (200 mg, 45%).

$^1$H NMR (400 MHz, $CDCl_3$). 8.03 (d, 1H), 7.87 (s, 1H), 7.72 (s, 2H), 7.25 (m, 1H), 5.84 (d, 1H), 4.68 (d, 1H), 4.46 (d, 1H), 4.0 (m, 1H), 3.37 (m, 1H), 3.03 (m, 1H), 2.64 (m, 1H), 1.79 (m, 4H), 1.41 (m, 2H), 1.28 (m, 4H), 0.86 (t, 3H), 0.73 (d, 3H).

[Step 2] Preparation of 5-{[(4S,5R)-5-[3,5-bis(trifluoromethyl)phenyl]-4-methyl-2-oxo-oxazolidin-3-yl]methyl}-6-[(cyclohexyl)(ethyl)amino]-pyridin-3-yl methanesulfonate

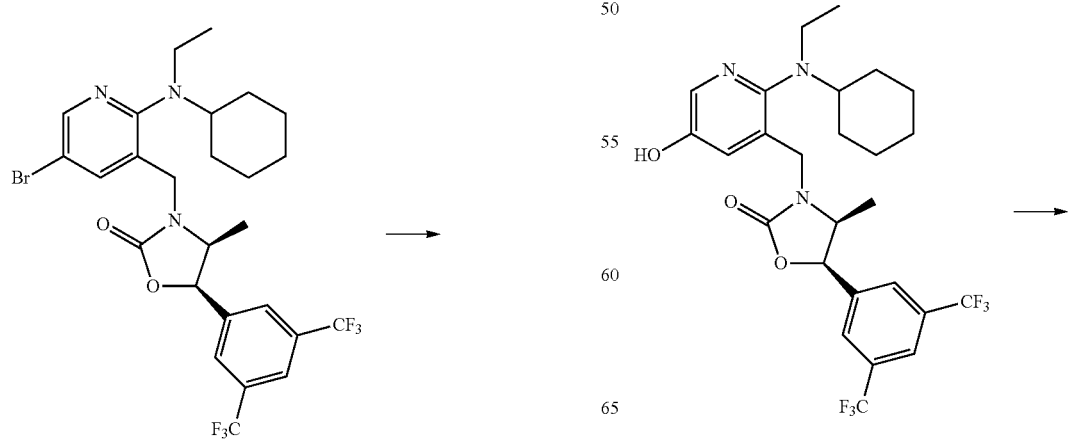

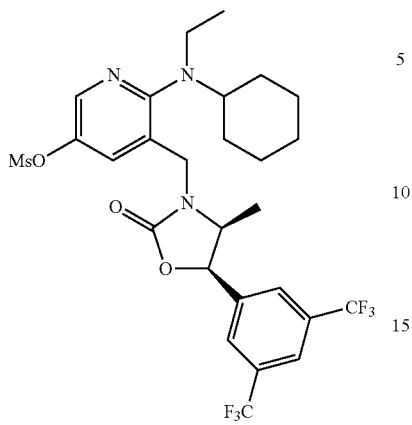

(4S,5R)-5-[3,5-bis(trifluoromethyl)phenyl]-4-methyl 3-({2-[cyclohexyl(ethyl)amino]-5-hydroxypyridin-3-yl}methyl)-oxazolidin-2-one of step 1 and MsCl were used in the same manner as in Example 32 to afford the title compound (18 mg, 12%).

$^1$H NMR (400 MHz, CDCl$_3$). 8.21 (s, 1H), 7.88 (s, 1H), 7.56 (s, 2H), 7.59 (s, 1H), 5.74 (d, 1H, J=8.4 Hz), 4.73 (d, 1H, J=16.0 Hz), 4.29 (d, 1H, J=16.0 Hz), 3.90 (m, 1H), 3.50 (m, 1H), 3.34 (s, 3H), 3.07 (m, 1H), 2.74 (m, 1H), 1.06~1.84 (m, 10H), 0.90 (t, 3H, J=7.0 Hz), 0.62 (d, 3H, J=6.8 Hz).

Example 56

(4S,5R)-5-[3,5-bis(trifluoromethyl)phenyl]-4-methyl-3-({[2-(ethyl)(cyclohexyl-4-yl)amino]-5-(1-methyl-1H-pyrrol-2-yl)pyridin-3-yl}methyl) oxazolidin-2-one

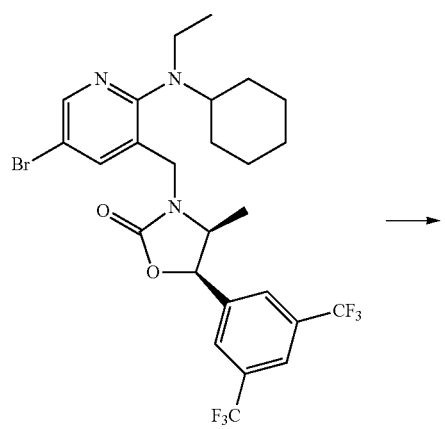

(4S,5R)-5-[3,5-bis(trifluoromethyl)phenyl]-4-methyl-3-({5-bromo-2-[cyclohexyl(ethyl)amino]pyridin-3-yl}methyl)-oxazolidin-2-one and 1-methyl-2-(tributylstannyl)-1H-pyrrole (137 mg, 0.37 mmol) were used in the same manner as in Example 50 to afford the title compound (45 mg, 30%).

$^1$H NMR (400 MHz, CDCl$_3$) 8.37 (s, 1H), 7.87 (s, 1H), 7.74 (s, 2H), 7.66 (s, 1H), 6.77 (s, 1H), 6.24 (m, 2H), 5.68 (d, 1H, J=7.6 Hz), 4.74 (m, 1H), 4.38 (m, 1H), 3.90 (m, 1H), 3.69 (s, 3H), 3.54 (m, 1H), 3.06 (m, 1H), 2.76 (m, 1H), 1.50~1.92 (m, 5H), 1.06~1.50 (m, 5H), 0.93 (m, 3H), 0.66 (m, 3H)

Example 57

(4S,5R)-5-[3,5-bis(trifluoromethyl)phenyl]-4-methyl-3-({[2-(methyl)(cyclohexyl-4-yl)amino]-5-(3,5-dimethylisoxazol-4-yl)pyridin-3-yl}methyl)-oxazolidin-2-one

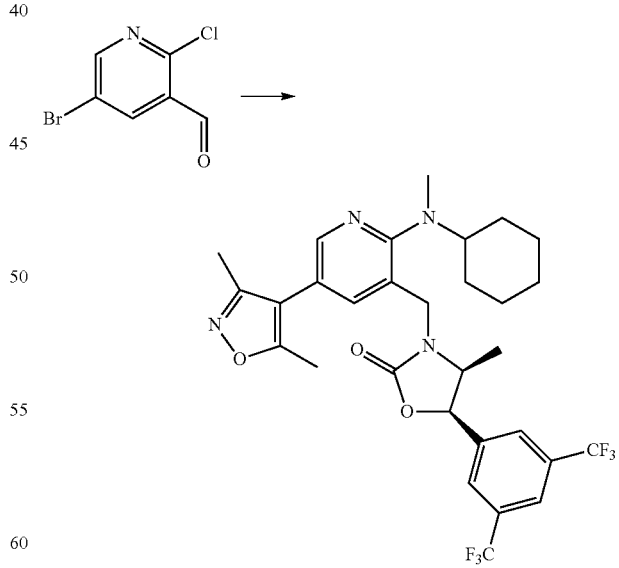

The same procedure as in Example 53 was repeated, with the exception that N-methyl-N-cyclohexylamine was used instead of N-ethyl-N-(tetrahydropyran-4-yl)amine, to afford 5-bromo-2-[cyclohexyl(methyl)amino]nicotine aldehyde. This compound was reacted with 3,5-dimethyl-4-(4,4,5,5- tetramethyl-1,3,2-dioxaborolan-2-yl)-isoxazole in the same procedure as in Example 56, with the exception that DME/H$_2$O (2/1) was used instead of 1,4-dioxane/H$_2$O, to afford the title compound (85 mg, 42%).

$^1$H NMR (400 MHz, CDCl$_3$) 8.18 (s, 1H), 7.88 (s, 1H), 7.73 (s, 2H), 7.53 (s, 1H), 5.68 (d, 1H), 4.78 (d, 1H), 4.33 (d, 1H), 3.92 (m, 1H), 3.00 (m, 1H), 2.79 (s, 3H), 2.44 (s, 3H), 2.29 (s, 3H), 1.83-1.13 (m, 10H), 0.70 (d, 3H).

Example 58

(4S,5R)-5-[3,5-bis(trifluoromethyl)phenyl]-4-methyl-3-({[2-(ethyl)(cyclohexyl)amino]-5-(3,5-dimethylisoxazol-4-yl)pyridin-3-yl}methyl)-oxazoli-clin-2-one

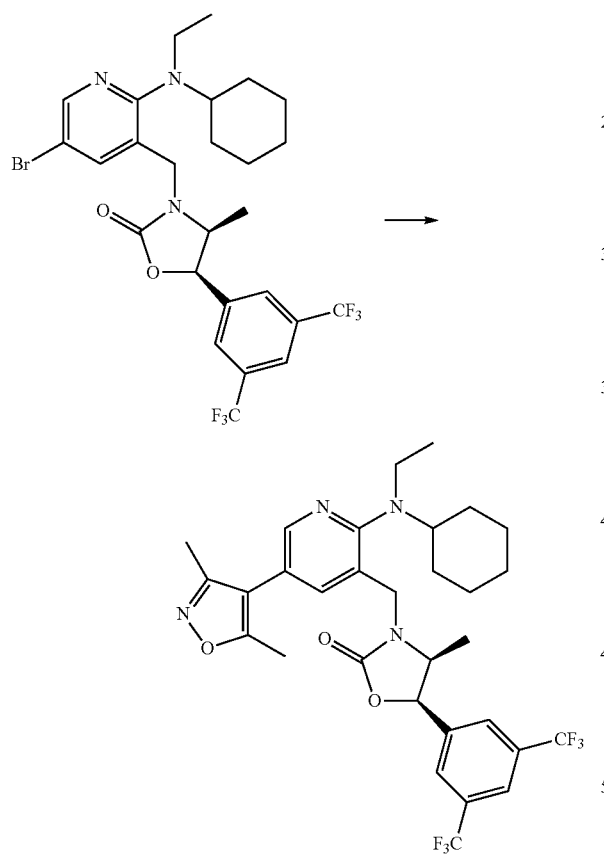

(4S,5R)-5-[3,5-bis(trifluoromethyl)phenyl]-4-methyl-3-({5-bromo-2-[cyclohexyl(ethyl)amino]pyridin-3-yl}methyl)-oxazolidin-2-one, obtained in step 4 of Example 54, and 3,5-dimethyl-4-(4,4,5,5-tetramethyl-1,3,2-dioxaborolan-2-yl)-isoxazole were used in the same manner as in Example 56 to afford the title compound (85 mg, 42%).

$^1$H NMR (400 MHz, CDCl$_3$) 8.21 (s, 1H), 7.88 (s, 1H), 7.74 (s, 2H), 7.57 (s, 1H), 5.68 (d, 1H, J=8.0 Hz), 4.73 (d, 1H, J=15.6 Hz), 4.37 (d, 1H, J=15.6 Hz), 3.94 (m, 1H), 3.52 (m, 1H), 3.11 (m, 1H), 2.78 (m, 1H), 2.50 (s, 3H), 2.31 (s, 3H), 1.50~1.90 (m, 4H), 1.43 (m, 2H), 1.25 (m, 2H), 1.12 (m, 2H), 0.95 (t, 3H, J=7.2 Hz), 0.70 (d, 3H, J=6.8 HZ).

Example 59

(4S,5R)-5-[3,5-bis(trifluoromethyl)phenyl]-4-methyl-3-({[2-(ethyl)(cyclohexyl)amino]-5-(1-methyl-1H-pyrazol-5-yl)pyridin-3-yl}methyl)-oxazolidin-2-one

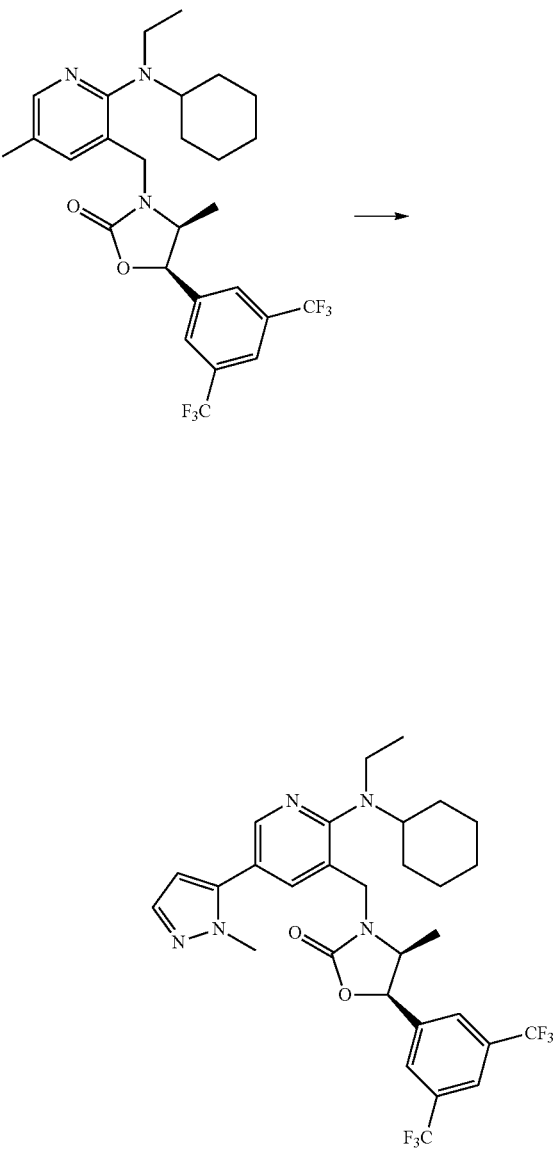

(4S,5R)-5-[3,5-bis(trifluoromethyl)phenyl]-4-methyl-3-({5-bromo-2-[cyclohexyl(ethyl)amino]pyridin-3-yl}methyl)-oxazolidin-2-one, obtained in step 4 of Example 54, and 1-methyl-2-(4,4,5,5-tetramethyl-1,3,2-dioxaborolan-2-yl)-1H-pyrazole were used in the same manner as in Example 50 to afford the title compound (300 mg, 90%).

$^1$H NMR (400 MHz, CDCl$_3$) 8.37 (s, 1H), 7.88 (s, 1H), 7.74 (s, 2H), 7.69 (s, 1H), 7.55 (s, 1H), 6.34 (s, 1H), 5.69 (d, 1H, J=8.0 Hz), 4.76 (d, 1H, J=15.6 Hz), 4.35 (d, 1H, J=16.0 Hz), 3.92 (s, 4H), 3.58 (m, 1H), 3.11 (m, 1H), 2.80 (m, 1H), 1.40~1.92 (m, 6H), 1.04~1.40 (m, 4H), 0.97 (m, 3H), 0.88 (m, 3H).

Example 60

(4S,5R)-5-[3,5-bis(trifluoromethyl)phenyl]-4-methyl-3-({[2-(ethyl)(cyclohexyl-4-yl)amino]-5-(1-methyl-1H-3-(trifluoromethyl)-pyrazol-5-yl)pyridin-3-yl}methyl)-oxazolidin-2-one

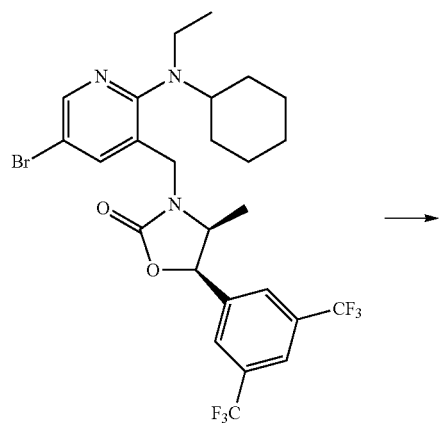

→

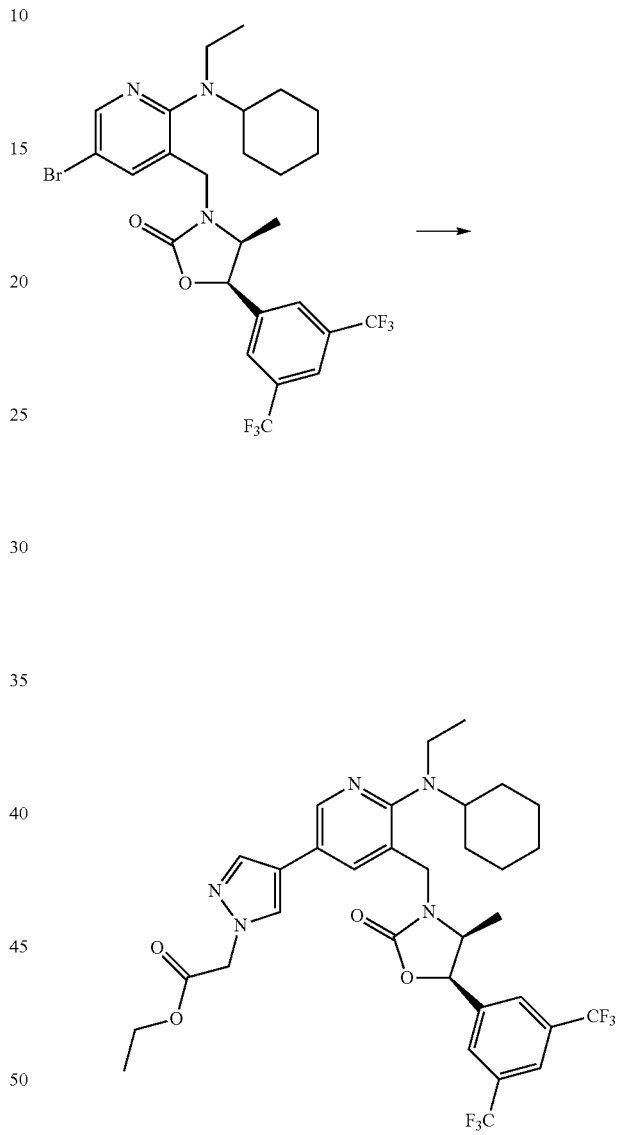

Example 61 ethyl (2-{4-[5-({(4S,5R)-5-[3,5-bis(trifluoromethyl)phenyl]-4-methyl-2-oxo-oxazolidin-3-yl}methyl)]-6-[(cyclohexyl)(ethyl)amino]pyridin-3-yl}-1H-pyrazol-1-yl)acetate

→

(4S,5R)-5-[3,5-bis(trifluoromethyl)phenyl]-4-methyl-3-({5-bromo-2-[cyclohexyl(ethyl)amino]pyridin-3-yl}methyl)-oxazolidin-2-one, prepared in step 4 of Example 54, and 1-methyl-3-trifluoromethyl-5-(4,4,5,5-tetramethyl-1,3,2-dioxaborolan-2-yl)-1H-pyrazole were used in the same manner as in Example 45 to afford the title compound (160 mg, 50%).

$^1$H NMR (400 MHz, CDCl$_3$) 8.34 (s, 1H), 7.89 (s, 1H), 7.74 (s, 2H), 7.68 (s, 1H), 6.57 (s, 1H), 5.70 (d, 1H, J=7.6 Hz), 4.74 (d, 1H, J=16.4 Hz), 4.34 (d, 1H, J=15.6 Hz), 2.85~4.00 (m, 4H), 3.56 (m, 1H), 3.16 (m, 1H), 2.84 (m, 1H), 1.40~1.90 (m, 6H), 1.03~1.39 (m, 4H), 0.98 (m, 3H), 0.97 (m, 3H), 0.68 (m, 3H).

(4S,5R)-5-[3,5-bis(trifluoromethyl)phenyl]-4-methyl-3-({5-bromo-2-[cyclohexyl(ethyl)amino]pyridin-3-yl}methyl)-oxazolidin-2-one, prepared in step 4 of Example 54, and methyl 3-(4-(4,4,5,5-tetramethyl-1,3,2-dioxaborolan-2-yl)-1H-pyrazol-1-yl)-propionate were used in the same manner as in Example 45 to afford the title compound (15 mg, 5%).

$^1$H NMR (400 MHz, CDCl$_3$) 8.46 (s, 1H), 7.87 (s, 1H), 7.82 (s, 1H), 7.71~7.45 (m, 4H), 5.70 (d, 1H, J=8.4 Hz), 4.97 (s, 2H), 4.75 (d, 1H, J=15.6 Hz), 4.38 (d, 1H, J=15.2 Hz), 4.28 (t, 2H, J=7.2 Hz), 3.89 (m, 1H), 3.53 (m, 1H), 3.05 (m, 1H), 2.72 (m, 1H), 1.08~1.91 (m, 13H), 0.92 (t, 3H, J=7.2 Hz), 0.69 (d, 3H, J=6.4 Hz).

Example 62

(4S,5R)-5-[3,5-bis(trifluoromethyl)phenyl]-4-methyl-3-({[2-(ethyl)(cyclohexyl)amino]-5-(1-methyl-1H-pyrazol-4-yl)pyridin-3-yl}methyl)-oxazolidin-2-one

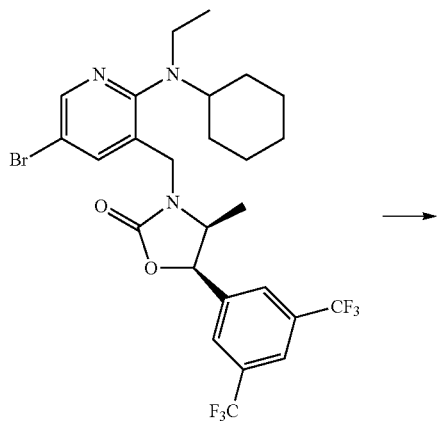

→

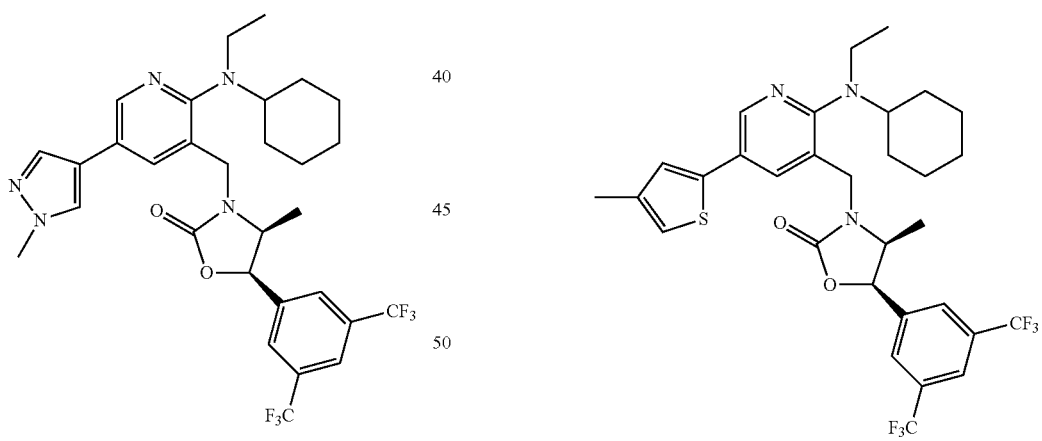

(4S,5R)-5-[3,5-bis(trifluoromethyl)phenyl]-4-methyl-3-({5-bromo-2-[cyclohexyl(ethyl)amino]pyridin-3-yl}methyl)-oxazolidin-2-one, prepared in step 4 of Example 54, and 1-methyl-4-(4,4,5,5-tetramethyl-1,3,2-dioxaborolan-2-yl)-1H-pyrazole were used in the same manner as in Example 50 to afford the title compound (100 mg, 50%).

$^1$H NMR (400 MHz, CDCl$_3$) 8.43 (s, 1H), 7.88 (s, 1H), 7.74 (s, 3H), 7.69 (s, 1H), 7.62 (s, 1H), 5.67 (d, 1H, J=8.0 Hz), 4.72 (d, 1H, J=16.4 Hz), 4.39 (d, 1H, J=15.6 Hz), 3.97 (s, 3H), 3.92 (m, 1H), 3.51 (m, 1H), 3.06 (m, 1H), 2.74 (m, 1H), 1.31~1.90 (m, 6H), 1.04~1.31 (m, 4H), 0.92 (m, 3H), 0.68 (m, 3H).

Example 63

(4S,5R)-5-[3,5-bis(trifluoromethyl)phenyl]-4-methyl-3-({[2-(ethyl)(cyclohexyl)amino]-5-(3-methyl-thiophen-5-yl)pyridin-3-yl}methyl)-oxazolidin-2-one

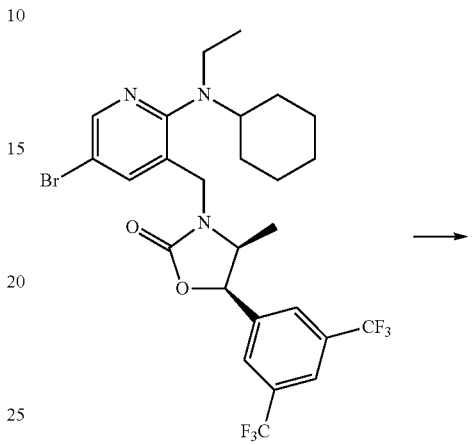

→

(4S,5R)-5-[3,5-bis(trifluoromethyl)phenyl]-4-methyl-3-({5-bromo-2-[cyclohexyl(ethyl)amino]pyridin-3-yl}methyl)-oxazolidin-2-one, prepared in step 4 of Example 54, and 3-methyl-5-(4,4,5,5-tetramethyl-1,3,2-dioxaborolan-2-yl)-thiophene were used in the same manner as in Example 50 to afford the title compound (50 mg, 25%).

$^1$H NMR (400 MHz, CDCl$_3$) 8.52 (s, 1H), 7.87 (s, 1H), 7.75 (s, 3H), 7.09 (s, 1H), 6.89 (s, 1H), 5.71 (d, 1H, J=8.4 Hz), 4.75 (d, 1H, J=16.0 Hz), 4.35 (d, 1H, J=16.0 Hz), 3.90 (m, 1H), 3.53 (m, 1H), 3.06 (m, 1H), 2.70 (m, 1H), 2.04 (s, 3H), 1.09~1.80 (m, 10H), 0.91 (m, 3H), 0.67 (m, 3H).

Example 64

(4S,5R)-5-[3,5-bis(trifluoromethyl)phenyl]-3-({[2-(ethyl)(cyclohexyl)amino]-5-(1,3,5-trimethyl-1H-pyrazol-4-yl}pyridin-3-yl}methyl)-oxazolidin-2-one

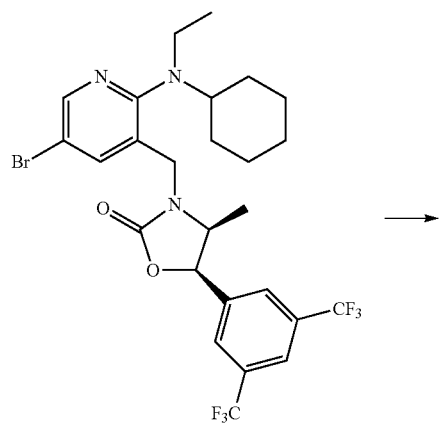

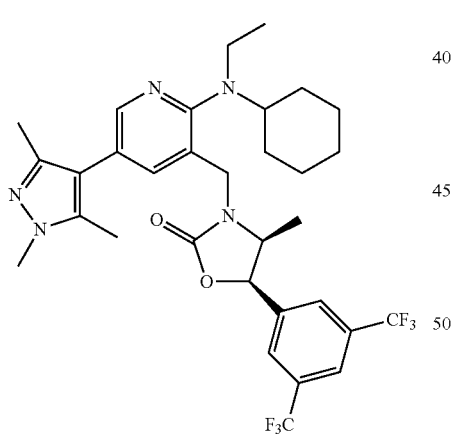

(4S,5R)-5-[3,5-bis(trifluoromethyl)phenyl]-4-methyl-3-({5-bromo-2-[cyclohexyl(ethyl)amino]pyridin-3-yl}methyl)-oxazolidin-2-one, prepared in step 4 of Example 54, and 1,3,5-trimethyl-4-(4,4,5,5-tetramethyl-1,3,2-dioxaborolan-2-yl)-1H-pyrazole were used in the same manner as in Example 45 to afford the title compound (30 mg, 8%).

$^1$H NMR (400 MHz, CDCl$_3$) 8.21 (s, 1H), 7.88 (s, 1H), 7.74 (s, 2H), 7.53 (s, 1H), 5.66 (d, 1H, J=7.6 Hz), 4.74 (d, 1H, J=15.6 Hz), 4.38 (d, 1H, J=15.2 Hz), 3.94 (m, 1H), 3.80 (s, 3H), 3.51 (m, 1H), 3.08 (m, 1H), 2.76 (m, 1H), 2.27 (s, 6H), 1.03~1.92 (m, 10H), 0.94 (m, 3H), 0.69 (m, 3H).

Example 65

(4S,5R)-5-[3,5-bis(trifluoromethyl)phenyl]-4-methyl-3-({[2-(ethyl)(cyclohexyl-4-yl)amino]-5-(3,5-dimethyl-1H-pyrazol-4-yl)pyridin-3-yl}methyl)-oxazolidin-2-one

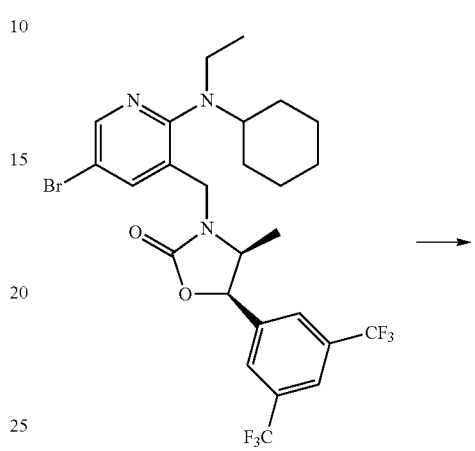

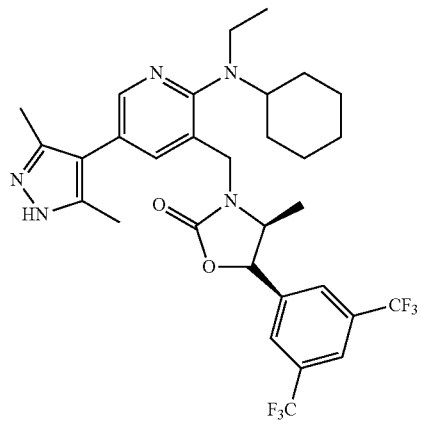

(4S,5R)-5-[3,5-bis(trifluoromethyl)phenyl]-4-methyl-3-({5-bromo-2-[cyclohexyl(ethyl)amino]pyridin-3-yl}methyl)-oxazolidin-2-one, prepared in step 4 of Example 54, and 3,5-dimethyl-4-(4,4,5,5-tetramethyl-1,3,2-dioxaborolan-2-yl)-1H-pyrazole-1-carboxylate were used in the same manner as in Example 50 to afford the title compound (42 mg, 35%).

$^1$H NMR (400 MHz, CDCl$_3$) 8.25 (s, 1H), 7.88 (s, 1H), 7.74 (s, 2H), 7.58 (s, 1H), 5.83 (bs, 1H), 5.68 (d, 1H), 4.77 (d, 1H), 4.41 (d, 1H), 3.94 (m, 1H), 3.52 (m, 1H), 3.08 (m, 1H), 2.76 (m, 1H), 2.33 (s, 6H), 1.87-1.13 (m, 10H), 1.02 (m, 3H), 0.71 (m, 3H).

Example 66

(4S,5R)-5-[3,5-bis(trifluoromethyl)phenyl]-4-methyl-3-({[2-(ethyl)(cyclohexyl)amino]-5-(1-methyl-1H-tetrazol-5-yl)pyridin-3-yl}methyl)-oxazolidin-2-one

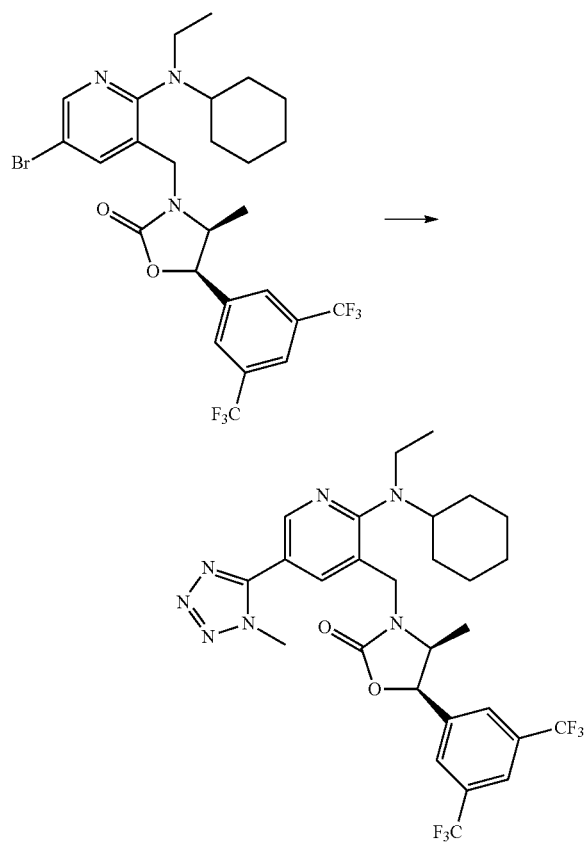

[Step 1] Preparation of (4S,5R)-5-[3,5-bis(trifluoromethyl)phenyl]-3-({2-[cyclohexyl(ethyl)amino]-4-methyl-5-(4,4,5,5-tetramethyl-1,3,2-dioxaborolan-2-yl)pyridin-3-yl}methyl)-oxazolidin-2-one

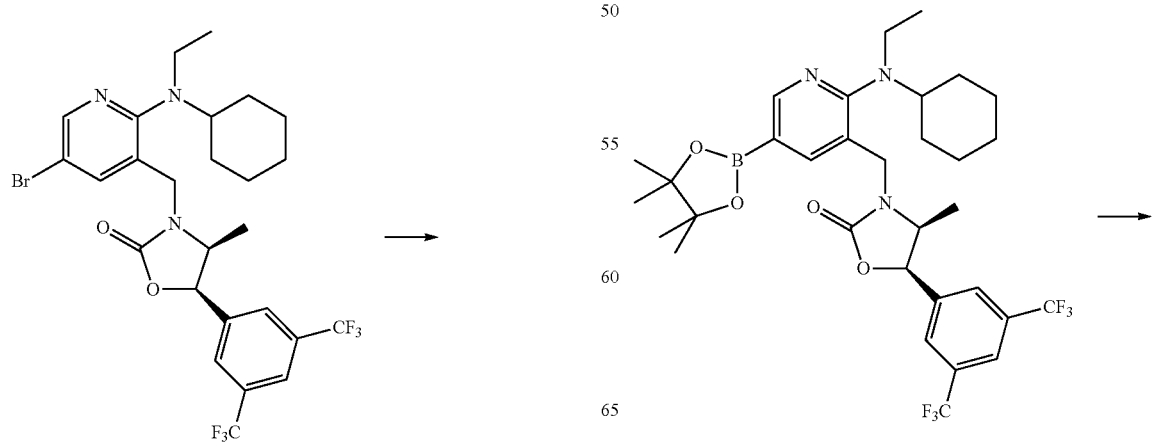

To a solution (4S,5R)-5-[3,5-bis(trifluoromethyl)phenyl]-4-methyl-3-({5-bromo-2-[cyclohexyl(ethyl)amino]pyridin-3-yl}methyl)-oxazolidin-2-one (1.0 g, 1.64 mmol), prepared in step 4 of Example 54, in toluene (4 ml) were dropwise added Pd(dppf)Cl (134 mg, 0.164 mmol), KOAc (483 mg, 4.92 mmol), and 4,4,4',4',5,5,5',5'-octamethyl-2,2'-bi(1,3,2-dioxaborolane) (500 mg, 1.97 mmol). The reaction mixture was refluxed at 100° C. for 5 hrs with stirring, and then cooled to room temperature, followed by extraction with dichloromethane. The organic layer thus formed was dried over anhydrous magnesium sulfate, filtered, and concentrated at a reduced pressure. The residue was purified by chromatography to afford a dioxaborolane compound (750 mg, 70%).

$^1$H NMR (400 MHz, CDCl$_3$) 8.61 (s, 1H), 7.95 (s, 1H), 7.87 (s, 1H), 7.75 (s, 2H), 5.70 (d, 1H), 4.78 (d, 1H), 4.28 (d, 1H), 3.83 (m, 1H), 3.59 (m, 1H), 3.08 (m, 1H), 2.78 (m, 1H), 1.95 (m, 5H), 1.34 (m, 5H), 1.24 (s, 12H), 0.92 (t, 3H), 0.64 (d, 3H).

[Step 2] Preparation of (4S,5R)-5-[3,5-bis(trifluoromethyl)phenyl]-4-methyl-3-({[2-(ethyl)(cyclohexyl)amino]-5-(1-methyl-1H-tetrazol-5-yl)pyridin-3-yl}methyl)-oxazolidin-2-one

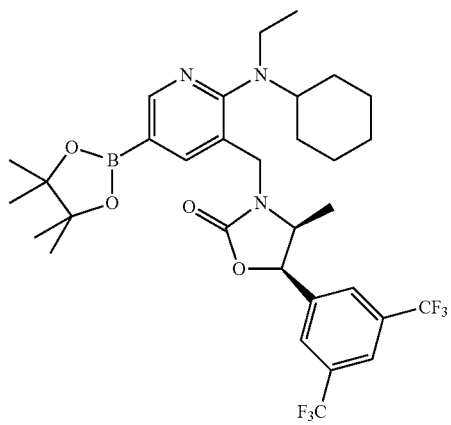

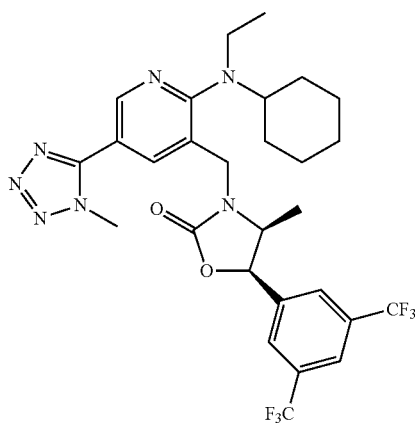

A solution of (4S,5R)-5-[3,5-bis(trifluoromethyl)phenyl]-3-({2-[cyclohexyl(ethyl)amino]-4-methyl-5-(4,4,5,5-tetramethyl-1,3,2-dioxaborolan-2-yl)pyridin-3-yl}methyl)-oxazolidin-2-one (200 mg, 0.30 mmol) of step 1 in DME/H2O (2/1, 4.5 ml) was added with drops of 1-methyl-5-iodo-tetrazole (90 mg, 0.46 mmol), $K_2CO_3$ (82 mg, 0.6 mmol), and $Pd(PPh_3)_4$ (50 mg, 0.03 mmol), and refluxed at 90° C. for 62 hrs with stirring. Cooling to room temperature was followed by extraction with ethyl acetate. The organic layer thus formed was dried over anhydrous magnesium sulfate, filtered, and concentrated at a reduced pressure. The residue was purified by chromatography to afford the title compound (17 mg, 9%).

$^1$H NMR (400 MHz, $CDCl_3$) 8.63 (d, 1H), 8.04 (d, 1 h), 7.88 (s, 1H), 7.75 (s, 2H), 5.76 (d, 1H), 4.84 (d, 1H), 4.28 (d, 1H), 4.22 (s, 3H), 3.95 (m, 1H), 3.67 (m 1H), 3.19 (m, 1H), 2.94 (m, 1H), 1.87 (m, 1H), 1.79 (m, 1H), 1.67 (m, 4H), 1.34 (m, 4H), 1.00 (t, 3H), 0.68 (d, 3H).

(4S,5R)-5-[3,5-bis(trifluoromethyl)phenyl]-4-methyl-3-({5-bromo-2-[cyclohexyl(ethyl)amino]pyridin-3-yl}methyl)-oxazolidin-2-one, prepared in step 4 of Example 54, and 1-isobutyl-4-(4,4,5,5-tetramethyl-1,3,2-dioxaborolan-2-yl)-1H-pyrazole were used in the same manner as in Example 45 to afford the title compound (60 mg, 28%).

$^1$H NMR (400 MHz, $CDCl_3$) 8.46 (d, 1H), 7.87 (s, 1H), 7.77 (s, 1H), 7.74 (s, 2H), 7.71 (d, 1H), 7.62 (s, 1H), 5.69 (d, 1H), 4.75 (d, 1H), 4.41 (d, 1H), 4.41 (d, 1H), 3.97 (m, 3H), 3.53 (m, 1H), 3.08 (m, 1H), 2.71 (m, 1H), 2.28 (m, 1H), 2.17-1.24 (m, 10H), 0.96 (m, 12H), 0.70 (d, 3H).

Example 67

(4S,5R)-5-[3,5-bis(trifluoromethyl)phenyl]-4-methyl-3-({2-(ethyl)(cyclohexyl)amino]-5-(1-isobutyl-1H-pyrazol-4-yl)pyridin-3-yl}methyl)-oxazolidin-2-one

Example 68

(4S,5R)-5-[3,5-bis(trifluoromethyl)phenyl]-4-methyl-3-({[2-(ethyl)(cyclohexyl)amino]-5-(1H-pyrazol-4-yl)pyridin-3-yl}methyl)-oxazolidin-2-one

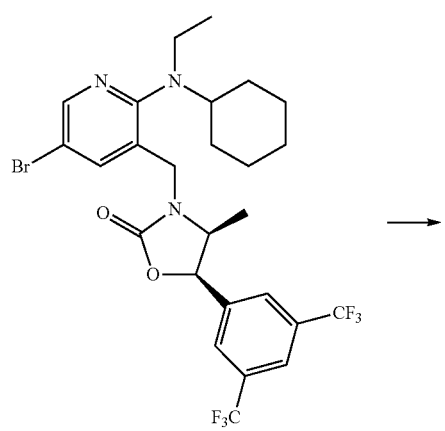

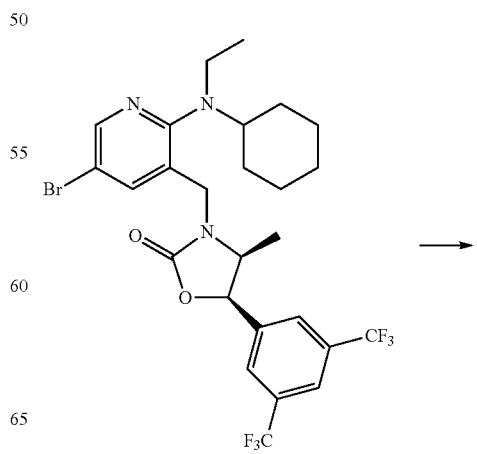

119

-continued

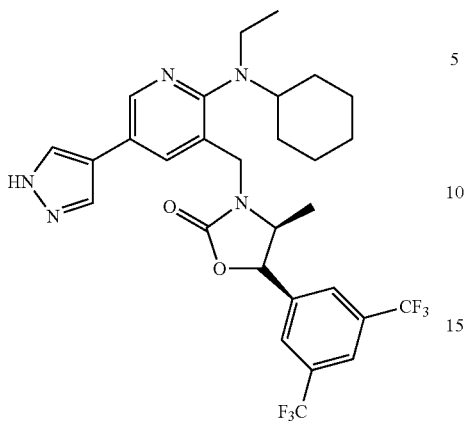

(4S,5R)-5-[3,5-bis(trifluoromethyl)phenyl]-4-methyl-3-({5-bromo-2-[cyclohexyl(ethyl)amino]pyridin-3-yl}methyl)-oxazolidin-2-one, prepared in step 4 of Example 54, and 1H-pyrazol-4-yl boronic acid were used in the same manner as in Example 45 to afford the title compound (50 mg, 25%).

$^1$H NMR (400 MHz, CDCl$_3$) 8.49 (d, 1H), 7.87 (s, 2H), 7.74 (s, 3H), 7.63 (s, 1H), 6.37 (bs, 1H), 5.69 (d, 1H), 4.77 (d, 1H), 4.42 (d, 1H), 3.93 (m, 1H), 3.54 (m, 1H), 3.09 (m, 1H), 2.73 (m, 1H), 1.88-1.50 (m, 6H), 1.40 (m, 2H), 1.14 (m, 2H), 0.94 (t, 3H), 0.70 (d, 3H).

Example 69

(4S,5R)-5-[3,5-bis(trifluoromethyl)phenyl]-4-methyl-3-({2-(ethyl)(cyclohexyl)amino]-5-(1,3-dimethyl-1H-pyrazol-4-yl)pyridin-3-yl}methyl)-oxazolidin-2-one

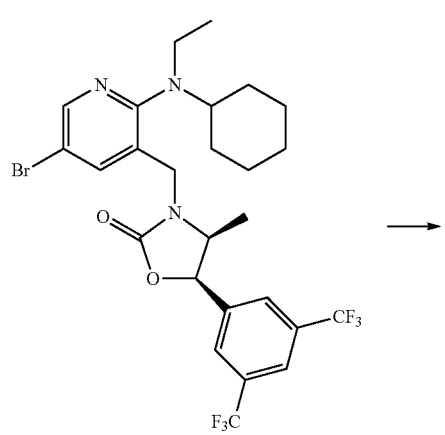

120

-continued

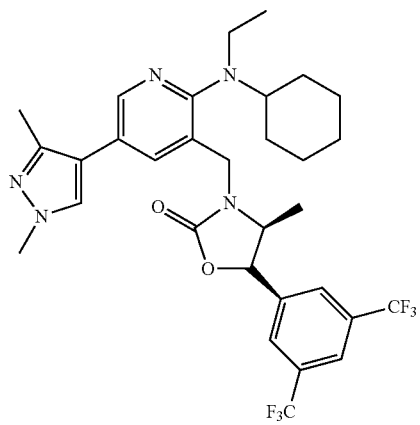

(4S,5R)-5-[3,5-bis(trifluoromethyl)phenyl]-4-methyl-3-({5-bromo-2-[cyclohexyl(ethyl)amino]pyridin-3-yl}methyl)-oxazolidin-2-one, prepared in step 4 of Example 54, and 1,3-dimethyl-4-(4,4,5,5-tetramethyl-1,3,2-dioxaborolan-2-yl)-1H-pyrazole were used in the same manner as in Example 45 to afford the title compound (56 mg, 54%).

$^1$H NMR (400 MHz, CDCl$_3$) 8.36 (s, 1H), 7.88 (s, 1H), 7.74 (s, 2H), 7.64 (s, 1H), 7.45 (s, 1H), 4.75 (d, 1H), 4.41 (d, 1H), 3.90 (s, 3H), 3.50 (m, 1H), 3.06 (m, 1H), 2.73 (m, 1H), 2.41 (m, 3H), 1.93-1.13 (m, 10H), 093 (m, 3H), 0.70 (d, 3H).

Example 70

(4S,5R)-5-[3,5-bis(trifluoromethyl)phenyl]-4-methyl-3-({[2-(ethyl)(cyclohexyl)amino]-5-(3-methoxy-thiophen-2-yl)pyridin-3-yl}methyl)-oxazolidin-2-one

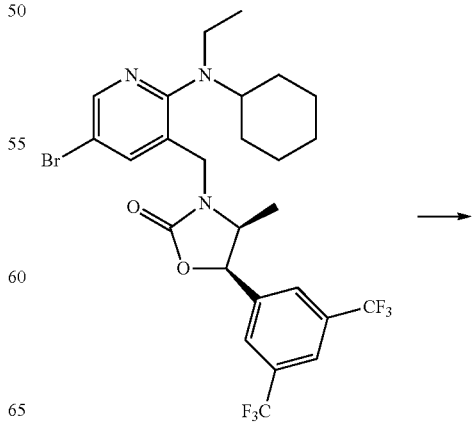

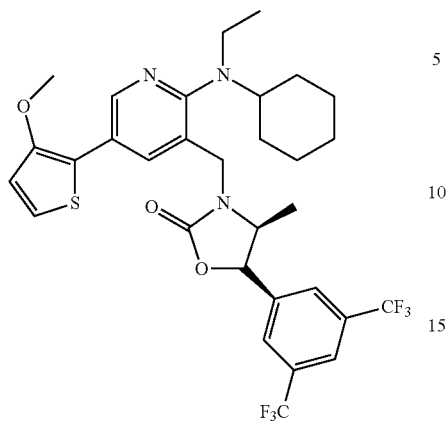

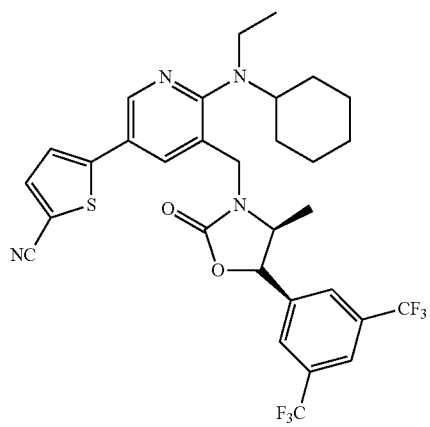

(4S,5R)-5-[3,5-bis(trifluoromethyl)phenyl]-4-methyl-3-({5-bromo-2-[cyclohexyl(ethyl)amino]pyridin-3-yl}methyl)-oxazolidin-2-one, prepared in step 4 of Example 54, and 3-methoxy-2-(4,4,5,5-tetramethyl-1,3,2-dioxoborolan-2-yl)-thiophene were used in the same manner as in Example 45 to afford the title compound (55 mg, 55%).

$^1$H NMR (400 MHz, CDCl$_3$) 8.64 (d, 1H), 8.00 (s, 1H), 7.87 (s, 1H), 7.76 (s, 2H), 7.20 (d, 1H), 6.96 (d, 1H), 5.69 (d, 1H), 4.79 (d, 1H), 4.36 (d, 1H), 3.94 (m, 4H), 3.56 (m, 1H), 3.07 (m, 1H), 2.75 (m, 1H), 1.87-1.33 (m, 7H), 1.14 (m, 3H), 0.94 (m, 3H), 0.68 (d, 3H).

(4S,5R)-5-[3,5-bis(trifluoromethyl)phenyl]-4-methyl-3-({5-bromo-2-[cyclohexyl(ethyl)amino]pyridin-3-yl}methyl)-oxazolidin-2-one, prepared in step 4 of Example 54, and 2-cyano-5-(4,4,5,5-tetramethyl-1,3,2-dioxoborolan-2-yl)-thiophene were used in the same manner as in Example 45 to afford the title compound (78 mg, 76%).

$^1$H NMR (400 MHz, CDCl$_3$) 8.52 (d, 1H), 7.88 (s, 1H), 7.80 (d, 1H), 7.74 (s, 2H), 7.62 (d, 1H), 7.24 (d, 1H), 5.70 (d, 1H), 4.76 (d, 1H), 4.34 (d, 1H), 3.92 (m, 1H), 3.58 (m, 1H), 3.58 (m, 1H), 3.15 (m, 1H), 2.84 (m, 1H), 1.84 (m, 2H), 1.64 (m, 2H), 1.49 (m, 2H), 1.30 (m, 2H), 1.20 (m, 2H), 0.96 (t, 3H), 0.68 (d, 1H).

Example 71

5-{5-({(4S,5S)-5-[3,5-bis(trifluoromethyl)phenyl]-4-methyl-2-oxo-oxazolidin-3-yl}methyl)-6-[(cyclohexyl)(ethyl)amino]pyridin-3-yl}-thiophene-2-carbonitrile Example 72

(4S,5R)-5-[3,5-bis(trifluoromethyl)phenyl]-4-methyl-3-({[2-(ethyl)(cyclohexyl)amino]-5-(3-(trifluoromethyl)-1H-pyrazol-4-yl)pyridin-3-yl}methyl)-oxazolidin-2-one

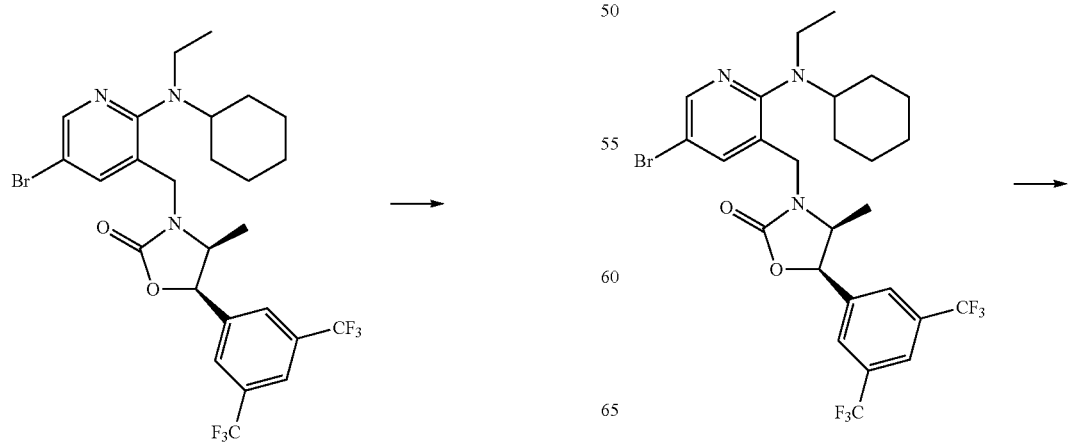

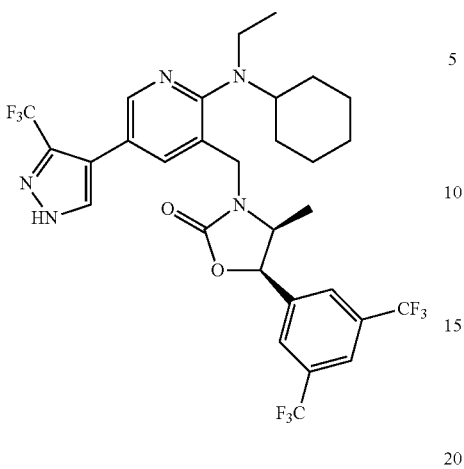

(4S,5R)-5-[3,5-bis(trifluoromethyl)phenyl]-4-methyl-3-({5-bromo-2-[cyclohexyl(ethyl)amino]pyridin-3-yl}methyl)-oxazolidin-2-one, prepared in step 4 of Example 54, and 3-(trifluoromethyl)-4-(4,4,5,5-tetramethyl-1,3,2-dioxaborolan-2-yl)-1H-pyrazole were used in the same manner as in Example 45 to afford the title compound (40 mg, 18%).

$^1$H NMR (400 MHz, CDCl$_3$) 8.32 (s, 1H), 7.88 (s, 1H), 7.75 (s, 3H), 7.72 (d, 1H), 5.72 (d, 1H), 4.78 (d, 1H), 4.37 (d, 1H), 3.94 (m, 1H), 3.57 (m, 1H), 3.12 (m, 1H), 2.78 (m, 1H), 1.87-1.00 (m, 10H), 0.96 (t, 3H), 0.67 (d, 3H).

Example 73 ethyl 4-{5-({(4S,5R)-5-[3,5-bis(trifluoromethyl)phenyl]-4-methyl-2-oxo-oxazolin-3-yl}methyl)-6-[(cyclohexyl)(ethyl)amino)]pyridin-3-yl}-3-methyl-isoxazole-5-carboxylate

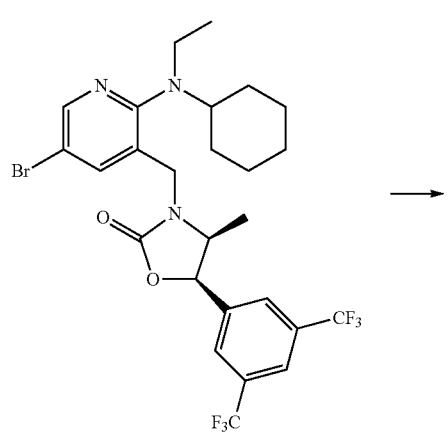

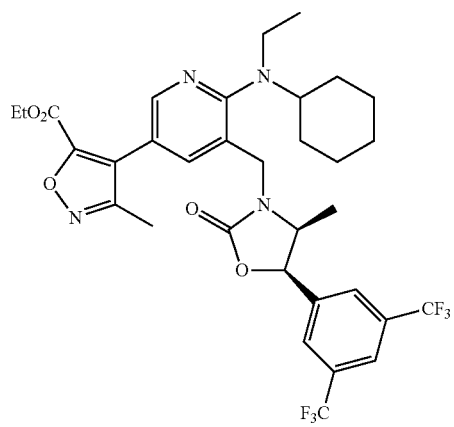

The same procedure as in Example 66 was repeated, with the exception that ethyl 4-bromo-3-methylisoxazole-5-carboxylate was used instead of 1-methyl-5-iodo-tetrazole, to afford the title compound (30 mg, 14%).

$^1$H NMR (400 MHz, CDCl$_3$) 8.69 (d, 1H), 8.30 (d, 1H), 7.87 (s, 1H), 7.81 (s, 2H), 5.98 (d, 1H), 7.87 (d, 1H), 4.36 (q, 2H), 4.23 (d, 1H), 4.15 (m, 1H), 3.73 (m, 1H), 3.11 (m, 1H), 2.96 (m, 1H), 2.52 (s, 3H), 1.94 (m, 1H), 1.69 (m 9H), 1.40 (t, 3H), 0.98 (t, 3H), 0.65 (d, 3H).

Example 74 ethyl 5-{5-({(4S,5R)-5-[3,5-bis(trifluoromethyl)phenyl]-4-methyl-2-oxo-oxazolin-3-yl}methyl)-6-[(cyclohexyl)(ethyl)amino)]pyridin-3-yl}-3-methyl-isoxazole-4-carboxylate

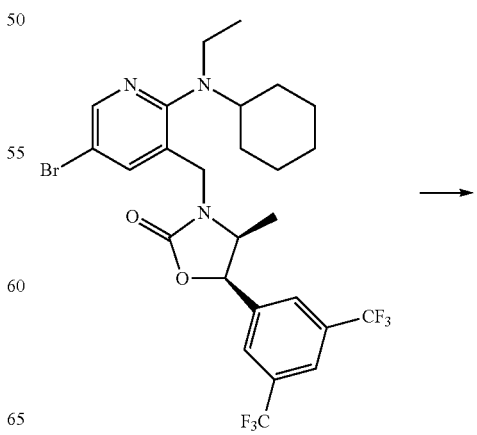

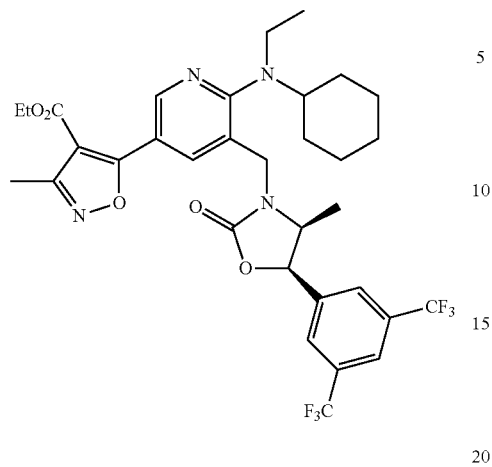

The same procedure as in Example 66 was repeated, with the exception that ethyl 5-bromo-3-methylisoxazole-4-carboxylate was used instead of 1-methyl-5-iodo-tetrazole, to afford the title compound (15 mg, 15%).

$^1$H NMR (400 MHz, CDCl$_3$) 8.69 (d, 1H), 7.88 (s, 2H), 7.82 (s, 1H), 7.75 (s, 1H), 5.69 (d, 1H), 4.71 (d, 1H), 4.42 (m, 2H), 4.15 (m, 1H), 3.92 (m, 1H), 3.70 (m, 1H), 3.50 (m, 1H), 2.40 (s, 3H), 1.82 (m, 10H), 1.43 (t, 3H), 0.94 (t, 3H), 0.66 (d, 3H).

Example 75

(4S,5R)-5-[3,5-bis(trifluoromethyl)phenyl]-4-methyl-3-({[2-(ethyl)(cyclohexyl)amino]-5-(2-methyl-furan-5-yl)pyridin-3-yl}methyl)-oxazolidin-2-one

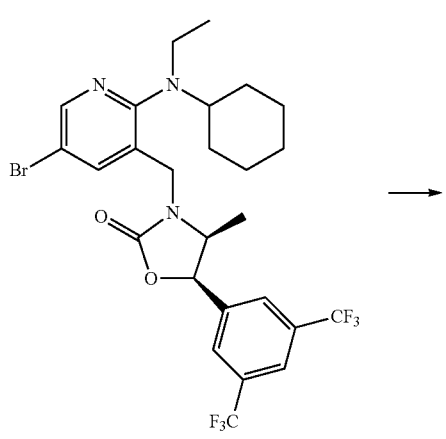

(4S,5R)-5-[3,5-bis(trifluoromethyl)phenyl]-4-methyl-3-({5-bromo-2-[cyclohexyl(ethyl)amino]pyridin-3-yl}methyl)-oxazolidin-2-one, prepared in step 4 of Example 54, and 5-methyl-2-(4,4,5,5-tetramethyl-1,3,2-dioxaborolan-2-yl)-furan were used in the same manner as in Example 45 to afford the title compound (30 mg, 15%).

$^1$H NMR (400 MHz, CDCl$_3$) 8.56 (d, 1H), 7.87 (s, 1H), 7.83 (d, 1H), 7.75 (s, 2H), 6.54 (d, 1H), 6.08 (d, 1H), 5.71 (d, 1H), 4.78 (d, 1H), 4.39 (d, 1H), 3.90 (m, 1H), 3.55 (m, 1H), 3.07 (m, 1H), 2.73 (m, 1H), 1.82-1.05 (m, 10H), 0.93 (t, 3H), 0.68 (d, 3H).

Example 76 t-butyl 2-{5-({(4S,5S)-5-[3,5-bis(trifluoromethyl)phenyl]-4-methyl-2-oxo-oxazolidin-3-yl}methyl)-6-[(cyclohexyl)(ethyl)amino]pyridin-3-yl}-1H-pyrrole-1-carboxylate

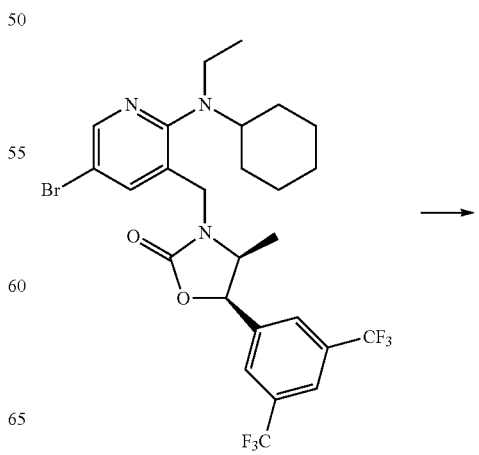

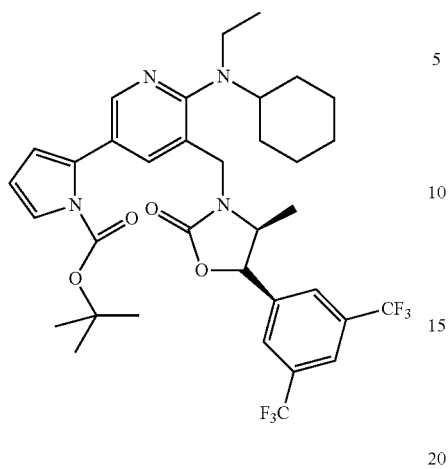

(4S,5R)-5-[3,5-bis(trifluoromethyl)phenyl]-4-methyl-3-({5-bromo-2-[cyclohexyl(ethyl)amino]pyridin-3-yl}methyl)-oxazolidin-2-one, prepared in step 4 of Example 54, and t-butyl 2-(4,4,5,5-tetramethyl-1,3,2-dioxaborolan-2-yl)-1H-pyrrole-1-carboxylate were used in the same manner as in Example 45 to afford the title compound (350 mg, 47%).

$^1$H NMR (400 MHz, CDCl$_3$) 8.27 (s, 1H), 7.87 (s, 1H), 7.75 (s, 2H), 7.72 (s, 1H), 7.38 (m, 1H), 6.26 (m, 1H), 5.77 (d, 1H), 4.88 (d, 1H), 4.32 (d, 1H), 3.99 (m, 1H), 3.62 (m, 1H), 3.05 (m, 1H), 2.73 (m, 1H), 1.90 (m, 10H), 1.48 (s, 9H), 097 (t, 3H), 0.68 (d, 3H).

Example 77

(4S,5R)-5-[3,5-bis(trifluoromethyl)phenyl]-4-methyl-3-({[2-(ethyl)(cyclohexyl)amino]-5-(thiophen-3-yl)pyridin-3-yl}methyl)-oxazolidin-2-one

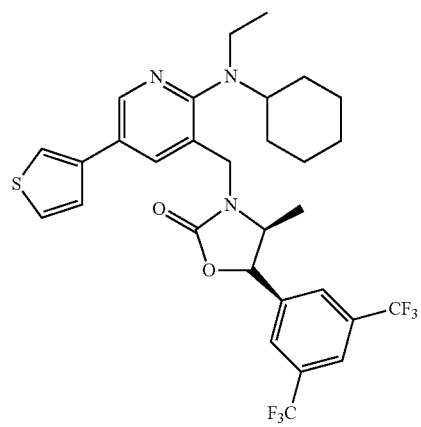

The same procedure as in Example 66 was repeated, with the exception that thiophene-3-boronic acid was used instead of 1-methyl-5-iodo-tetrazole, to afford the title compound (130 mg, 64%).

$^1$H NMR (400 MHz, CDCl$_3$) 8.56 (s, 1H), 7.87 (s, 1H), 7.82 (s, 1H), 7.74 (s, 2H), 7.46 (m, 2H), 7.37 (d, 1H), 5.69 (d, 1H), 4.79 (d, 1H), 4.40 (d, 1H), 3.91 (m, 1H), 3.57 (m, 1H), 3.09 (m, 1H), 2.78 (m, 1H), 1.89-1.06 (m, 10H), 0.95 (t, 3H), 0.69 (d, 3H).

Example 78

(4S,5R)-5-[3,5-bis(trifluoromethyl)phenyl]-4-methyl-3-({[2-(ethyl)(cyclohexyl)amino]-5-(3-methyl-thiophen-2-yl)pyridin-3-yl}methyl)-oxazolidin-2-one

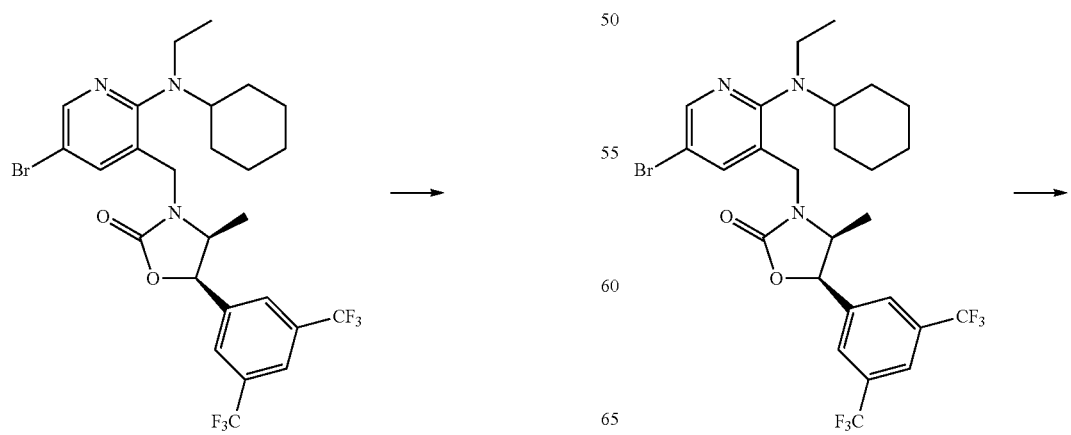

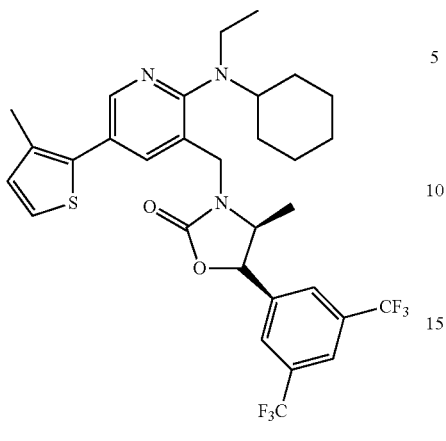

(4S,5R)-5-[3,5-bis(trifluoromethyl)phenyl]-4-methyl-3-({5-bromo-2-[cyclohexyl(ethyl)amino]pyridin-3-yl}methyl)-oxazolidin-2-one, prepared in step 4 of Example 54, and 3-methyl-2-(4,4,5,5-tetramethyl-1,3,2-dioxaborolan-2-yl)-1H-thiophene were used in the same manner as in Example 45 to afford the title compound (110 mg, 53%).

¹H NMR (400 MHz, CDCl₃) 8.41 (d, 1H), 7.88 (s, 1H), 7.75 (s, 2H), 7.71 (s, 1H), 7.26 (d, 1H), 6.97 (d, 1H), 5.70 (d, 1H), 4.79 (d, 1H), 4.38 (d, 1H), 3.94 (m, 1H), 3.58 (m, 1H), 3.11 (m, 1H), 2.78 (m, 1H), 2.35 (s, 3H), 1.72-1.07 (m, 10H), 0.96 (t, 3H), 0.70 (d, 3H).

(4S,5R)-5-[3,5-bis(trifluoromethyl)phenyl]-4-methyl-3-({5-bromo-2-[cyclohexyl(ethyl)amino]pyridin-3-yl}methyl)-oxazolidin-2-one, prepared in step 4 of Example 54, and 2-methyl-5-(4,4,5,5-tetramethyl-1,3,2-dioxaborolan-2-yl)-thiophenyl were used in the same manner as in Example 45 to afford the title compound (30 mg, 42%).

¹H NMR (400 MHz, CDCl₃) 8.52 (d, 1H), 7.87 (s, 1H), 7.77 (d, 1H), 7.75 (s, 2H), 7.09 (s, 1H), 6.89 (s, 1H), 5.70 (d, 1H), 4.78 (d, 1H), 4.37 (d, 1H), 3.93 (m, 1H), 3.58 (m, 1H), 3.10 (m, 1H), 2.78 (m, 1H), 1.89-1.02 (m, 10H), 0.94 (t, 3H), 0.68 (d, 3H).

Example 79

(4S,5R)-5-[3,5-bis(trifluoromethyl)phenyl]-4-methyl-3-({[2-(ethyl)(cyclohexyl)amino]-5-(2-methyl-thiophen-5-yl)pyridin-3-yl}methyl)-oxazolidin-2-one Example 80

(4S,5R)-5-[3,5-bis(trifluoromethyl)phenyl]-4-methyl-3-({[2-(ethyl)(cyclohexyl)amino]-5-(thiophen-2-yl)pyridin-3-yl}methyl)-oxazolidin-2-one

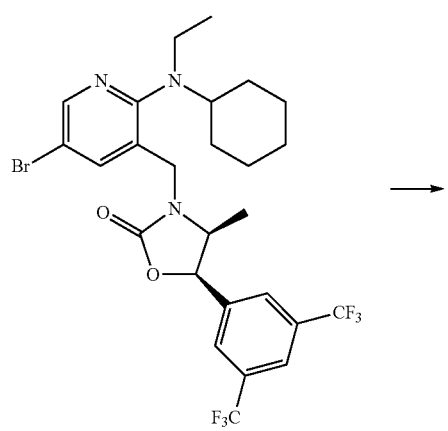

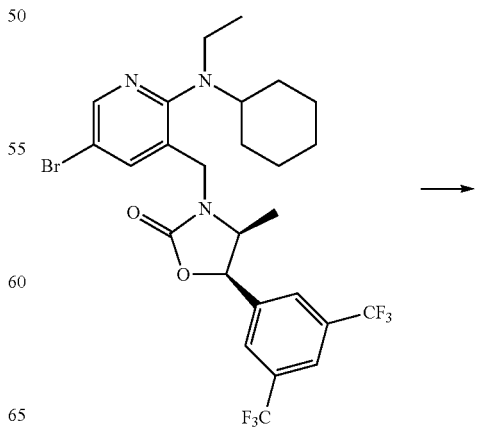

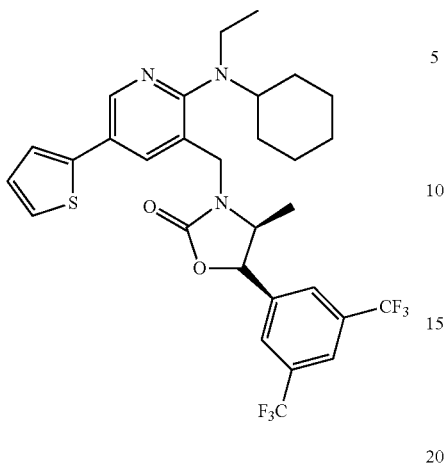

(4S,5R)-5-[3,5-bis(trifluoromethyl)phenyl]-4-methyl-3-({5-bromo-2-[cyclohexyl(ethyl)amino]pyridin-3-yl}methyl)-oxazolidin-2-one, prepared in step 4 of Example 54, and tributyl(thiophen-2-yl)stannane were used in the same manner as in Example 50 to afford the title compound (33 mg, 16%). 2¹H NMR (400 MHz, CDCl₃) 8.56 (d, 1H), 7.87 (s, 1H), 7.81 (d, 1H), 7.75 (d, 2H), 7.33 (d, 1H), 7.29 (d, 1H), 7.13 (t, 1H), 5.70 (d, 1H), 4.78 (d, 1H), 4.38 (d, 1H), 3.94 (m, 1H), 3.57 (m, 1H), 3.12 (m, 1H), 2.79 (m, 1H), 1.89-1.069 (m, 10H), 0.95 (t, 3H), 0.69 (d, 3H).

Example 81

(4S,5R)-5-[3,5-bis(trifluoromethyl)phenyl]-4-methyl-3-({[2-(ethyl)(cyclohexyl)amino]-5-(thiazol-4-yl)pyridin-3-yl}methyl)-oxazolidin-2-one

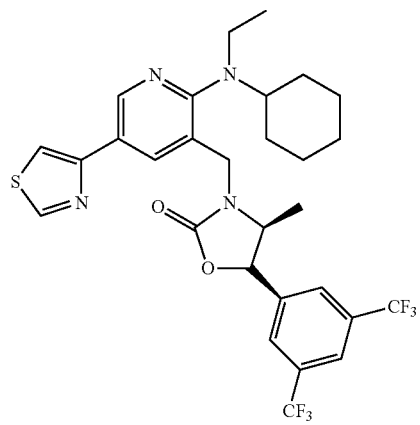

The same procedure as in Example 66 was repeated, with the exception that 4-bromothiazole was used instead of 1-methyl-5-iodo-tetrazole, to afford the title compound (85 mg, 45%). ¹H NMR (400 MHz, CDCl₃) 8.91 (d, 1H), 8.83 (d, 1H), 8.17 (d, 1H), 7.87 (s, 1H), 7.75 (s, 2H), 7.54 (d, 1H), 5.72 (d, 1H), 4.82 (d, 1H), 4.40 (d, 1H), 3.94 (m, 1H), 3.59 (m, 1H), 3.12 (m, 1H), 2.83 (m, 1H), 1.90 (m, 4H), 1.46 (m, 2H), 1.34 (m, 2H), 1.16 (m, 2H), 0.96 (t, 3H), 0.68 (d, 3H).

Example 82

3-{5-({(4S,5S)-5-[3,5-bis(trifluoromethyl)phenyl]-4-methyl-2-oxo-oxazolidin-3-yl}methyl)-6-[(cyclohexyl)(ethyl)amino]pyridin-3-yl}-thiophene-2-carbonitrile

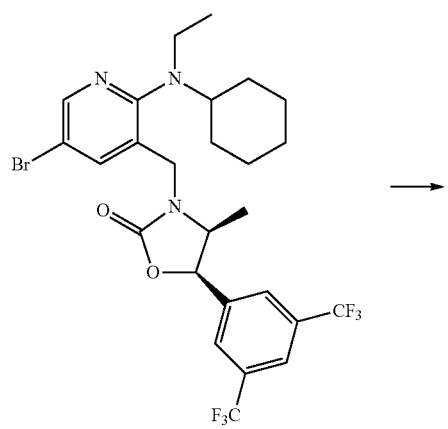

→

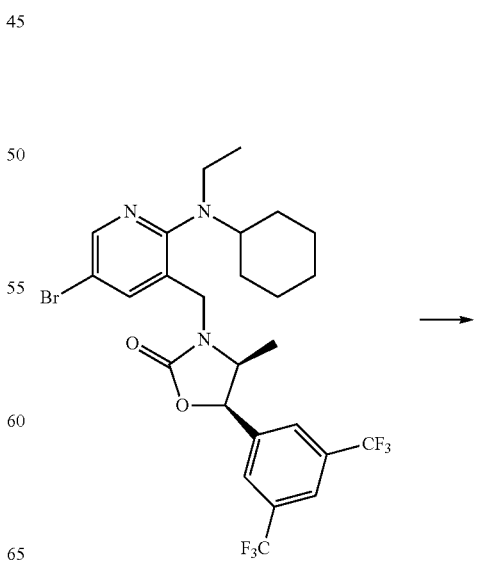

→

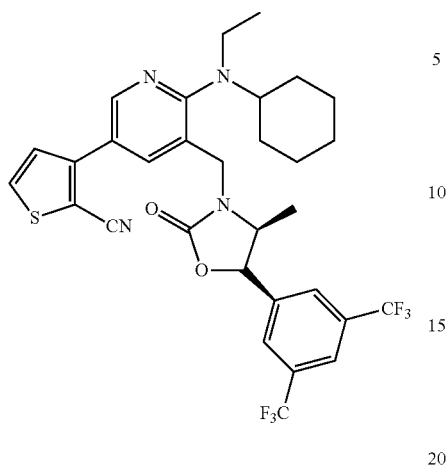

The same procedure as in Example 66 was repeated, with the exception that 3-bromo-2-cyanothiophene was used instead of 1-methyl-5-iodo-tetrazole, to afford the title compound (80 mg, 38%).

$^1$H NMR (400 MHz, CDCl$_3$) 8.45 (s, 1H), 8.07 (s, 1H), 7.86 (s, 1H), 7.81 (s, 2H), 7.68 (d, 1H), 7.30 (d, 1H), 6.06 (d, 1H), 4.88 (d, 1H), 4.32 (d, 1H), 4.12 (m, 1H), 3.65 (m, 1H), 3.06 (m, 1H), 2.85 (m, 1H), 1.95-1.13 (m, 10H), 1.11 (m, 3H), 0.67 (d, 3H).

Example 83 t-butyl 4-[5-({(4S,5S)-5-[3,5-bis(trifluoromethyl)phenyl]-4-methyl-2-oxo-oxazolidin-3-yl}methyl)-6-[cyclohexyl(ethyl)amino]pyridin-3-yl]-5-methylisoxazol-3-yl-carbamate (4S,5R)-5-[3,5-bis(trifluoromethyl)phenyl]-4-methyl-3-({5-bromo-2-[cyclohexyl(ethyl)amino]pyridin-3-yl}methyl)-oxazolidin-2-one, prepared in step 4 of Example 54, and t-butyl 5-methyl-4-(4,4,5,5-tetramethyl-1,3,2-dioxaborolan-2-yl)-isoxazol-3-yl-carboxylate were used in the same manner as in Example 45 to afford the title compound (50 mg, 16%).

$^1$H NMR (400 MHz, CDCl$_3$) 8.35 (d, 1H), 7.88 (s, 1H), 7.75 (s, 2H), 7.65 (d, 1H), 5.70 (d, 1H), 4.76 (d, 1H), 4.37 (d, 1H), 3.96 (m, 1H), 3.57 (m, 1H), 3.15 (m, 1H), 2.81 (m, 1H), 2.07 (s, 3H), 2.48 (s, 3H), 1.89-1.07 (m, 10H), 0.96 (t, 3H), 0.69 (d, 3H).

Example 84

(4S,5R)-5-[3,5-bis(trifluoromethyl)phenyl]-4-methyl-3-({[2-(ethyl)(cyclohexyl)amino]-5-(2,4-dimethyl-thiazol-5-yl)pyridin-3-yl}methyl)-oxazolidin-2-one

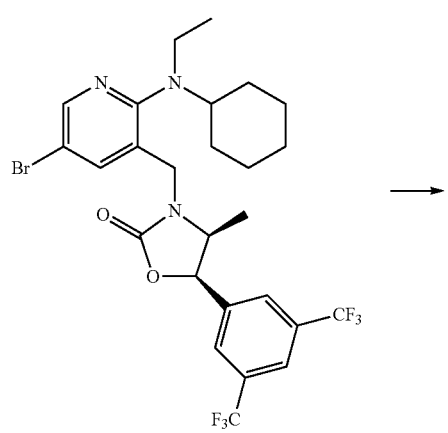 →

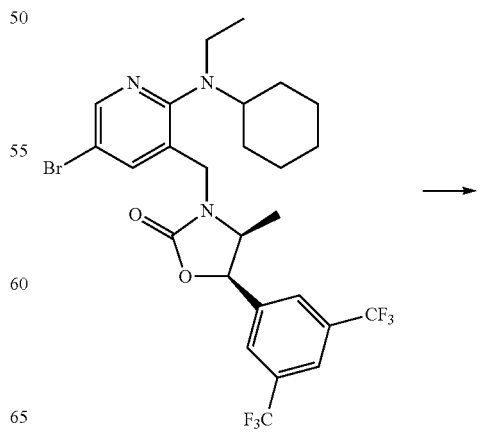 →

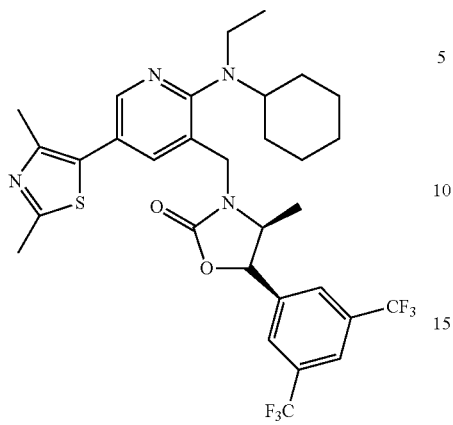

(4S,5R)-5-[3,5-bis(trifluoromethyl)phenyl]-4-methyl-3-({5-bromo-2-[cyclohexyl(ethyl)amino]pyridin-3-yl}methyl)-oxazolidin-2-one, prepared in step 4 of Example 54, and 2,4-dimethyl-5-(4,4,5,5-tetramethyl-1,3,2-dioxaborolan-2-yl)-thiazole were used in the same manner as in Example 45 to afford the title compound (70 mg, 33%).

$^1$H NMR (400 MHz, CDCl$_3$) 8.35 (d, 1H), 7.88 (s, 1H), 7.75 (s, 2H), 7.65 (d, 1H), 5.70 (d, 1H), 4.76 (d, 1H), 4.37 (d, 1H), 3.96 (m, 1H), 3.57 (m, 1H), 3.15 (m, 1H), 2.81 (m, 1H), 2.07 (s, 3H), 2.48 (s, 3H), 1.89-1.07 (m, 10H), 0.96 (t, 3H), 0.69 (d, 3H).

Example 85

(4S,5R)-5-[3,5-bis(trifluoromethyl)phenyl]-4-methyl-3-({[2-(ethyl)(cyclohexyl)amino]-5-(3-amino-5-methyl-isoxazol-4-yl)pyridin-3-yl}methyl)-oxazolidin-2-one

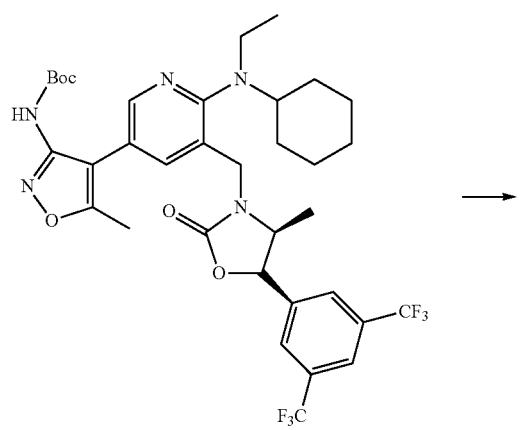

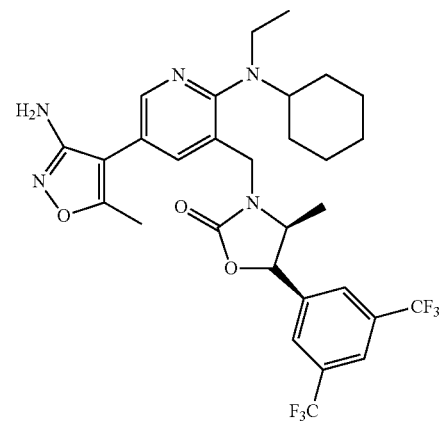

t-Butyl 4-[5-({(4S,5S)-5-[3,5-bis(trifluoromethyl)phenyl]-4-methyl-2-oxo-oxazolidin-3-yl}methyl)-6-[cyclohexyl(ethyl)amino]pyridin-3-yl]-5-methylisoxazol-3-yl-carbamate of Example 83 was used in the same manner as in Example 28 to afford the title compound (30 mg, 50%).

$^1$H NMR (400 MHz, CDCl$_3$) 8.28 (d, 1H), 7.89 (s, 1H), 7.75 (s, 2H), 7.65 (d, 1H), 5.72 (d, 1H), 4.74 (d, 1H), 4.37 (d, 1H), 3.99 (m, 4H), 3.56 (m, 1H), 3.13 (m, 1H), 2.79 (m, 1H), 2.39 (s, 1H), 1.89-1.04 (m, 10H), 0.96 (t, 3H), 0.72 (d, 3H).

Example 86

(4S,5R)-5-[3,5-bis(trifluoromethyl)phenyl]-4-methyl-3-({[2-(ethyl)(cyclohexyl)amino]-5-(3-methyl-thiophen-4-yl)pyridin-3-yl}methyl)-oxazolidin-2-one

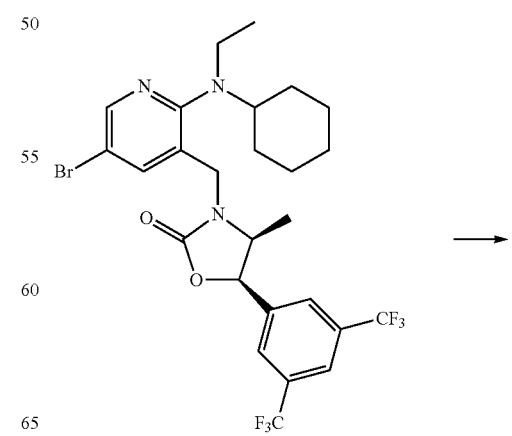

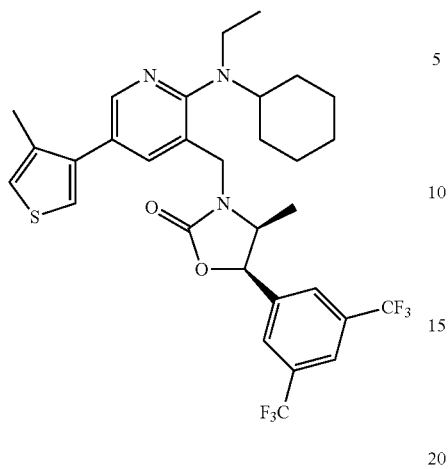

The same procedure as in Example 66 was repeated, with the exception that 3-bromo-4-methylthiophene was used instead of 1-methyl-5-iodo-tetrazole to afford the title compound (40 mg, 19%).

$^1$H NMR (400 MHz, CDCl$_3$) 8.36 (d, 1H), 7.87 (s, 1H), 7.74 (s, 1H), 7.68 (d, 1H), 7.25 (d, 1H), 7.08 (d, 1H), 5.69 (d, 1H), 4.78 (d, 1H), 4.40 (d, 1H), 3.94 (m, 1H), 3.57 (m, 1H), 3.11 (m, 1H), 2.77 (m, 1H), 2.31 (s, 3H), 1.90-1.01 (m, 10H), 0.96 (t, 3H), 0.70 (d, 3H).

The same procedure as in Example 66 was repeated, with the exception that 4-bromo-3-methylisothiazole was used instead of 1-methyl-5-iodo-tetrazole to afford the title compound (70 mg, 34%).

$^1$H NMR (400 MHz, CDCl$_3$) 8.53 (s, 1H), 8.35 (d, 1H), 7.88 (s, 1H), 7.74 (s, 2H), 7.69 (d, 1H), 5.69 (d, 1H), 4.78 (d, 1H), 4.40 (d, 1H), 3.97 (m, 1H), 3.57 (m, 1H), 3.16 (m, 1H), 2.82 (m, 1H), 2.58 (s, 3H), 1.90-1.08 (m, 10H), 0.97 (t, 3H), 0.71 (d, 3H).

Example 87

(4S,5R)-5-[3,5-bis(trifluoromethyl)phenyl]-4-methyl-3-({[2-(ethyl)(cyclohexyl)amino]-5-(3-methyl-isothioxazol-4-yl)pyridin-3-yl}methyl)-oxazolidin-2-one

Example 88

(4S,5R)-5-[3,5-bis(trifluoromethyl)phenyl]-4-methyl-3-({[2-(ethyl)(cyclohexyl)amino]-5-(pyrrolidin-1-yl)pyridin-3-yl}methyl)-oxazolidin-2-one

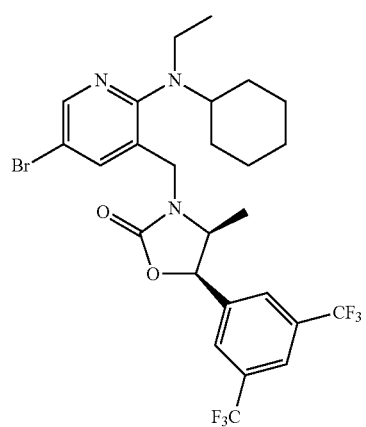 →

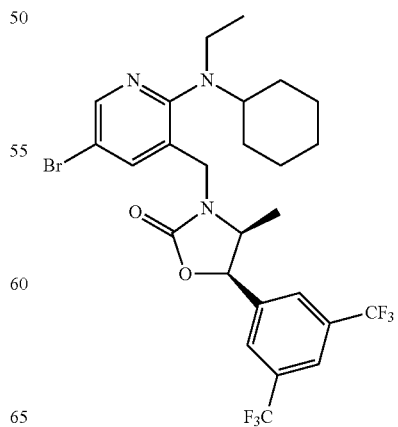 →

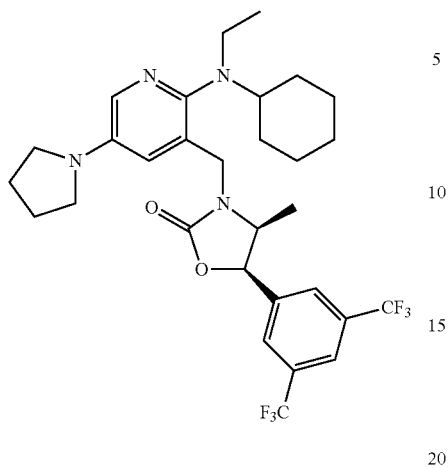

(4S,5R)-5-[3,5-bis(trifluoromethyl)phenyl]-4-methyl-3-({5-bromo-2-[cyclohexyl(ethyl)amino]pyridin-3-yl}methyl)-oxazolidin-2-one, prepared in step 4 of Example 54, and pyrrolidine were used in the same manner as in Example 41 to afford the title compound (60 mg, 60%).

$^1$H NMR (400 MHz, CDCl$_3$) 7.88 (s, 1H), 7.76 (s, 3H), 6.84 (s, 1H), 5.66 (d, 1H, J=7.6 Hz), 4.67 (d, 1H, J=15.2 Hz), 4.49 (d, 1H, J=16.0 Hz), 3.97 (m, 1H), 3.28 (s, 4H), 3.00 (m, 1H), 2.64 (m, 1H), 2.03 (s, 4H), 1.60~1.83 (m, 5H), 0.98~1.38 (m, 6H), 0.84 (m, 3H), 0.72 (m, 3H).

Example 89

(4S,5R)-5-[3,5-bis(trifluoromethyl)phenyl]-4-methyl-3-({[2-(ethyl)(cyclohexyl)amino]-5-(2-methyl-pyrrolidin-1-yl)pyridin-3-yl}methyl)-oxazolidin-2-one

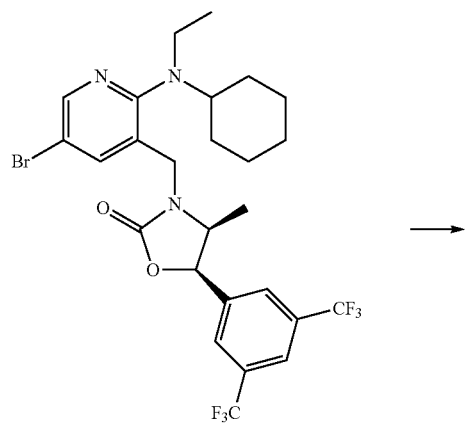

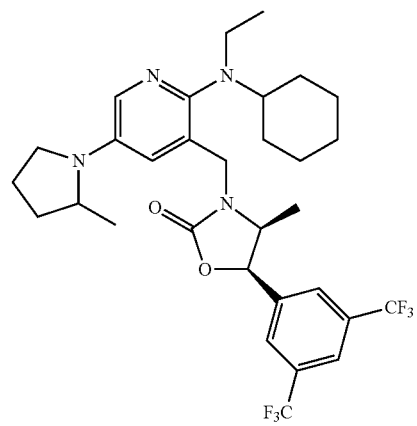

(4S,5R)-5-[3,5-bis(trifluoromethyl)phenyl]-4-methyl-3-({5-bromo-2-[cyclohexyl(ethyl)amino]pyridin-3-yl}methyl)-oxazolidin-2-one, prepared in step 4 of Example 54, and 2-methyl pyrrolidine were used in the same manner as in Example 41 to afford the title compound (110 mg, 50%).

$^1$H NMR (400 MHz, CDCl$_3$) 7.87 (s, 1H), 7.76~7.78 (m, 3H), 6.85 (s, 1H), 5.68 (m, 1H), 4.67 (d, 1H, J=15.6 Hz), 4.49 (m, 1H), 3.98 (m, 1H), 3.85 (m, 1H), 3.43 (m, 1H), 3.30 (m, 1H), 3.13 (m, 1H), 3.00 (m, 1H), 2.64 (m, 1H), 1.02~2.07 (m, 14H), 1.18 (d, 3H, J=7.2 Hz), 0.85 (m, 3H), 0.73 (d, 3H, J=6.0 Hz)

Example 90

(4S,5R)-5-[3,5-bis(trifluoromethyl)phenyl]-4-methyl-3-({[2-(ethyl)(cyclohexyl)amino]-5-(2-ethyl-pyrrolidin-1-yl)pyridin-3-yl}methyl)-oxazolidin-2-one

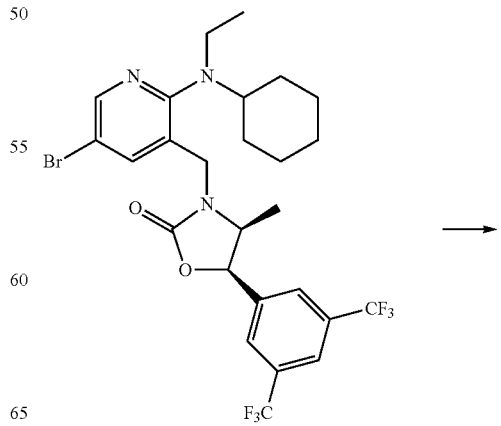

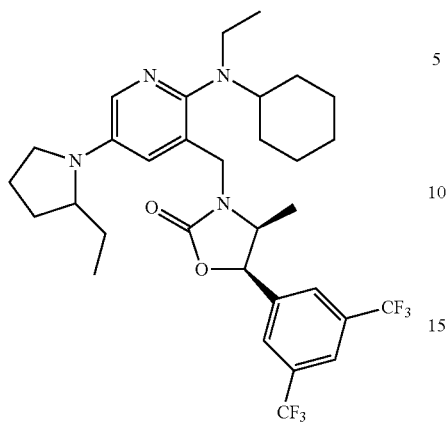

The same procedure as in Example 88 was repeated, with the exception that 2-ethyl pyrrolidine was used instead of pyrrolidine, to afford the title compound (30 mg, 15%).

¹H NMR (400 MHz, CDCl₃) 7.88 (s, 1H), 7.76 (s, 3H), 6.84 (s, 1H), 5.69 (dd, 1H), 4.69 (d, 1H), 4.50 (dd, 1H), 3.99 (m, 1H), 3.54 (m, 1H), 3.43 (m, 1H), 3.30 (m, 1H), 3.11 (m, 1H), 3.01 (m, 1H), 2.64 (m, 1H), 2.00 (m, 4H), 1.85 (m, 6H), 1.32 (m, 4H), 0.96 (m, 3H), 0.87 (t, 3H), 0.74 (d, 3H).

Example 91

(4S,5R)-5-[3,5-bis(trifluoromethyl)phenyl]-4-methyl-3-({[2-(ethyl)(cyclohexyl)amino]-5-(3,3-difluoro-pyrrolidin-1-yl)pyridin-3-yl}methyl)-oxazolidin-2-one

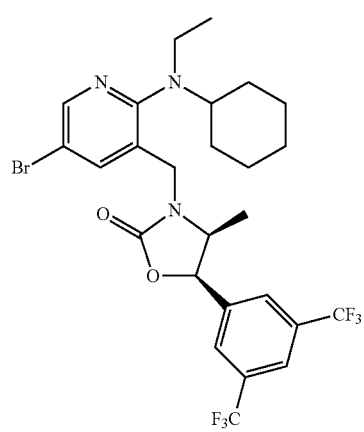

→

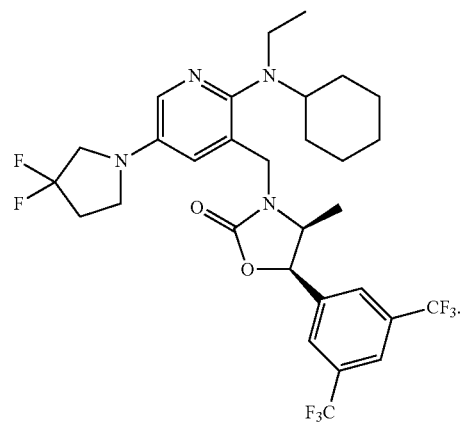

(4S,5R)-5-[3,5-bis(trifluoromethyl)phenyl]-4-methyl-3-({5-bromo-2-[cyclohexyl(ethyl)amino]pyridin-3-yl}methyl)-oxazolidin-2-one, prepared in step 4 of Example 54, and 3,3-difluoro pyrrolidine were used in the same manner as in Example 41 to afford the title compound (110 mg, 50%).

¹H NMR (400 MHz, CDCl₃) 7.88 (s, 1H), 7.76 (m, 3H), 6.90 (d, 1H), 5.68 (d, 1H), 4.68 (d, 1H), 4.50 (d, 1H), 3.99 (m, 1H), 3.70 (t, 2H), 3.55 (m, 2H), 3.36 (m, 1H), 3.05 (m, 1H), 2.66 (m, 1H), 2.56 (m, 2H), 1.83 (m, 6H), 1.42-1.00 (m, 4H), 0.88 (t, 3H), 0.73 (d, 3H).

Example 92

(4S,5R)-5-[3,5-bis(trifluoromethyl)phenyl]-4-methyl-3-({[2-(ethyl)(cyclohexyl)amino]-5-(2-(trifluoromethyl)-pyrrolidin-1-yl)pyridin-3-yl}methyl)-oxazolidin-2-one

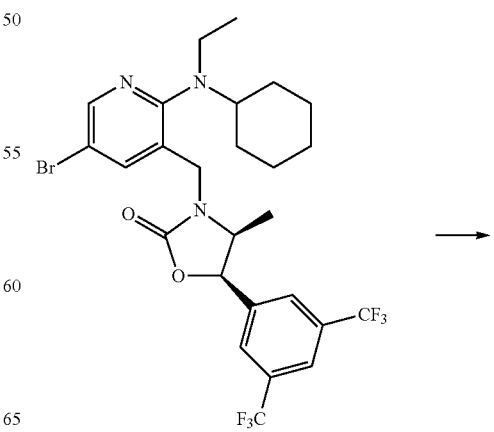

→

-continued

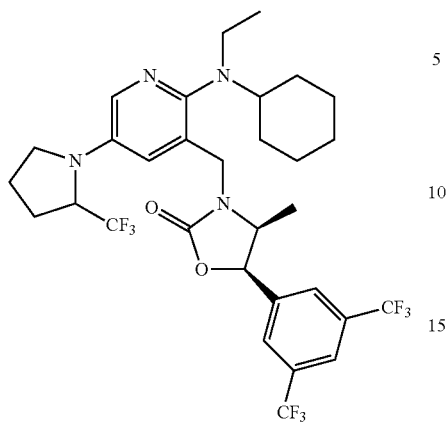

The same procedure as in Example 88 was repeated, with the exception that 2-trifluoromethyl pyrrolidine was used instead of pyrrolidine to afford the title compound (140 mg, 70%).

$^1$H NMR (400 MHz, CDCl$_3$) 7.94 (d, 1H, major), 7.91 (d, 1H, minor), 7.88 (s, 1H), 7.76 (s, 2H), 7.75 (s, 1H), 5.70 (d, 1H, major), 5.64 (d, 1H, minor), 4.72 (m, 1H), 4.50 (m, 1H), 4.20 (m, 1H), 4.04 (m, 1H), 3.92 (m, 1H, minor), 3.72 (m, 1H), 3.41 (m, 1H, minor), 3.31 (m, 2H), 3.11 (m, 1H), 2.98 (m, 1H, minor), 2.67 (m, 1H), 2.29 (m, 4H), 1.82 (m, 5H), 1.44 (m, 5H), 0.91 (m, 3H), 0.69 (d, 3H).

Example 93

3-[5-({(4S,5R)-5-[3,5-bis(trifluoromethyl)phenyl]-4-methyl-2-oxo-oxazolidin-3-yl}methyl)-6-[(cyclohexyl)(ethyl)amino]pyridin-3-yl]-1,2,4-oxadiazol-5(H)-one

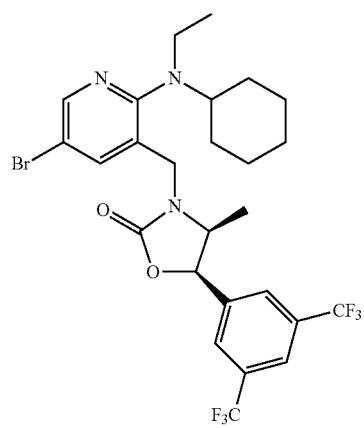

-continued

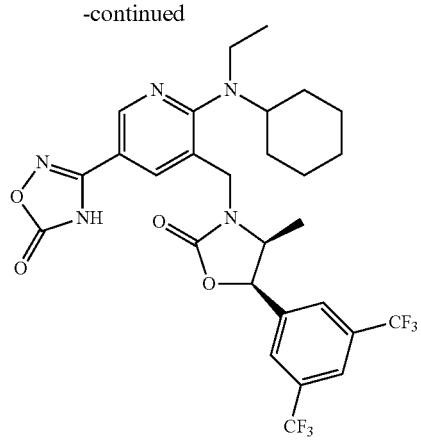

[Step 1] Preparation of (Z)-5-({(4S,5R)-5-[3,5-bis(trifluoromethyl)phenyl]-4-methyl-2-oxooxazolidin-3-yl}methyl)-6-[cyclohexyl(ethyl)amino]-N'-hydroxynicotinamide To a solution of 5-({4S,5R)-5-[3,5-bis(trifluoromethyl)phenyl]-4-methyl-2-oxo-1,3-oxazolidin-3-yl}methyl)-6-[(cyclohexyl)(ethyl)amino]nicotinonitrile (200 mg, 0.36 mmol) of Example 54 in IPA (2 ml) was added 20 equivalents of a 50% ammonia solution. Stirring at 80° C. for 24 hrs was followed by extraction with ethyl acetate. The organic layer thus formed was dried, filtered, and concentrated at a reduced pressure. The residue was purified by chromatography to afford the title compound (110 mg, 45%).

$^1$H NMR (400 MHz, CDCl$_3$) 8.51 (s, 1H), 7.88 (s, 2H), 7.77 (s, 2H), 5.78 (d, 1H, J=7.6 Hz), 4.93 (s, 2H), 4.77 (d, 1H, J=15.6 Hz), 4.27 (d, 1H, J=15.2 Hz), 3.86 (m, 1H), 3.56 (m, 1H), 3.04 (m, 1H), 2.78 (m, 1H), 1.60~1.88 (m, 6H), 1.26 (m, 2H), 1.10 (m, 2H), 0.90 (m, 3H), 0.64 (m, 3H).

[Step 2] Preparation of 3-[5-({(4S,5R)-5-[3,5-bis(trifluoromethyl)phenyl]-4-methyl-2-oxooxazolidin-3-yl}methyl)-6-[cyclohexyl(ethyl)amino]pyridin-3-yl]-1,2,4-oxadiazol-5(4H)-one

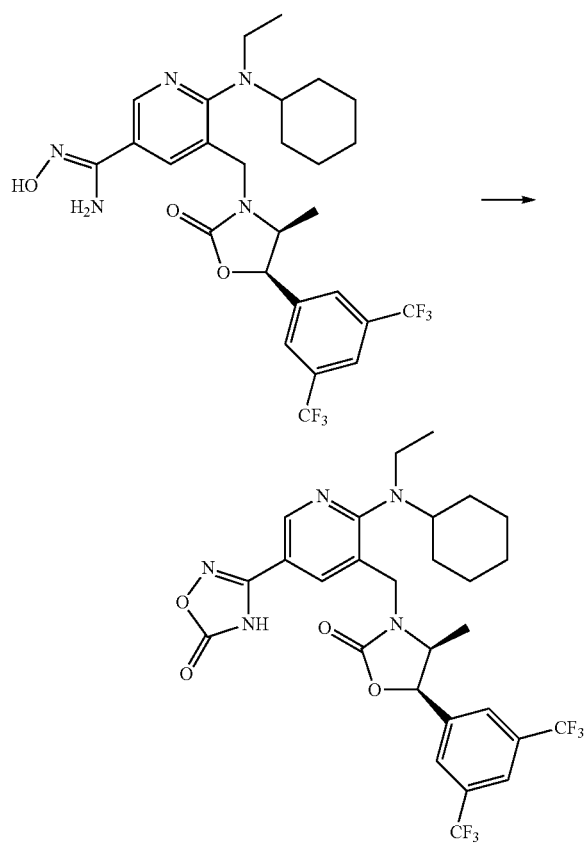

To a solution of (Z)-5-({(4S,5R)-5-[3,5-bis(trifluoromethyl)phenyl]-4-methyl-2-oxooxazolidin-3-yl}methyl)-6-[cyclohexyl(ethyl)amino]-N'-hydroxynicotinamide of step 1 in dichloromethane (2 m) l was dropwise added CDI (carbonyl diimidazole) (61.6 mg, 0.38 mmol), followed by stirring at 80° C. for 2 hrs. The reaction mixture was cooled to room temperature, and quenched with water. Extraction was performed with dichloromethane. The organic layer thus formed was dried over anhydrous magnesium sulfate, filtered, and concentrated at a reduced pressure. The residue was purified by chromatography to afford the title compound (71 mg, 62%).

$^1$H NMR (400 MHz, CDCl$_3$) 8.61 (s, 1H), 7.89 (s, 2H), 7.76 (s, 2H), 5.73 (d, 1H, J=8.4 Hz), 5.23 (s, 1H), 4.75 (d, 1H, J=14.8 Hz), 4.26 (d, 1H, J=14.2 Hz), 3.90 (m, 1H), 3.59 (m, 1H), 3.12 (m, 1H), 2.85 (m, 1H), 1.51~1.84 (m, 6H), 1.26 (m, 2H), 1.23 (m, 2H), 0.94 (m, 3H), 0.65 (d, 3H, J=6.4 Hz).

Example 94

(4S,5R)-5-[3,5-bis(trifluoromethyl)phenyl]-4-methyl-3-{[2-(cyclohexylamino)-5-(3,5-dimethyl-isoxazol-4-yl)pyrazin-3-yl]methyl}-oxazolidin-2-one

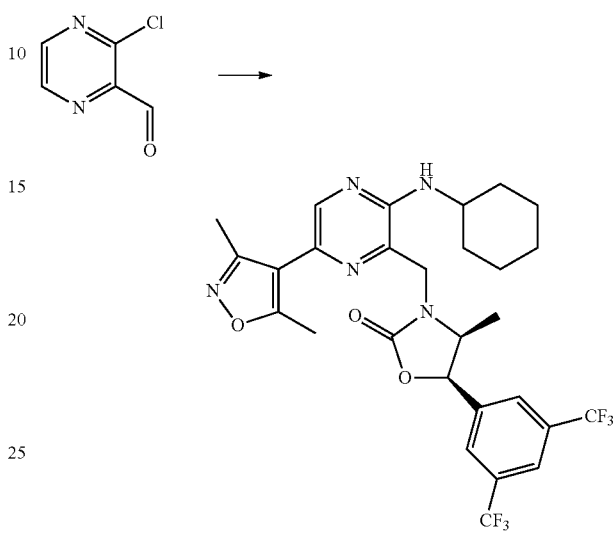

[Step 1] Preparation of (3-chloropyrazin-2-yl)methanol

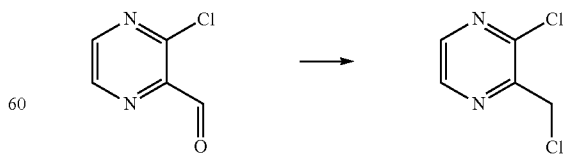

To a solution of 3-chloropyrazine-2-carbaldehyde (700 mg, 4.91 mmol) in methanol (10 ml) was dropwise NaBH$_4$ (223 mg, 5.89 mmol). The reaction mixture was stirred at room temperature for 1 hr, and the reaction was terminated with a saturated aqueous ammonium solution, followed by extraction with ethyl acetate. The organic layer was dried over anhydrous magnesium sulfate, filtered, and concentrated in a vacuum.

[Step 2] Preparation of 2-chloro-3-(chloromethyl)pyrazine

To (3-chloropyrazin-2-yl)methanol of step 1 was dropwise added a solution of SOCl$_2$ (700 mg, 5.89 mmol) in DMF (10 ml) at 0° C. Stirring at 0° C. for 30 min was followed by extraction with ethyl acetate. The organic layer was washed with a saturated NaHCO₃ solution, dried over anhydrous magnesium sulfate, filtered, and concentrated in a vacuum. The residue was used in a subsequent step without further purification.

[Step 3] Preparation of (4S,5S)-5-[3,5-bis(trifluoromethyl)phenyl]-4-methyl-3-[(3-chloropyrazin-2-yl)methyl]-oxazolidin-2-one

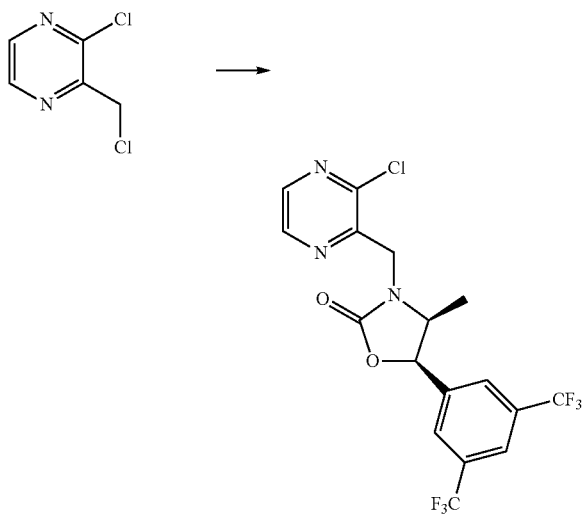

To a solution of (4S,5R)-5-[3,5-bis(trifluoromethyl)phenyl]-4-methyloxazolidin-2-one (1.84 g, 5.89 mmol) in DMF (10 ml) was dropwise added NaHMDS (5.4 ml, 5.4 mmol) at −40° C. After being stirred for 30 min, the reaction mixture was slowly added with drops of a dilution of 2-chloro-3-(chloromethyl)pyrazine, obtained in step 2, in DMF (10 ml). The resulting reaction mixture was warmed to room temperature, stirred for 3 hrs, diluted with ethyl acetate (200 ml), and quenched with water (200 ml). The organic layer was washed with water, dried over anhydrous magnesium sulfate, filtered, and concentrated in a vacuum. The residue was purified by chromatography to afford the title compound (900 mg, 35%).

¹H NMR (400 MHz, CDCl₃) 8.51 (d, 1H), 8.36 (d, 1H), 7.90 (s, 1H), 7.83 (s, 2H), 5.85 (d, 1H), 5.05 (d, 1H), 4.50 (d, 1H), 4.45 (m, 1H), 0.81 (d, 3H).

[Step 4] Preparation of (4S,5S)-5-[3,5-bis(trifluoromethyl)phenyl]-4-methyl-3-{[3-(cyclohexylamino)pyrazin-2-yl]methyl}-oxazolidin-2-one

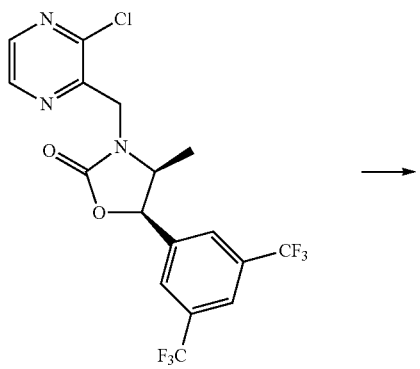

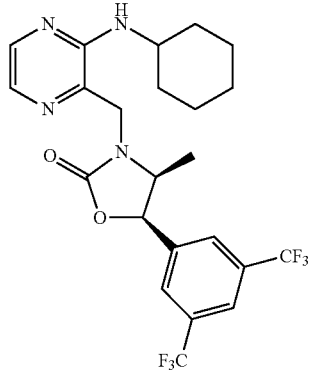

To (4S,5S)-5-[3,5-bis(trifluoromethyl)phenyl]-4-methyl-3[(3-chloropyrazin-2-yl)methyl]-oxazolidin-2-one (910 mg, 2.07 mmol) of step 3 was added cyclohexylamine (1 ml, 8.28 mmol), and the reaction mixture was stirred at 100° C. for 4 hrs. After cooling, chromatographic purification afforded the title compound (650 mg, 75%).

¹H NMR (400 MHz, CDCl₃) 7.97 (s, 1H), 7.87 (s, 1H), 7.70 (s, 2H), 7.60 (d, 1H), 5.82 (d, 1H), 5.69 (d, 1H), 4.68 (d, 1H), 4.32 (d, 1H), 4.14 (m, 1H), 3.89 (m, 1H), 2.03 (m, 2H), 1.76 (m, 2H), 1.61-1.24 (m, 6H), 0.79 (d, 3H).

[Step 5] Preparation of (4S,5S)-5-[3,5-bis(trifluoromethyl)phenyl]-4-methyl-3-{[6-bromo-3-(cyclohexylamino)pyrazin-2-yl]methyl}-oxazolidin-2-one

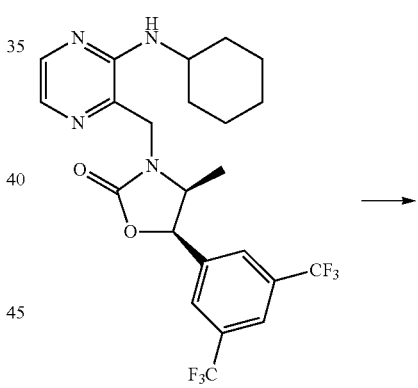

To a solution of (4S,5S)-5-[3,5-bis(trifluoromethyl)phenyl]-4-methyl-3-{[3-(cyclohexylamino)pyrazin-2-yl]methyl}-oxazolidin-2-one (300 mg, 0.6 mmol) of step 4 in DMF (3 ml) was dropwise added NBS (N-bromo succinic imide) (128 mg, 0.72 mmol) at 0° C. The reaction mixture was stirred for 2 hrs and quenched with water. Extraction afforded the title compound (370 mg, 92%).

$^1$H NMR (400 MHz, CDCl$_3$) 8.06 (s, 1H), 7.90 (s, 1H), 7.72 (s, 2H), 6.01 (d, 1H), 5.73 (d, 1H), 4.63 (d, 1H), 4.32 (d, 1H), 4.23 (m, 1H), 3.85 (m, 1H), 2.06 (m, 10H), 0.83 (d, 3H).

[Step 6] Preparation of (4S,5R)-5-[3,5-bis(trifluoromethyl)phenyl]-4-methyl-3-{[2-(cyclohexylamino)-5-(3,5-dimethyl-isoxazol-4-yl)pyrazin-3-yl]methyl}-oxazolidin-2-one

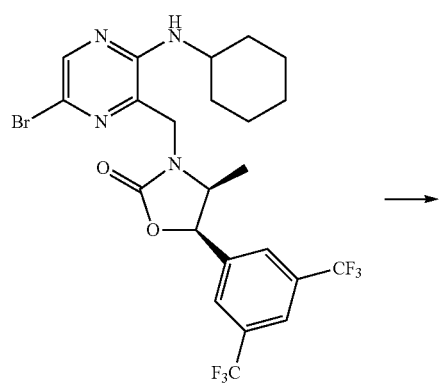

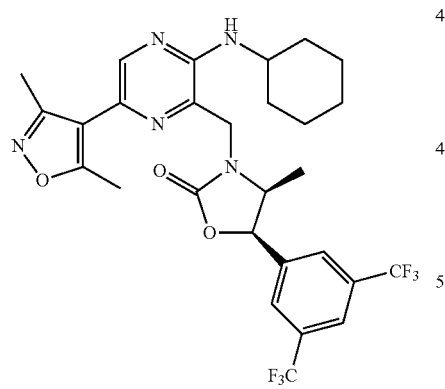

(4S,5S)-5-[3,5-bis(trifluoromethyl)phenyl]-4-methyl-3-{[6-bromo-3-(cyclohexylamino)pyrazin-2-yl]methyl}-oxazolidin-2-one and 3,5-dimethyl-4-(4,4,5,5-tetramethyl-1,3,2-dioxaborolan-2-yl)-isoxazole were used in the same manner as in Example 45 to afford the title compound (340 mg, 72%).

$^1$H NMR (400 MHz, CDCl$_3$) 8.06 (s, 1H), 7.90 (s, 1H), 7.72 (s, 2H), 6.02 (bd, 1H), 5.73 (d, 1H), 475 (d, 1H), 4.35 (d, 1H), 4.22 (m, 1H), 3.94 (m, 1H), 2.50 (s, 3H), 2.36 (s, 3H), 2.10 (m, 2H), 1.83 (m, 2H), 1.68 (m, 2H), 1.49 (m, 4H), 0.88 (d, 3H).

Example 95

(4S,5R)-5-[3,5-bis(trifluoromethyl)phenyl]-4-methyl-3-({[2-(methyl)(cyclohexyl)amino]-5-(3,5-dimethyl-isoxazol-4-yl)pyrazin-3-yl}methyl)-oxazolidin-2-one

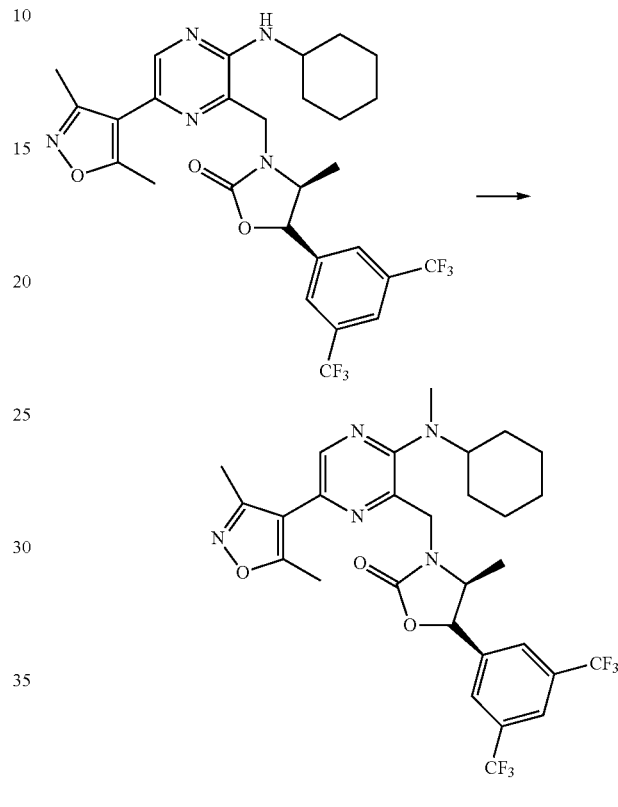

(4S,5R)-5-[3,5-bis(trifluoromethyl)phenyl]-4-methyl-3-{[2-(cyclohexylamino)-5-(3,5-dimethyl-isoxazol-4-yl)pyrazin-3-yl]methyl}-oxazolidin-2-one of Example 94, and methyl iodide were used in the same manner as in Example 6 to afford the title compound (5 mg, 4%).

$^1$H NMR (400 MHz, CDCl$_3$) 8.20 (s, 1H), 7.89 (s, 1H), 7.74 (2H), 5.69 (d, 1H), 5.01 (d, 1H), 4.24 (d, 1H), 4.18 (m, 1H), 3.32 (m, 1H), 2.85 (s, 3H), 2.61 (s, 3H), 2.47 (s; 3H), 1.89-1.12 (m, 10H), 0.74 (d, 3H).

Example 96

(4S,5R)-5-[3,5-bis(trifluoromethyl)phenyl]-4-methyl-3-({[2-(ethyl)(cyclohexyl)amino]-5-(3,5-dimethyl-isoxazol-4-yl)pyrazin-3-yl}methyl)-oxazolidin-2-one

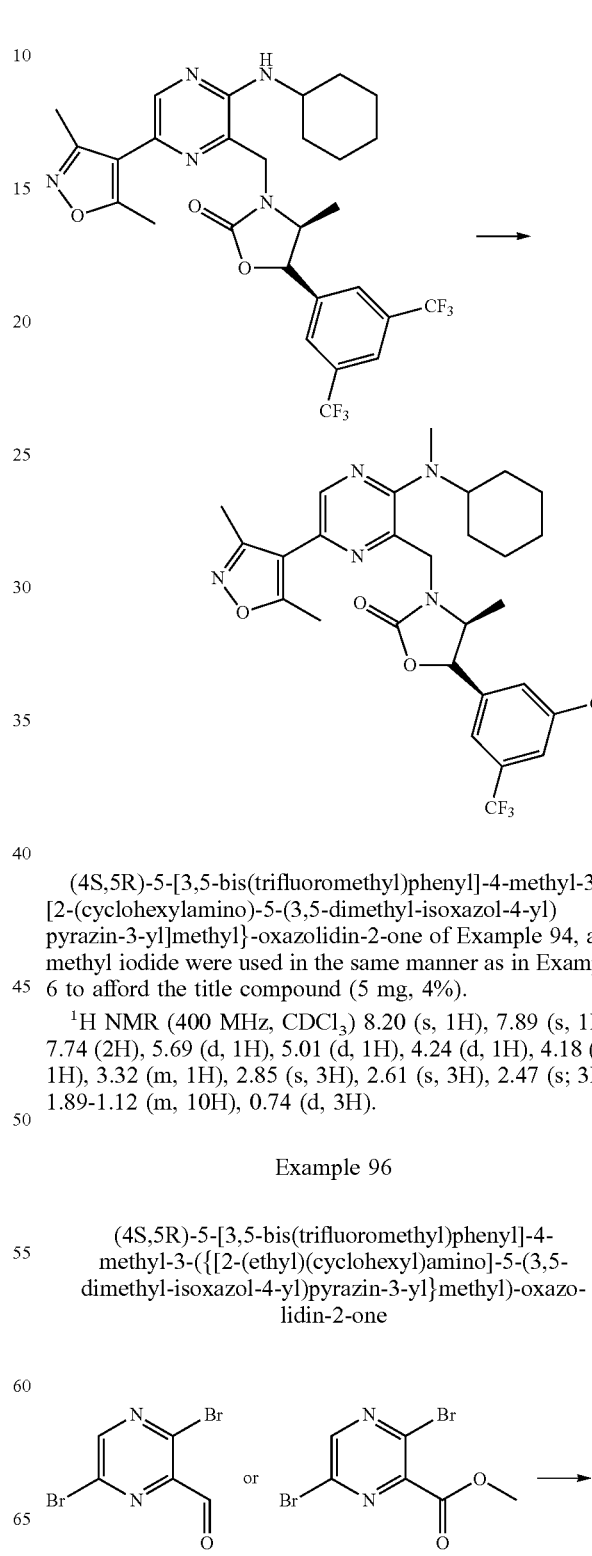

-continued

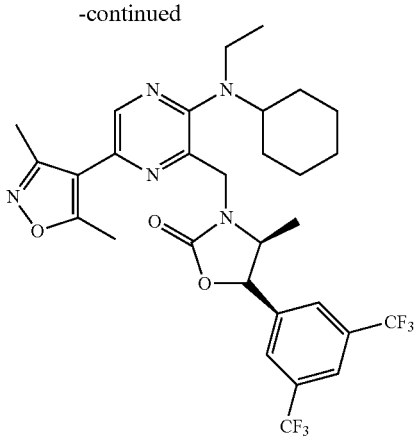

Method 1

[Step 1] Preparation of 6-bromo-3-[cyclohexyl (ethyl)amino]pyrazine-2-carbaldehyde

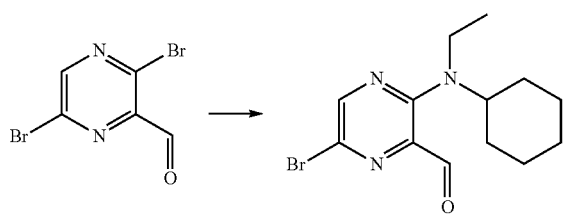 [SMILES: O=Cc1nc(Br)cnc1Br ; CCN(c1ncc(Br)nc1C=O)C1CCCCC1]

To a solution of 2,5-dibromopyrazine carbaldehyde (300 mg, 1.13 mmol) in toluene (6 ml) were dropwise added $K_2CO_3$ (314 mg, 2.26 mmol) and N-ethyl-N-cyclohexylamine (0.26 ml, 1.69 mmol). The reaction mixture was stirred at 60° C. for 10 min and then cooled to room temperature. After concentration in a vacuum, the residue was purified by chromatography to afford the title compound (80 mg, 23%).

$^1$H NMR (400 MHz, CDCl$_3$) 9.85 (s, 1H), 8.18 (s, 1H),3.87 (m 1H), 3.58 (m 2H), 1.88 (m, 2H), 1.68 (m, 4H), 1.36 (m 2H), 1.03 (t, 3H).

[Step 2] Preparation of {6-bromo-3-[cyclohexyl (ethyl)amino]pyrazin-2-yl}methanol

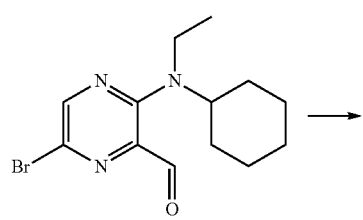

To a solution of 6-bromo-3-[cyclohexyl(ethyl)amino] pyrazine-2-carbaldehyde (80 mg, 0.26 mmol) of step 1 in methanol (1 ml) was dropwise added NaBH$_4$ (30 mg, 0.79 mmol). The reaction mixture was stirred at room temperature for 30 min, and extracted with ethyl acetate. The extract was purified by chromatography to afford the title compound (40 mg, 50%).

$^1$H NMR (400 MHz, CDCl$_3$) 8.23 (s, 1H), 4.64 (s, 2H), 3.31 (q, 2H), 3.07 (m, 1H), 1.81~1.42 (m, 8H), 1.17 (m, 2H), 1.03 (t, 3H).

[Step 3] Preparation of 5-bromo-3-(chloromethyl)-N-cyclohexyl-N-ethylpyrazine-2-amine

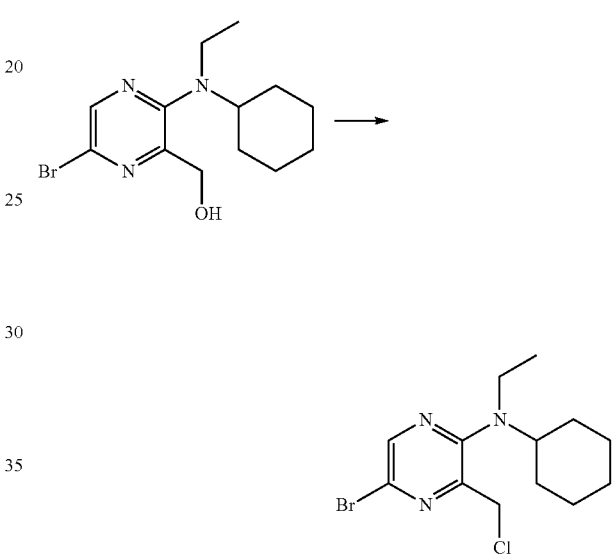

To a solution of {6-bromo-3-[cyclohexyl(ethyl)amino] pyrazin-2-yl}methanol (40 mg, 0.127 mmol) in DMF (1 ml) was dropwise added SOCl$_2$ (18 mg, 0.153 mmol). The reaction mixture was stirred at room temperature for 30 min, quenched with water, and then extracted with ethyl acetate. The organic layer thus formed was dried over anhydrous magnesium sulfate, filtered, and concentrated in a vacuum. The concentrate was used in a subsequent step without further purification.

[Step 4] Preparation of (4S,5R)-5-[3,5-bis(trifluoromethyl)phenyl]-3-({6-bromo-3-[cyclohexyl(ethyl) amino]pyrazin-2-yl}methyl)-4-methyl-oxazolidin-2-one

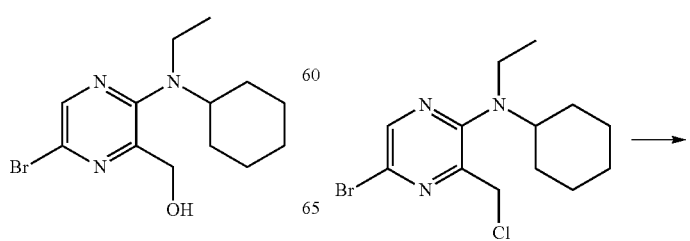

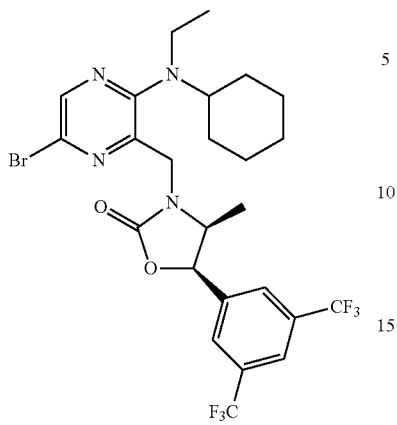

The same procedure as in step 4 of Example 54 was repeated, with the exception that 5-bromo-3-(chloromethyl)-N-cyclohexyl-N-ethylpyrazine-2-amine was used instead of 5-bromo-3-(chloromethyl)-N-cyclohexyl-N-ethylpyridine-2-amine, to afford the title compound (150 mg, 80%).

$^1$H NMR (400 MHz, CDCl$_3$) 8.23 (s, 1H), 7.89 (s, 1H), 7.79 (s, 1H), 5.82 (d, 1H), 4.91 (d, 1H), 4.28 (m, 1H), 4.21 (d, 1H), 3.42 (m, 1H), 3.23 (m, 1H), 3.03 (m, 1H), 1.83 (m, 10H), 0.96 (t, 3H), 0.72 (d, 3H).

[Step 5] Preparation of (4S,5R)-5-[3,5-bis(trifluoromethyl)phenyl]-4-methyl-3-({[2-(ethyl)(cyclohexyl)amino]-5-(3,5-dimethyl-isoxazol-4-yl)pyrazin-3-yl}methyl)-oxazolidin-2-one

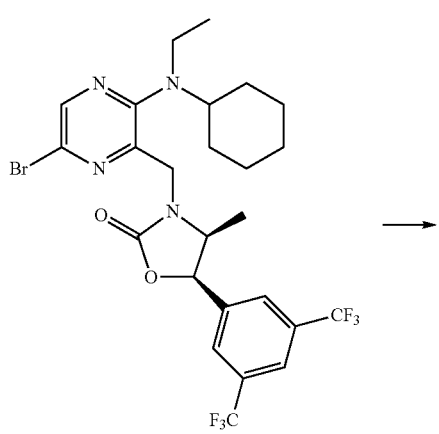

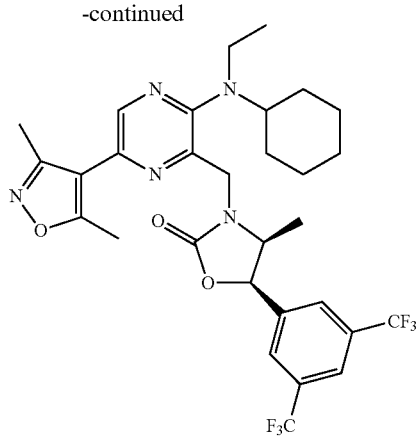

The same procedure as in Example 58 was repeated, with the exception that (4S,5R)-5-[3,5-bis(trifluoromethyl)phenyl]-3-({6-bromo-3-[cyclohexyl(ethyl)amino]pyrazin-2-yl}methyl)-4-methyl-oxazolidin-2-one was used instead of (4S,5R)-5-[3,5-bis(trifluoromethyl)phenyl]-4-methyl-3-({5-bromo-2-[cyclohexyl(ethyl)amino]pyridin-3-yl}methyl)-oxazolidin-2-one, to afford the title compound 5 (30 mg, 70%) $^1$H NMR (400 MHz, CDCl$_3$) $^1$H NMR (400 MHz, CDCl$_3$) 8.27 (s, 1H), 7.89 (s, 1H), 7.74 (s, 2H), 5.69 (d, 1H), 4.96 (d, 1H), 4.14 (m, 1H), 3.54 (m, 1H), 3.22 (m, 1H), 3.04 (m, 1H), 2.64 (s, 3H), 2.50 (m, 3H), 1.91-1.45 (m, 10H), 1.00 (t, 3H), 0.72 (d, 3H).

Method 2

[Step 1] Preparation of methyl 6-bromo-3-[cyclohexyl(ethyl)amino]pyrazine-2-carboxylate

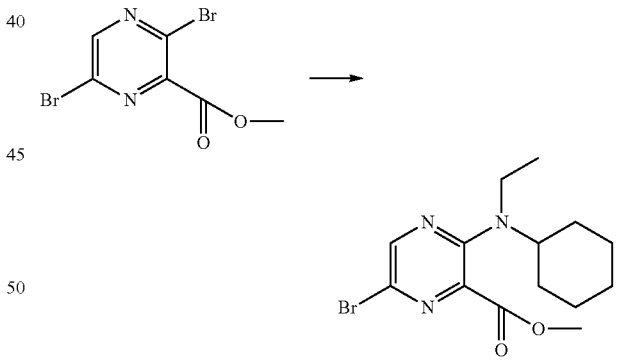

To a solution of methyl 2,5-dibromo pyrazine carboxylate (40 g, 135 mmol) in toluene (300 ml) were dropwise added K$_2$CO$_3$ (28 g, 202 mmol) and N-ethyl-N-cyclohexylamine (35 g, 270 mmol). The reaction mixture was refluxed at 120° C. for 3 with stirring, and then cooled to room temperature. After extraction with ethyl acetate, the organic layer thus formed was washed with 2N HCl and further with water. Then, the organic layer was dried over anhydrous magnesium sulfate, filtered and concentrated in a vacuum to afford the title compound (46 g, 99%).

$^1$H NMR (400 MHz, CDCl$_3$) 8.15 (s, 1H), 3.92 (s, 3H), 3.50 (3H), 1.81 (m, 4H), 1.66 (m, 2H), 1.57 (m, 2H), 1.28 (m 2H), 1.12 (t, 3H).

[Step 2] Preparation of methyl 3-[cyclohexyl(ethyl)amino]-6-(3,5-dimethylisoxazol-4-yl)pyrazine-2-carboxylate

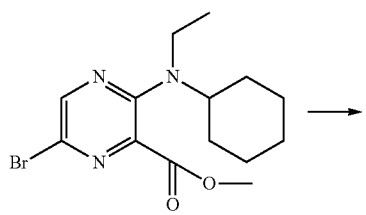

Methyl 6-bromo-3-[cyclohexyl(ethyl)amino]pyrazine-2-carboxylate of step 1 and 3,5-dimethyl-4-(4,4,5,5-tetramethyl-1,3,2-dioxaborolan-2-yl)-isoxazole were used in the same manner as in Example 45 to afford the title compound (33 g, 68%).

¹H NMR (400 MHz, CDCl₃) 8.15 (s, 1H), 3.96 (s, 3H), 3.54 (m, 3H), 2.49 (s, 3H), 2.39 (s, 3H), 1.85 (m, 4H), 1.67 (m, 2H), 1.59 (m, 2H), 1.31 (m, 2H), 1.16 (t, 3H).

[Step 3] Preparation of {6-bromo-3-[cyclohexyl(ethyl)amino]pyrazin-2-yl}methanol

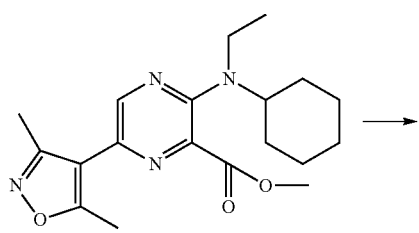

To a solution of methyl 3-[cyclohexyl(ethyl)amino]-6-(3,5-dimethylisoxazol-4-yl)pyrazine-2-carboxylate (4.0 g, 11.16 mmol) of step 2 in ethylether (50 ml) were dropwise methanol (1 ml) and 2M LiBH₄ (12.3 ml, 24.6 mmol) at 0° C. One hour later, methanol (1 ml) and LiBH₄ (12.3 ml, 24.6 mmol) were added again. The reaction mixture was also added with methanol (30 ml) and then with NaBH₄ (422 mg, 11.26 mmol), and stirred for 30 min at room temperature. The reaction was terminated with a saturated aqueous ammonium solution, followed by extraction with ethyl acetate. The organic layer thus formed was dried over anhydrous magnesium sulfate, filtered, and concentrated in a vacuum. The residue was purified by chromatography to afford the title compound (2.5 g, 68%).

¹H NMR (400 MHz, CDCl₃) 8.18 (s, 1H), 4.71 (s, 2H), 4.34 (s, 1H, exchangeable proton), 3.39 (q, 2H), 3.19 (m, 1H), 2.58 (s, 3H), 2.44 (s, 3H), 1.81 (m, 4H), 1.68 (m, 4H), 1.31 (m, 2H), 1.03 (t, 3H).

[Step 4] Preparation of (4S,5R)-5-[3,5-bis(trifluoromethyl)phenyl]-4-methyl-3-({[2-(ethyl)(cyclohexyl)amino]-5-(3,5-dimethyl-isoxazol-4-yl)pyrazin-3-yl}methyl)-oxazolidin-2-one

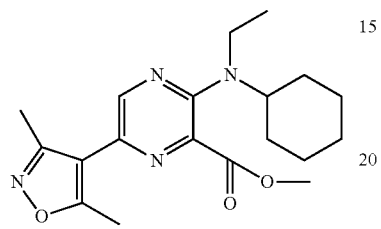

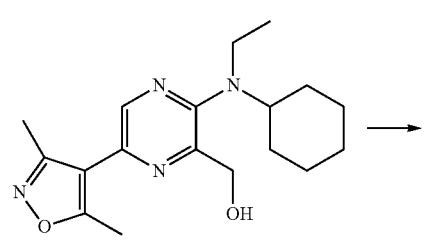

{6-Bromo-3-[cyclohexyl(ethyl)amino]pyrazin-2-yl}methanol of Step 3 was used in the same manner as in steps 3 and 4 of Example 7, with the exception that {3-[cyclohexyl(ethyl)amino]-6-(3,5-dimethylisoxazol-4-yl)pyrazin-2-yl}methanol was used instead of (2-[ethyl(tetrahydro-2H-pyran-4-yl)amino)-5-(trifluoromethyl)pyridin-3-yl) methanol, to afford the title compound (5.0 g, 70%).

¹H NMR (400 MHz, CDCl₃) 8.27 (s, 1H), 7.89 (s, 1H), 7.74 (s, 2H), 5.69 (d, 1H), 4.96 (d, 1H), 4.14 (m, 1H), 3.54 (m, 1H), 3.22 (m, 1H), 3.04 (m, 1H), 2.64 (s, 3H), 2.50 (m, 3H), 1.91-1.45 (m, 10H), 1.00 (t, 3H), 0.72 (d, 3H).

Example 97

(4S,5R)-5-[3,5-bis(trifluoromethyl)phenyl]-3-({[2-(cyclopropyl)(cyclohexyl)amino]-5-(3,5-dimethyl-isoxazol-4-yl)pyrazin-3-yl}methyl)-4-methyloxazolidin-2-one

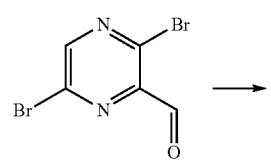

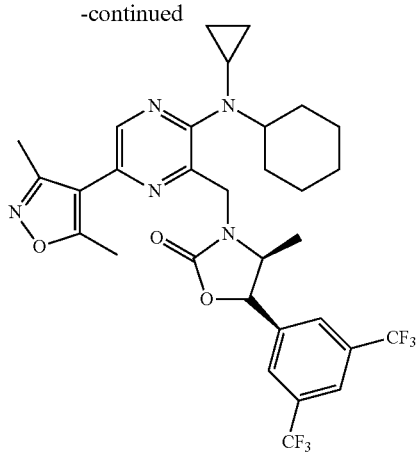

The same procedure as in method 1 of Example 96 was repeated, with the exception that N-cyclopropyl-N-cyclohexylamine was used instead of N-ethyl-N-cyclohexylamine, to afford the title compound (32 mg, 70%).

$^1$H NMR (400 MHz, CDCl$_3$) 8.28 (s, 1H), 7.89 (s, 1H), 7.78 (s, 2H), 5.80 (d, 1H), 4.95 (d, 1H), 4.33 (m, 1H), 4.18 (m, 1H), 3.10 (m, 1H), 2.74 (m, 1H), 1.81-1.13 (m, 14H), 0.74 (d, 3H).

Example 98

(4S,5S)-5-[3,5-bis(trifluoromethyl)phenyl]-3-{[6-(3,5-dimethylisoxazol-4-yl)-3-(piperidin-1-yl)pyrazin-2-yl]methyl}-4-methyloxazolidin-2-one

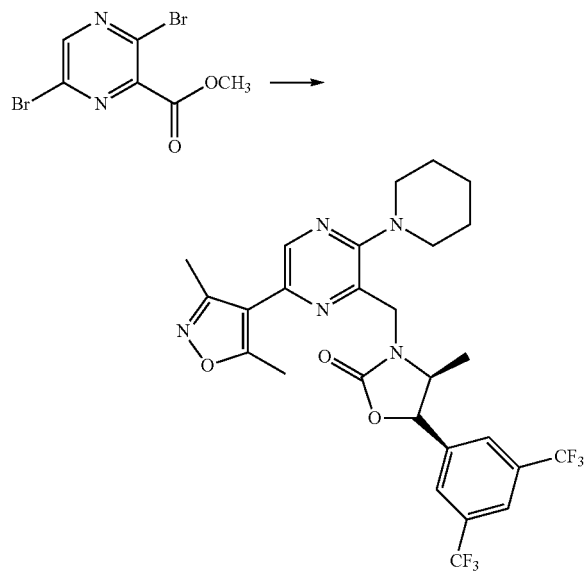

The same procedure as in method 2 of Example 96 was repeated, with the exception that piperidine was used instead of N-ethyl-N-cyclohexylamine, to afford the title compound (520 mg, 74%).

$^1$H NMR (400 MHz, CDCl$_3$) 8.24 (s, 1H), 7.89 (s, 1H), 7.75 (s, 2H), 5.71 (d, 1H), 5.03 (d, 1H), 4.29 (d, 1H), 4.23 (m, 1H), 3.24 (m, 2H), 3.16 (m, 2H), 2.60 (s, 3H), 2.46 (s, 3H), 1.80 (m, 6H), 0.77 (d, 3H).

Example 99

(4S,5S)-5-[3,5-bis(trifluoromethyl)phenyl]-3-{[6-(3,5-dimethylisoxazol-4-yl)-3-(2,6-dimethyl morpholino)pyrazin-2-yl]methyl}-4-methyloxazolidin-2-one

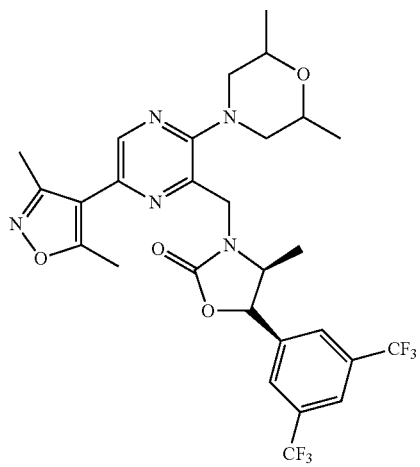

The same procedure as in method 2 of Example 96 was repeated, with the exception that 2,6-dimethylmorpholine was used instead of N-ethyl-N-cyclohexylamine to afford the title compound (510 mg, 71%).

$^1$H NMR (400 MHz, CDCl$_3$) 8.26 (s, 1H), 7.90 (s, 1H), 7.75 (s, 2H), 5.72 (d, 1H), 5.05 (d, 1H), 4.27 (m, 2H), 3.94 (m, 1H), 3.83 (m, 1H), 3.43 (dd, 2H), 2.84 (m, 1H), 2.68 (m, 3H), 2.46 (s, 3H), 1.27 (d, 6H), 0.73 (d, 3H).

Example 100

(4S,5S)-5-[3,5-bis(trifluoromethyl)phenyl]-3-{[6-(3,5-dimethylisoxazol-4-yl)-3-[3-(trifluoromethyl)piperidin-1-yl]pyrazin-2-yl]methyl}-4-methyloxazolidin-2-one

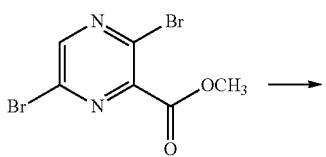

-continued

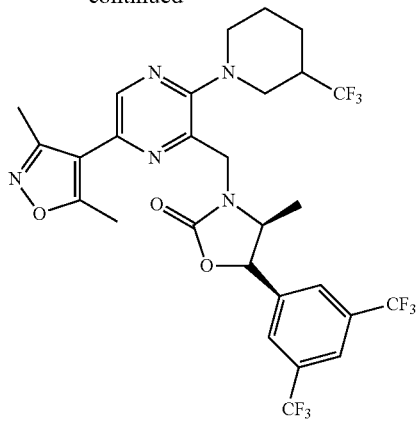

The same procedure as in method 2 of Example 96 was repeated, with the exception that 3-(2,2,2-trifluoromethyl)piperidine was used instead of N-ethyl-N-cyclohexylamine, to afford the title compound (50 mg, 48%).

¹H NMR (400 MHz, CDCl₃) 8.29 (s, 1H), 8.28 (s, 1H), 7.75 (s, 2H), 5.71 (d, 1H), 5.03 (d, 1H), 4.29 (m, 2H), 3.75 (m, 1H), 3.48 (m, 1H), 3.05 (m, 2H), 2.82 (m, 1H), 2.63 (m, 8H), 2.13 (m, 2H), 1.94 (m, 2H), 1.61 (m, 8H), 0.79 (m, 6H),

Example 101

(4S,5R)-5-[3,5-bis(trifluoromethyl)phenyl]-3-({[3-(cyclopentylmethyl)(ethyl)amino]-4-methyl 6-(3,5-dimethylisoxazol-4-yl)pyrazin-3-yl}methyl)-oxazolidin-2-one

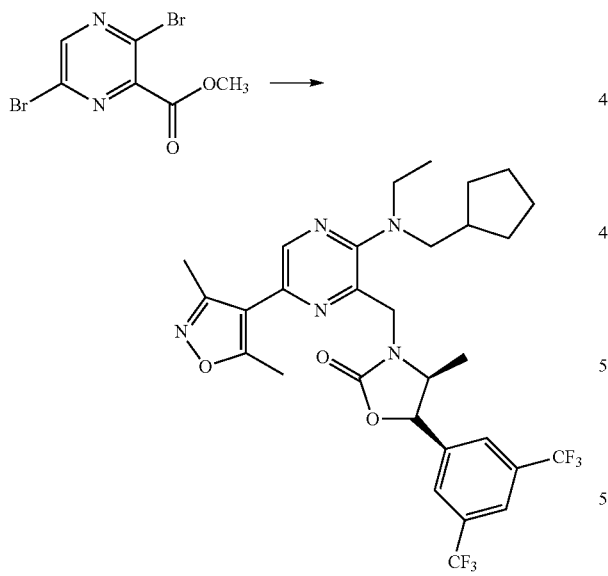

The same procedure as in step 2 of Example 96 was repeated, with the exception that N-(cyclopentylmethyl)ethaneamine was used instead of N-ethyl-N-cyclohexylamine, to afford the title compound (100 mg, 30%).

¹H NMR (400 MHz, CDCl₃) 8.24 (s, 1H), 7.89 (s, 1H), 7.74 (s, 2H), 5.70 (d, 1H), 4.99 (d, 1H), 4.30 (d, 1H), 4.18 (m, 1H), 3.40 (m, 2H), 3.12 (m, 1H), 2.62 (s, 3H), 2.48 (s, 3H), 2.14 (m, 1H), 1.68 (m, 8H), 1.17 (t, 3H), 0.73 (d, 3H).

Example 102 trans-4-({[3-({(4S,5S)-5-[3,5-bis(trifluoromethyl)phenyl]-4-methyl-2-oxazolidin-3-yl}methyl)-5-(3,5-dimethyloxazol-4-yl)pyrazin-2-yl]{[N-(ethyl)aminomethyl]cyclohexyl})acetic acid

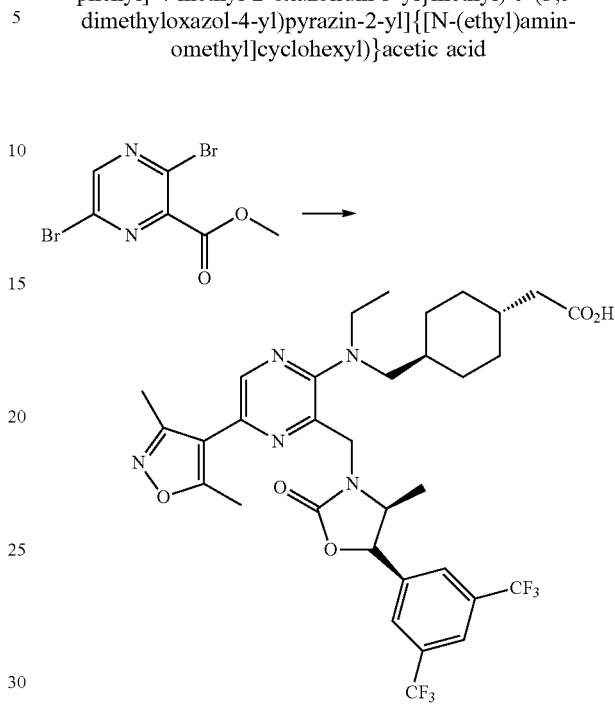

[Step 1] Preparation of ethyl trans-4-({[3-({(4S,5S)-5-[3,5-bis(trifluoromethyl)phenyl]-4-methyl-2-oxazolidin-3-yl}methyl)-5-bromo-pyrazin-2-yl]{[N-(ethyl)aminomethyl]cyclohexyl)}acetate

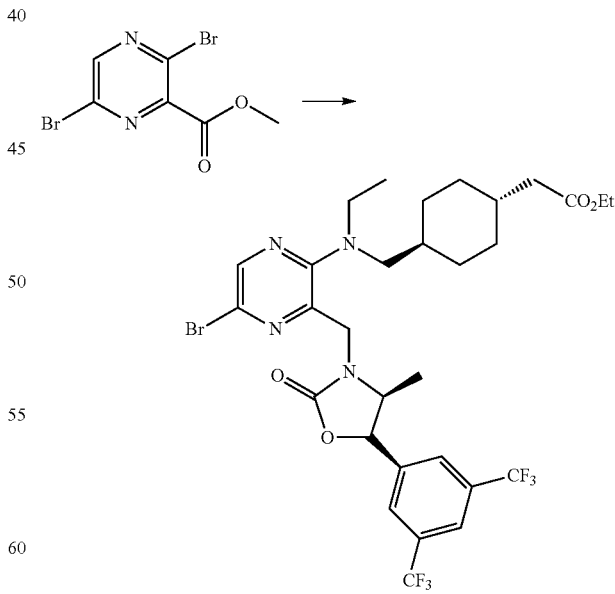

The same procedure as in method 2 of Example 96 was repeated, with the exception that ethyl trans-{4-[(N-ethylamino)methyl]cyclohexyl}acetate was used instead of N-ethyl-N-cyclohexylamine, to afford the title compound ethyl trans-4-({[3-({(4S,5S)-5-[3,5-bis(trifluoromethyl)phenyl]-4-methyl-2-oxazolidin-3-yl}methyl)-5-bromo-pyrazin-2-yl]{([N-(ethyl)aminomethyl]cyclohexyl)}acetate (120 mg, 77%).

¹H NMR (400 MHz, CDCl₃): 8.16 (s, 1H), 7.87 (s, 1H), 7.77 (s, 2H), 5.78 (d, 1H, J=8.4 Hz), 4.87 (d, 1H, J=16.8 Hz), 4.31-4.27 (m, 1H), 4.15-4.05 (m, 3H), 3.23-3.01 (m, 4H), 2.11 (d, 2H, J=6.8 Hz), 1.73-1.71 (m, 5H), 1.46-1.38 (m, 1H), 1.21 (t, 3H, J=7.2 Hz), 1.10 (t, 3H, J=7.2 Hz), 0.91-0.88 (m, 4H), 0.70 (d, 3H, J=6.8 Hz).

[Step 2] Preparation of ethyl trans-4-({[3-({(4S,5S)-5-[3,5-bis(trifluoromethyl)phenyl]-4-methyl-2-oxazolidin-3-yl}methyl)-5-(3,5-dimethyloxazol-4-yl)pyrazin-2-yl]{[N-(ethyl)aminomethyl]cyclohexyl)}acetate

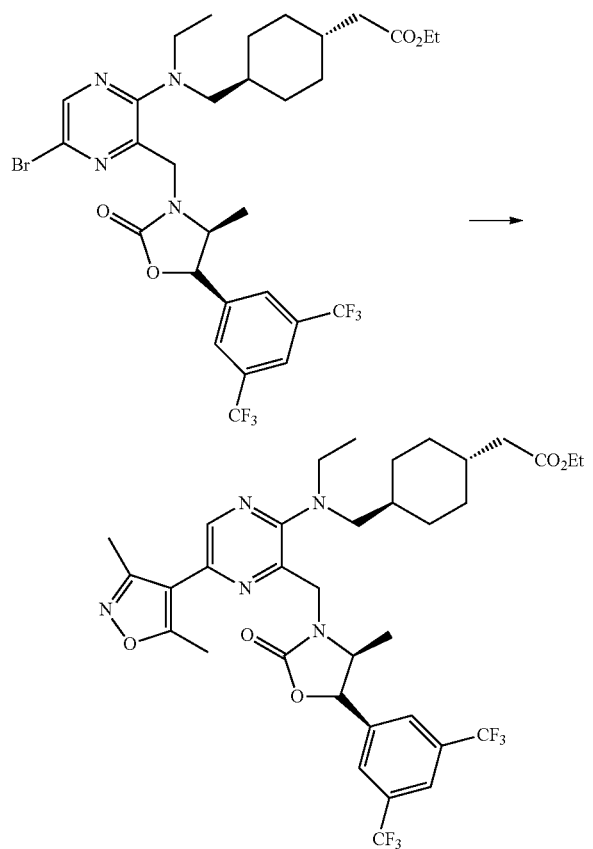

The title compound ethyl trans-4-({[3-({(4S,5S)-5-[3,5-bis(trifluoromethyl)phenyl]-4-methyl-2-oxazolidin-3-yl}methyl)-5-(3,5-dimethyloxazol-4-yl)pyrazin-2-yl]{[N-(ethyl)aminomethyl]cyclohexyl)}acetate (66 mg, 49%) were prepared in the same as in Example 58.

¹H NMR (600 MHz, CDCl₃): 8.23 (s, 1H), 7.89 (s, 1H), 7.74 (s, 2H), 5.68 (d, 1H, J=8.4 Hz), 4.96 (d, 1H, J=16.8 Hz), 4.26 (d, 1H, J=16.8 Hz), 4.18-4.16 (m, 1H), 4.11-4.07 (m, 2H), 3.34-3.22 (m, 3H), 3.34-3.01 (m, 1H), 2.62 (s, 3H), 2.48 (s, 3H), 2.14 (d, 2H, J=6.6 Hz), 1.78-1.71 (m, 5H), 1.52-1.48 (m, 1H), 1.23 (t, 3H, J=7.2 Hz), 1.14 (t, 3H, J=7.2 Hz), 0.97-0.84 (m, 4H), 0.71 (d, 3H, J=6.6 Hz).

[Step 3] Preparation of trans-4-({[3-({(4S,5S)-5-[3,5-bis(trifluoromethyl)phenyl]-4-methyl-2-oxazolidin-3-yl}methyl)-5-(3,5-dimethyloxazol-4-yl)pyrazin-2-yl]{[N-(ethyl)aminomethyl]cyclohexyl)}acetic acid

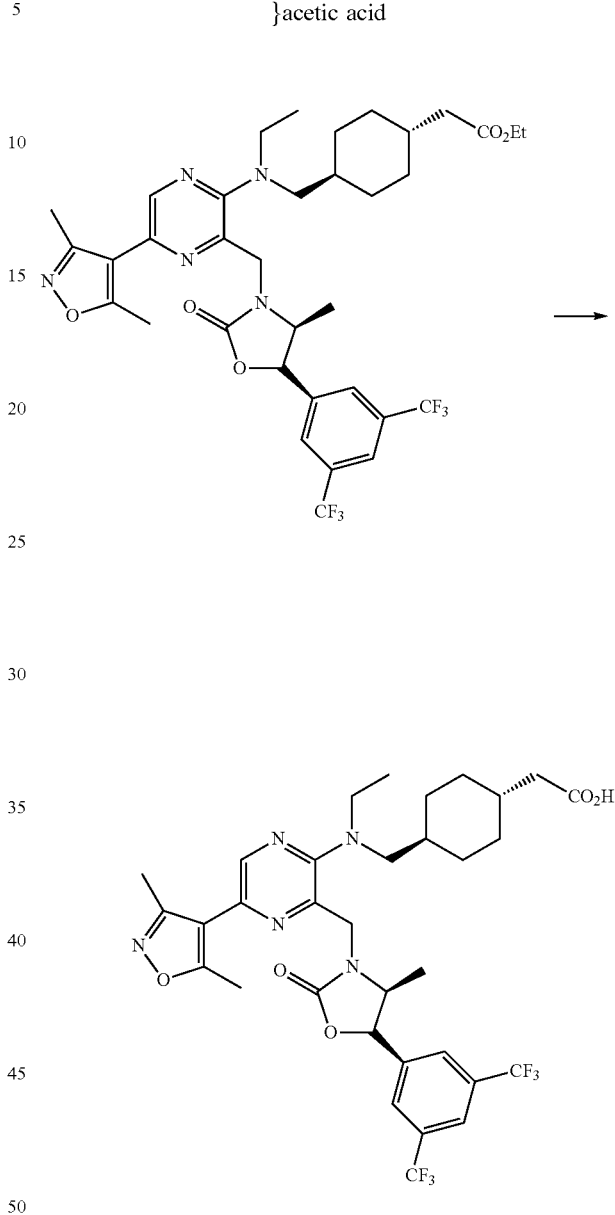

To a solution of ethyl trans-4-({[3-({(4S,5S)-5-[3,5-bis(trifluoromethyl)phenyl]-4-methyl-2-oxazolidin-3-yl}methyl)-5-(3,5-dimethyloxazol-4-yl)pyrazin-2-yl]{[N-(ethyl)aminomethyl]cyclohexyl)}acetate (18 mg) of step 2 in ethanol (2 mL) was dropwise added 4N NaOH (0.8 mL), followed by stirring at room temperature for 6 hrs. After neutralization with 2N HCl, the reaction mixture was extracted with ethyl acetate, and the organic layer was dried and concentrated in a vacuum. The residue was purified through a column to afford the title compound (50 mg, 50%).

¹H NMR (600 MHz, CDCl₃): 8.23 (s, 1H), 7.89 (s, 1H), 7.74 (s, 2H), 5.68 (d, 1H, J=8.4 Hz), 4.96 (d, 1H, J=16.8 Hz), 4.26 (d, 1H, J=16.8 Hz), 4.18-4.16 (m, 1H), 3.34-3.22 (m, 3H), 3.34-3.01 (m, 1H), 2.62 (s, 3H), 2.48 (s, 3H), 2.14 (d, 2H, J=6.6 Hz), 1.78-1.71 (m, 5H), 1.52-1.48 (m, 1H), 1.14 (t, 3H, J=7.2 Hz), 0.97-0.84 (m, 4H), 0.71 (d, 3H, J=6.6 Hz).

Example 103 trans-4-({[3-({(4S,5S)-5-[3,5-bis(trifluoromethyl)phenyl]-4-methyl-2-oxazolidin-3-yl}methyl)-5-(pyrrolidin-1-yl)pyrazin-2-yl]{[N-(ethyl)aminomethyl]cyclohexyl)}acetic acid

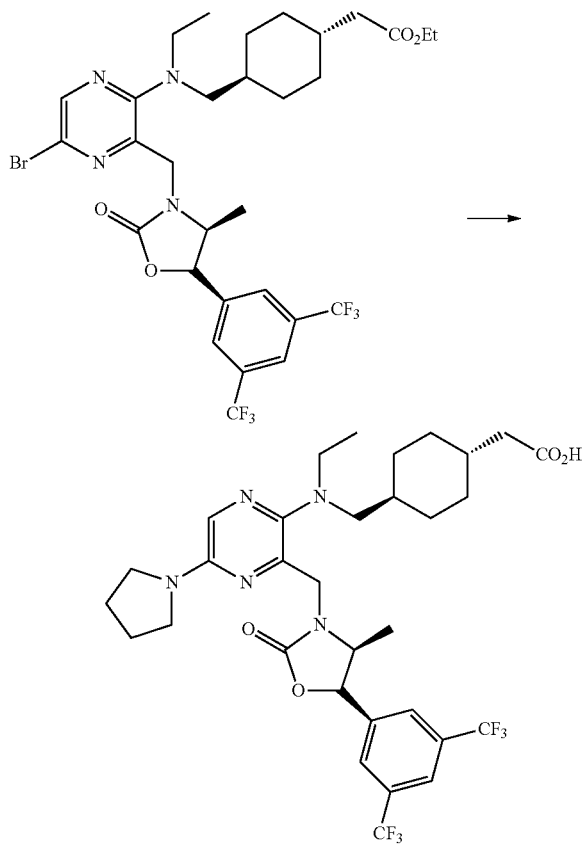

[Step 1] Preparation of ethyl trans-4-({[3-({(4S,5S)-5-[3,5-bis(trifluoromethyl)phenyl]-4-methyl-2-oxazolidin-3-yl}methyl)-5-(pyrrolidin-1-yl)pyrazin-2-yl]{[N-(ethyl)aminomethyl]cyclohexyl)}acetate

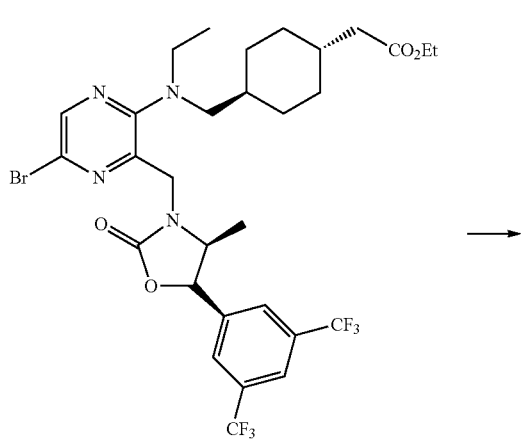

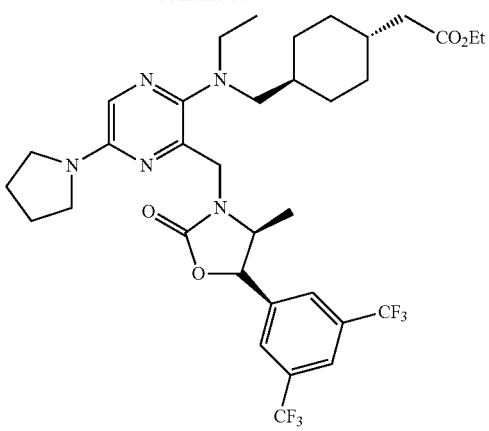

Ethyl trans-4-({[3-({(4S,5S)-5-[3,5-bis(trifluoromethyl)phenyl]-4-methyl-2-oxazolidin-3-yl}methyl)-5-(3,5-dimethyloxazol-4-yl)pyrazin-2-yl]{[N-(ethyl)aminomethyl]cyclohexyl)}acetate of step 2 of Example 102 was used in the same manner as in Example 88 to afford the title compound ethyl trans-4-({[3-({(4S,5S)-5-[3,5-bis(trifluoromethyl)phenyl]-4-methyl-2-oxazolidin-3-yl}methyl)-5-(pyrrolidin-1-yl)pyrazin-2-yl]{[N-(ethyl)aminomethyl]cyclohexyl)}acetate (35 mg, 51%).

$^1$H NMR (600 MHz, CDCl$_3$): 7.88 (s, 1H), 7.77 (s, 1H), 7.60 (s, 2H), 5.73 (d, 1H, J=8.4 Hz), 4.82 (d, 1H, J=16.8 Hz), 4.36-4.30 (m, 2H), 4.10-4.07 (m, 2H), 3.51-3.42 (m, 4H), 2.96-2.88 (m, 3H), 2.74-2.71 (m, 1H), 2.12 (d, 2H, J=6.6 Hz), 2.04-2.01 (m, 4H), 1.82-1.70 (m, 4H), 1.30-1.25 (m, 1H), 1.22 (t, 3H, J=7.2 Hz), 0.97 (t, 3H, J=7.2 Hz), 0.96-0.85 (m, 4H), 0.73 (d, 3H, J=6.0 Hz).

[Step 2] Preparation of trans-4-({[3-({(4S,5S)-5-[3,5-bis(trifluoromethyl)phenyl]-4-methyl-2-oxazolidin-3-yl}methyl)-5-(pyrrolidin-1-yl)pyrazin-2-yl]{[N-(ethyl)aminomethyl]cyclohexyl)}acetic acid

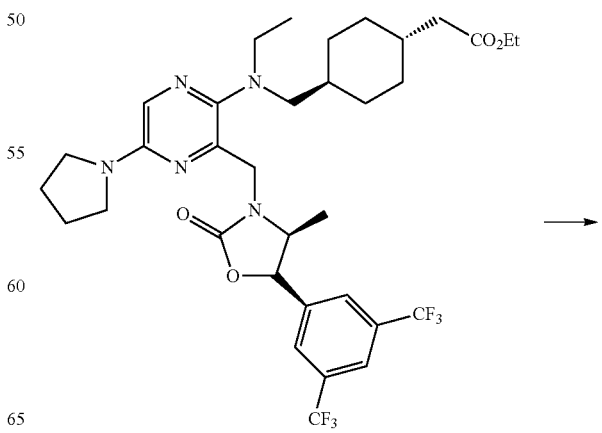

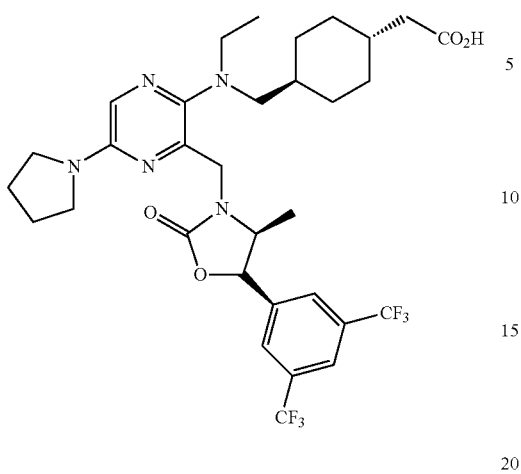

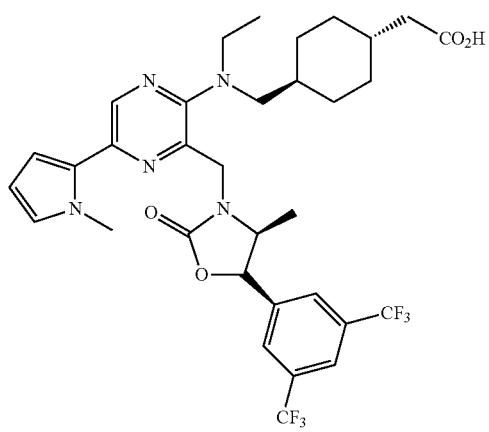

The compound of step 1 was used in the same manner as in step 3 of Example 102 to afford the title compound (15 mg, 98%).

$^1$H NMR (600 MHz, CDCl$_3$): 7.88 (s, 1H), 7.77 (s, 1H), 7.61 (s, 2H), 5.73 (d, 1H, J=9.0 Hz), 4.83 (d, 1H, J=17.4 Hz), 4.36-4.30 (m, 2H), 3.51-3.44 (m, 4H), 3.00-2.85 (m, 3H), 2.71-2.78 (m, 1H), 2.17 (d, 2H, J=7.2 Hz), 2.04-2.01 (m, 4H), 1.82-1.69 (m, 5H), 0.98-0.85 (m, 7H), 0.73 (d, 3H, J=6.0 Hz).

The title compound (23 mg, 98%) was prepared in the same manner as in Example 102, with the exception that the different reactant was used.

$^1$H NMR (600 MHz, CDCl3): 8.45 (s, 1H), 7.88 (s, 1H), 7.73 (s, 2H), 6.76 (s, 1H), 6.61-6.60 (m, 1H), 6.21-6.20 (m, 1H), 5.66 (d, 1H, J=8.4 Hz), 4.92 (d, 1H, J=17.4 Hz), 4.31 (d, 1H, J=16.2 Hz), 4.14-4.09 (m, 1H), 3.96 (s, 3H), 3.35-3.12 (m, 3H), 3.11-2.88 (m, 1H), 2.18 (d, 2H, J=7.2 Hz), 1.78-1.63 (m, 5H), 1.48-1.42 (m, 1H), 1.10 (t, 3H, J=7.2 Hz), 0.98-0.84 (m, 4H), 0.67 (d, 3H, J=6.6 Hz). *CO$_2$H was not observed.

Example 104 trans-4-({[3-({(4S,5S)-5-[3,5-bis(trifluoromethyl)phenyl]-4-methyl-2-oxazolidin-3-yl}methyl)-5-(1-methyl-1H-pyrrol-2-yl)pyrazin-2-yl]{[N-(ethyl)aminomethyl]cyclohexyl)}acetic acid

Example 105 trans-4-({[3-({(4S,5S)-5-[3,5-bis(trifluoromethyl)phenyl]-4-methyl-2-oxazolidin-3-yl}methyl)-5-(thiophen-3-yl)pyrazin-2-yl]{[N-(ethyl)aminomethyl]cyclohexyl)}acetic acid

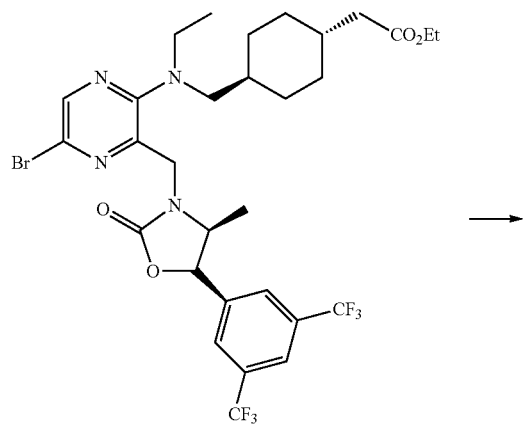 →

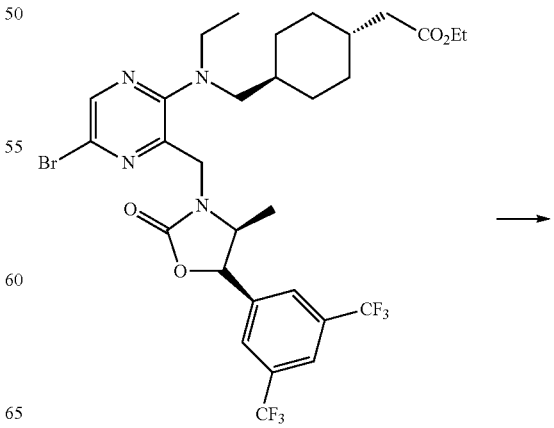 →

167

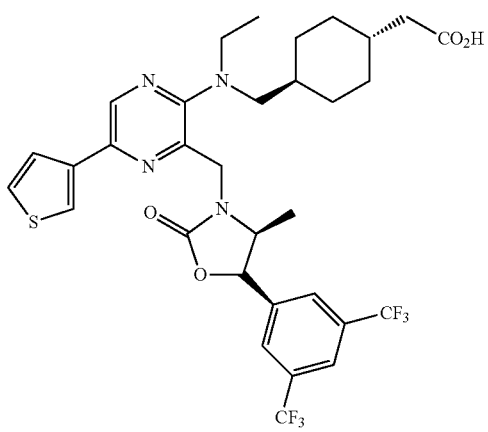

The title compound (60 mg, 78%) was prepared in the same manner as in Example 102, with the exception that the different reactant was used.

$^1$H NMR (600 MHz, CDCl3): 8.50 (s, 1H), 7.88 (s, 1H), 7.82-7.81 (m, 1H), 7.76 (s, 2H), 7.62-7.61 (m, 1H), 7.43-7.42 (m, 1H), 5.74 (d, 1H, J=9.0 Hz), 4.97 (d, 1H, J=16.8 Hz), 4.27-4.21 (m, 2H), 3.35-3.19 (m, 3H), 3.02-2.98 (m, 1H), 2.18 (d, 2H, J=6.6 Hz), 1.78-1.65 (m, 5H), 1.52-1.45 (m, 1H), 1.12 (t, 3H, J=7.2 Hz), 0.98-0.87 (m, 4H), 0.72 (d, 3H, J=6.6 Hz).

Example 106 trans-4-({[3-({(4S,5S)-5-[3,5-bis(trifluoromethyl)phenyl]-4-methyl-2-oxazolidin-3-yl}methyl)-5-(1-methyl-1H-pyrazol-5-yl)pyrazin-2-yl]{[N-(ethyl)aminomethyl]cyclohexyl)}acetic acid

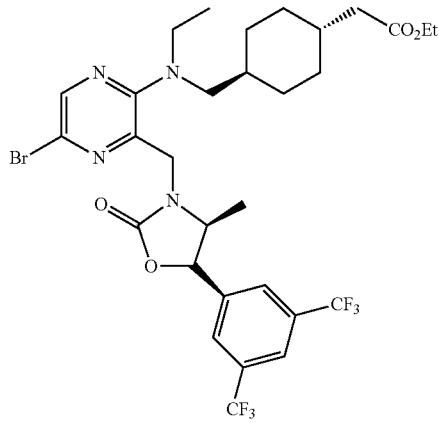

⟶

168

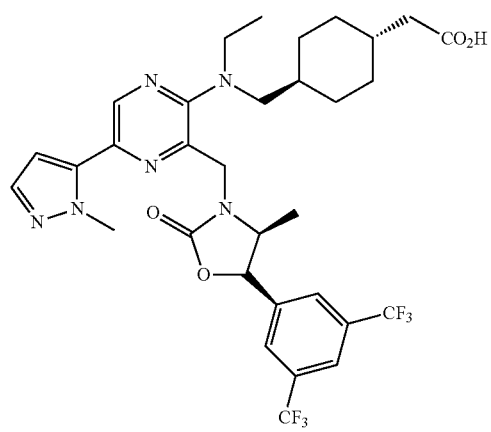

The title compound (32 mg, 84%) was prepared in the same manner as in Example 102, with the exception that the different reactant was used.

$^1$H NMR (600 MHz, CDCl3): 8.45 (s, 1H), 7.89 (s, 1H), 7.73 (s, 2H), 7.53 (d, 1H, J=1.8 Hz), 7.59 (d, 1H, J=1.8 Hz), 5.68 (d, 1H, J=9.0 Hz), 4.98 (d, 1H, J=16.2 Hz), 4.19 (s, 3H), 4.17-4.12 (m, 1H), 3.41-3.22 (m, 3H), 3.03-3.02 (m, 1H), 2.19 (d, 2H, J=7.2 Hz), 1.79-1.75 (m, 5H), 1.52-1.45 (m, 1H), 1.15 (t, 3H, J=7.2 Hz), 0.99-0.85 (m, 4H), 0.69 (d, 3H, J=6.6 Hz).

Example 107 trans-4-({[3-({(4S,5S)-5-[3,5-bis(trifluoromethyl)phenyl]-4-methyl-2-oxazolidin-3-yl}methyl)-5-(1,3-dimethyl-1H-pyrazol-5-yl)pyrazin-2-yl]{[N-(ethyl)aminomethyl]cyclohexyl)}acetic acid

⟶

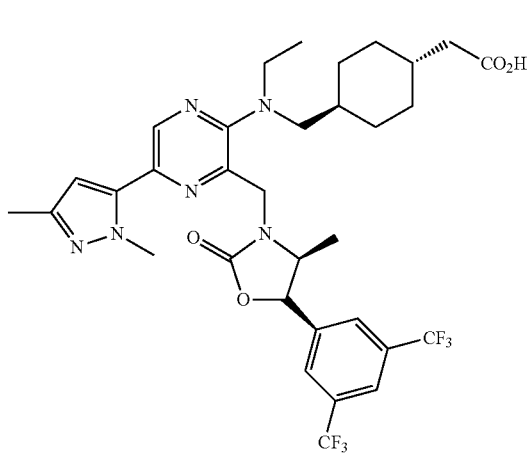

The title compound (60 mg, 96%) was prepared in the same manner as in Example 102, with the exception that the different reactant was used.

¹H NMR (400 MHz, CDCl3): 8.39 (s, 1H), 7.87 (s, 1H), 7.71 (s, 2H), 6.35 (s, 1H), 5.65 (d, 1H, J=8.0 Hz), 4.95 (d, 1H, J=16.8 Hz), 4.23 (d, 1H, J=16.8 Hz), 4.10-4.04 (m, 6H), 3.39-3.18 (m, 3H), 3.00-2.95 (m, 1H), 2.30 (s, 3H), 2.11 (d, 2H, J=6.0 Hz), 1.79-1.68 (m, 5H), 1.52-1.45 (m, 1H), 1.22-1.16 (m, 3H), 1.13 (t, 3H, J=6.8 Hz), 0.98-0.85 (m, 4H), 0.67 (d, 3H, J=6.4 Hz).

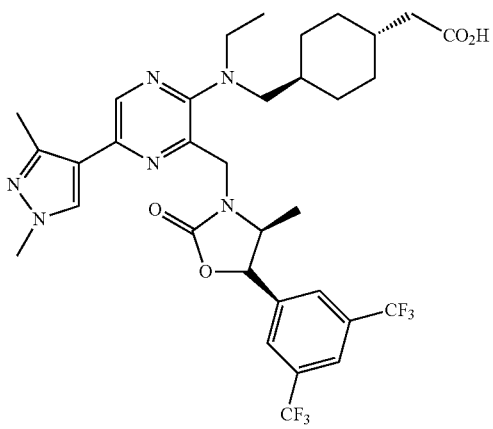

The title compound (34 mg, 89%) was prepared in the same manner as in Example 102, with the exception that the different reactant was used.

¹H NMR (400 MHz, CDCl3): 8.39 (s, 1H), 7.87 (s, 1H), 7.71 (s, 2H), 6.35 (s, 1H), 5.65 (d, 1H, J=8.0 Hz), 4.95 (d, 1H, J=16.8 Hz), 4.23 (d, 1H, J=16.8 Hz), 4.10-4.04 (m, 6H), 3.39-3.18 (m, 3H), 3.00-2.95 (m, 1H), 2.30 (s, 3H), 2.11 (d, 2H, J=6.0 Hz), 1.79-1.68 (m, 5H), 1.52-1.45 (m, 1H), 1.22-1.16 (m, 3H), 1.13 (t, 3H, J=6.8 Hz), 0.98-0.85 (m, 4H), 0.67 (d, 3H, J=6.4 Hz). ¹H NMR (600 MHz, CDCl3): 8.32 (s, 1H), 7.88 (s, 1H), 7.74 (s, 2H), 7.73 (s, 1H), 5.69 (d, 1H, J=8.4 Hz), 4.94 (d, 1H, J=16.8 Hz), 4.28 (d, 1H, J=16.8 Hz), 4.17-4.12 (m, 1H), 3.90 (s, 3H), 3.31-3.13 (m, 3H), 2.95-2.92 (m, 1H), 2.31 (s, 3H), 2.18 (d, 2H, J=7.2 Hz), 1.78-1.70 (m, 5H), 1.48-1.42 (m, 1H), 1.10 (t, 3H, J=7.2 Hz), 0.97-0.85 (m, 4H), 0.69 (d, 3H, J=6.6 Hz).

Example 108 trans-4-({[3-({(4S,5S)-5-[3,5-bis(trifluoromethyl)phenyl]-4-methyl-2-oxazolidin-3-yl}methyl)-5-(1,3-dimethyl-1H-pyrazol-4-yl)pyrazin-2-yl]{[N-(ethyl)aminomethyl]cyclohexyl)}acetic acid

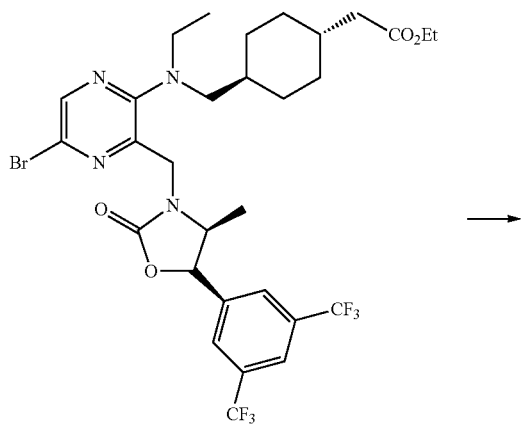 →

Example 109 trans-4-({[3-({(4S,5S)-5-[3,5-bis(trifluoromethyl)phenyl]-4-methyl-2-oxazolidin-3-yl}methyl)-5-(3-methoxythiophen-2-yl)pyrazin-2-yl]{[N-(ethyl)aminomethyl]cyclohexyl)}acetic acid

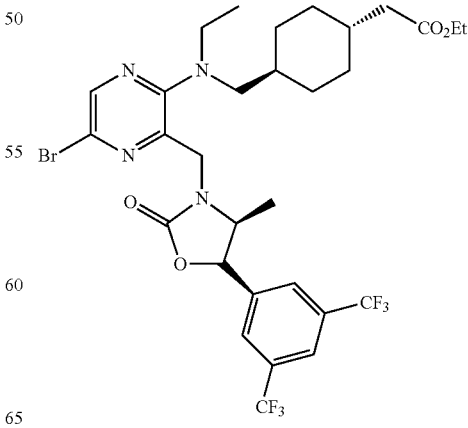 →

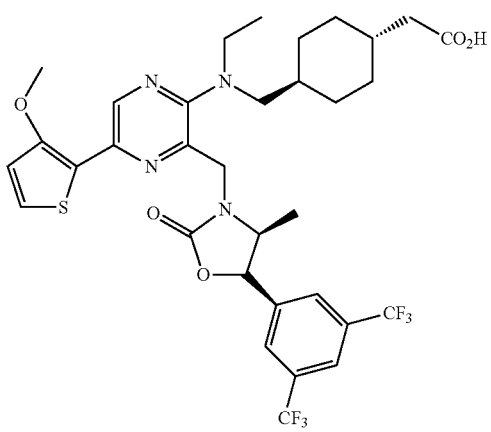

The title compound (110 mg, 95%) was prepared in the same manner as in Example 102, with the exception that the different reactant was used.

$^1$H NMR (600 MHz, CDCl3): 8.90 (s, 1H), 7.88 (s, 1H), 7.80 (s, 2H), 7.26 (s, 1H), 6.94 (d, 1H, J=5.4 Hz), 5.88 (d, 1H, J=8.4 Hz), 4.95 (d, 1H, J=16.2 Hz), 4.43-4.38 (m, 2H), 4.20 (d, 1H, J=17.4 Hz), 3.99 (s, 3H), 3.28-3.16 (m, 3H), 3.02-2.99 (m, 1H), 2.18 (d, 2H, J=7.2 Hz), 1.79-1.69 (m, 5H), 1.48-1.42 (m, 1H), 1.11 (t, 3H, J=7.2 Hz), 0.96-0.84 (m, 4H), 0.74 (d, 3H, J=6.6 Hz).

The title compound (140 mg, 95%) was prepared in the same manner as in Example 102, with the exception that the different reactant was used.

$^1$H NMR (600 MHz, CDCl3): 8.47 (s, 1H), 7.88 (s, 1H), 7.80 (s, 2H), 7.31 (s, 1H), 6.95 (s, 1H), 5.87 (d, 1H, J=8.4 Hz), 4.97 (d, 1H, J=17.4 Hz), 4.43-4.40 (m, 1H), 4.20 (d, 1H, J=16.2 Hz), 3.28-3.21 (m, 3H), 3.07-3.04 (m, 1H), 2.31 (s, 3H), 2.19 (d, 2H, J=7.2 Hz), 1.79-1.70 (m, 5H), 1.48-1.45 (m, 1H), 1.13 (t, 3H, J=6.6 Hz), 0.93-0.88 (m, 4H), 0.75 (d, 3H, J=6.6 Hz).

Example 110 trans-4-({[3-({(4S,5S)-5-[3,5-bis(trifluoromethyl)phenyl]-4-methyl-2-oxazolidin-3-yl}methyl)-5-(4-methylthiophen-???yl)pyrazin-2-yl]{[N-(ethyl)aminomethyl]cyclohexyl})acetic acid

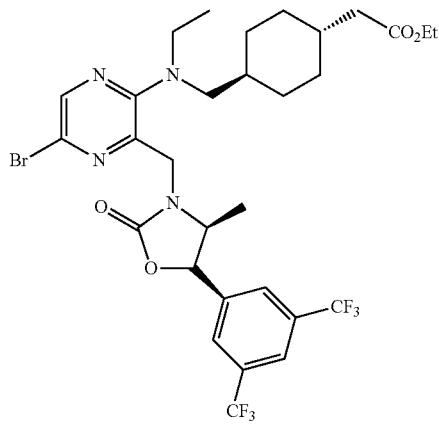

Example 111 trans-4-({[3-({(4S,5S)-5-[3,5-bis(trifluoromethyl)phenyl]-4-methyl-2-oxazolidin-3-yl}methyl)-5-(3-methylthiophen-2-yl)pyrazin-2-yl]{[N-(ethyl)aminomethyl]cyclohexyl})acetic acid

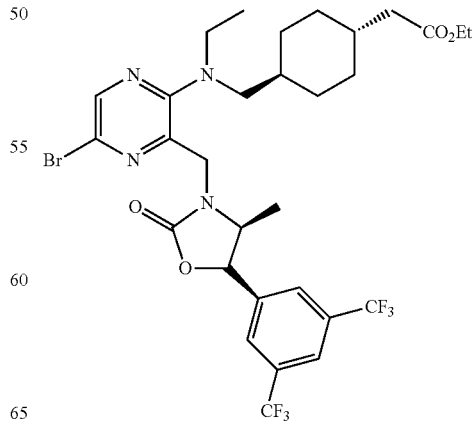

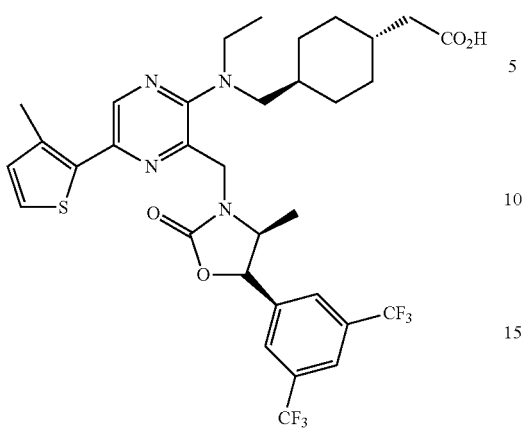

The title compound (35 mg, 99%) was prepared in the same manner as in Example 102, with the exception that the different reactant was used.

1H NMR (600 MHz, CDCl3): 8.45 (s, 1H), 7.88 (s, 1H), 7.79 (s, 2H), 7.27 (s, 1H), 6.94-6.93 (m, 1H), 5.87 (d, 1H, J=8.4 Hz), 4.98 (d, 1H, J=16.8 Hz), 4.45-4.42 (m, 1H), 4.21 (d, 1H, J=17.4 Hz), 3.30-3.23 (m, 3H), 3.08-3.05 (m, 1H), 2.52 (s, 3H), 2.19 (d, 2H, J=6.6 Hz), 1.78-1.71 (m, 5H), 1.52-1.48 (m, 1H), 1.14 (t, 3H, J=6.6 Hz), 0.96-0.91 (m, 4H), 0.75 (d, 3H, J=6.6 Hz).

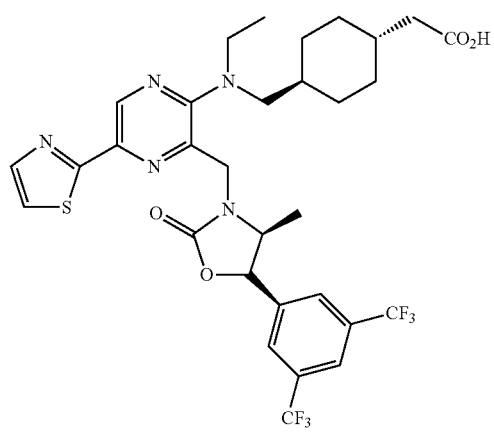

The title compound (70 mg, 93%) was prepared in the same manner as in Example 102, with the exception that the different reactant was used.

$^1$H NMR (600 MHz, CDCl3): 8.92 (s, 1H), 7.89 (m, 2H), 7.79 (s, 2H), 7.38 (s, 1H), 5.84 (d, 1H, J=7.8 Hz), 4.97 (d, 1H, J=17.4 Hz), 4.35-4.33 (m, 1H), 4.22 (d, 1H, J=16.2 Hz), 3.39-3.32 (m, 3H), 3.18-3.15 (m, 1H), 2.19 (d, 2H, J=7.2 Hz), 1.79-1.60 (m, 5H), 1.58-1.52 (m, 1H), 1.18 (t, 3H, J=6.6 Hz), 0.98-0.91 (m, 4H), 0.76 (d, 3H, J=6.6 Hz).

Example 112 trans-4-({[3-({(4S,5S)-5-[3,5-bis(trifluoromethyl) phenyl]-4-methyl-2-oxazolidin-3-yl}methyl)-5-(thi-azol-2-yl)pyrazin-2-yl]{[N-(ethyl)aminomethyl] cyclohexyl})acetic acid

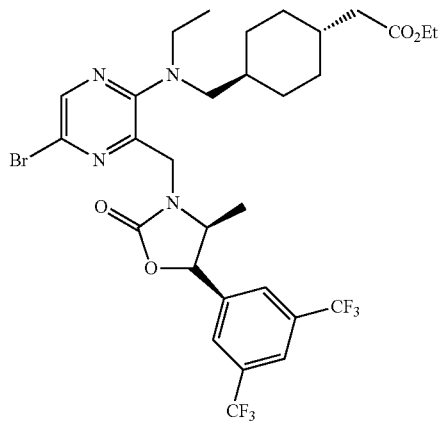

→

Example 113 trans-4-({[3-({(4S,5S)-5-[3,5-bis(trifluoromethyl) phenyl]-4-methyl-2-oxazolidin-3-yl}methyl)-5-(thi-azol-4-yl)pyrazin-2-yl]{[N-(ethyl)aminomethyl] cyclohexyl})acetic acid

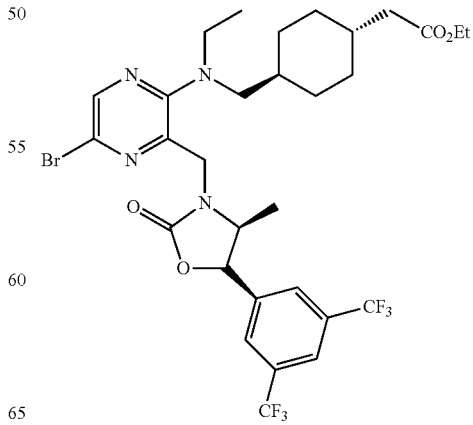

→

175

-continued

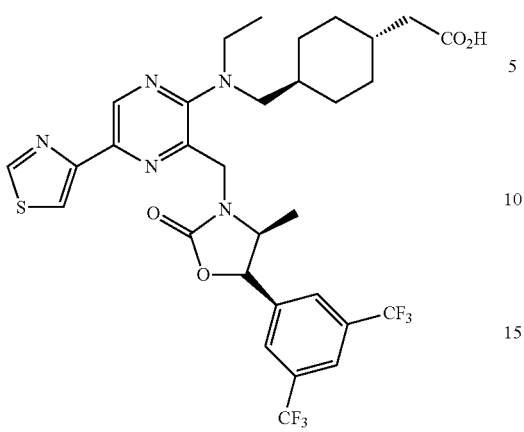

The title compound (160 mg, 95%) was prepared in the same manner as in Example 102, with the exception that the different reactant was used.

$^1$H NMR (600 MHz, CDCl3): 8.95-8.91 (m, 2H), 7.95-7.79 (m, 2H), 7.75 (s, 2H), 5.73 (d, 1H, J=8.4 Hz), 4.97 (d, 1H, J=16.8 Hz), 4.28 (d, 1H, J=16.2 Hz), 4.15-4.10 (m, 1H), 3.40-3.24 (m, 3H), 3.05-3.01 (m, 1H), 2.17 (d, 2H, J=7.2 Hz), 1.78-1.68 (m, 5H), 1.52-1.48 (m, 1H), 1.14 (t, 3H, J=7.2 Hz), 0.95-0.86 (m, 4H), 0.70 (d, 3H, J=6.6 Hz).

Example 114 trans-4-({[3-({(4S,5S)-5-[3,5-bis(trifluoromethyl)phenyl]-4-methyl-2-oxazolidin-3-yl}methyl)-5-(thiophen-2-yl)pyrazin-2-yl]{[N-(ethyl)aminomethyl]cyclohexyl})acetic acid

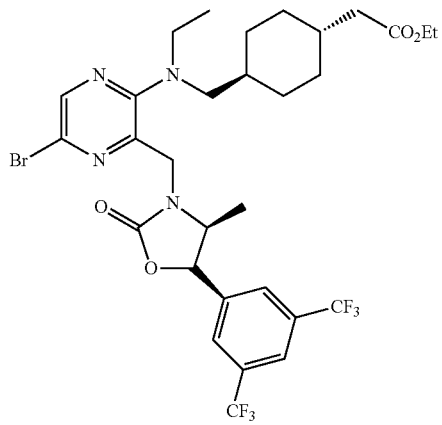

176

-continued

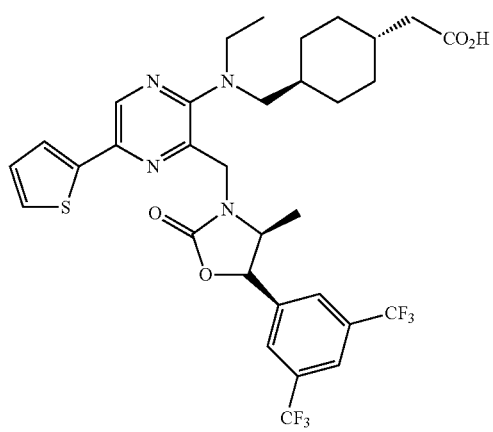

The title compound (110 mg, 88%) was prepared in the same manner as in Example 102, with the exception that the different reactant was used.

$^1$H NMR (600 MHz, CDCl$_3$): 8.50 (s, 1H), 7.86 (s, 1H), 7.78 (s, 2H), 7.49 (dd, J=1.2, 4.2 Hz), 7.34 (d, 1H, J=4.8 Hz), 7.10 (dd, 1H, J=4.2, 4.8 Hz), 5.86 (d, 1H, J=8.4 Hz), 4.95 (d, 1H, J=17.4 Hz), 4.43~4.38 (m, 1H), 4.19 (d, 1H, J=17.4 Hz), 3.27~3.19 (m, 3H), 3.06~3.02 (m, 1H), 2.16 (d, 2H, J=7.2 Hz), 1.77~1.68 (m, 5H), 1.51~1.43 (m, 1H), 1.12 (t, 3H, J=7.2 Hz), 0.95~0.86 (m, 4H), 0.74 (d, 3H, J=6.6 Hz)

Example 115 trans-4-({[3-({(4S,5S)-5-[3,5-bis(trifluoromethyl)phenyl]-4-methyl-2-oxazolidin-3-yl}methyl)-5-(5-acetylthiophen-2-yl)pyrazin-2-yl]{[N-(ethyl)aminomethyl]cyclohexyl})acetic acid

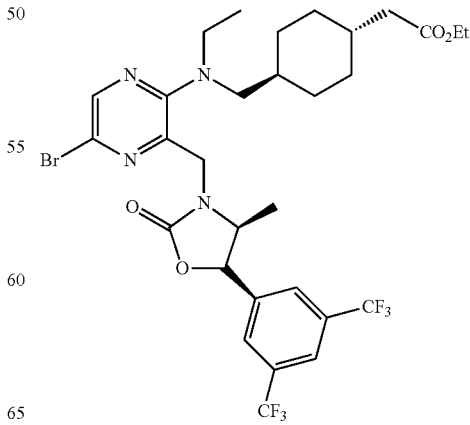

177
-continued

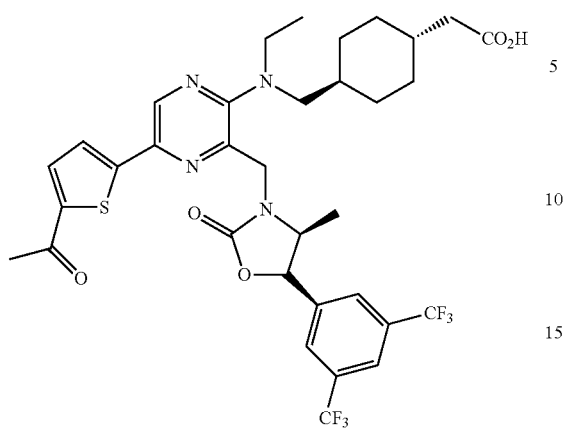

The title compound (109 mg, 90%) was prepared in the same manner as in Example 102, with the exception that the different reactant was used.

$^1$H NMR (400 MHz, CDCl$_3$): 8.50 (s, 1H), 7.86 (s, 1H), 7.78 (s, 2H), 7.66 (d, 1H, J=4.0 Hz), 7.46 (d, 1H, J=4.0 Hz), 5.85 (d, 1H, J=8.4 Hz), 4.96 (d, 1H, J=16.4 Hz), 4.50~4.45 (m, 1H), 4.15 (d, 1H, J=16.4 Hz), 3.33~3.14 (m, 4H), 2.55 (s, 3H), 2.15 (d, 2H, J=6.8 Hz), 1.76~1.64 (m, 5H), 1.54~1.45 (m, 1H), 1.15 (t, 3H, J=6.8 Hz), 0.77 (d, 3H, J=6.8 Hz).

178
-continued

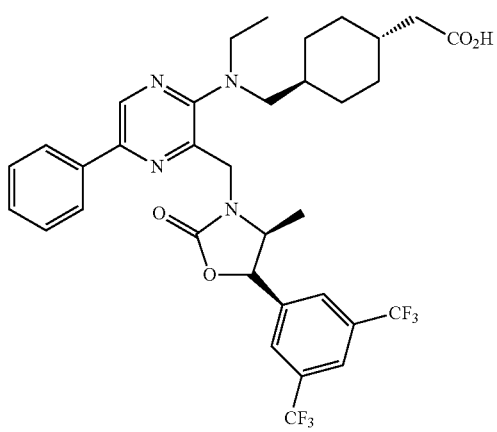

The title compound (112 mg, 78%) was prepared in the same manner as in Example 102, with the exception that the different reactant was used.

$^1$H NMR (600 MHz, CDCl$_3$): 8.60 (s, 1H), 7.95 (d, 2H, J=7.8 Hz), 7.86 (s, 1H), 7.74 (s, 2H), 7.46 (t, 2H, J=7.8 Hz), 7.38 (t, 1H, J=7.8 Hz), 5.72 (d, 1H, J=9.0 Hz), 4.99 (d, 1H, J=16.8 Hz), 4.26 (d, 1H, J=16.2 Hz), 4.25~4.22 (m, 1H), 3.33~3.21 (m, 3H), 3.05~3.01 (m, 1H), 2.16 (d, 2H, J=6.6 Hz), 1.78~1.63 (m, 5H), 1.52~1.45 (m, 1H), 1.12 (t, 3H, J=6.6 Hz), 0.96~0.85 (m, 4H), 0.71 (d, 3H, J=6.6 Hz)

Example 116 trans-4-({[3-({(4S,5S)-5-[3,5-bis(trifluoromethyl)phenyl]-4-methyl-2-oxazolidin-3-yl}methyl)-5-phenylpyrazin-2-yl]{[N-(ethyl)aminomethyl]cyclohexyl})acetic acid

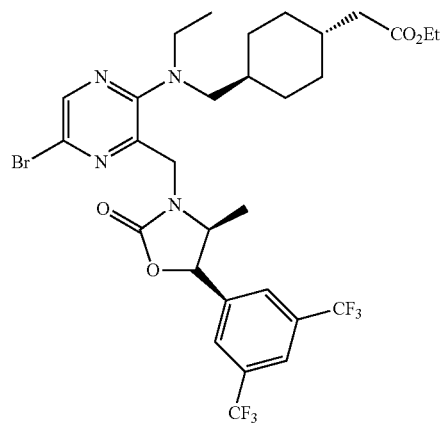 →

Example 117 trans-4-({[3-({(4S,5S)-5-[3,5-bis(trifluoromethyl)phenyl]-4-methyl-2-oxazolidin-3-yl}methyl)-5-(4-cyanophenyl)pyrazin-2-yl]{[N-(ethyl)aminomethyl]cyclohexyl})acetic acid

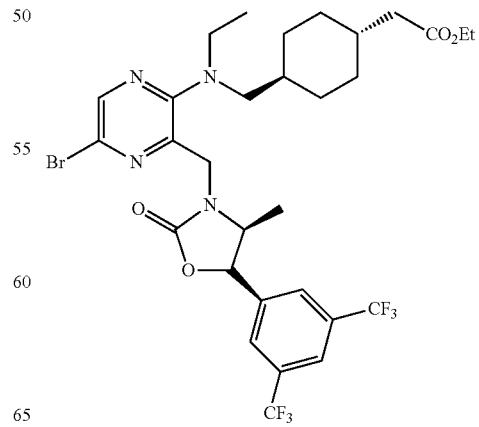 →

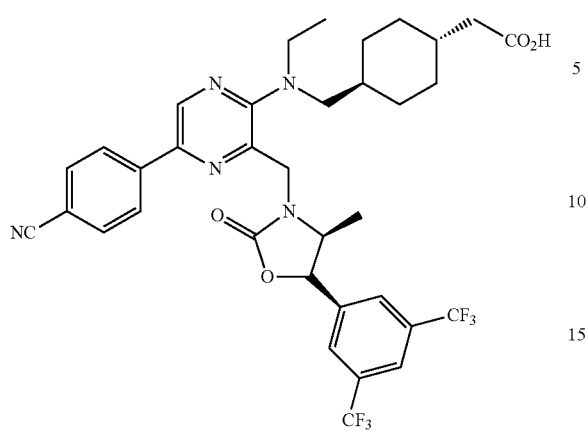

The title compound (70 mg, 45%) was prepared in the same manner as in Example 102, with the exception that the different reactant was used.

$^1$H NMR (600 MHz, CDCl3): 8.62 (s, 1H), 8.07-8.06 (m, 2H), 7.89 (s, 1H), 7.76-7.74 (m, 4H), 5.71 (d, 1H, J=7.8 Hz), 4.98 (d, 1H, J=16.2 Hz), 4.26 (d, 1H, J=16.2 Hz), 4.16-4.11 (m, 1H), 3.40-3.30 (m, 3H), 3.14-3.11 (m, 1H), 2.19 (d, 2H, J=6.6 Hz), 1.77-1.66 (m, 5H), 1.54-1.50 (m, 1H), 1.17 (t, 3H, J=6.6 Hz), 0.98-0.83 (m, 4H), 0.72 (d, 3H, J=6.0 Hz).

The title compound (25 mg, 16%) was prepared in the same manner as in Example 102, with the exception that the different reactant was used.

$^1$H NMR (600 MHz, CDCl3): 8.61 (s, 1H), 7.97 (d, 2H, J=8.4 Hz), 7.88 (s, 1H), 7.75 (s, 2H), 7.48 (d, 2H, J=8.4 Hz), 5.73 (d, 1H, J=8.4 Hz), 5.00 (d, 1H, J=16.2 Hz), 4.77 (s, 2H), 4.29-4.22 (m, 2H), 3.36-3.24 (m, 3H), 3.07-3.03 (m, 1H), 2.19 (d, 2H, J=7.2 Hz), 1.82-1.69 (m, 5H), 1.52-1.48 (m, 1H), 1.15 (t, 3H, J=7.2 Hz), 0.99-0.87 (m, 4H), 0.73 (d, 3H, J=6.0 Hz).

Example 118 trans-4-({[3-({(4S,5S)-5-[3,5-bis(trifluoromethyl)phenyl]-4-methyl-2-oxazolidin-3-yl}methyl)-5-(4-hydroxymethylphenyl)pyrazin-2-yl]{[N-(ethyl)aminomethyl]cyclohexyl)}acetic acid Example 119 trans-4-({[3-({(4S,5S)-5-[3,5-bis(trifluoromethyl)phenyl]-4-methyl-2-oxazolidin-3-yl}methyl)-5-(pyridin-3-yl)pyrazin-2-yl]{[N-(ethyl)aminomethyl]cyclohexyl)}acetic acid

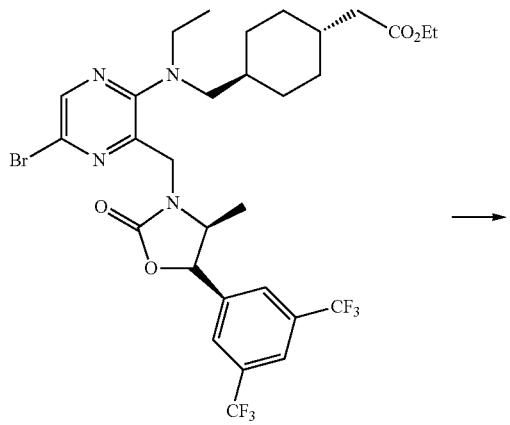 →

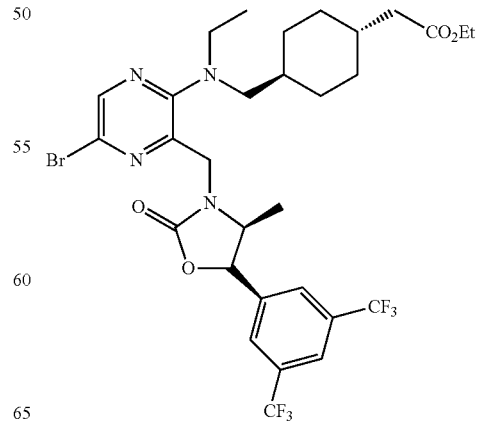 →

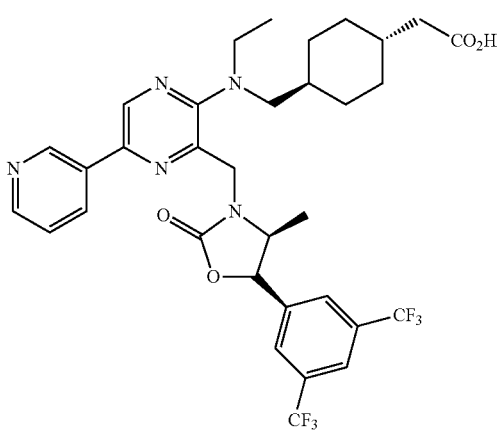

The title compound (140 mg, 88%) was prepared in the same manner as in Example 102, with the exception that the different reactant was used.

$^1$H NMR (600 MHz, CDCl3): 9.23 (s, 1H), 8.61 (m, 2H), 8.27 (d, 1H, J=7.8 Hz), 7.88 (s, 1H), 7.77 (s, 2H), 7.46-7.43 (m, 1H), 5.80 (d, 1H, J=8.4 Hz), 5.01 (d, 1H, J=16.2 Hz), 4.33-4.19 (m, 2H), 3.37-3.27 (m, 3H), 3.13-3.10 (m, 1H), 2.18 (d, 2H, J=7.2 Hz), 1.82-1.68 (m, 5H), 1.56-1.50 (m, 1H), 1.17 (t, 3H, J=6.6 Hz), 0.98-0.84 (m, 4H), 0.74 (d, 3H, J=6.6 Hz).

*CO$_2$H was not observed.

The title compound (140 mg, 91%) was prepared in the same manner as in Example 102, with the exception that the different reactant was used.

$^1$H NMR (600 MHz, CDCl3): 9.01 (s, 1H), 8.60 (s, 1H), 8.47 (s, 1H), 7.95 (d, 1H, J=9.0 Hz), 7.88 (s, 1H), 7.76 (s, 2H), 5.76 (d, 1H, J=8.4 Hz), 5.00 (d, 1H, J=16.2 Hz), 4.27-4.23 (m, 2H), 3.38-3.33 (m, 3H), 3.17-3.13 (m, 1H), 2.19 (d, 2H, J=7.2 Hz), 1.82-1.68 (m, 5H), 1.54-1.50 (m, 1H), 1.18 (t, 3H, J=6.6 Hz), 0.97-0.87 (m, 4H), 0.75 (d, 3H, J=6.6 Hz).

Example 120 trans-4-({[3-({(4S,5S)-5-[3,5-bis(trifluoromethyl)phenyl]-4-methyl-2-oxazolidin-3-yl}methyl)-5-(5-fluoropyridin-3-yl)pyrazin-2-yl]{[N-(ethyl)aminomethyl]cyclohexyl})acetic acid

Example 121 trans-4-({[3-({(4S,5S)-5-[3,5-bis(trifluoromethyl)phenyl]-4-methyl-2-oxazolidin-3-yl}methyl)-5-(cyclopropylpyrazin-2-yl)]{[N-(ethyl)aminomethyl]cyclohexyl})acetic acid

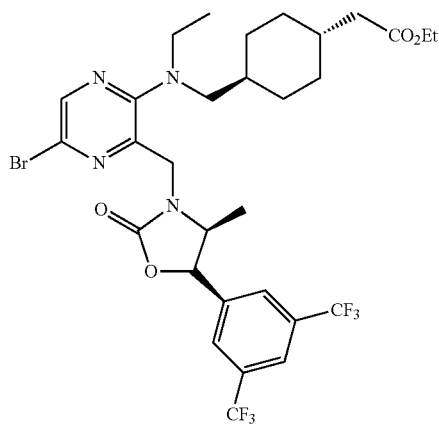

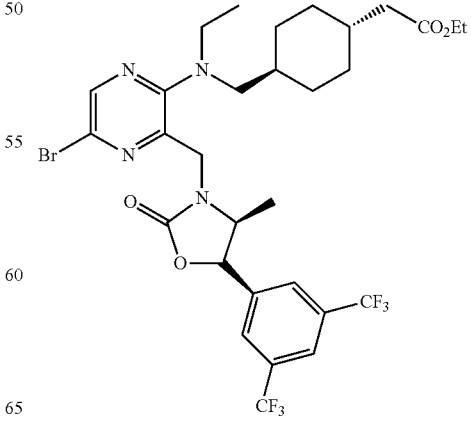

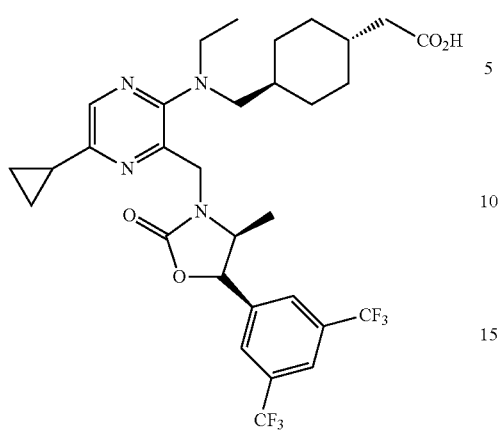

The title compound (60 mg, 91%) was prepared in the same manner as in Example 102, with the exception that the different reactant was used.

$^1$H NMR (400 MHz, CDCl3): 8.07 (s, 1H), 7.87 (s, 1H), 7.75 (s, 2H), 5.70 (d, 1H, J=8.4 Hz), 4.83 (d, 1H, J=16.8 Hz), 4.21-4.09 (m, 2H), 3.18-3.03 (m, 3H), 2.92-2.87 (m, 1H), 2.16 (d, 2H, J=6.8 Hz), 2.03-1.97 (m, 1H), 1.75-1.68 (m, 5H), 1.41-1.32 (m, 1H), 1.06-0.87 (m, 11H), 0.67 (d, 3H, J=6.4 Hz).

The title compound (100 mg, 90%) was prepared in the same manner as in Example 102, with the exception that the different reactant was used.

$^1$H NMR (600 MHz, CDCl$_3$): 7.96 (s, 1H), 7.87 (s, 1H), 7.75 (s, 2H), 5.75 (d, 1H, J=8.4 Hz), 4.92 (d, 1H, J=16.2 Hz), 4.28~4.24 (m, 1H), 4.23 (d, 1H, J=16.8 Hz), 3.66~3.57 (m, 1H), 3.20~3.09 (m, 3H), 2.95~2.91 (m, 1H), 2.32~2.27 (m, 4H), 2.15 (d, 2H, J=7.2 Hz), 2.08~2.03 (m, 1H), 1.96~1.88 (m, 1H), 1.79~1.62 (m, 5H), 1.41~1.33 (m, 1H), 1.23~1.18 (m, 1H), 1.06 (t, 3H, J=6.6 Hz), 0.95~0.80 (m, 4H), 0.70 (d, 3H, J=6.6 Hz)

Example 122 trans-4-({[3-({(4S,5S)-5-[3,5-bis(trifluoromethyl) phenyl]-4-methyl-2-oxazolidin-3-yl}methyl)-5-(cyclobutylpyrazin-2-yl)]}{[N-(ethyl)aminomethyl]cyclohexyl)}acetic acid Example 123 trans-4-({[3-({(4S,5S)-5-[3,5-bis(trifluoromethyl) phenyl]-4-methyl-2-oxazolidin-3-yl}methyl)-5-(3,5-dimethyloxazol-4-yl)pyrazin-2-yl]{[N-(propyl)aminomethyl]cyclohexyl)}acetic acid

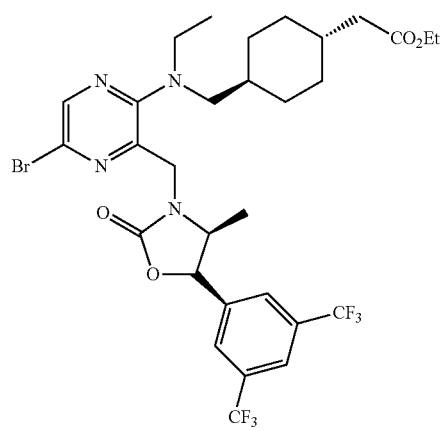

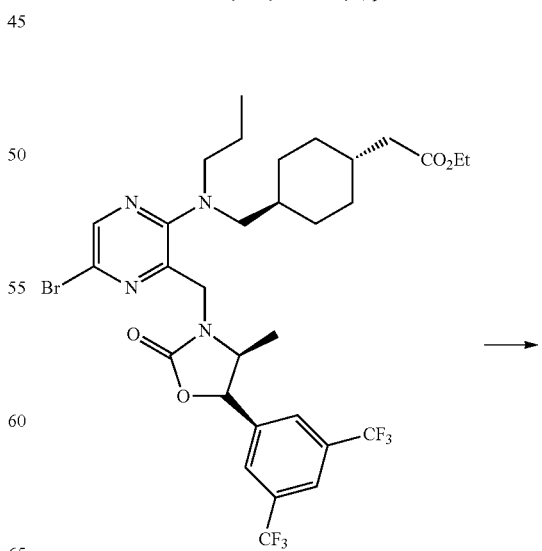

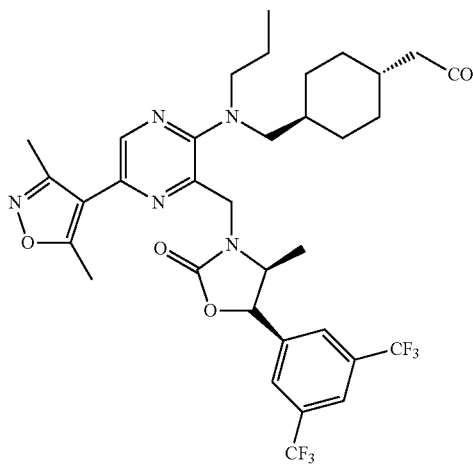

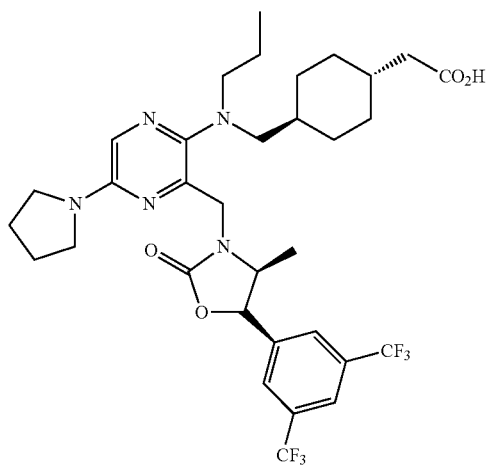

The title compound (35 mg, 98%) was prepared in the same manner as in Example 102, with the exception that the different reactant was used.

$^1$H NMR (400 MHz, CDCl$_3$): 8.20 (s, 1H), 7.87 (s, 1H), 7.72 (s, 2H), 5.65 (d, 1H, J=8.4 Hz), 4.94 (d, 1H, J=16.8 Hz), 4.23 (d, 1H, J=16.4 Hz), 4.17-4.07 (m, 1H), 3.32-3.02 (m, 4H), 2.60 (s, 3H), 2.46 (s, 3H), 2.17 (d, 2H, J=7.2 Hz), 1.78-1.48 (m, 9H), 0.92-0.81 (m, 7H), 0.99 (d, 3H, J=6.8 Hz).

The title compound (90 mg, 98%) was prepared in the same manner as in Example 102, with the exception that the different reactant was used.

$^1$H NMR (600 MHz, CDCl$_3$): 7.88 (s, 1H), 7.77 (s, 2H), 7.59 (s, 1H), 5.74 (d, 1H, J=7.2 Hz), 4.81 (d, 1H, J=16.8 Hz), 4.37-4.30 (m, 2H), 3.57-3.43 (m, 4H), 2.92-2.17 (m, 4H), 2.11 (d, 2H, J=6.6 Hz), 2.05-1.98 (m, 4H), 1.78-1.61 (m, 5H), 1.48-1.38 (m, 2H), 1.26-1.21 (m, 1H), 0.94-0.82 (m, 7H), 0.64 (d, 3H, J=7.2 Hz).

Example 124 trans-4-({[3-({(4S,5S)-5-[3,5-bis(trifluoromethyl)phenyl]-4-methyl-2-oxazolidin-3-yl}methyl)-5-(pyrrolidin-1-yl)pyrazin-2-yl]{[N-(propyl)aminomethyl]cyclohexyl)}acetic acid Example 125 trans-4-({[3-({(4S,5S)-5-[3,5-bis(trifluoromethyl)phenyl]-4-methyl-2-oxazolidin-3-yl}methyl)-5-(cyclohexylpyrazin-2-yl)]{[N-(propyl)aminomethyl]cyclohexyl)}acetic acid

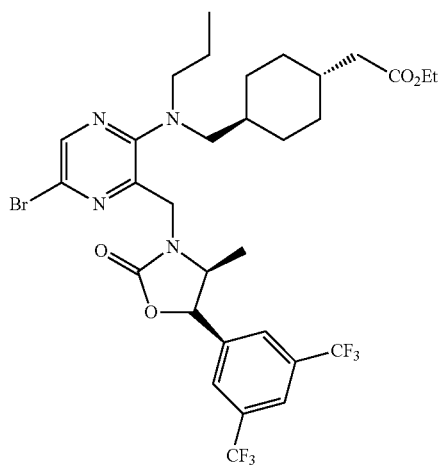

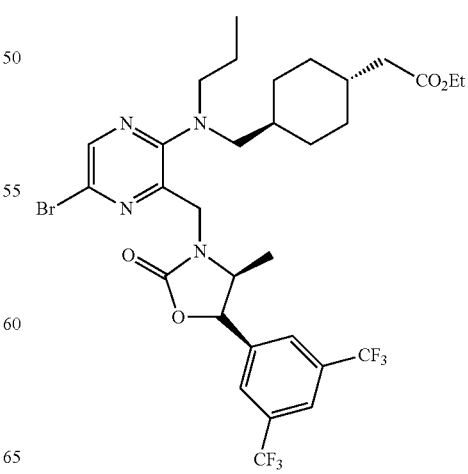

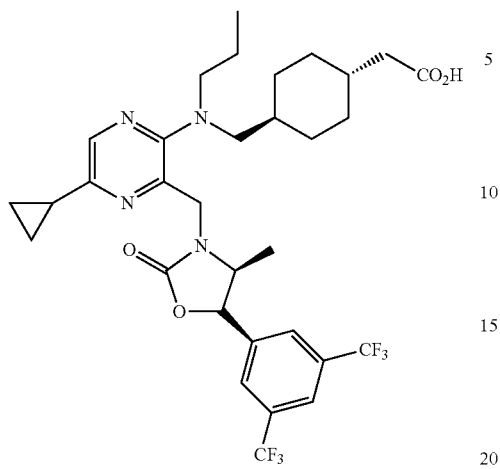

The title compound (80 mg, 99%) was prepared in the same manner as in Example 102, with the exception that the different reactant was used.

$^1$H NMR (600 MHz, CDCl3): 8.08 (s, 1H), 7.89 (s, 1H), 7.77 (s, 2H), 5.71 (d, 1H, J=7.8 Hz), 4.85 (d, 1H, J=16.2 Hz), 4.21-4.14 (m, 2H), 3.21-2.94 (m, 4H), 2.18 (d, 2H, J=6.0 Hz), 2.04-2.01 (m, 1H), 1.77-1.65 (m, 5H), 1.58-1.38 (m, 3H), 1.01-0.82 (m, 11H), 0.68 (d, 3H, J=4.8 Hz).

The title compound (70 mg, 99%) was prepared in the same manner as in Example 102, with the exception that the different reactant was used.

$^1$H NMR (400 MHz, CDCl$_3$): 8.17 (s, 1H), 7.87 (s, 1H), 7.72 (s, 2H), 5.66 (d, 1H, J=8.4 Hz), 5.00 (d, 1H, J=16.8 Hz), 4.23 (d, 1H, J=16.0 Hz), 3.26~3.06 (m, 2H), 2.94 (s, 3H), 2.58 (s, 3H), 2.44 (s, 3H), 2.20 (d, 2H, J=7.2 Hz), 1.82~1.58 (m, 6H), 1.03~0.88 (m, 4H), 0.71 (d, 3H, J=6.4 Hz)

Example 126 trans-4-({[3-({(4S,5S)-5-[3,5-bis(trifluoromethyl)phenyl]-4-methyl-2-oxazolidin-3-yl}methyl)-5-(3,5-dimethyloxazol-4-yl)pyrazin-2-yl]{[N-(methyl)aminomethyl]cyclohexyl)}acetic acid

Example 127 trans-4-({[3-({(4S,5S)-5-[3,5-bis(trifluoromethyl)phenyl]-4-methyl-2-oxazolidin-3-yl}methyl)-5-(pyrrolidin-1-yl)pyrazin-2-yl]{[N-(methyl)aminomethyl]cyclohexyl)}acetic acid

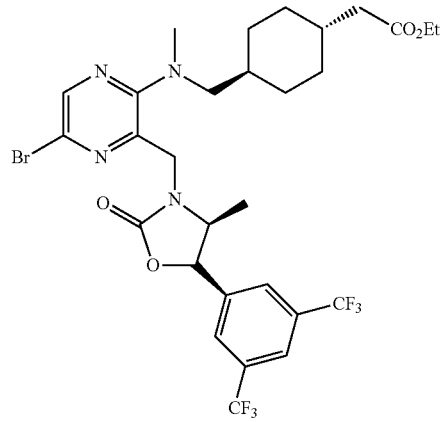

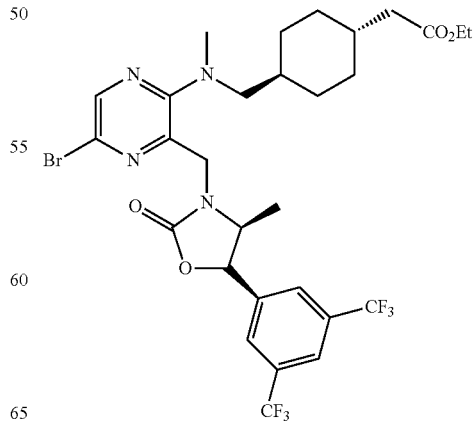

189

-continued

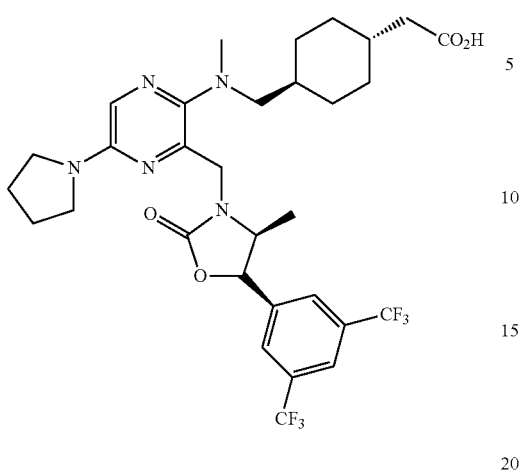

The title compound (70 mg, 92%) was prepared in the same manner as in Example 102, with the exception that the different reactant was used.

$^1$H NMR (400 MHz, CDCl$_3$): 7.87 (s, 1H), 7.76 (s, 2H), 7.55 (s, 1H), 5.72 (d, 1H, J=8.8 Hz), 4.82 (d, 1H, J=17.2 Hz), 4.36-4.28 (m, 2H), 3.52-3.38 (m, 4H), 2.86-2.78 (m, 1H), 2.74-2.66 (m, 1H), 2.59 (s, 3H), 2.18 (d, 2H, J=6.8 Hz), 2.04-1.98 (m, 4H), 1.86-1.72 (m, 5H), 1.42-1.36 (m, 1H), 0.98-0.84 (m, 4H), 0.73 (d, 3H, J=6.4 Hz).

Example 128 trans-4-({[3-({(4S,5S)-5-[3,5-bis(trifluoromethyl)phenyl]-4-methyl-2-oxazolidin-3-yl}methyl)-5-(cyclobutylpyrazin-2-yl)]{[N-(methyl)aminomethyl]cyclohexyl})acetic acid

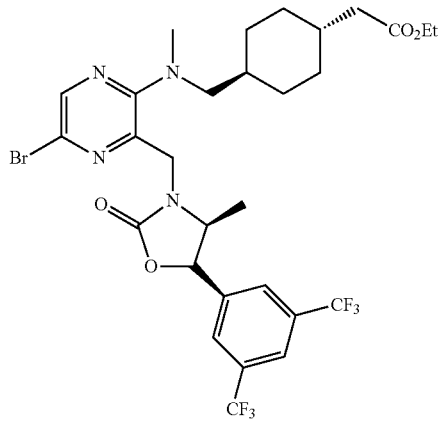

→

190

-continued

The title compound (60 mg, 92%) was prepared in the same manner as in Example 102, with the exception that the different reactant was used.

$^1$H NMR (400 MHz, CDCl$_3$): 7.93 (s, 1H), 7.87 (s, 1H), 7.75 (s, 2H), 5.75 (d, 1H, J=8.0 Hz), 4.96 (d, 1H, J=16.8 Hz), 4.30~4.24 (m, 2H), 3.62~3.57 (m, 1H), 3.12~3.07 (m, 1H), 3.00~2.93 (m, 1H), 2.83 (s, 3H), 2.32~2.26 (m, 3H), 2.19 (d, 2H, J=6.4 Hz), 2.11~1.99 (m, 1H), 1.96~1.89 (m, 1H), 1.81~1.50 (m, 7H), 1.00~0.82 (m, 4H), 0.72 (d, 3H, J=6.8 Hz)

Example 129 trans-4-({[3-({(4S,5S)-5-[3,5-bis(trifluoromethyl)phenyl]-4-methyl-2-oxazolidin-3-yl}methyl)-5-(cyclopentylpyrazin-2-yl)]{[N-(methyl)aminomethyl]cyclohexyl})acetic acid

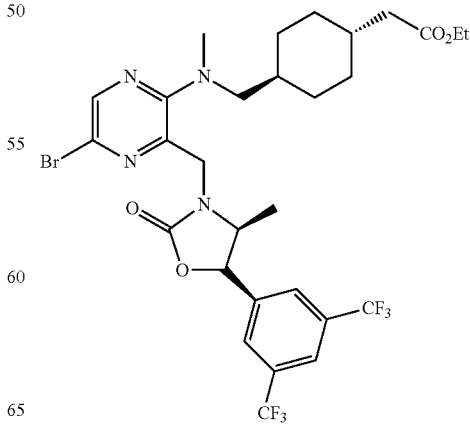

→

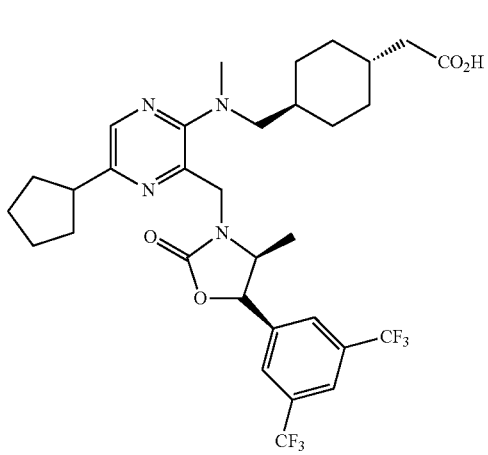

The title compound (50 mg, 79%) was prepared from the same manner as in Example 102, with the exception that trans-{4-[(N-methylamino)methyl]cyclohexyl}acetatein and a different reactant were used.

¹H NMR (400 MHz, CDCl₃): 7.97 (s, 1H), 7.86 (s, 1H), 7.74 (s, 2H), 5.71 (d, 1H, J=8.0 Hz), 4.93 (d, 1H, J=16.8 Hz), 4.23~4.17 (m, 2H), 3.15~3.05 (m, 2H), 2.98~2.83 (m, 1H), 2.81 (s, 3H), 2.18 (d, 2H, J=6.8 Hz), 2.08~1.97 (m, 2H), 1.83~1.56 (m, 12H), 1.00~0.85 (m, 4H), 0.70 (d, 3H, J=6.8 Hz).

A solution of trans-4-({[3-({(4S,5S)-5-[3,5-bis(trifluoromethyl)phenyl]-4-methyl-2-oxazolidin-3-yl}methyl)-5-(3,5-dimethyloxazol-4-yl)pyrazin-2-yl]{[N-(ethyl)aminomethyl]cyclohexyl)}acetic acid (100 mg, 0.14 mmol), prepared in Example 102, in THF (2 ml) was cooled to 0° C. and slowly added with drops of LAH (11 mg, 0.28 mmol). Then, the solution was stirred for 1 hr, added with drops of sodium sulfate decahydrate, and stirred again for 6 hrs. The reaction mixture was filtered through a celite-pad, concentrated in a vacuum, and purified through a column to afford the title compound (25 mg, 26%).

¹H NMR (600 MHz, CDCl3): 8.23 (s, 1H), 7.89 (s, 1H), 7.74 (s, 2H), 5.68 (d, 1H, J=9.0 Hz), 4.97 (d, 1H, J=16.8 Hz), 4.27 (d, 1H, J=16.8 Hz), 4.18-4.15 (m, 1H), 3.69-3.65 (m, 2H), 3.33-3.21 (m, 3H), 3.04-3.00 (m, 1H), 2.62 (s, 3H), 2.48 (s, 3H), 1.78-1.74 (m, 5H), 1.45-1.30 (m, 3H), 1.14 (t, 3H, J=7.2 Hz), 0.94-0.83 (m, 4H), 0.71 (d, 3H, J=6.6 Hz).

Example 130 trans-4-({[3-({(4S,5S)-5-[3,5-bis(trifluoromethyl)phenyl]-4-methyl-2-oxazolidin-3-yl}methyl)-5-(3,5-dimethyloxazol-4-yl)pyrazin-2-yl]{[N-(ethyl)aminomethyl]cyclohexyl)}propanol Example 131 trans-4-({[3-({(4S,5S)-5-[3,5-bis(trifluoromethyl)phenyl]-4-methyl-2-oxazolidin-3-yl}methyl)-5-(pyrrolidin-4-yl)pyrazin-2-yl]{[N-(ethyl)aminomethyl]cyclohexyl)}propanol

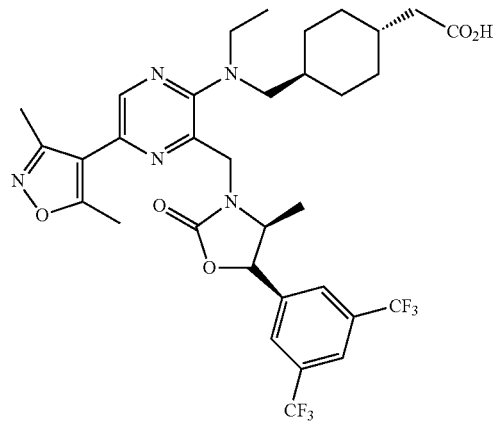

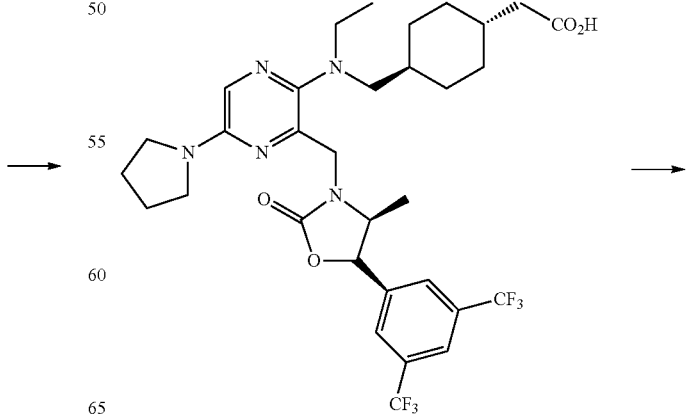

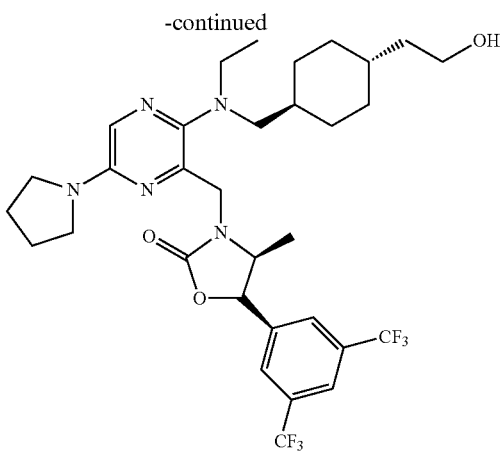

The title compound (70 mg, 51%) was prepared in the same manner as in Example 102, with the exception that the compound of Example 103 was used as a reactant.

$^1$H NMR (600 MHz, CDCl3): 7.88 (s, 1H), 7.77 (s, 2H), 7.60 (s, 1H), 5.73 (d, 1H, J=9.0 Hz), 4.83 (d, 1H, J=17.4 Hz), 4.35 (d, 1H, J=16.8 Hz), 4.33-4.30 (m, 1H), 3.65 (t, 2H, J=6.6 Hz), 3.52-3.40 (m, 4H), 2.97-2.90 (m, 3H), 2.74-2.71 (m, 1H), 2.05-2.02 (m, 4H), 1.82-1.70 (m, 5H), 1.44-1.25 (m, 3H), 0.97 (t, 3H, J=7.2 Hz), 0.90-0.81 (m, 4H), 0.73 (d, 3H, J 7.2 Hz).

Test Example 1

In Vivo Assay for Inhibitory Activity Against CETP in Human Blood

A CETP activity kit (#RB-CETP) was purchased from Roar Biochemical, Inc. A donor and an acceptor (each, 4 ul), a 10× assay buffer (177 ul), and each of dilutions of test compounds in dimethylsulfoxide (DMSO, Sigma-Aldrich) (0.01 nM~10000 nM) were added to each well of black round-bottom 96-well plates (Corning #3792). Plasma samples from healthy men were diluted in the assay buffer (1:10=plasma:assay buffer), and added to each well. The plates were sealed with a sealing film (Sigma-Aldrich, #Z369659), and incubated in a 37° C. incubator microplate shaker (#SLST-3, Seolin Bio) for 3 hrs. After removal of the sealing film, fluorescence was read on Spectra Max Gemini EM (Molecular devices) with an excitation wavelength of 465 nm and an emission wavelength of 535 nm. Measurements were calculated according to the following formula.

Calculated value=(Fluorescence Intensity with both compound and plasma−Fluorescence Intensity with compound but without plasma)/(Fluorescence Intensity with plasma but without compound−Fluorescence Intensity with neither compound nor plasma)

From the calculated value, a sigmoidal curve (y=start+ (end-start)x$^n$/k$^n$+x$^n$) was drawn using Origin Software (OriginLab Corporation, ver. 8.0724) to obtain IC$_{50}$ values. IC$_{50}$ values of the compounds of the Examples are summarized in Table 2, below. As their IC$_{50}$ values were measured to be less than 10 μM, particularly, below 0.5 μM, the compounds exhibited excellent inhibitory activity against CEPT.

TABLE 2

In vivo Inhibition of CETP Activity in Human Plasma

| Ex. No. | IC$_{50}$ (μM) |
|---|---|
| 1 | 0.112 |
| 2 | 0.143 |
| 3 | 0.194 |
| 6 | 0.049 |
| 7 | 0.0063 |
| 8 | 0.014 |
| 9 | 0.068 |
| 10 | 0.060 |
| 11 | 0.317 |
| 14 | 0.098 |
| 15 | 0.010 |
| 16 | 0.075 |
| 17 | 0.379 |
| 18 | 0.091 |
| 20 | 0.059 |
| 21 | 0.114 |
| 22 | 0.010 |
| 23 | 0.0444 |
| 24 | 0.1854 |
| 25 | 0.108 |
| 26 | 0.100 |
| 27 | 0.430 |
| 29 | 0.54 |
| 31 | 0.108 |
| 32 | 0.410 |
| 33 | 0.0399 |
| 34 | 0.062 |
| 35 | 0.020 |
| 36 | 0.220 |
| 37 | 0.498 |
| 38 | 0.0193 |
| 39 | 0.492 |
| 40 | 0.0198 |
| 41 | 0.0024 |
| 43 | 0.0079 |
| 44 | 0.0570 |
| 45 | 0.0269 |
| 46 | 0.0280 |
| 47 | 0.0450 |
| 48 | 0.133 |
| 49 | 0.0237 |
| 50 | 0.0111 |
| 51 | 0.0127 |
| 52 | 0.0734 |
| 53 | 0.0052 |
| 54 | 0.019 |
| 55 | 0.0111 |
| 56 | 0.0109 |
| 57 | 0.0167 |
| 58 | 0.0027 |
| 59 | 0.0057 |
| 60 | 0.0347 |
| 62 | 0.1507 |
| 63 | 0.0189 |
| 64 | 0.0293 |
| 65 | 0.2235 |
| 66 | 0.0463 |
| 68 | 0.3336 |
| 69 | 0.0134 |
| 70 | 0.0099 |
| 71 | 0.0067 |
| 72 | 0.1695 |
| 74 | 0.0632 |
| 75 | 0.0311 |
| 76 | 0.0874 |
| 77 | 0.0021 |
| 78 | 0.0177 |
| 79 | 0.0243 |
| 80 | 0.022 |
| 81 | 0.0265 |
| 82 | 0.2459 |
| 84 | 0.0297 |
| 85 | 0.0319 |
| 86 | 0.0304 |
| 87 | 0.0056 |

TABLE 2-continued

In vivo Inhibition of
CETP Activity in Human Plasma

| Ex. No. | IC$_{50}$ (µM) |
|---|---|
| 88 | 0.0107 |
| 89 | 0.007 |
| 90 | 0.0118 |
| 91 | 0.0267 |
| 92 | 0.048 |
| 95 | 0.0038 |
| 96 | 0.002 |
| 97 | 0.01161 |
| 98 | 0.00261 |
| 99 | 0.0831 |
| 100 | 0.0156 |
| 101 | 0.00345 |
| 102 | 0.00065 |
| 103 | 0.00326 |
| 104 | 0.0038 |
| 105 | 0.0008 |
| 106 | 0.0303 |
| 107 | 0.0370 |
| 108 | 0.0459 |
| 109 | 0.00384 |
| 110 | 0.05617 |
| 111 | 0.00311 |
| 112 | 0.03744 |
| 113 | 0.01604 |
| 114 | 0.0103 |
| 116 | 0.00629 |
| 117 | 0.01172 |
| 119 | 0.07816 |
| 120 | 0.02475 |
| 121 | 0.00388 |
| 122 | 0.00468 |
| 123 | 0.00719 |
| 124 | 0.00713 |
| 125 | 0.04027 |
| 126 | 0.0170 |
| 127 | 0.043 |
| 128 | 0.0239 |
| 129 | 0.03401 |
| 130 | 0.00886 |
| 131 | 0.00498 |

Test Example 21

Effect on CETP Activity in Hamster Administered with Single Dose

Each of the compounds of the Examples was orally administered at a dose of 100 mg/kg to three 7-week-old male Golden Syrian hamsters per group. Blood samples were taken from the retro-orbital plexus before administration and 0.5, 1, 2, 4, 6, 8, and 24 hrs after administration, and measured for blood CETP activity using a Roar CETP activity assay kit (Cat#: RB-CETP, Roar Biomedical Inc.).

As shown in Table 3, compounds of Examples 50, 56, 58, 77, 87, 88, 89, 96, 103, 105, 124 and 125 inhibited CETP activity by 45~72% to the maximum, compared to pre-treatment.

TABLE 3

Inhibition of CETP Activity in Hamsters
Administered with Single Dose

| Example | Relative Maximal Inhibition of CETP Activity to Pre-Administration (%) |
|---|---|
| 50 | 57 |
| 56 | 49 |
| 58 | 55 |
| 77 | 50 |
| 87 | 59 |
| 88 | 45 |
| 89 | 53 |
| 96 | 56 |
| 103 | 52 |
| 105 | 72 |
| 124 | 52 |
| 125 | 56 |

Test Example 3

Assay for Blood Lipid Level and Drug Concentration in Hamster Administered with Multiple Doses Each of the compounds of Examples 58, 96, 103 and 125 was orally administered at a dose of 10 mg/kg to 10 7-week-old male Golden Syrian Hamsters per group, every day for two weeks. Two hours after the final administration, blood samples were taken from the hamsters which then underwent an autopsy to analyze blood lipid levels and drug concentrations in blood and tissues (adipose tissues and liver)

As shown in Table 4, the compounds of the Examples effectively increased HDL levels.

TABLE 4

Effect of Compounds on Blood HDL-C
Level in Multi-Dosed Hamsters

| Example | Relative Increase HDL-C (%) to VC (Vehicle) |
|---|---|
| 58 | 47 |
| 96 | 48 |
| 103 | 47 |
| 125 | 27 |

In addition, as is understood from data of Table 5, compounds of Examples 58 and 96 were detected at low levels in blood and liver tissues, but at high levels in adipose tissues, showing a liphophilic distribution mode. In most animal species, fats are known as a main organ expressing CETP. Particularly, there is a correlation of CETP expression between fat and blood in humans and hamsters (*Atherosclerosis*, 1998; 139: 369-376, *J Lipid Res.* 34: 845-852). The compounds with lipophilicity are considered to effectively inhibit CETP in adipose tissues after CETP is generated from adipose tissues, and thus, can effectively improve HDL-C, as shown in Table 4, in spite of their low blood concentrations.

TABLE 5

Concentrations of Drug in Blood and Tissues
of Hamsters Administered with Multiple Doses

| | Drug Concentration | | |
|---|---|---|---|
| Example | Blood (ng/ml) | Liver Tissue (ng/g) | Adipose Tissue (ng/g) |
| 58 | 605.8 | 415 | 10190 |
| 96 | 309.4 | 128 | 7902 |

The invention claimed is:
1. A compound represented by the following Chemical Formula 1:

[Chemical Formula 1]

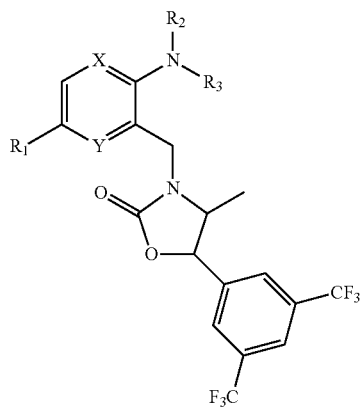

wherein,

X is N, Y is N or CH;

$R_1$ is selected from the group consisting of hydrogen, cyano, halogen, halogen-substituted or unsubstituted C1 to C6 alkyl, —$NR_4R_5$, —(O)$SO_2R_6$ which is optionally substituted with C1-C4 alkyl or may not be, substituted or unsubstituted C3 to C20 cycloalkyl, substituted or unsubstituted C3 to C20 heterocyclic, substituted or unsubstituted C6 to C40 aryl, and substituted or unsubstituted C3 to C40 heteroaryl;

$R_4$ and $R_5$ are independently selected from the group consisting of hydrogen, C1 to C4 alkyl, and C3 to C6 cycloalkyl with a proviso that when $R_4$ and $R_5$ are independently C1 to C4 alkyl, $R_4$ and $R_5$ may be linked to each other to form a hetero cycle containing N;

the substituted C3 to C20 cycloalky or the C3 to C20 heterocyclic in $R_1$ may be substituted with a functional radical selected from the group consisting of halogen, halogen-substituted or unsubstituted C1 to C4 alkyl, C1 to C4 hydroxyalkyl, —($CH_2$)$nCOR_7$, and —($CH_2$)nCO(O)$R_7$;

the substituted C6 to C40 aryl in $R_1$ may be substituted with a functional radical selected from the group consisting of halogen, cyano, nitryl, C1 to C4 alkyl, C1 to C4 hydroxyalkyl, and C1 to C4 alkoxy;

the C3 to 40 heteroaryl in $R_1$ may be substituted with cyano, nitryl, oxo, —$NR_8R_9$, halogen, halogen-substituted or unsubstituted C1 to C4 alkyl, C1 to C4 hydroxyalkyl, C1 to C4 alkoxy, —($CH_2$)$nCOR_{10}$, and —($CH_2$)nCO(O)$R_{10}$;

$R_2$ is selected from the group consisting of hydrogen, hydroxy-substituted or unsubstituted C1 or C6 alkyl, C3 to C7 cycloalkyl, and —($CH_2$)nCO(O)$R_{11}$;

$R_3$ is selected from the group consisting of C1 to C6 alkyl which may be substituted with substituted or unsubstituted C3 to C7 cycloalkyl or may not be, substituted or unsubstituted C3 to C7 cycloalkyl, substituted or unsubstituted C3 to C20 heterocyclic, and substituted or unsubstituted C6 to C20 spirocyclic heterocyclic;

$R_2$ and $R_3$ may be linked to each other to form a heterocycle containing N, said heterocycle being substituted with halogen-substituted or unsubstituted C1 to C4 alkyl or not;

the C3 to C7 cycloalkyl in $R_3$ may be substituted with a functional radical selected from the group consisting of oxo, —$NR_{12}R_{13}$, C1 to C4 hydroxyalkyl, and —($CH_2$)nCO(O)$R_{14}$;

the substituted C3 to C20 heterocycle and the substituted C6 to C20 spirocyclic heterocyclic in $R_3$ may be independently substituted with a functional radical selected from the group consisting of oxo, C1 to C4 alkyl, C1 to C4 alkoxy, ($CH_2$)nCO(O)$R_{15}$, —$COR_{16}$, and —$SO_2R_{17}$;

$R_{16}$ and $R_{17}$ are independently C1 to C4 alkyl or —$NR_{18}R_{19}$;

$R_6$, $R_7$, $R_8$, $R_9$, $R_{10}$, $R_{11}$, $R_{12}$, $R_{13}$, $R_{14}$, $R_{15}$, $R_{18}$ and $R_{19}$ are independently hydrogen or C1 to C4 alkyl;

n is an integer of 0, 1 or 2; an isomer thereof, or a pharmaceutically acceptable salt thereof.

2. The compound of claim 1, wherein X is N, and Y is N; an isomer thereof, or a pharmaceutically acceptable salt thereof.

3. The compound of claim 2,
wherein
$R_1$ is unsubstituted C3 to C20 cycloalkyl, or C3 to C40 heteroaryl substituted with C1 to C4 alkyl;
$R_2$ is C1 to C6 alkyl or C3 to C7 cycloalkyl, $R_3$ is C3 to C7 cycloalkyl, or C1 to C6 alkyl substituted with substituted C3 to C7 cycloalkyl;
$R_2$ and $R_3$ are linked to each other to form a heterocycle which may be substituted with halogen-substituted or unsubstituted C1 to C4 alkyl or may not be; an isomer thereof, or a pharmaceutically acceptable salt thereof.

4. The compound of claim 1, selected from the group consisting of the following compounds 1 to 93:

| | |
|---|---|
| 1 | (4S,5R)-5-[3,5-bis(trifluoromethyl)phenyl]-4-methyl-3-[(2-(methyl(tetrahydrofuran-3-yl)amino)-5-(trifluoromethyl)pyridin-3-yl)methyl]-oxazolidin-2-one |
| 2 | (4S,5R)-5-[3,5-bis(trifluoromethyl)phenyl]-4-methyl-3-{(2-[ethyl(tetrahydrofuran-3-yl)amino]-5-(trifluoromethyl)pyridin-3-yl)methyl}-oxazolidin-2-one |
| 3 | (4S,5R)-5-[3,5-bis(trifluoromethyl)phenyl]-4-methyl-3-({2-[(3R,4R)-4-ethoxytetrahydrofuran-3-yl)(methyl)amino]-5-(trifluoromethyl)pyridin-3-yl}methyl)-oxazolidin-2-one |
| 4 | (4S,5R)-5-[3,5-bis(trifluoromethyl)phenyl]-4-methyl-3-({2-[(3S,4R)-ethoxytetrahydrofuran-3-yl)(methyl)amino]-5-(trifluoromethyl)pyridin-3-yl}methyl)-oxazolidin-2-one |
| 5 | (4S,5R)-5-[3,5-bis(trifluoromethyl)phenyl]-4-methyl-3-({2-[(tetrahydro-2H-pyran-4-yl)amino]-5-(trifluoromethyl)pyridin-3-yl}methyl)-oxazolidin-2-one |
| 6 | (4S,5S)-5-[3,5-bis(trifluoromethyl)phenyl]-4-methyl-3-({[2-(methyl)(tetrahydro-2H-pyran-4-yl)amino]-5-(trifluoromethyl)pyridin-3-yl}methyl)-oxazolidin-2-one |
| 7 | (4S,5R)-5-[3,5-bis(trifluoromethyl)phenyl]-4-methyl-3-({[2-(ethyl)(tetrahydro-2H-pyran-4-yl)amino]-5-(trifluoromethyl)pyridin-3-yl}methyl)-oxazolidin-2-one |
| 8 | (4S,5R)-5-[3,5-bis(trifluoromethyl)phenyl]-4-methyl-3-({[2-(propyl)(tetrahydro-2H-pyran-4-yl)amino]-5-(trifluoromethyl)pyridin-3-yl}methyl)-oxazolidin-2-one |
| 9 | (4S,5R)-5-[3,5-bis(trifluoromethyl)phenyl]-4-methyl-3-({[2-(butyl)(tetrahydro-2H-pyran-4-yl)amino]-5-(trifluoromethyl)pyridin-3-yl}methyl)-oxazolidin-2-one |
| 10 | (4S,5R)-5-[3,5-bis(trifluoromethyl)phenyl]-4-methyl-3-{[2-(cyclopropyl)(tetrahydro-2H-pyran-4-yl)amino]-5-(trifluoromethyl)pyridin-3-yl}methyl)-oxazolidin-2-one |
| 11 | (4S,5R)-5-[3,5-bis(trifluoromethyl)phenyl]-4-methyl-3-({[2-(cyclobutyl)(tetrahydro-2H-pyran-4-yl)amino]-5-(trifluoro)methylpyridin-3-yl}methyl)-oxazolidin-2-one |
| 12 | t-butyl [3-({(4S,5R)-5-[3,5-bis(trifluoromethyl)phenyl]-4-methyl-2-oxo-oxazolidin-3-yl}methyl)-5-(trifluoromethyl)pyridin-2-yl]-(tetrahydro-2H-pyran-4-yl)-carbamate |

| | |
|---|---|
| 13 | ethyl [3-({(4S,5R)-5-[3,5-bis(trifluoromethyl)phenyl]-4-methyl-2-oxo-oxazolidin-3-yl}methyl)-5-(trifluoromethyl]pyridin-2-yl]-(tetrahydro-2H-pyran-4-yl)-carbamate |
| 14 | (4S,5R)-5-[3,5-bis(trifluoromethyl)phenyl]-4-methyl-3-({[2-ethyl(tetrahydro-2H-pyran-4-yl)amino]-pyridin-3-yl}methyl)-oxazolidin-2-one |
| 15 | (4S,5R)-5-[3,5-bis(trifluoromethyl)phenyl]-4-methyl-3-({[2-ethyl(tetrahydro-2H-pyran-3-yl)amino]-5-(trifluoromethyl)pyridin-3-yl}methyl)-oxazolidin-2-one |
| 16 | (4S,5R)-5-[3,5-bis(trifluoromethyl)phenyl]-4-methyl-3-({2-[ethyl(tetrahydro-2H-pyran-4-yl)amino]-5-fluoropyridin-3-yl}methyl)-oxazolidin-2-one |
| 17 | t-butyl 2-([3-({(4S,5R)-5-[3,5-bis(trifluoromethyl)phenyl]-4-methyl-2-oxo-oxazolidin-3-yl}methyl)-5-(trifluoromethyl)pyridin-2-yl]-(tetrahydro-2H-pyran-4-yl)amino)-acetate |
| 18 | (4S,5R)-5-[3,5-bis(trifluoromethyl)phenyl]-4-methyl-3-({[2-(hydroxyethyl)(tetrahydro-2H-pyran-4-yl)amino]-5-(trifluoromethyl)pyridin-3-yl}methyl)-oxazolidin-2-one |
| 19 | (4S,5R)-5-[3,5-bis(trifluoromethyl)phenyl]-4-methyl-3-({[2-(oxepan-4-yl)amino]-5-(trifluoromethyl)pyridin-3-yl}methyl)-oxazolidin-2-one |
| 20 | (4S,5R)-5-[3,5-bis(trifluoromethyl)phenyl]-4-methyl-3-({[2-(methyl)(oxepen-4-yl)amino]-5-(trifluoromethyl)pyridin-3-yl}methyl)-oxazolidin-2-one |
| 21 | (4S,5R)-5-[3,5-bis(trifluoromethyl)phenyl]-4-methyl-3-({[2-(ethyl)(1,4-dioxaspiro[4.5]decan-8-yl)amino]-5-trifluoromethylpyridin-3-yl}methyl)-oxazolidin-2-one |
| 22 | (4S,5R)-5-[3,5-bis(trifluoromethyl)phenyl]-4-methyl-3-({[2-(ethyl)(4-oxocyclohexyl)amino]-5-(trifluoromethyl)pyridin-3-yl}methyl)-oxazolidin-2-one |
| 23 | (4S,5R)-5-[3,5-bis(trifluoromethyl)phenyl]-4-methyl-3-({[2-(ethyl)(4-ethylaminocyclohexyl)amino]-5-(trifluoromethyl)pyridin-3-yl}methyl)-oxazolidin-2-one |
| 24 | methyl 2-(4-{[3-({(4S,5R)-5-[3,5-bis(trifluoromethyl)phenyl]-4-methyl-2-oxo-oxazolidin-3-yl}methyl)-5-(trifluoromethyl)pyridin-2-yl](ethyl)amino}cyclohexyl)acetate |
| 25 | (4S,5R)-5-[3,5-bis(trifluoromethyl)phenyl]-4-methyl-3-({[2-(ethyl)(tetrahydro-2H-thiopyran-4-yl)amino]-5-(trifluoromethyl)pyridin-3-yl}methyl)-oxazolidin-2-one |
| 26 | (4S,5R)-5-[3,5-bis(trifluoromethyl)phenyl]-4-methyl-3-({[2-(ethyl)(1-oxidotetrahydro-2H-thiopyran-4-yl)amino]-5-(trifluoromethyl)pyridin-3-yl}methyl)-oxazolidin-2-one |
| 27 | t-butyl 4-{[3-({(4S,5R)-5-[3,5-bis(trifluoromethyl)phenyl]-4-methyl-2-oxo-oxazolidin-3-yl}methyl)-5-(trifluoromethyl)pyridin-2-yl]amino}piperidine-1-carboxylate |
| 28 | (4S,5R)-5-[3,5-bis(trifluoromethyl)phenyl]-3-({[2-(ethyl)(piperidin-4-yl)amino]-5-(trifluoromethyl)pyridin-3-yl}methyl)-4-methyloxazolidin-2-one |
| 29 | (4S,5R)-5-[3,5-bis(trifluoromethyl)phenyl]-4-methyl-3-({[2-(ethyl)(1-methylpiperidin-4-yl)amino]-5-(trifluoromethyl)pyridin-3-yl}methyl)-oxazolidin-2-one |
| 30 | (4S,5R)-5-[3,5-bis(trifluoromethyl)phenyl]-4-methyl-3-({[2-(ethyl)(1,1-dimethylpiperidin-4-yl)amino]-5-(trifluoromethyl)pyridin-3-yl}methyl)-oxazolidin-2-one |
| 31 | ((4S,5R)-5-[3,5-bis(trifluoromethyl)phenyl]-4-methyl-3-({[2-(ethyl)(1-propylpiperidin-4-yl)amino]-5-trifluoromethylpyridin-3-yl}methyl)-oxazolidin-2-one |
| 32 | (4S,5R)-5-[3,5-bis(trifluoromethyl)phenyl]-4-methyl-3-({[2-(ethyl)(1-methanesulfonylpiperidin-4-yl)amino]-5-trifluoromethylpyridin-3-yl}methyl)-oxazolidin-2-one |
| 33 | (4S,5R)-5-[3,5-bis(trifluoromethyl)phenyl]-4-methyl-3-({[2-(ethyl)(1-acetylpiperidin-4-yl)amino]-5-(trifluoromethyl}pyridin-3-yl}methyl)-oxazolidin-2-one |
| 34 | (4S,5R)-5-[3,5-bis(trifluoromethyl)phenyl]-4-methyl-3-({[2-(ethyl)(1-propionylpiperidin-4-yl)amino]-5-(trifluoromethyl)pyridin-3-yl}methyl)-oxazolidin-2-one |
| 35 | methyl 4-{[3-({(4S,5R)-5-[3,5-bis(trifluoromethyl)phenyl]-4-methyl-2-oxo-oxazolidin-3-yl}methyl)-5-(trifluoromethyl)pyridin-2-yl](ethyl)amino}piperidine-1-carboxylate |
| 36 | ethyl 4-{[3-({(4S,5R)-5-[3,5-bis(trifluoromethyl)phenyl]-4-methyl-2-oxo-oxazolidin-3-yl}methyl)-5-(trifluoromethyl)pyridin-2-yl](ethyl)amino}piperidine-1-carboxylate |
| 37 | methyl 4-{[3-({(4S,5R)-5-[3,5-bis(trifluoromethyl)phenyl]-4-methyl-2-oxo-oxazolidin-3-yl}methyl)-5-(trifluoromethyl)pyridin-2-yl](ethyl)amino}-N,N-dimethylpiperidine-1-carboxamide |
| 38 | methyl 2-(4-{[3-({(4S,5R)-5-[3,5-bis(trifluoromethyl)phenyl]-4-methyl-2-oxo-oxazolidin-3-yl}methyl)-5-(trifluoromethyl)pyridin-2-yl](ethyl)amino}piperidin-1-yl)acetate |
| 39 | 2-(4-{[3-({(4S,5R)-5-[3,5-bis(trifluoromethyl)phenyl]-4-methyl-2-oxo-oxazolidin-3-yl}methyl)-5-(trifluoromethyl)pyridin-2-yl](ethyl)amino}piperidin-1-yl)acetic acid |
| 40 | (4S,5R)-5-[3,5-bis(trifluoromethyl)phenyl]-4-methyl-3-({[2-(ethyl)(tetrahydro-2H-pyran-4-yl)amino]-5-bromopyridin-3-yl}methyl)-oxazolidin-2-one |
| 41 | (4S,5R)-5-[3,5-bis(trifluoromethyl)phenyl]-4-methyl-3-({[2-(ethyl)(tetrahydro-2H-pyran-4-yl)amino]-5-(pyrrolidin-1-yl)pyridin-3-yl}methyl)-oxazolidin-2-one |
| 42 | methyl 2-(4-{5-({(4S,5R)-5-[3,5-bis(trifluoromethyl)phenyl]-4-methyl-2-oxo-oxazolidin-3-yl}methyl)-6-[ethyl(tetrahydro-2H-pyran-4-yl)amino]pyridin-3-yl}piperazin-1-yl)acetate |
| 43 | (4S,5R)-5-[3,5-bis(trifluoromethyl)phenyl]-4-methyl-3-({[2-(ethyl)(tetrahydro-2H-pyran-4-yl)amino]-5-(azetidin-1-yl)pyridin-3-yl}methyl)-oxazolidin-2-one |
| 44 | (4S,5R)-5-[3,5-bis(trifluoromethyl)phenyl]-4-methyl-3-({[2-(ethyl)(tetrahydro-2H-pyran-4-yl)amino]-5-(piperidin-1-yl)pyridin-3-yl}methyl)-oxazolidin-2-one |
| 45 | (4S,5R)-5-[3,5-bis(trifluoromethyl)phenyl]-4-methyl-3-({[2-(ethyl)(tetrahydro-2H-pyran-4-yl)amino]-5-phenylpyridin-3-yl}methyl)-oxazolidin-2-one |
| 46 | (4S,5R)-5-[3,5-bis(trifluoromethyl)phenyl]-4-methyl-3-({[2-(ethyl)(tetrahydro-2H-pyran-4-yl)amino]-5-(3-methylphenyl)pyridin-3-yl}methyl)-oxazolidin-2-one |
| 47 | (4S,5R)-5-[3,5-bis(trifluoromethyl)phenyl]-4-methyl-3-({[2-(ethyl)(tetrahydro-2H-pyran-4-yl)amino]-5-(3-fluorophenyl)pyridin-3-yl}methyl)-oxazolidin-2-one |
| 48 | (4S,5R)-5-[3,5-bis(trifluoromethyl)phenyl]-4-methyl-3-({[2-(ethyl)(tetrahydro-2H-pyran-4-yl)amino]-5-(3-ethoxyphenyl)pyridin-3-yl}methyl)-oxazolidin-2-one |
| 49 | (4S,5R)-5-[3,5-bis(trifluoromethyl)phenyl]-4-methyl-3-({[2-(ethyl)(tetrahydro-2H-pyran-4-yl)amino]-5-(furan-2-yl)pyridin-3-yl}methyl)-oxazolidin-2-one |
| 50 | (4S,5R)-5-[3,5-bis(trifluoromethyl)phenyl]-4-methyl-3-({[2-(ethyl)(tetrahydro-2H-pyran-4-yl)amino]-5-(1-methyl-1H-pyrrol-2-yl)pyridin-3-yl}methyl)-oxazolidin-2-one |
| 51 | (4S,5R)-5-[3,5-bis(trifluoromethyl)phenyl]-4-methyl-3-({[2-(ethyl)(tetrahydro-2H-pyran-4-yl)amino]-5-(3,5-dimethyl-isoxazol-4-yl)pyridin-3-yl}methyl)-oxazolidin-2-one |
| 52 | (4S,5R)-5-[3,5-bis(trifluoromethyl)phenyl]-4-methyl-3-({[2-(ethyl)(tetrahydro-2H-pyran-4-yl)amino]-pyridin-3-yl}methyl)-oxazolidin-2-one |
| 53 | (4S,5R)-5-[3,5-bis(trifluoromethyl)phenyl]-4-methyl-3-({[2-(ethyl)(cyclohexyl)amino]-5-(trifluoromethyl)pyridin-3-yl}methyl)-oxazolidin-2-one |
| 54 | 5-({4S,5R)-5-[3,5-bis(trifluoromethyl)phenyl]-4-methyl-2-oxo-1,3-oxazolidin-3-yl}methyl)-6-[(cyclohexyl)(ethyl)amino]nicotinonitrile |
| 55 | 5-{[(4S,5R)-5-[3,5-bis(trifluoromethyl)phenyl]-4-methyl-2-oxo-oxazolidin-3-yl]methyl}-6-[(cyclohexyl)(ethyl)amino]-pyridin-3-yl methanesulfonate |
| 56 | (4S,5R)-5-[3,5-bis(trifluoromethyl)phenyl]-4-methyl-3-({[2-(ethyl)(cyclohexyl-4-yl)amino]-5-(1-methyl-1H-pyrrol-2-yl)pyridin-3-yl}methyl)-oxazolidin-2-one |
| 57 | (4S,5R)-5-[3,5-bis(trifluoromethyl)phenyl]-4-methyl-3-({[2-(methyl)(cyclohexyl-4-yl)amino]-5-(3,5-dimethylisoxazol-4-yl)pyridin-3-yl}methyl)-oxazolidin-2-one |
| 58 | (4S,5R)-5-[3,5-bis(trifluoromethyl)phenyl]-4-methyl-3-({[2-(ethyl)(cyclohexyl)amino]-5-(3,5-dimethylisoxazol-4-yl)pyridin-3-yl}methyl)-oxazolidin-2-one |
| 59 | (4S,5R)-5-[3,5-bis(trifluoromethyl)phenyl]-4-methyl-3-({[2-(ethyl)(cyclohexyl)amino]-5-(1-methyl-1H-pyrazol-5-yl)pyridin-3-yl}methyl)-oxazolidin-2-one |

| | |
|---|---|
| 60 | (4S,5R)-5-[3,5-bis(trifluoromethyl)phenyl]-4-methyl-3-({[2-(ethyl)(cyclohexyl-4-yl)amino]-5-(1-methyl-1H-3-(trifluoromethyl)-pyrazol-5-yl)pyridin-3-yl}methyl)-oxazolidin-2-one |
| 61 | ethyl (2-{4-[5-({(4S,5R)-5-[3,5-bis(trifluoromethyl)phenyl]-4-methyl-2-oxo-oxazolidin-3-yl}methyl)]-6-[(cyclohexyl)(ethyl)amino]pyridin-3-yl]-1H-pyrazol-1-yl)acetate |
| 62 | (4S,5R)-5-[3,5-bis(trifluoromethyl)phenyl]-4-methyl-3-({[2-(ethyl)(cyclohexyl)amino]-5-(1-methyl-1H-pyrazol-4-yl)pyridin-3-yl}methyl)-oxazolidin-2-one |
| 63 | (4S,5R)-5-[3,5-bis(trifluoromethyl)phenyl]-4-methyl-3-({[2-(ethyl)(cyclohexyl)amino]-5-(3-methyl-thiophen-5-yl)pyridin-3-yl}methyl)-oxazolidin-2-one |
| 64 | (4S,5R)-5-[3,5-bis(trifluoromethyl)phenyl]-3-({[2-(ethyl)(cyclohexyl)amino]-5-(1,3,5-trimethyl-1H-pyrazol-4-yl)pyridin-3-yl}methyl)-oxazolidin-2-one |
| 65 | (4S,5R)-5-[3,5-bis(trifluoromethyl)phenyl]-4-methyl-3-({[2-(ethyl)(cyclohexyl-4-yl)amino]-5-(3,5-dimethyl-1H-pyrazol-4-yl)pyridin-3-yl}methyl)-oxazolidin-2-one |
| 66 | (4S,5R)-5-[3,5-bis(trifluoromethyl)phenyl]-4-methyl-3-({[2-(ethyl)(cyclohexyl)amino]-5-(1-methyl-1H-tetrazol-5-yl)pyridin-3-yl}methyl)-oxazolidin-2-one |
| 67 | (4S,5R)-5-[3,5-bis(trifluoromethyl)phenyl]-4-methyl-3-({[2-(ethyl)(cyclohexyl)amino]-5-(1-isobutyl-1H-pyrazol-4-yl)pyridin-3-yl}methyl)-oxazolidin-2-one |
| 68 | (4S,5R)-5-[3,5-bis(trifluoromethyl)phenyl]-4-methyl-3-({[2-(ethyl)(cyclohexyl)amino]-5-(1H-pyrazol-4-yl)pyridin-3-yl}methyl)-oxazolidin-2-one |
| 69 | (4S,5R)-5-[3,5-bis(trifluoromethyl)phenyl]-4-methyl-3-({[2-(ethyl)(cyclohexyl)amino]-5-(1,3-dimethyl-1H-pyrazol-4-yl)pyridin-3-yl}methyl)-oxazolidin-2-one |
| 70 | (4S,5R)-5-[3,5-bis(trifluoromethyl)phenyl]-4-methyl-3-({[2-(ethyl)(cyclohexyl)amino]-5-(3-methoxy-thiophen-2-yl)pyridin-3-yl}methyl)-oxazolidin-2-one |
| 71 | 5-{5-({(4S,5S)-5-[3,5-bis(trifluoromethyl)phenyl]-4-methyl-2-oxo-oxazolidin-3-yl}methyl)-6-[(cyclohexyl)(ethyl)amino]pyridin-3-yl}-thiophene-2-carbonitrile |
| 72 | (4S,5R)-5-[3,5-bis(trifluoromethyl)phenyl]-4-methyl-3-({[2-(ethyl)(cyclohexyl)amino]-5-(3-(trifluoromethyl)-1H-pyrazol-4-yl)pyridin-3-yl}methyl)-oxazolidin-2-one |
| 73 | ethyl 4-{5-({(4S,5R)-5-[3,5-bis(trifluoromethyl)phenyl]-4-methyl-2-oxo-oxazolin-3-yl}methyl)-6-[(cyclohexyl)(ethyl)amino)]pyridin-3-yl}-3-methylisoxazole-5-carboxylate |
| 74 | ethyl 5-{5-({(4S,5R)-5-[3,5-bis(trifluoromethyl)phenyl]-4-methyl-2-oxo-oxazolin-3-yl}methyl)-6-[(cyclohexyl)(ethyl)amino)]pyridin-3-yl}-3-methylisoxazole-4-carboxylate |
| 75 | (4S,5R)-5-[3,5-bis(trifluoromethyl)phenyl]-4-methyl-3-({[2-(ethyl)(cyclohexyl)amino]-5-(2-methyl-furan-5-yl)pyridin-3-yl}methyl)-oxazolidin-2-one |
| 76 | t-butyl 2-{5-({(4S,5S)-5-[3,5-bis(trifluoromethyl)phenyl]-4-methyl-2-oxo-oxazolidin-3-yl}methyl)-6-[(cyclohexyl)(ethyl)amino]pyridin-3-yl}-1H-pyrrole-1-carboxylate |
| 77 | (4S,5R)-5-[3,5-bis(trifluoromethyl)phenyl]-4-methyl-3-({[2-(ethyl)(cyclohexyl)amino]-5-(thiophen-3-yl)pyridin-3-yl}methyl)-oxazolidin-2-one |
| 78 | (4S,5R)-5-[3,5-bis(trifluoromethyl)phenyl]-4-methyl-3-({[2-(ethyl)(cyclohexyl)amino]-5-(3-methyl-thiophen-2-yl)pyridin-3-yl}methyl)-oxazolidin-2-one |
| 79 | (4S,5R)-5-[3,5-bis(trifluoromethyl)phenyl]-4-methyl-3-({[2-(ethyl)(cyclohexyl)amino]-5-(2-methyl-thiophen-5-yl)pyridin-3-yl}methyl)-oxazolidin-2-one |
| 80 | (4S,5R)-5-[3,5-bis(trifluoromethyl)phenyl]-4-methyl-3-({[2-(ethyl)(cyclohexyl)amino]-5-(thiophen-2-yl)pyridin-3-yl}methyl)-oxazolidin-2-one |
| 81 | (4S,5R)-5-[3,5-bis(trifluoromethyl)phenyl]-4-methyl-3-({[2-(ethyl)(cyclohexyl)amino]-5-(thiazol-4-yl)pyridin-3-yl}methyl)-oxazolidin-2-one |
| 82 | 3-{5-({(4S,5S)-5-[3,5-bis(trifluoromethyl)phenyl]-4-methyl-2-oxo-oxazolidin-3-yl}methyl)-6-[(cyclohexyl)(ethyl)amino]pyridin-3-yl}-thiophene-2-carbonitrile |
| 83 | t-butyl 4-[5-({(4S,5S)-5-[3,5-bis(trifluoromethyl)phenyl]-4-methyl-2-oxo-oxazolidin-3-yl}methyl)-6-[cyclohexyl(ethyl)amino]pyridin-3-yl]-5-methylisoxazol-3-yl-carbamate |
| 84 | (4S,5R)-5-[3,5-bis(trifluoromethyl)phenyl]-4-methyl-3-({[2-(ethyl)(cyclohexyl)amino]-5-(2,4-dimethyl-thiazol-5-yl)pyridin-3-yl}methyl)-oxazolidin-2-one |
| 85 | (4S,5R)-5-[3,5-bis(trifluoromethyl)phenyl]-4-methyl-3-({[2-(ethyl)(cyclohexyl)amino]-5-(3-amino-5-methyl-isoxazol-4-yl)pyridin-3-yl}methyl)-oxazolidin-2-one |
| 86 | (4S,5R)-5-[3,5-bis(trifluoromethyl)phenyl]-4-methyl-3-({[2-(ethyl)(cyclohexyl)amino]-5-(3-methyl-thiophen-4-yl)pyridin-3-yl}methyl)-oxazolidin-2-one |
| 87 | (4S,5R)-5-[3,5-bis(trifluoromethyl)phenyl]-4-methyl-3-({[2-(ethyl)(cyclohexyl)amino]-5-(3-methyl-isothioxazol-4-yl)pyridin-3-yl}methyl)-oxazolidin-2-one |
| 88 | (4S,5R)-5-[3,5-bis(trifluoromethyl)phenyl]-4-methyl-3-({[2-(ethyl)(cyclohexyl)amino]-5-(pyrrolidin-1-yl)pyridin-3-yl}methyl)-oxazolidin-2-one |
| 89 | (4S,5R)-5-[3,5-bis(trifluoromethyl)phenyl]-4-methyl-3-({[2-(ethyl)(cyclohexyl)amino]-5-(2-methyl-pyrrolidin-1-yl)pyridin-3-yl}methyl)-oxazolidin-2-one |
| 90 | (4S,5R)-5-[3,5-bis(trifluoromethyl)phenyl]-4-methyl-3-({[2-(ethyl)(cyclohexyl)amino]-5-(2-ethyl-pyrrolidin-1-yl)pyridin-3-yl}methyl)-oxazolidin-2-one |
| 91 | (4S,5R)-5-[3,5-bis(trifluoromethyl)phenyl]-4-methyl-3-({[2-(ethyl)(cyclohexyl)amino]-5-(3,3-difluoro-pyrrolidin-1-yl)pyridin-3-yl}methyl)-oxazolidin-2-one |
| 92 | (4S,5R)-5-[3,5-bis(trifluoromethyl)phenyl]-4-methyl-3-({[2-(ethyl)(cyclohexyl)amino]-5-(2-(trifluoromethyl)-pyrrolidin-1-yl)pyridin-3-yl}methyl)-oxazolidin-2-one |
| 93 | 3-[5-({(4S,5R)-5-[3,5-bis(trifluoromethyl)phenyl]-4-methyl-2-oxo-oxazolidin-3-yl}methyl)-6-[(cyclohexyl)(ethyl)amino]pyridin-3-yl]-1,2,4-oxadiazol-5(4H)-one; | or an isomer thereof, or a pharmaceutically acceptable salt thereof.

5. The compound of claim 1, selected from the group consisting of the following compounds 94 to 131:

| | |
|---|---|
| 94 | (4S,5R)-5-[3,5-bis(trifluoromethyl)phenyl]-4-methyl-3-{[2-(cyclohexylamino)-5-(3,5-dimethyl-isoxazol-4-yl)pyrazin-3-yl]methyl}-oxazolidin-2-one |
| 95 | (4S,5R)-5-[3,5-bis(trifluoromethyl)phenyl]-4-methyl-3-({[2-(methyl)(cyclohexyl)amino]-5-(3,5-dimethyl-isoxazol-4-yl)pyrazin-3-yl}methyl)-oxazolidin-2-one |
| 96 | (4S,5R)-5-[3,5-bis(trifluoromethyl)phenyl]-4-methyl-3-({[2-(ethyl)(cyclohexyl)amino]-5-(3,5-dimethyl-isoxazol-4-yl)pyrazin-3-yl}methyl)-oxazolidin-2-one |
| 97 | (4S,5R)-5-[3,5-bis(trifluoromethyl)phenyl]-3-({[2-(cyclopropyl)(cyclohexyl)amino]-5-(3,5-dimethyl-isoxazol-4-yl)pyrazin-3-yl}methyl)-4-methyloxazolidin-2-one |
| 98 | (4S,5S)-5-[3,5-bis(trifluoromethyl)phenyl]-3-{[6-(3,5-dimethylisoxazol-4-yl)-3-(piperidin-1-yl)pyrazin-2-yl]methyl}-4-methyloxazolidin-2-one |
| 99 | (4S,5S)-5-[3,5-bis(trifluoromethyl)phenyl]-3-{[6-(3,5-dimethylisoxazol-4-yl)-3-(2,6-dimethylmorpholino)pyrazin-2-yl]methyl}-4-methyloxazolidin-2-one |
| 100 | (4S,5S)-5-[3,5-bis(trifluoromethyl)phenyl]-3-{[6-(3,5-dimethylisoxazol-4-yl)-3-[3-(trifluoromethyl)piperidin-1-yl]pyrazin-2-yl]methyl}-4-methyloxazolidin-2-one |
| 101 | (4S,5R)-5-[3,5-bis(trifluoromethyl)phenyl]-3-({[3-(cyclopentylmethyl)(ethyl)amino]-4-methyl6-(3,5-dimethylisoxazol-4-yl)pyrazin-3-yl}methyl)-oxazolidin-2-one |
| 102 | trans-4-({[3-({(4S,5S)-5-[3,5-bis(trifluoromethyl)phenyl]-4-methyl-2-oxazolidin-3-yl}methyl)-5-(3,5-dimethyloxazol-4-yl)pyrazin-2-yl]{[N-(ethyl)aminomethyl]cyclohexyl})acetic acid |
| 103 | trans-4-({[3-({(4S,5S)-5-[3,5-bis(trifluoromethyl)phenyl]-4-methyl-2-oxazolidin-3-yl}methyl)-5-(pyrrolidin-1-yl)pyrazin-2-yl]{[N-(ethyl)aminomethyl]cyclohexyl})acetic acid |

| | |
|---|---|
| 104 | trans-4-({[3-({(4S,5S)-5-[3,5-bis(trifluoromethyl)phenyl]-4-methyl-2-oxazolidin-3-yl}methyl)-5-(1-methyl-1H-pyrrol-2-yl)pyrazin-2-yl]{[N-(ethyl)aminomethyl]cyclohexyl})acetic acid |
| 105 | trans-4-({[3-({(4S,5S)-5-[3,5-bis(trifluoromethyl)phenyl]-4-methyl-2-oxazolidin-3-yl}methyl)-5-(thiophen-3-yl)pyrazin-2-yl]{[N-(ethyl)aminomethyl]cyclohexyl})acetic acid |
| 106 | trans-4-({[3-({(4S,5S)-5-[3,5-bis(trifluoromethyl)phenyl]-4-methyl-2-oxazolidin-3-yl}methyl)-5-(1-methyl-1H-pyrazol-5-yl)pyrazin-2-yl]{[N-(ethyl)aminomethyl]cyclohexyl})acetic acid |
| 107 | trans-4-({[3-({(4S,5S)-5-[3,5-bis(trifluoromethyl)phenyl]-4-methyl-2-oxazolidin-3-yl}methyl)-5-(1,3-dimethyl-1H-pyrazol-5-yl)pyrazin-2-yl]{[N-(ethyl)aminomethyl]cyclohexyl})acetic acid |
| 108 | trans-4-({[3-({(4S,5S)-5-[3,5-bis(trifluoromethyl)phenyl]-4-methyl-2-oxazolidin-3-yl}methyl)-5-(1,3-dimethyl-1H-pyrazol-4-yl)pyrazin-2-yl]{[N-(ethyl)aminomethyl]cyclohexyl})acetic acid |
| 109 | trans-4-({[3-({(4S,5S)-5-[3,5-bis(trifluoromethyl)phenyl]-4-methyl-2-oxazolidin-3-yl}methyl)-5-(3-methoxythiophen-2-yl)pyrazin-2-yl]{[N-(ethyl)aminomethyl]cyclohexyl})acetic acid |
| 110 | trans-4-({[3-({(4S,5S)-5-[3,5-bis(trifluoromethyl)phenyl]-4-methyl-2-oxazolidin-3-yl}methyl)-5-(4-methylthio펜-일)pyrazin-2-yl]{[N-(ethyl)aminomethyl]cyclohexyl})acetic acid |
| 111 | trans-4-({[3-({(4S,5S)-5-[3,5-bis(trifluoromethyl)phenyl]-4-methyl-2-oxazolidin-3-yl}methyl)-5-(3-methylthiophen-2-yl)pyrazin-2-yl]{[N-(ethyl)aminomethyl]cyclohexyl})acetic acid |
| 112 | trans-4-({[3-({(4S,5S)-5-[3,5-bis(trifluoromethyl)phenyl]-4-methyl-2-oxazolidin-3-yl}methyl)-5-(thiazol-2-yl)pyrazin-2-yl]{[N-(ethyl)aminomethyl]cyclohexyl})acetic acid |
| 113 | trans-4-({[3-({(4S,5S)-5-[3,5-bis(trifluoromethyl)phenyl]-4-methyl-2-oxazolidin-3-yl}methyl)-5-(thiazol-4-yl)pyrazin-2-yl]{[N-(ethyl)aminomethyl]cyclohexyl})acetic acid |
| 114 | trans-4-({[3-({(4S,5S)-5-[3,5-bis(trifluoromethyl)phenyl]-4-methyl-2-oxazolidin-3-yl}methyl)-5-(thiophen-2-yl)pyrazin-2-yl]{[N-(ethyl)aminomethyl]cyclohexyl})acetic acid |
| 115 | trans-4-({[3-({(4S,5S)-5-[3,5-bis(trifluoromethyl)phenyl]-4-methyl-2-oxazolidin-3-yl}methyl)-5-(5-acetylthiophen-2-yl)pyrazin-2-yl]{[N-(ethyl)aminomethyl]cyclohexyl})acetic acid |
| 116 | trans-4-({[3-({(4S,5S)-5-[3,5-bis(trifluoromethyl)phenyl]-4-methyl-2-oxazolidin-3-yl}methyl)-5-phenylpyrazin-2-yl]{[N-(ethyl)aminomethyl]cyclohexyl})acetic acid |
| 117 | trans-4-({[3-({(4S,5S)-5-[3,5-bis(trifluoromethyl)phenyl]-4-methyl-2-oxazolidin-3-yl}methyl)-5-(4-cyanophenyl)pyrazin-2-yl]{[N-(ethyl)aminomethyl]cyclohexyl})acetic acid |
| 118 | trans-4-({[3-({(4S,5S)-5-[3,5-bis(trifluoromethyl)phenyl]-4-methyl-2-oxazolidin-3-yl}methyl)-5-(4-hydroxymethylphenyl)pyrazin-2-yl]{[N-(ethyl)aminomethyl]cyclohexyl})acetic acid |
| 119 | trans-4-({[3-({(4S,5S)-5-[3,5-bis(trifluoromethyl)phenyl]-4-methyl-2-oxazolidin-3-yl}methyl)-5-(pyridin-3-yl)pyrazin-2-yl]{[N-(ethyl)aminomethyl]cyclohexyl})acetic acid |
| 120 | trans-4-({[3-({(4S,5S)-5-[3,5-bis(trifluoromethyl)phenyl]-4-methyl-2-oxazolidin-3-yl}methyl)-5-(5-fluoropyridin-3-yl)pyrazin-2-yl]{[N-(ethyl)aminomethyl]cyclohexyl})acetic acid |
| 121 | trans-4-({[3-({(4S,5S)-5-[3,5-bis(trifluoromethyl)phenyl]-4-methyl-2-oxazolidin-3-yl}methyl)-5-(cyclopropylpyrazin-2-yl)]{[N-(ethyl)aminomethyl]cyclohexyl})acetic acid |
| 122 | trans-4-({[3-({(4S,5S)-5-[3,5-bis(trifluoromethyl)phenyl]-4-methyl-2-oxazolidin-3-yl}methyl)-5-(cyclobutylpyrazin-2-yl)]{[N-(ethyl)aminomethyl]cyclohexyl})acetic acid |
| 123 | trans-4-({[3-({(4S,5S)-5-[3,5-bis(trifluoromethyl)phenyl]-4-methyl-2-oxazolidin-3-yl}methyl)-5-(3,5-dimethyloxazol-4-yl)pyrazin-2-yl]{[N-(propyl)aminomethyl]cyclohexyl})acetic acid |
| 124 | trans-4-({[3-({(4S,5S)-5-[3,5-bis(trifluoromethyl)phenyl]-4-methyl-2-oxazolidin-3-yl}methyl)-5-(pyrrolidin-1-yl)pyrazin-2-yl]{[N-(propyl)aminomethyl]cyclohexyl})acetic acid |
| 125 | trans-4-({[3-({(4S,5S)-5-[3,5-bis(trifluoromethyl)phenyl]-4-methyl-2-oxazolidin-3-yl}methyl)-5-(cyclohexylpyrazin-2-yl)]{[N-(propyl)aminomethyl]cyclohexyl})acetic acid |
| 126 | trans-4-({[3-({(4S,5S)-5-[3,5-bis(trifluoromethyl)phenyl]-4-methyl-2-oxazolidin-3-yl}methyl)-5-(3,5-dimethyloxazol-4-yl)pyrazin-2-yl]{[N-(methyl)aminomethyl]cyclohexyl})acetic acid |
| 127 | trans-4-({[3-({(4S,5S)-5-[3,5-bis(trifluoromethyl)phenyl]-4-methyl-2-oxazolidin-3-yl}methyl)-5-(pyrrolidin-1-yl)pyrazin-2-yl]{[N-(methyl)aminomethyl]cyclohexyl})acetic acid |
| 128 | trans-4-({[3-({(4S,5S)-5-[3,5-bis(trifluoromethyl)phenyl]-4-methyl-2-oxazolidin-3-yl}methyl)-5-(cyclobutylpyrazin-2-yl)]{[N-(methyl)aminomethyl]cyclohexyl})acetic acid |
| 129 | trans-4-({[3-({(4S,5S)-5-[3,5-bis(trifluoromethyl)phenyl]-4-methyl-2-oxazolidin-3-yl}methyl)-5-(cyclopentylpyrazin-2-yl)]{[N-(methyl)aminomethyl]cyclohexyl})acetic acid |
| 130 | trans-4-({[3-({(4S,5S)-5-[3,5-bis(trifluoromethyl)phenyl]-4-methyl-2-oxazolidin-3-yl}methyl)-5-(3,5-dimethyloxazol-4-yl)pyrazin-2-yl]{[N-(ethyl)aminomethyl]cyclohexyl})propanol |
| 131 | trans-4-({[3-({(4S,5S)-5-[3,5-bis(trifluoromethyl)phenyl]-4-methyl-2-oxazolidin-3-yl}methyl)-5-(pyrrolidin-4-yl)pyrazin-2-yl]{[N-(ethyl)aminomethyl]cyclohexyl})propanol; | or an isomer thereof, or a pharmaceutically acceptable salt thereof.

6. A method for preparing the compound of claim 1, comprising:

introducing a leaving group to a compound of Chemical Formula 2-1 to give a compound of Chemical Formula 2-2;

reacting the compound of Chemical Formula 2-2 with (4S,5R)-5-[3,5-bis(trifluoromethyl)phenyl])-4-methyl-oxazolidin-2-one to form a compound of Chemical Formula 3; and coupling the compound of Chemical Formula 3 with an amine group (—NR$_2$R$_3$) to afford the compound of Chemical Formula 1:

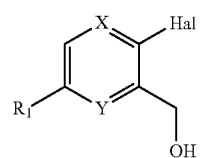

[Chemical Formula 2-1]

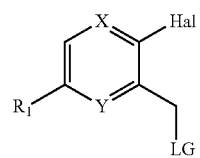

[Chemical Formula 2-2]

[Chemical Formula 3]

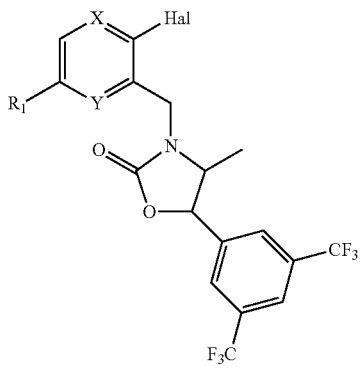

wherein, Hal represents halogen, LG represents a leaving group selected from among halogen and methanesulfonyl, and X, Y, $R_1$, $R_2$, and $R_3$ are as defined in Chemical Formula 1.

7. The method of claim 6, wherein the compound of Chemical Formula 2-1 is obtained by reducing a compound of Chemical Formula 2:

[Chemical Formula 2]

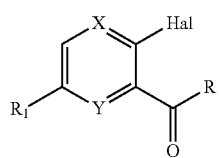

wherein, R is hydrogen or C1 to C4 alkoxy, for example, methoxy, and Hal and $R_1$ are as defined in Chemical Formula 2-1.

8. A method for preparing the compound of claim 1, comprising:
introducing a leaving group to a compound of Chemical Formula 4-1 to give a compound of Chemical Formula 4-2; and
reacting the compound of Chemical Formula 4-2 with (4S,5R)-5-[3,5-bis(trifluoromethyl)phenyl])-4-methyl-oxazolidin-2-one:

[Chemical Formula 4-1]

[Chemical Formula 4-2]

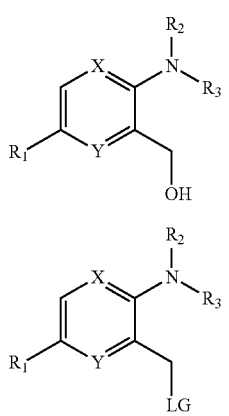

wherein, LG represents a leaving group selected from among halogen and sulfanyl group, and X, Y, $R_1$, $R_2$ and $R_3$ are as defined in Chemical Formula 1.

9. The method of claim 8, further comprising, prior to the formation of the compound of Chemical Formula 4-2:
coupling a compound of Chemical Formula 2 with an amine group (—$NR_2R_3$) to form a compound of Chemical Formula 4; and
reducing the compound of Chemical Formula 4 into the compound of Chemical Formula 4-1:

[Chemical Formula 2]

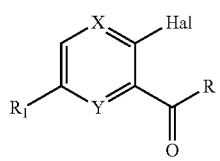

[Chemical Formula 4]

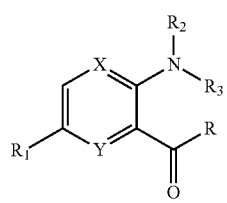

wherein, Hal represents halogen, R is hydrogen or C1 to C4 alkoxy, and X, Y, $R_1$, $R_2$ and $R_3$ are as defined in Chemical Formula 1.

10. The method of claim 8, further comprising, prior to the formation of the compound of Chemical Formula 4-2:
introducing at least one of $R_2$ and $R_3$ to the amine group on a compound of Chemical Formula 5 to give a compound of Chemical Formula 6;
performing acyl substitution on the compound of Chemical Formula 6 to form a compound of Chemical Formula 4; and
reducing the compound of Chemical Formula 4 to a compound of Chemical Formula 4-1;

[Chemical Formula 5]

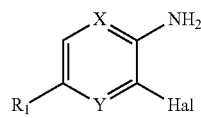

[Chemical Formula 6]

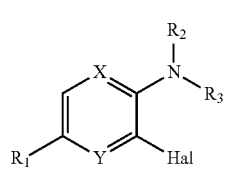

[Chemical Formula 4]

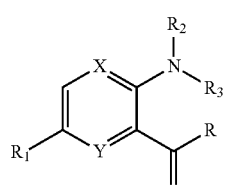

-continued

[Chemical Formula 4-1]

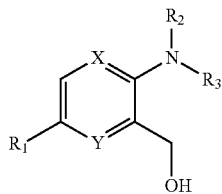

wherein, Hal represents halogen, R is hydrogen or C1 to C4 alkoxy, and X, Y, $R_1$, $R_2$ and $R_3$ are as defined in Chemical Formula 1.

11. The method of claim 8, further comprising, prior to the formation of the compound of Chemical Formula 4-2:
   coupling a compound of Chemical Formula 2b with an amine group (—$NR_2R_3$) to give a compound of Chemical Formula 4b';
   introducing $R_1$ to the compound of Chemical Formula 4b' to form a compound of Chemical Formula 4 (exception that $R_1$ is hydrogen or halogen); and
   reducing the compound of Chemical Formula 4 to a compound of Chemical Formula 4-1:

[Chemical Formula 2b]

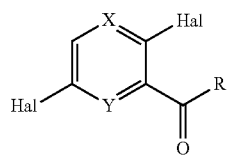

[Chemical Formula 4b']

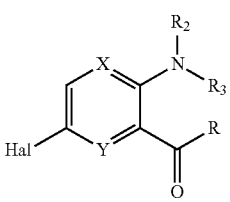

[Chemical Formula 4]

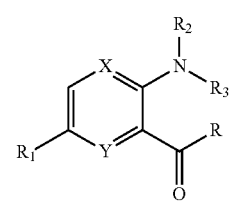

[Chemical Formula 4-1]

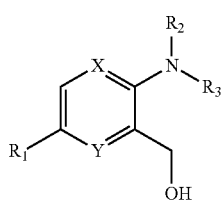

wherein, Hal represents halogen, R is hydrogen or C1 to C4 alkoxy, and X, Y, $R_1$, $R_2$ and $R_3$ are as defined in Chemical Formula 1, with a proviso that $R_1$ is not hydrogen nor halogen.

12. A method for preparing the compound of claim 1, comprising:
   introducing a leaving group to a compound of Chemical Formula 2a-1 to form a compound of Chemical Formula 2a-2;
   reacting the compound of Chemical Formula 2a-2 with (4S,5R)-5-[3,5-bis(trifluoromethyl)phenyl])-4-methyl-oxazolidin-2-one to form a compound of Chemical Formula 3a;
   coupling the compound of Chemical Formula 3a with an amine group (—$NR_2R_3$) to form a compound of Chemical Formula 1a'; and
   introducing $R_1$ to the compound of Chemical Formula 1a' to afford the compound of Chemical Formula 1 (with the exception that $R_1$ is hydrogen):

[Chemical Formula 2a-1]

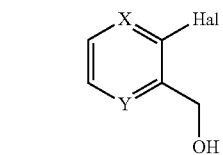

[Chemical Formula 2a-2]

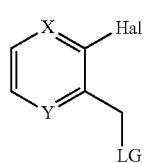

[Chemical Formula 3a]

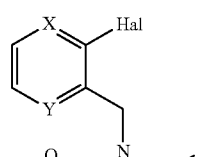

[Chemical Formula 1a']

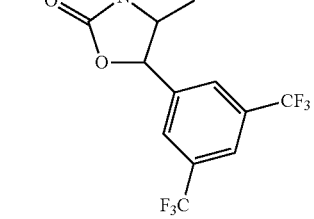

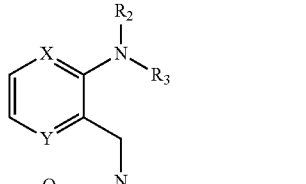

wherein, Hal represents halogen, LG represents a leaving group selected from among halogen and methanesulfonyl, and X, Y, $R_1$, $R_2$ and $R_3$ are as defined in Chemical Formula 1, with a proviso that $R_1$ is not hydrogen.

13. A method for preparing the compound of claim 1, comprising:
   introducing a leaving group to the compound of Chemical Formula 4a-1 to give a compound of Chemical Formula 4a-2;

reacting the compound of Chemical Formula 4a-2 with (4S,5R)-5-[3,5-bis(trifluoromethyl)phenyl])-4-methyl-oxazolidin-2-one to form a compound of Chemical Formula 1a'; and introducing $R_1$ to a compound of Chemical Formula 1a' to afford the compound of Chemical Formula 1 (with exception that $R_1$ is hydrogen):

[Chemical Formula 4a-1]

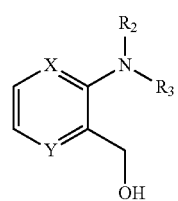

[Chemical Formula 4a-2]

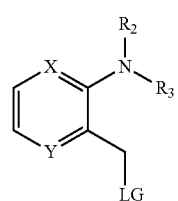

[Chemical Formula 1a']

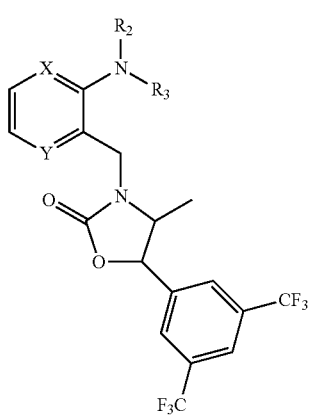

wherein, LG represents a leaving group selected from among halogen and methanesulfonyl, and X, Y, $R_1$, $R_2$ and $R_3$ are as defined in Chemical Formula 1, with a proviso that $R_1$ is not hydrogen.

14. A method for preparing the compound of claim 1, comprising:

introducing a leaving group to the compound of Chemical Formula 4a-1 to give a compound of Chemical Formula 4a-2;

reacting the compound of Chemical Formula 4a-2 with (4S,5R)-5-[3,5-bis(trifluoromethyl)phenyl])-4-methyl-oxazolidin-2-one to form a compound of Chemical Formula 1a'; and introducing $R_1$ to a compound of Chemical Formula 1a' to afford the compound of Chemical Formula 1 (with exception that $R_1$ is hydrogen):

[Chemical Formula 4a-1]

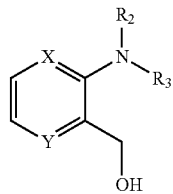

[Chemical Formula 4a-2]

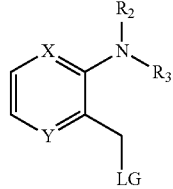

[Chemical Formula 1a']

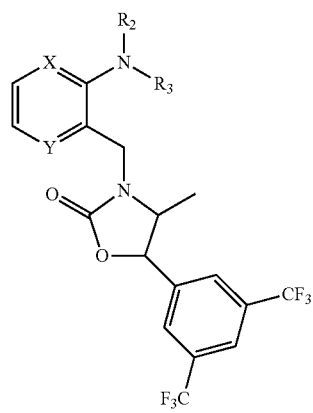

wherein, LG represents a leaving group selected from among halogen and methanesulfonyl, and X, Y, $R_1$, $R_2$ and $R_3$ are as defined in Chemical Formula 1, with a proviso that $R_1$ is not hydrogen.

15. The method of claim 12, wherein the introducing of $R_1$ comprises:

halogenating the compound of Chemical Formula 1a' to the compound of Chemical Formula 1b', and substituting the halogen on the compound of Chemical Formula 1b' with $R_1$

[Chemical Formula 1b']

1b'

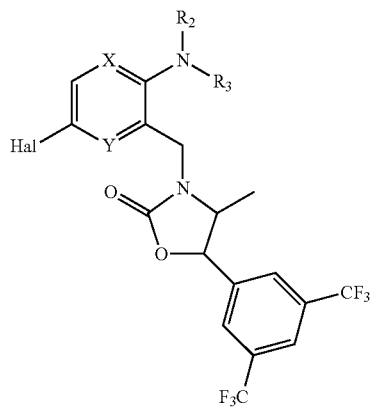

wherein, LG represents a leaving group selected from among halogen and methanesulfonyl, and X, Y, $R_1$, $R_2$ and $R_3$ are as defined in Chemical Formula 1, with a proviso that $R_1$ is not hydrogen.

16. A method for preparing the compound of claim 1, comprising:

introducing a leaving group to a compound of Chemical Formula 4b'-1 to give a compound of Chemical Formula 4b'-2;

reacting the compound of Chemical Formula 4b'-2 with (4S,5R)-5-[3,5-bis(trifluoromethyl)phenyl])-4-methyl-oxazolidin-2-one to form a compound of Chemical Formula 1b'; and substituting the halogen on the compound of Chemical Formula 1b' with $R_1$ to afford the compound of Chemical Formula 1 (with exception that $R_1$ is hydrogen):

[Chemical Formula 4b'-1]

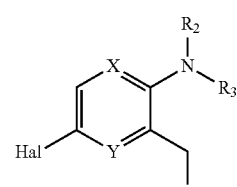

[Chemical Formula 4b'-2]

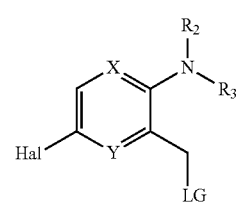

[Chemical Formula 1b']

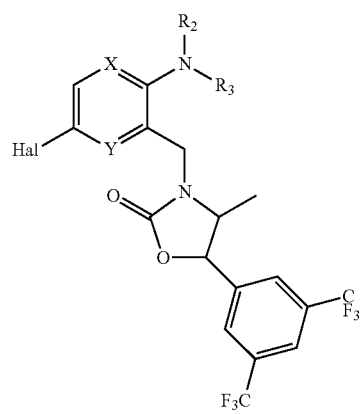

wherein Hal represents halogen, LG represents a leaving group selected from among halogen and methanesulfonyl, and X, Y, $R_1$, $R_2$ and $R_3$ are as defined in Chemical Formula 1, with a proviso that $R_1$ is not hydrogen nor halogen.

17. A method for preparing the compound of claim 1, comprising:

introducing a leaving group to a compound of Chemical Formula 2b-1 to give a compound of Chemical Formula 2b-2;

reacting the compound of Chemical Formula 2b-2 with (4S,5R)-5-[3,5-bis(trifluoromethyl)phenyl])-4-methyl-oxazolidin-2-one to form a compound of Chemical Formula 3b'; and coupling the compound of Chemical Formula 3b' with an amino group (—$NR_2R_3$) to form a compound of Chemical Formula 1b'; substituting the halogen on the compound of Chemical Formula 1b' with $R_1$ to afford the compound of Chemical Formula 1 (with exception that $R_1$ is hydrogen or halogen):

[Chemical Formula 2b-1]

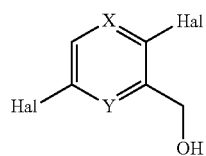

[Chemical Formula 2b-2]

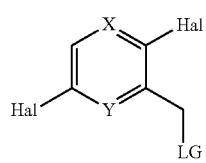

[Chemical Formula 3b']

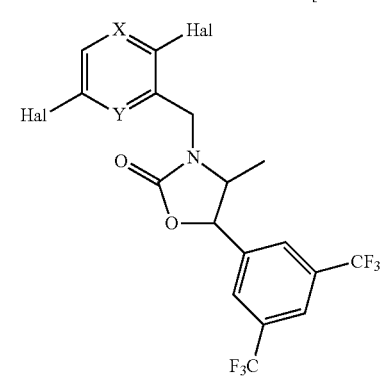

[Chemical Formula 1b']

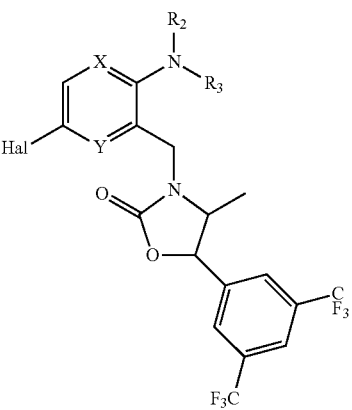

wherein, Hal represents halogen, LG represents a leaving group selected from among halogen and methanesulfonyl, and X, Y, $R_1$, $R_2$ and $R_3$ are as defined in Chemical Formula 1, with a proviso that $R_1$ is not hydrogen nor halogen.

18. A method for preparing the compound of claim 1, comprising:

introducing a leaving group to a compound of Chemical Formula 2b-1 to give a compound of Chemical Formula 2b-2;

reacting the compound of Chemical Formula 2b-2 with (4S,5R)-5-[3,5-bis(trifluoromethyl)phenyl])-4-methyl-oxazolidin-2-one to form a compound of Chemical Formula 3b';

substituting the halogen on the compound of Chemical Formula 3b' with $R_1$ to form a compound of Chemical Formula 3 (with exception that $R_1$ is not hydrogen nor halogen); and coupling the compound of Chemical Formula 3 with an amino group ($-NR_2R_3$) to afford a compound of Chemical Formula 1:

[Chemical Formula 2b-1]

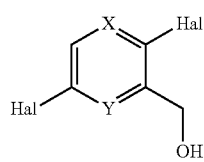

[Chemical Formula 2b-2]

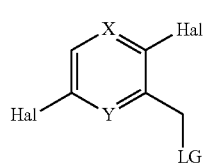

[Chemical Formula 3b']

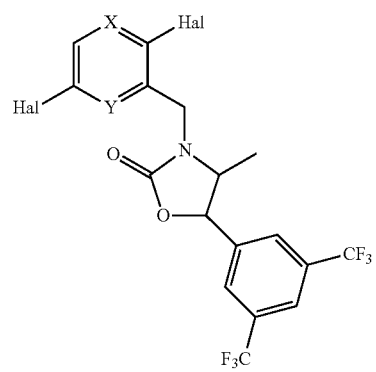

[Chemical Formula 3]

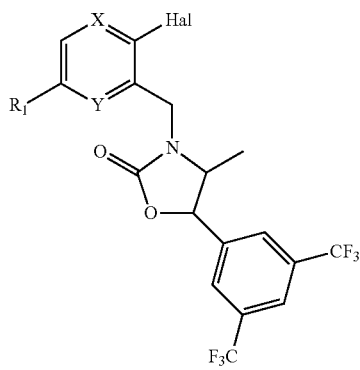

wherein, Hal represents halogen, LG represents a leaving group selected from among halogen and methanesulfonyl, and X, Y, $R_1$, $R_2$ and $R_3$ are as defined in Chemical Formula 1, with a proviso that $R_1$ is not hydrogen nor halogen.

19. The method of claim 6, wherein the coupling of the amine group ($-NR_2R_3$) is carried out either by using $NHR_2R_3$ as a reactant or by using $NHR_2$ or $NHR_3$ as a reactant, and then by introducing $R_2$ or $R_3$.

20. The method of claim 6, wherein $R_2$ is a hydroxy-containing substituent, and wherein the method further comprises protecting the hydroxy group with a protecting group, and finally removing the hydroxy-protecting group.

21. A pharmaceutical composition with inhibitory activity against CETP, comprising the compound of claim 1, an isomer thereof, or a pharmaceutically acceptable salt thereof.

22. The pharmaceutical composition of claim 21, being therapeutic of dyslipidemia, atherosclerosis or coronary heart disease.

23. A method of treating a disease related with cholesterylester transfer protein (CETP) activity, wherein the disease is dyslipidemia, atherosclerosis or coronary heart disease, comprising administering the compound of claim 1, an isomer thereof, or a pharmaceutically acceptable salt thereof to a subject in need thereof.

* * * * *